US012576099B2

(12) United States Patent
Zhang et al.

(10) Patent No.: US 12,576,099 B2

(45) Date of Patent: Mar. 17, 2026

(54) RIBOSE-MODIFIED CAP ANALOG AND USE THEREOF

(71) Applicant: Beijing Youcare Kechuang Pharmaceutical Technology Co., Ltd., Beijing (CN)

(72) Inventors: Honglei Zhang, Beijing (CN); Gengshen Song, Beijing (CN); Yangjian Liu, Beijing (CN); Kai Dong, Beijing (CN); Yuqing Ma, Beijing (CN); Chao Zhang, Beijing (CN); Yanfeng Wang, Beijing (CN); Guoliang Zhang, Beijing (CN); Lili Jiang, Beijing (CN); Jinyu Zhang, Beijing (CN)

(73) Assignee: Beijing Youcare Kechuang Pharmaceutical Technology Co., Ltd., Beijing (CN)

( * ) Notice: Subject to any disclaimer, the term of this patent is extended or adjusted under 35 U.S.C. 154(b) by 0 days.

(21) Appl. No.: 19/066,352

(22) Filed: Feb. 28, 2025

(65) Prior Publication Data

US 2025/0332189 A1 Oct. 30, 2025

(30) Foreign Application Priority Data

Apr. 26, 2024 (CN) ......................... 202410514555.1
Jun. 24, 2024 (CN) ......................... 202410814191.9

(51) Int. Cl.

| | |
|---|---|
| ***A61K 31/7105*** | (2006.01) |
| ***A61K 9/1272*** | (2025.01) |
| ***A61K 9/51*** | (2006.01) |
| ***A61K 47/02*** | (2006.01) |
| ***A61K 47/24*** | (2006.01) |
| ***C07H 21/02*** | (2006.01) |
| ***C12N 9/14*** | (2006.01) |

(52) U.S. Cl.

CPC ........ *A61K 31/7105* (2013.01); *A61K 9/1272* (2013.01); *A61K 9/5123* (2013.01); *A61K 47/02* (2013.01); *A61K 47/24* (2013.01); *C07H 21/02* (2013.01); *C12N 9/14* (2013.01); *C12Y 306/01001* (2013.01)

(58) Field of Classification Search

CPC ............ A61K 31/7105; A61K 31/7089; A61K 9/1272; A61K 9/5123; C07H 21/02; C12N 15/67

USPC ......................................................... 536/1.11

See application file for complete search history.

(56) References Cited

U.S. PATENT DOCUMENTS

| | | | | |
|---|---|---|---|---|
| 12,171,876 B2 * | 12/2024 | Song | ...................... | A61K 45/06 |
| 2019/0270766 A1 * | 9/2019 | Hogrefe | ............... | A61K 31/712 |
| 2023/0304058 A1 | 9/2023 | Hu et al. | | |

FOREIGN PATENT DOCUMENTS

| | | | | |
|---|---|---|---|---|
| CN | 115745820 A | 3/2023 | | |
| CN | 115803333 A | 3/2023 | | |
| CN | 115260264 B | 6/2023 | | |
| CN | 116751827 B | 1/2024 | | |
| CN | 117510565 A | 2/2024 | | |
| CN | 117534719 * | 2/2024 | ........... | A61K 9/5123 |
| CN | 117534719 A | 2/2024 | | |
| CN | 117886873 A | 4/2024 | | |
| EP | 4328217 A1 | 2/2024 | | |
| WO | 2017066797 A1 | 4/2017 | | |
| WO | 2021214204 A1 | 10/2021 | | |
| WO | 2022006368 A2 | 1/2022 | | |
| WO | 2022051677 A1 | 3/2022 | | |
| WO | 2022212710 A1 | 10/2022 | | |
| WO | 2023025073 A1 | 3/2023 | | |
| WO | 2023073190 A1 | 5/2023 | | |
| WO | 2023133946 A1 | 7/2023 | | |
| WO | WO 2023/147352 A1 * | 8/2023 | ............. | C07H 21/02 |
| WO | 2023201294 A1 | 10/2023 | | |
| WO | 2024044741 A2 | 2/2024 | | |
| WO | 2024153245 A1 | 7/2024 | | |
| WO | 2025024563 A2 | 1/2025 | | |

OTHER PUBLICATIONS

Eygeris et al, Accounts of Chemical Research, 2022, 55, 2-12.*
Jul. 31, 2024 1st Chinese Office Action issued in Chinese Patent Application No. 202410814191.9.
Jul. 25, 2024 Chinese First Search Report issued in Chinese Patent Application No. 202410814191.9.
Aug. 31, 2024 2nd Chinese Office Action issued in Chinese Patent Application No. 202410814191.9.
Sep. 6, 2024 Supplementary Chinese Search Report issued in Chinese Patent Application No. 202410814191.9.
Yulia Eygeris et al., Chemistry of Lipid Nanoparticles for RNA Delivery, Accounts of chemical research, 2022, 55 (1): 2-12.
Sep. 24, 2025 The partial European search report issued in European Patent Application No. 25158385.2.
Oct. 14, 2025 First Office Action issued in Eurasian Patent Application Patent Application No. 202591015.
Sep. 2, 2025 First Office Action issued in Japanese Patent Application No. 2025-036773.
Nov. 11, 2025 First Office Action issued in Taiwanese Patent Application No. 114106604.

* cited by examiner

*Primary Examiner* — Ganapathy Krishnan

(57) ABSTRACT

The present disclosure provides a ribose-modified cap analog and a use thereof, and belongs to the technical field of chemical and biological engineering. The ribose-modified cap analog has a structure of formula (I). The ribose-modified cap analog described herein can improve the stability of mRNA and/or the translation efficiency of mRNA.

5 Claims, 4 Drawing Sheets

RIBOSE-MODIFIED CAP ANALOG AND USE THEREOF

CROSS-REFERENCE TO RELATED APPLICATION

The present application claims priority from Chinese Patent Application No. 202410514555.1 filed on Apr. 26, 2024 and Chinese Patent Application No. 202410814191.9 filed on Jun. 24, 2024, the contents of which are incorporated herein by reference in their entirety.

TECHNICAL FIELD

The present disclosure belongs to the technical field of chemical and biological engineering, and relates to a ribose-modified cap analog and a use thereof.

BACKGROUND

The chemical nature of a cap structure is a special structure at the 5' end of mRNA formed by modification during mRNA transcription, namely an m7GPPPN structure, also known as a methylguanosine cap. It is formed under the co-catalysis of RNA triphosphatase, guanylyltransferase, mRNA (guanine-N7) methyltransferase, and mRNA (nucleoside-2') methyltransferase. Depending on the degree of methylation, three types of caps can be formed, namely CAP0, CAP1, and CAP2, which are m7G5'ppp5'Np, m7G5'ppp5'NmpNp, and m7G5'ppp5'NmpNmpNp, respectively.

The cap structure is necessary for the initiation of mRNA translation, which provides a signal for the recognition of mRNA by the ribosome, assists the ribosome in binding to the mRNA, and enables translation to start from AUG. Meanwhile, the cap structure can increase the stability of mRNA and protect the mRNA from 5'→3' exonuclease attack.

To put it simply, the cap structure is like a steel helmet for mRNA, which can not only protect the mRNA from being destroyed, but also imprint the helmet through chemical modification to facilitate recognition by other members. In addition to the natural cap structure, cap structure analogs are also mostly used to improve the stability of mRNA structures during in vitro transcription, with ARCA and Cap1 structure analogs being the common ones.

Studies have shown that the cap structure of mRNA is importantly linked to mRNA quality control and innate immunity of the organism. Therefore, the invention of a novel cap analog is of great significance for increasing the stability of mRNA and improving the translation efficiency of mRNA.

Content of the Present Invention

In response to the deficiencies of the prior art, the present disclosure aims to provide a ribose-modified cap analog and a use thereof. The ribose-modified cap analog of the present disclosure can improve the stability of mRNA and/or the translation efficiency of mRNA.

To achieve the foregoing objective, the present disclosure adopts the following technical solutions:

A first aspect of the present disclosure provides a ribose-modified cap analog, or a stereoisomer, a pharmaceutically acceptable salt, or a solvate thereof, wherein the ribose-modified cap analog has a structure of formula (I):

(I)

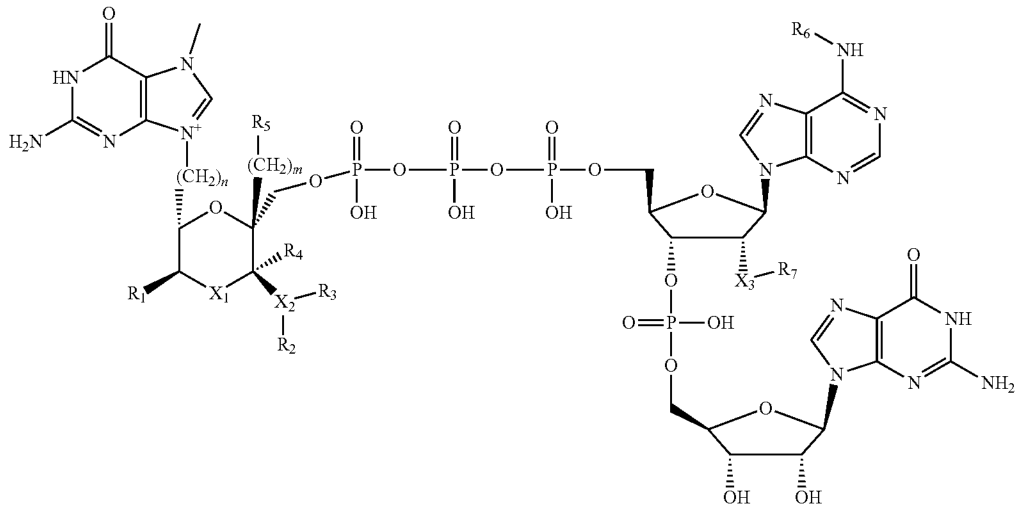

wherein n is selected from 1 or 0; m is selected from 1 or 0;

$X_1$ is selected from —C(OH)H— or a single bond;

$X_2$ is selected from —CH—, —O—, —CN, —C(O)—,

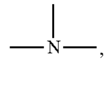

or a single bond;

$X_3$ is selected from —$CH_2$, —CFH—, or —O—;

$R_1$ is selected from —OH or —NHAc;

$R_2$ is selected from —$CH_3$, —F, —H, or absent;

$R_3$ is selected from —$OR_6$, —$NHC(O)R_7$, —$N(R_8)_2$, —CN, —F, —$C(O)N(R_9)_2$, substituted or unsubstituted $C_1$-$C_3$ alkyl, —H, or absent;

$R_4$ is selected from —$CH_3$, —F, or —H;

$R_5$ is selected from —$OR_{10}$, —$NHC(O)R_{11}$, —$N(R_{12})_2$, —$CF_2H$, —F, —$C(O)N(R_{13})_2$, substituted or unsubstituted $C_1$-$C_3$ alkyl, or absent;

$R_6$, $R_8$, $R_{10}$, $R_{11}$, $R_{12}$, and $R_{13}$ are each independently selected from unsubstituted $C_1$-$C_3$ alkyl or —H;

$R_7$ is selected from —$OR_{14}$, —$NHC(O)R_{15}$, —F, or substituted or unsubstituted $C_1$-$C_3$ alkyl;

$R_9$ is selected from unsubstituted $C_2$-$C_3$ alkyl;

$R_{14}$ and $R_{15}$ are each independently selected from unsubstituted $C_1$-$C_3$ alkyl.

Compared to the ribose-modified cap analogs in the prior art, the ribose-modified cap analogs of the present disclosure can result in a significant increase in the in vitro transcription yield of mRNA, the capping rate, the translation efficiency of mRNA, and the amount and duration of protein expression by mRNA in mice, as well as a significant decrease in the decapping rate.

A second aspect of the present disclosure provides a use of the ribose-modified cap analog, or the stereoisomer, the pharmaceutically acceptable salt, or the solvate thereof according to the first aspect of the present disclosure in the preparation of an in vitro co-transcription mRNA capping reagent.

A third aspect of the present disclosure provides an RNA molecule comprising the ribose-modified cap analog, or the stereoisomer, the pharmaceutically acceptable salt, or the solvate thereof according to the first aspect of the present disclosure as a cap structure or a cap structure fragment.

A fourth aspect of the present disclosure provides a pharmaceutical composition comprising the RNA molecule according to the third aspect of the present disclosure.

A fifth aspect of the present disclosure provides a method for synthesizing an mRNA molecule for non-disease diagnostic and therapeutic purposes comprising the steps of: co-incubating the ribose-modified cap analog, or the stereoisomer, the pharmaceutically acceptable salt, or the solvate thereof according to the first aspect of the present disclosure with a polynucleotide template for template transcription.

A sixth aspect of the present disclosure provides a capped mRNA transcription reaction system for non-disease diagnostic and therapeutic purposes comprising:

(1) the ribose-modified cap analog, or the stereoisomer, the pharmaceutically acceptable salt, or the solvate thereof according to the first aspect of the present disclosure; and (2) a polynucleotide template, NTPs (nucleoside triphosphates), and an RNA polymerase.

A seventh aspect of the present disclosure provides a kit comprising: (1) the ribose-modified cap analog, or the stereoisomer, the pharmaceutically acceptable salt, or the solvate thereof according to the first aspect of the present disclosure; and (2) a nucleotide triphosphate molecule and an RNA polymerase.

An eighth aspect of the present disclosure provides a method for improving intracellular stability of an RNA, comprising incorporating the ribose-modified cap analog, or the stereoisomer, the pharmaceutically acceptable salt, or the solvate thereof according to the first aspect of the present disclosure into the RNA.

A ninth aspect of the present disclosure provides a method for introducing RNA into a cell, comprising contacting the cell with the ribose-modified cap analog, or the stereoisomer, the pharmaceutically acceptable salt, or the solvate thereof according to the first aspect of the present disclosure, or the pharmaceutical composition according to the fourth aspect of the present disclosure.

A tenth aspect of the present disclosure provides a method for inhibiting RNA translation in a cell, comprising contacting the cell with the ribose-modified cap analog, or the stereoisomer, the pharmaceutically acceptable salt, or the solvate thereof according to the first aspect of the present disclosure, or the pharmaceutical composition according to the fourth aspect of the present disclosure.

An eleventh aspect of the present disclosure provides a use of the ribose-modified cap analog, or the stereoisomer, the pharmaceutically acceptable salt, or the solvate thereof according to the first aspect of the present disclosure, or the pharmaceutical composition according to the fourth aspect of the present disclosure in the preparation of a vaccine.

In relation to the prior art, the present disclosure has the following beneficial effects:

Compared to the ribose-modified cap analogs in the prior art, the ribose-modified cap analogs of the present disclosure can result in a significant increase in the in vitro transcription yield of mRNA, the capping rate, the translation efficiency of mRNA, and the amount and duration of protein expression by mRNA in mice, as well as a significant decrease in the decapping rate.

DETAILED DESCRIPTION OF THE PREFERRED EMBODIMENT

Figure 1:
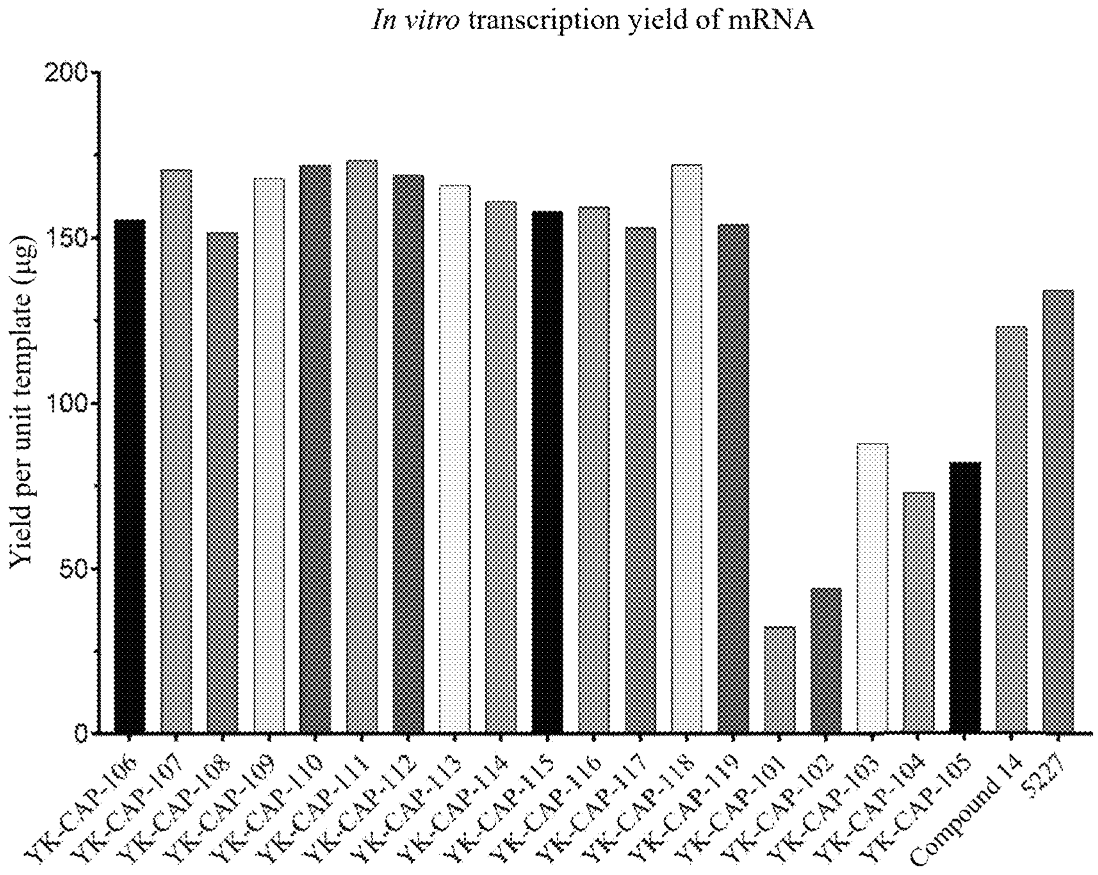
FIG. 1 is a graph showing the results of in vitro transcription yield of mRNA using YK-CAP-106, YK-CAP-107, YK-CAP-108, YK-CAP-109, YK-CAP-110, YK-CAP-111, YK-CAP-112, YK-CAP-113, YK-CAP-114, YK-CAP-115, YK-CAP-116, YK-CAP-117, YK-CAP-118, YK-CAP-119, YK-CAP-101, YK-CAP-102, YK-CAP-103, YK-CAP-104, YK-CAP-105, compound 14, and 5227 as cap analogs.

The technical solutions of the present disclosure are further described below through specific embodiments. It should be understood by those skilled in the art that the examples are only for facilitating the understanding of the present disclosure, and should not be construed as a specific limitation of the present disclosure.

The present disclosure may be embodied in other specific forms without departing from the essential attributes of the present disclosure. It should be understood that any and all embodiments of the present disclosure may be combined with technical features in any other embodiment or a plurality of other embodiments to obtain additional embodiments under the premise of no conflict. The present disclosure includes additional embodiments obtained from such combinations.

Except in the examples or otherwise indicated, all numbers stating quantitative properties, such as doses, in the present disclosure should be understood as modified in all instances by the term "about". It should also be understood that any numerical range recited in the present disclosure is intended to include all sub-ranges within the range and any combination of the various endpoints of the range or sub-ranges.

Unless otherwise defined, all terms (including technical and scientific terms) used in the present disclosure have the same meaning as commonly understood by those of ordinary skill in the art to which the present disclosure pertains. Terms, such as those defined in commonly used dictionaries, should be interpreted as having a meaning consistent with their meaning in the context of the relevant art and shall not be interpreted in an idealized or overly formal sense unless expressly so defined in the present disclosure.

As used herein, the term "$C_1$-$C_3$" refers to a group having any integral number of carbon atoms within the range of 1 to 3 in the main chain, such as 1, 2, or 3 carbon atoms. The term "$C_{6-15}$" refers to a group having any integral number of carbon atoms within the range of 6 to 15, such as 6, 7, 8, 9, 10, 11, 12, 13, 14, or 15 carbon atoms. The limitation of other ranges of carbon atoms, and so on, all indicate that the limited number of carbon atoms of a group may be any integer value within the limited range.

As used herein, the term "alkyl" refers to a saturated aliphatic hydrocarbon group having a linear or branched chain; non-limiting examples include methyl, ethyl, propyl, isopropyl, etc.

As used herein, the term "salt" refers to a corresponding salt of a modified nucleoside compound (or nucleotide compound) of the present disclosure that can be conveniently or desirably prepared, purified, and/or treated, such as a pharmaceutically acceptable salt. Unless otherwise indicated, references to a specific compound in the present disclosure also include a salt form thereof.

As used herein, "cap analog" refers to a structure at the 5' end of a mature mRNA formed by post-transcriptional modification in eukaryotes, namely an m7GPPPN structure, also known as a methylguanosine cap. The structure can prevent the degradation of mRNA at the 5' end, help RNA transcripts pass through the selective pores of the nuclear membrane and enter the cytoplasm, enhance translation, and help complete the entire splicing process.

The words "comprising", "including", or "containing" and similar words used in the present disclosure mean that the element appearing before the word covers the elements listed after the word and their equivalents, and does not exclude unrecited elements. The term "comprising" or "including (containing)" as used herein can be open, semi-closed, and closed. In other words, the term also includes "consisting essentially of" or "consisting of".

The term "pharmaceutically acceptable" in the present disclosure means that a compound or composition is chemically and/or toxicologically compatible with the other ingredients making up the preparation and/or with the human or mammal in which it is used to prevent or treat a disease or condition.

The term "solvate" in the present disclosure refers to a complex formed by combining a compound of formula (I) or a pharmaceutically acceptable salt thereof with a solvent (e.g., ethanol or water). It should be understood that any solvate of a compound of formula I for use in the treatment of a disease or condition may provide different properties (including pharmacokinetic properties), however will result in the compound of formula I upon absorbed into a subject, such that the use of the compound of formula I encompasses the use of any solvate of the compound of formula I respectively.

It should be further understood that the compound of formula I or the pharmaceutically acceptable salt thereof may be isolated in the form of a solvate, and therefore any such solvate is included within the scope of the present disclosure. For example, the compound of formula I or the pharmaceutically acceptable salt thereof may exist in an unsolvated form as well as a solvated form with a pharmaceutically acceptable solvent (e.g., water, ethanol).

The present disclosure also includes a salt of the compound described herein, especially a pharmaceutically acceptable salt. The compounds of the present disclosure having sufficiently acidic or sufficiently basic functional groups can react with a wide variety of bases or acids to form salts. Alternatively, compounds that are inherently charged (e.g., compounds having a quaternary nitrogen) may form salts with appropriate counterions (e.g., halide ions such as bromide ions, chloride ions, or fluoride ions, especially bromide ions).

The pharmaceutically acceptable salt of the present disclosure may be, for example, an acid addition salt of the compound of the present disclosure which is sufficiently basic and bears a nitrogen atom in a chain or ring of the compound of formula (I), for example, an acid addition salt formed with an inorganic acid, such as hydrochloric acid, hydrobromic acid, hydroiodic acid, sulfuric acid, phosphoric acid, or nitric acid, or an acid addition salt formed with an organic acid, such as formic acid, acetic acid, acetoacetic acid, pyruvic acid, trifluoroacetic acid, propionic acid, butyric acid, hexanoic acid, heptanoic acid, undecanoic acid, lauric acid, benzoic acid, salicylic acid, 2-(4-hydroxybenzoyl)benzoic acid, camphoric acid, cinnamic acid, cyclopentylpropionic acid, 3-hydroxy-2-naphthoic acid, nicotinic acid, pamoic acid, pectinic acid, persulfuric acid, 3-phenylpropionic acid, picric acid, pivalic acid, 2-hydroxyethanesulfonic acid, itaconic acid, sulfamic acid, trifluoromethanesulfonic acid, dodecylsulfuric acid, ethanesulfonic acid, benzenesulfonic acid, p-toluenesulfonic acid, methanesulfonic acid, 2-naphthalenesulfonic acid, naphthalenedisulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, glucoheptanoic acid, glycerophosphoric acid, aspartic acid, sulfosalicylic acid, or thiocyanic acid.

Additionally, another suitable pharmaceutically acceptable salt of the compound of the present disclosure which is sufficiently acidic is an alkali metal salt such as a sodium or potassium salt, an alkaline earth metal salt such as a calcium or magnesium salt, an ammonium salt (e.g., a salt formed with $NH_3$ or ammonia water), or a salt formed with an organic base which provides a physiologically acceptable cation, for example, a salt formed with triethylamine, N-methylglucamine, dimethylglucamine, ethylglucamine, lysine, dicyclohexylamine, 1,6-hexanediamine, ethanolamine, glucosamine, sarcosine, serinol, tris(hydroxymethyl)aminomethane, aminopropanediol, 1-amino-2,3,4-butanetriol. Furthermore, basic nitrogen-containing groups can be quaternized with the following reagents: lower alkyl halides such as methyl, ethyl, propyl, and butyl chlorides, bromides, and iodides; dialkyl sulfates such as dimethyl, diethyl, dibutyl, and diamyl sulfates; long chain halides such as decyl, lauryl, myristyl, and stearyl chlorides, bromides, and iodides; aralkyl halides such as benzyl and phenethyl bromides.

It will also be recognized by those skilled in the art that acid addition salts of the compound of formula (I) of the present disclosure can be prepared by reacting the compound with a suitable inorganic or organic acid by any one of the known methods. Alternatively, base addition salts of the acidic compound of the present disclosure are prepared by reacting the compound with a suitable base by various known methods.

The present disclosure includes all possible salts of the compound of formula (I) of the present disclosure, which may be a single salt or any mixture of the salt in any ratio.

Certain compounds of the present disclosure may exist as one or more stereoisomers. Stereoisomers include geometric isomers, diastereomers, and enantiomers. Accordingly, the compound of formula (I) of the present disclosure also includes racemic mixtures, single stereoisomers, and optically active mixtures. It should be understood by those skilled in the art that one stereoisomer may have better efficacy and/or lower side effects than other stereoisomers. Single stereoisomers and optically active mixtures can be obtained by methods such as chiral source synthesis, chiral catalysis, and chiral resolution. The racemate can be chirally resolved by chromatographic resolution or chemical resolution. For example, a chiral acid resolution reagent such as chiral tartaric acid and chiral malic acid can be added to form a salt with the compound of the present disclosure, and the physicochemical properties of the product, such as the difference in solubility, can be utilized for separation.

In the present disclosure, when the name of a compound is inconsistent with the structural formula, the structural formula shall prevail.

The specification of the present disclosure should be construed to be consistent with the laws and principles of chemical bonding. In some instances, a hydrogen atom may be removed to accommodate a substituent at a given position.

It should be understood that the term "compound of the present disclosure" as used herein may include a compound of formula (I), a solvate thereof, a pharmaceutically acceptable salt thereof, a stereoisomer thereof, or mixtures thereof according to the context.

A first aspect of the present disclosure provides a ribose-modified cap analog, or a stereoisomer, a pharmaceutically acceptable salt, or a solvate thereof, wherein the ribose-modified cap analog has a structure of formula (I):

(I)

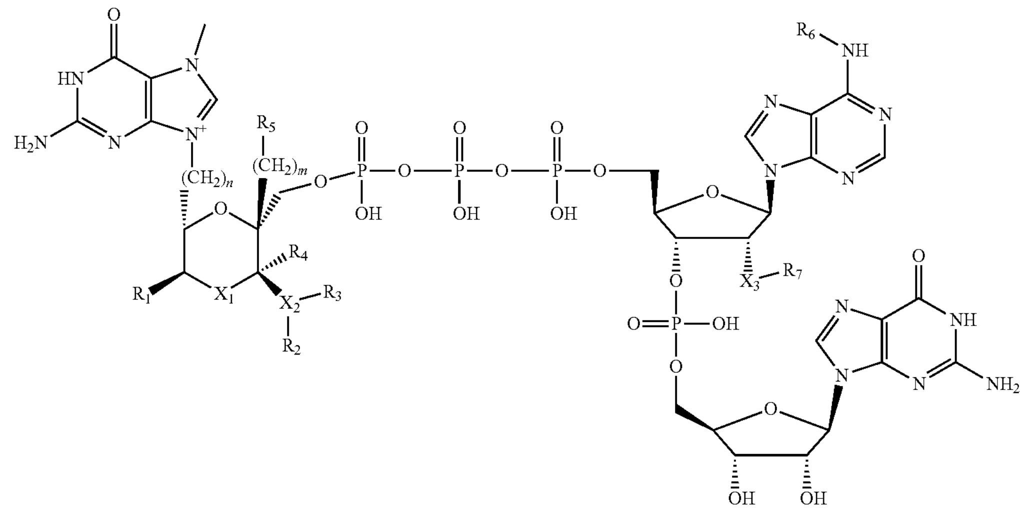

wherein n is selected from 1 or 0; m is selected from 1 or 0;

$X_1$ is selected from —C(OH)H— or a single bond;

$X_2$ is selected from —CH—, —O—, —CN, —C(O)—,

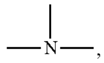

or a single bond;

$X_3$ is selected from —$CH_2$, —CFH—, or —O—;

$R_1$ is selected from —OH or —NHAc;

$R_2$ is selected from —$CH_3$, —F, —H, or absent;

$R_3$ is selected from —$OR_6$, —$NHC(O)R_7$, —$N(R_8)_2$, —CN, —F, —$C(O)N(R_9)_2$, substituted or unsubstituted $C_1$-$C_3$ alkyl, —H, or absent;

$R_4$ is selected from —$CH_3$, —F, or —H;

$R_5$ is selected from —$OR_{10}$, —$NHC(O)R_{11}$, —$N(R_{12})_2$, —$CF_2H$, —F, —$C(O)N(R_{13})_2$, substituted or unsubstituted $C_1$-$C_3$ alkyl, or absent;

$R_6$, $R_8$, $R_{10}$, $R_{11}$, $R_{12}$, and $R_{13}$ are each independently selected from unsubstituted $C_1$-$C_3$ alkyl or —H;

$R_7$ is selected from —$OR_{14}$, —$NHC(O)R_{15}$, —F, or substituted or unsubstituted $C_1$-$C_3$ alkyl;

$R_9$ is selected from unsubstituted $C_2$-$C_3$ alkyl;

$R_{14}$ and $R_{15}$ are each independently selected from unsubstituted $C_1$-$C_3$ alkyl.

In one embodiment, $X_2$ is —O—.

In one embodiment, $X_2$ is —O— and $R_2$ is absent.

In one embodiment, $X_2$ is —O— and $R_3$ is —H.

In one embodiment, $X_2$ is —O—, $R_2$ is absent, and $R_3$ is —H.

In one embodiment, $X_2$ is —CH—.

In one embodiment, $X_2$ is —CH— and $R_2$ is —H, —$CH_3$, or —F.

In one embodiment, $X_2$ is —CH— and $R_3$ is —$N(CH_3)_2$, —$C(O)CH_3$, —$OCH_3$, —$NHC(O)CH_3$, or —F.

In one embodiment, $X_2$ is —CH—, $R_2$ is —H, —$CH_3$, or —F, and $R_3$ is —$N(CH_3)_2$, —$C(O)CH_3$, —$OCH_3$, —NHC(O)$CH_3$, or —F.

In one embodiment, $X_2$ is —CN.

In one embodiment, $X_2$ is —CN and $R_2$ is absent.

In one embodiment, $X_2$ is —CN, $R_2$ is absent, and $R_3$ is absent.

In one embodiment, $X_2$ is

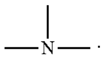

and $R_2$ is absent.

In one embodiment, $X_2$ is

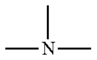

and $R_3$ is absent.

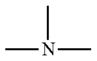

In one embodiment, $X_2$ is

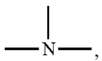, $R_2$ is absent, and $R_3$ is absent.

In one embodiment, $X_2$ is —C(O)—.

In one embodiment, $X_2$ is —C(O)— and $R_2$ is absent.

In one embodiment, $X_2$ is —C(O)— and $R_3$ is —$N(CH_2CH_3)_2$ or —$N(CH_2CH_2CH_3)_2$.

In one embodiment, $X_2$ is —C(O)—, $R_2$ is absent, and $R_3$ is —$N(CH_2CH_3)_2$ or —$N(CH_2CH_2CH_3)_2$.

In one embodiment, $X_3$ is —O—.

In one embodiment, $X_3$ is —O— and $R_7$ is —$CH_3$ or —$OCH_3$.

In one embodiment, $X_3$ is —$CH_2$—.

In one embodiment, $X_3$ is —$CH_2$— and $R_7$ is —$OCH_3$, —$NHC(O)CH_3$, or —F.

In one embodiment, $X_3$ is —CFH—.

In one embodiment, $X_3$ is —CFH— and $R_7$ is —F.

In one embodiment, m is 1.

In one embodiment, m is 1 and $R_5$ is —$OCH_3$, —F, or —$CF_2H$; preferably, m is 1 and $R_5$ is —$OCH_3$.

In one embodiment, $R_6$ is —H.

In one embodiment, the ribose-modified cap analog is YK-CAP-101, YK-CAP-102, YK-CAP-103, YK-CAP-104, YK-CAP-105, YK-CAP-106, YK-CAP-107, YK-CAP-108, YK-CAP-109, YK-CAP-110, YK-CAP-111, YK-CAP-112, YK-CAP-113, YK-CAP-114, YK-CAP-115, YK-CAP-116, YK-CAP-117, YK-CAP-118, or YK-CAP-119 as shown below:

YK-CAP-101

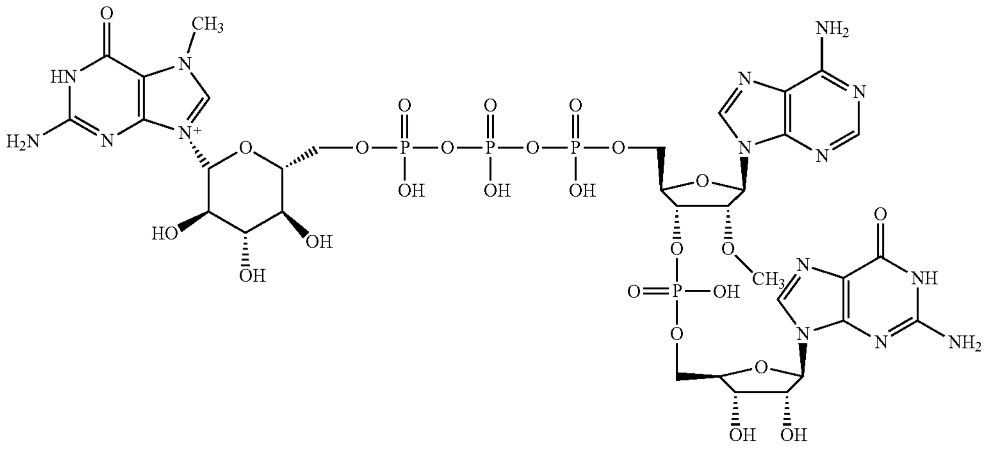

-continued
YK-CAP-102
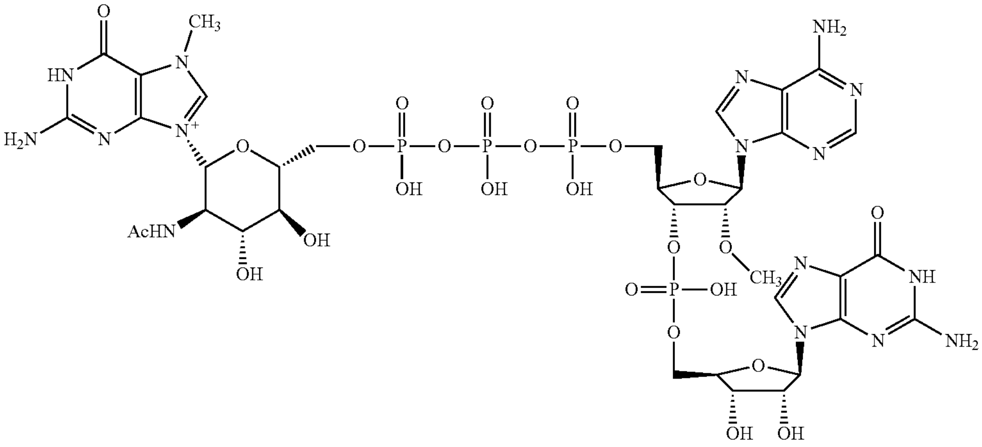
YK-CAP-103
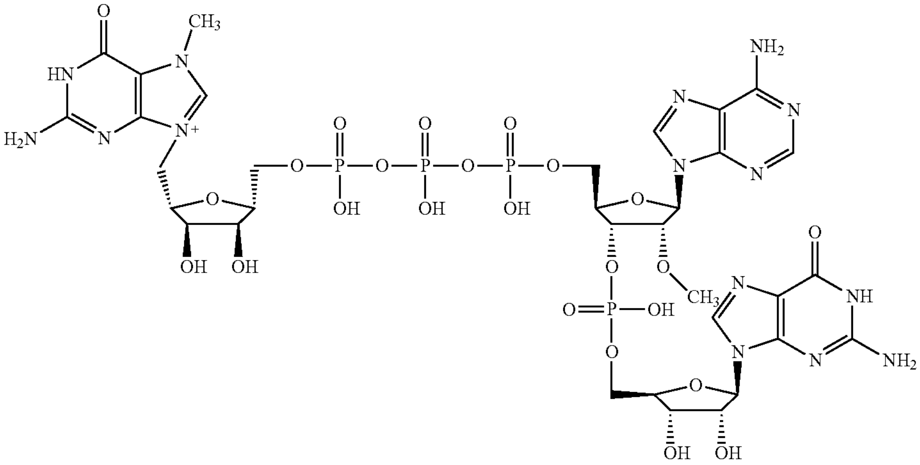
YK-CAP-104
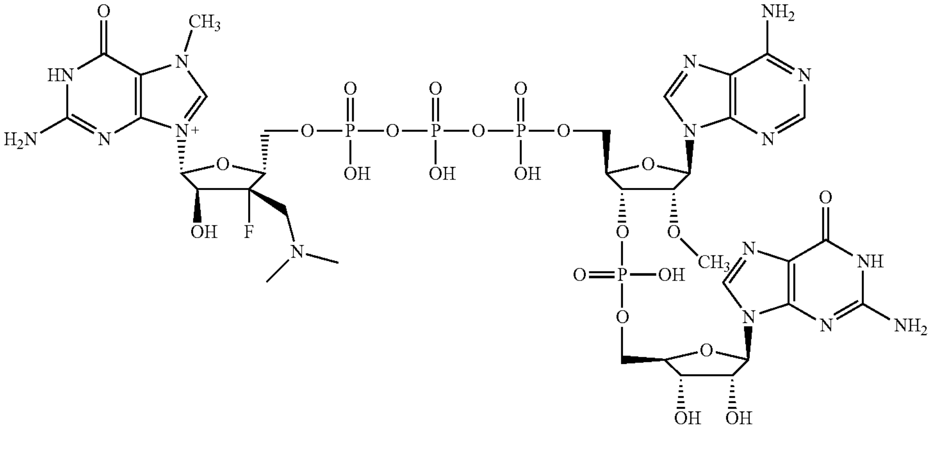

-continued
YK-CAP-105
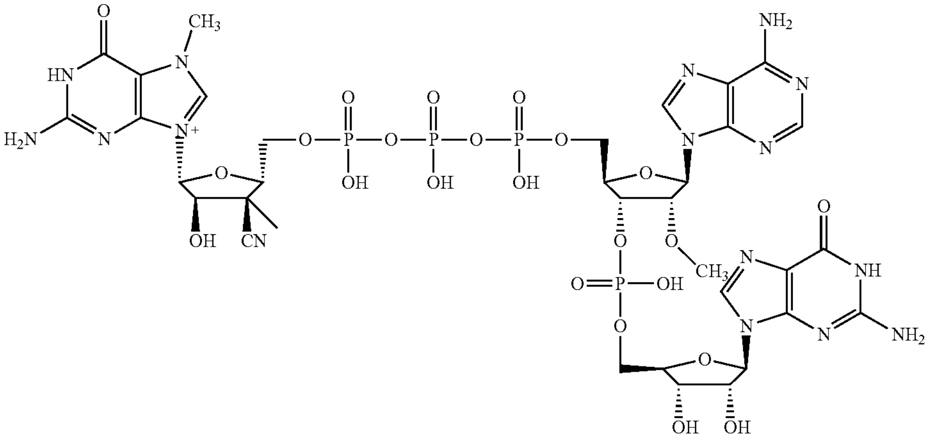
YK-CAP-106
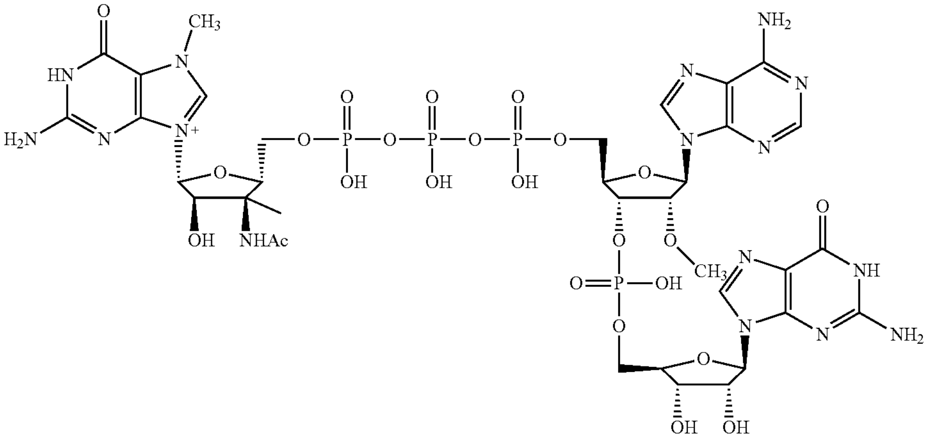
YK-CAP-107
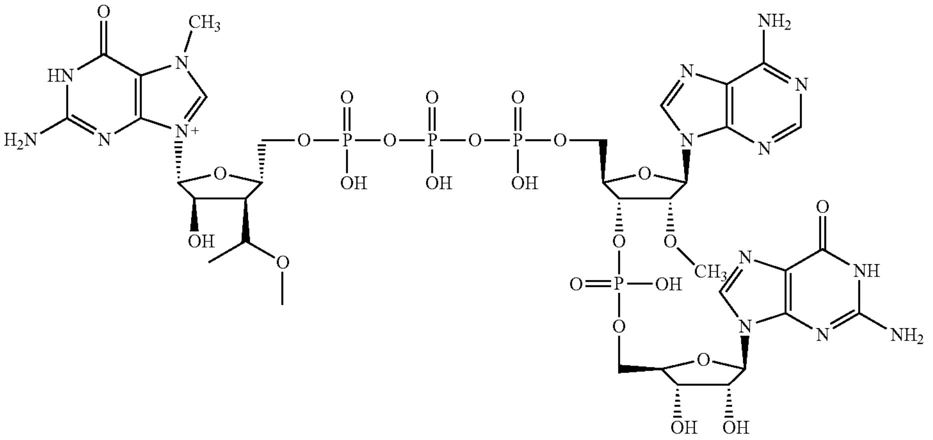

-continued
YK-CAP-108
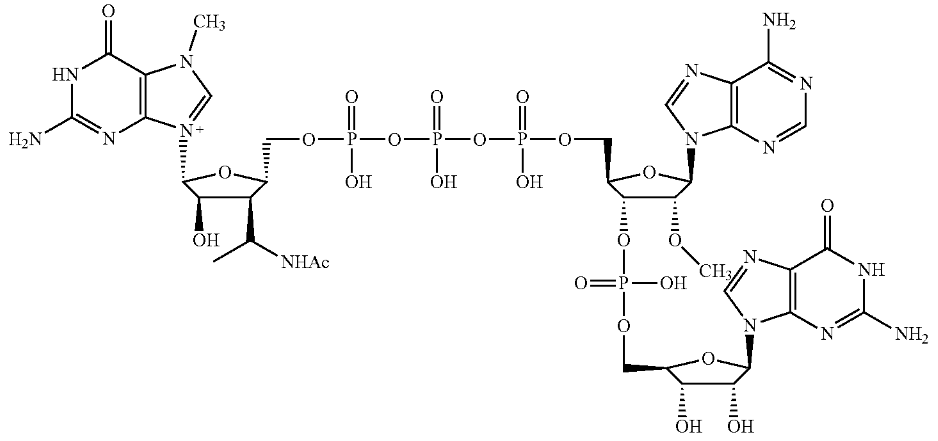
YK-CAP-109
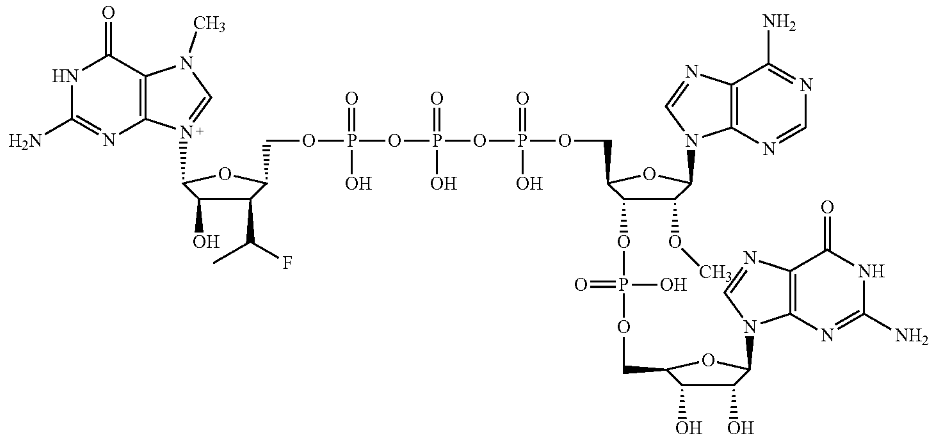
YK-CAP-110
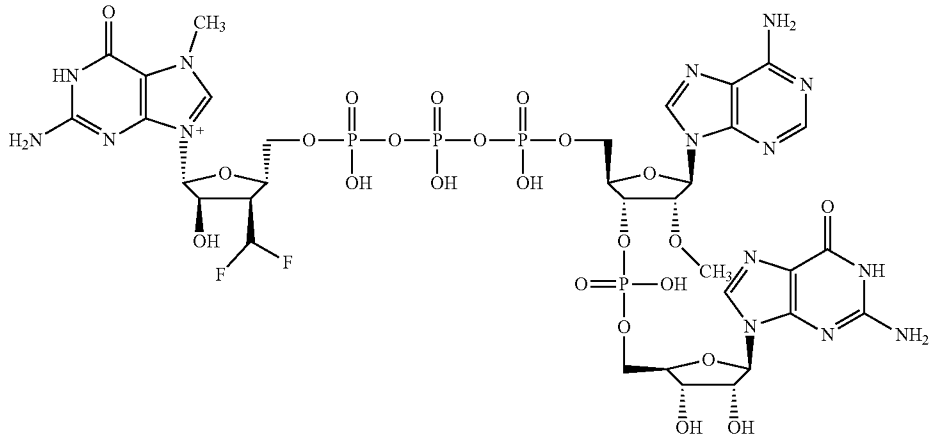

-continued
YK-CAP-111
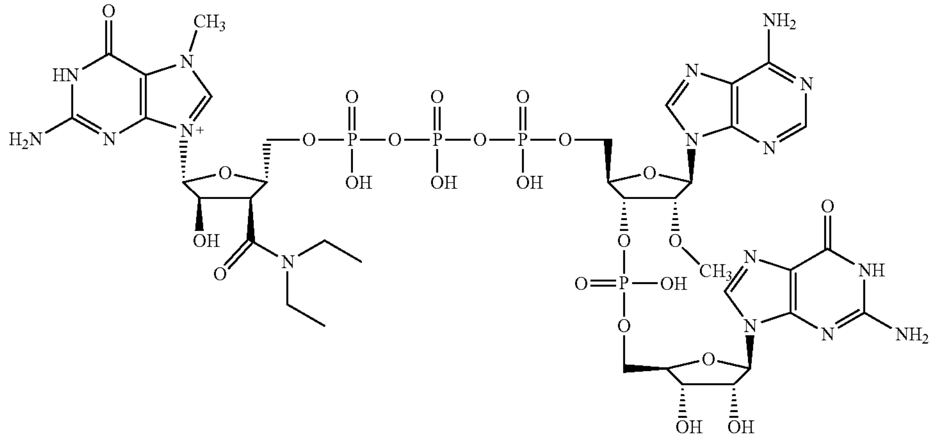
YK-CAP-112
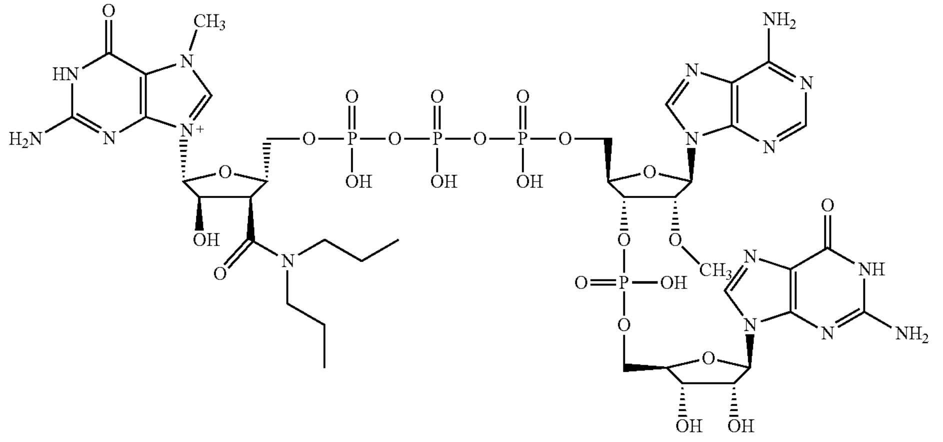
YK-CAP-113
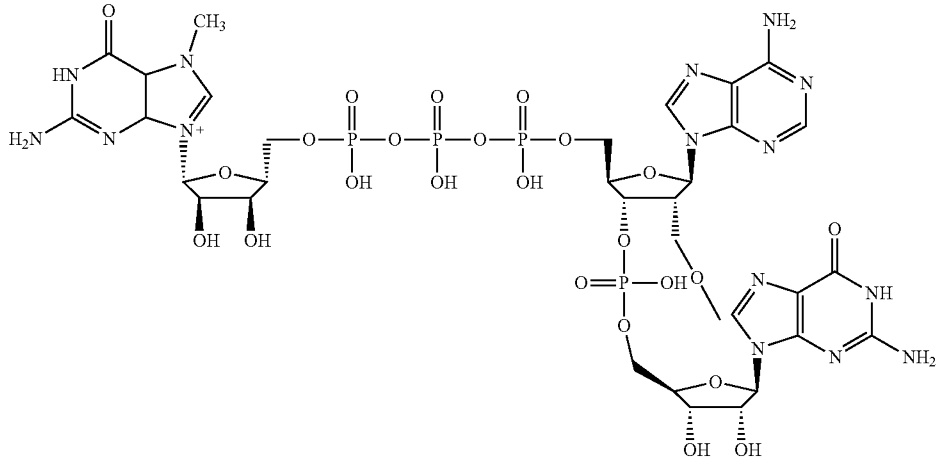

-continued
YK-CAP-114
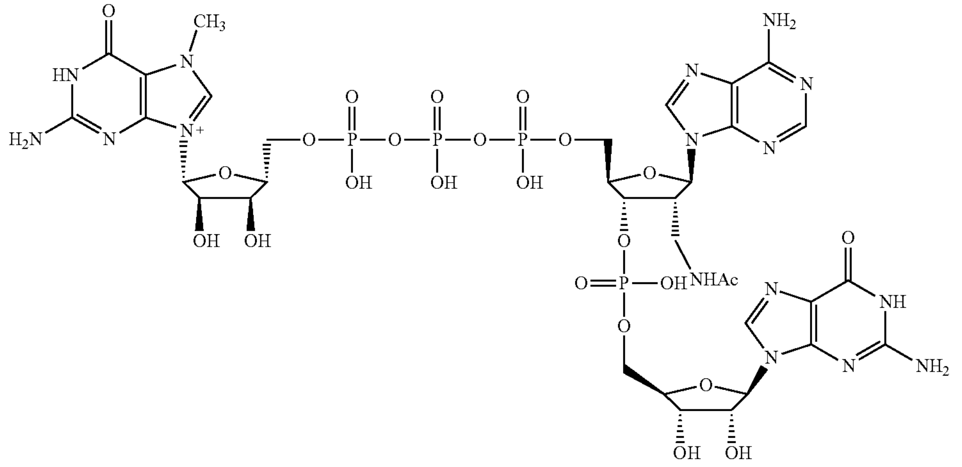
YK-CAP-115
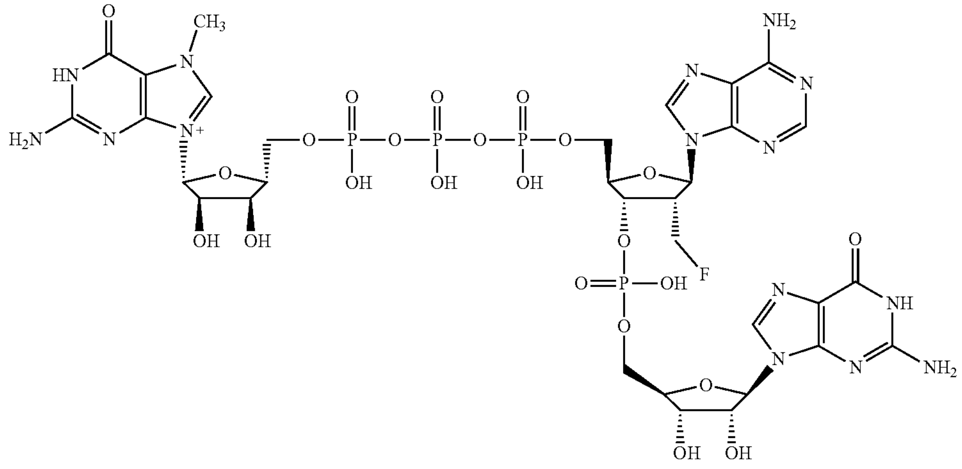
YK-CAP-116
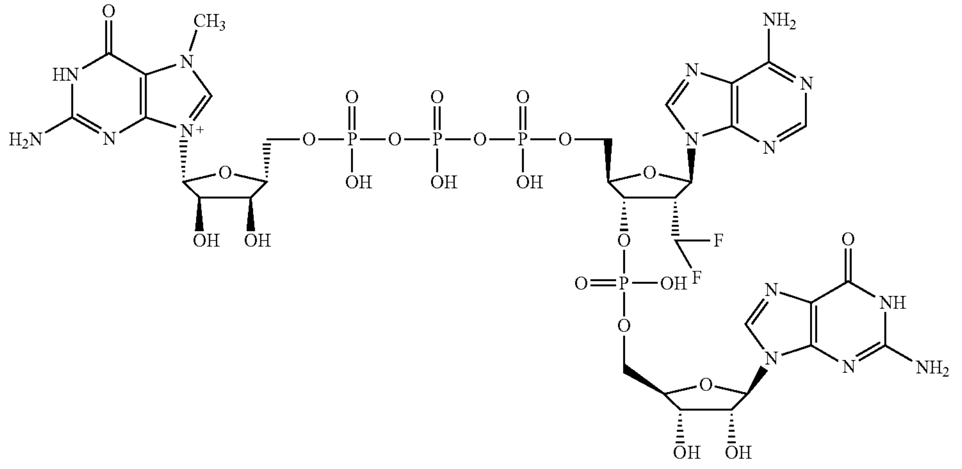

-continued

YK-CAP-117

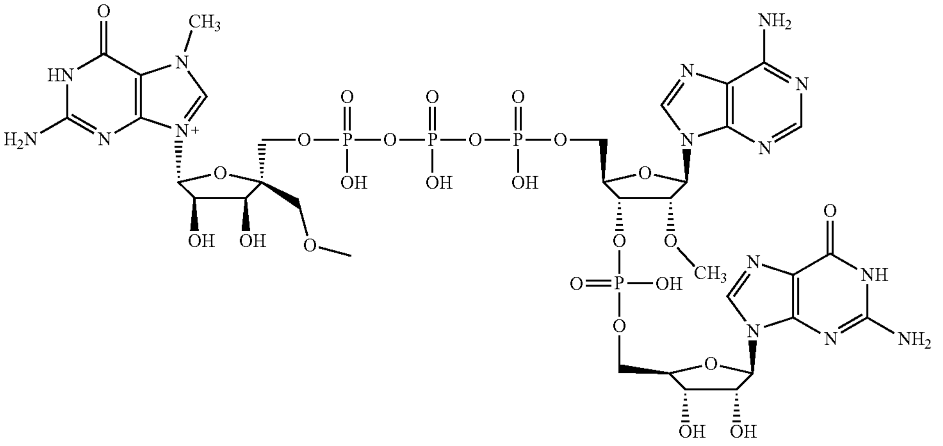

YK-CAP-118

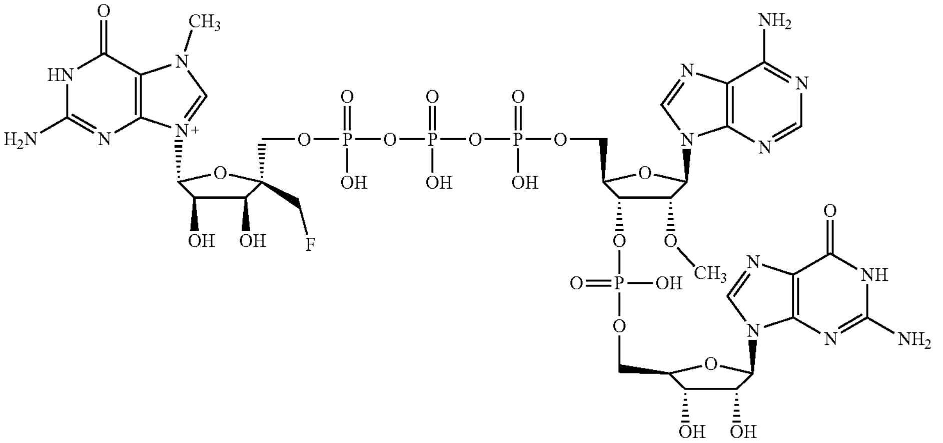

YK-CAP-119

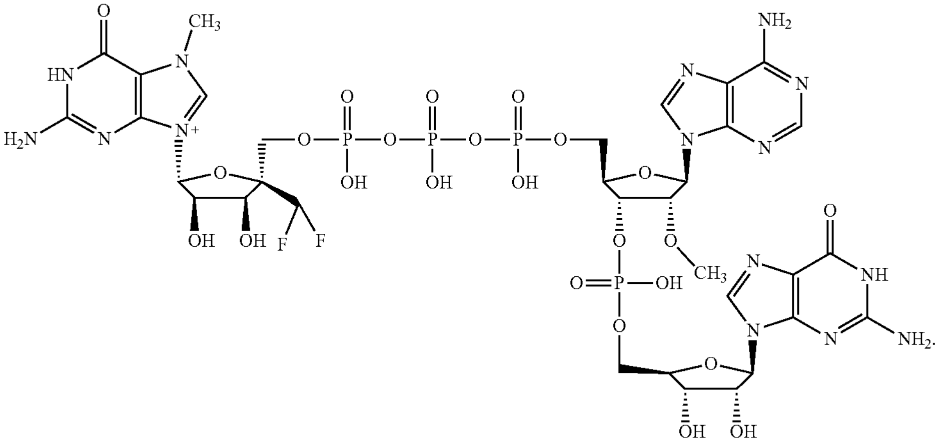

A second aspect of the present disclosure provides a use of the ribose-modified cap analog, or the stereoisomer, the pharmaceutically acceptable salt, or the solvate thereof according to the first aspect of the present disclosure in the preparation of an in vitro co-transcription mRNA capping reagent.

A third aspect of the present disclosure provides an RNA molecule comprising the ribose-modified cap analog, or the stereoisomer, the pharmaceutically acceptable salt, or the solvate thereof according to the first aspect of the present disclosure as a cap structure or a cap structure fragment.

A fourth aspect of the present disclosure provides a pharmaceutical composition comprising the RNA molecule according to the third aspect of the present disclosure.

In one embodiment, the pharmaceutical composition further comprises at least one RNA delivery agent.

The RNA delivery agent may be, for example, lipid nanoparticles (LNPs). Lipid nanoparticles are widely used in small molecule drug and nucleic acid delivery. mRNA encapsulated by LNPs can be protected from extracellular ribonucleases and facilitates intracellular delivery of mRNA. For lipid nanoparticles, please refer to the review "Chemistry of Lipid Nanoparticles for RNA Delivery. Acc Chem Res. 2022 Jan. 4; 55(1):2-12".

In one embodiment, the at least one RNA delivery agent comprises at least one cationic lipid.

The term "cationic lipid" as used herein refers to a lipid that is positively charged at a selected pH value. For example, please refer to the cationic lipids disclosed in literatures such as WO2023133946A1, CN115745820A, and "Chemistry of Lipid Nanoparticles for RNA Delivery. Acc Chem Res. 2022 Jan. 4; 55(1):2-12".

In one embodiment, the cationic lipid is selected from one or a combination of at least two of the following compounds:

(1) a compound of formula (II), or an N-oxide, a solvate, a pharmaceutically acceptable salt, or a stereoisomer thereof, wherein $G_1$ is $C_{1-6}$ alkylene; $G_2$ is $C_{2-8}$ alkylene; $G_3$ is $C_{1-3}$ alkylene; $L_1$ is $C_{6-15}$ linear alkyl; $L_2$ is $C_{12-25}$ branched alkyl;

(II)

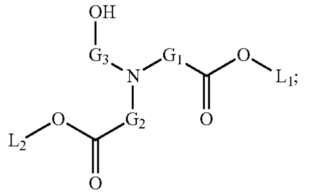

(2) a compound of formula (III), or an N-oxide, a solvate, a pharmaceutically acceptable salt, or a stereoisomer thereof, wherein $G_1$ is $C_{2-8}$ alkylene; $G_2$ is $C_{2-8}$ alkylene; $L_1$ is —C(O)O— or —OC(O)—; $L_2$ is —C(O)O— or —OC(O)—; $R_1$ is $C_{6-25}$ linear or branched alkyl; $R_2$ is $C_{6-25}$ linear or branched alkyl; $G_3$ is $HO(CH_2)_2$— or $HO(CH_2)_3$—; $G_4$ is $HO(CH_2)_2$— or $HO(CH_2)_3$—; L is $(CH_2)_2$—, —$(CH_2)_3$—, or —$(CH_2)_4$—;

(III)

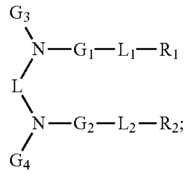

(3) a compound of formula (IV), or an N-oxide, a solvate, a pharmaceutically acceptable salt, or a stereoisomer thereof, wherein $G_1$ is $C_{1-6}$ alkylene; $G_2$ is $C_{2-8}$ alkylene; $R_1$ is $C_{6-20}$ linear or branched alkyl; $R_2$ is $C_{12-25}$ branched alkyl; $G_3$ is $HO(CH_2)_2N(CH_3)(CH_2)_2$—, $HO(CH_2)_2N(CH_2CH_3)(CH_2)_2$—, $(HO(CH_2)_2)_2N(CH_2)_2$—, $CH_3O(CH_2)_2N(CH_3)(CH_2)_2$—, $(CH_3)_2N(CH_2)_3SC(O)O(CH_2)_2$—, $(CH_3)_2N(CH_2)_3SC(O)$—, $CH_3NH(CH_2)_2N(CH_3)(CH_2)_2$—, or $CH_3CH_2NH(CH_2)_2$—;

(IV)

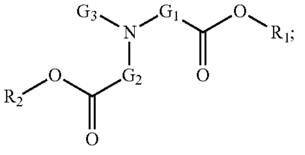

(4) a compound of formula (V), or an N-oxide, a solvate, a pharmaceutically acceptable salt, or a stereoisomer thereof, wherein $G_1$ is $C_{1-8}$ alkylene; $G_2$ is $C_{2-8}$ alkylene; $R_1$ is $C_{6-25}$ linear or branched alkyl; $R_2$ is $C_{12-25}$ linear or branched alkyl; $G_3$ is $HO(CH_2)_2N(R_3)CH_2CH(OH)CH_2$—, wherein $R_3$ is —$CH_3$, —$CH_2CH_3$, or —$CH_2CH_2OH$;

(V)

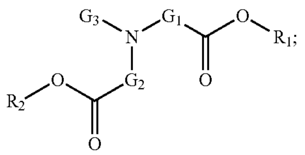

(5) a compound of formula (VI), or an N-oxide, a solvate, a pharmaceutically acceptable salt, or a stereoisomer thereof, wherein $G_1$ and $G_2$ are each independently unsubstituted $C_6$-$C_{10}$ alkylene; $G_3$ is unsubstituted $C_1$-$C_{12}$ alkylene; $R^1$ and $R^2$ are each independently $C_6$-$C_{24}$ alkyl or $C_6$-$C_{24}$ alkenyl; $R^3$ is $OR^5$, N, —C(=O) $OR^4$, —OC(=O) $R^4$, or —$NR^5C$(=O)$R^4$; $R^4$ is $C_1$-$C_{12}$ hydrocarbyl; and $R^5$ is H or $C_1$-$C_6$ hydrocarbyl;

(VI)

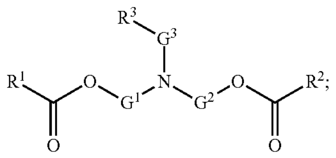

(6) a compound of formula (VII), or an N-oxide, a solvate, a pharmaceutically acceptable salt, or a stereoisomer thereof, wherein $R_4$ is selected from —$(CH_2)_nQ$ and —$(CH_2)_nCHQR$; Qis selected from the group consisting of —OR, —OH, —$O(CH_2)$, $N(R)_2$, —OC(O)R, —$CX_3$, —CN, —N(R)C(O)R, —N(H)C(O)R, —N(R)$S(O)_2R$, —N(H)$S(O)_2R$, —N(R)C(O)$N(R)_2$, —N(H)C(O)$N(R)_2$, —N(H)C(O)N(H)(R), —N(R)C(S)$N(R)_2$, —N(H)C(S)$N(R)_2$, —N(H)C(S)N(H)(R), —N(R)S$(O)_2$ $R_8$, and heterocycle; n is 1, 2, or 3;

(VII)

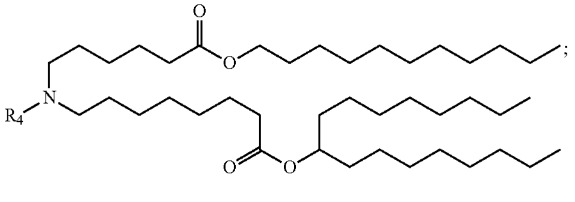

(7) a compound of formula (VIII), or an N-oxide, a solvate, a pharmaceutically acceptable salt, or a stereoisomer thereof, (VIII)

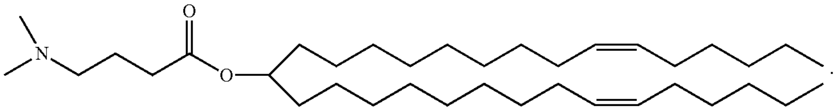

In a preferred embodiment, the cationic lipid is selected from one or a combination of at least two of YK-009, YK-401, YK-305, ALC0315, SM102, or DLIN-MC3-DMA:

YK-009

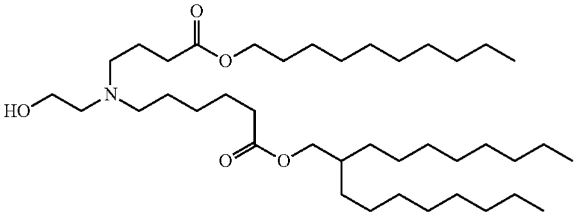

YK-401

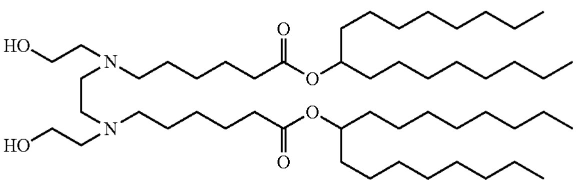

YK-305

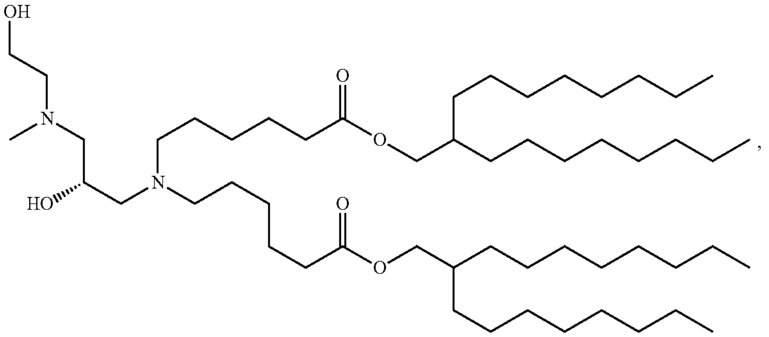

ALC-0315

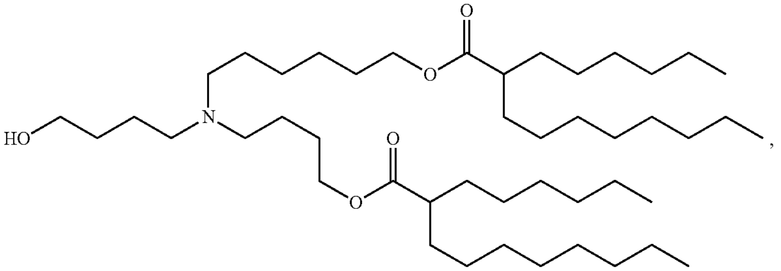

SM-102

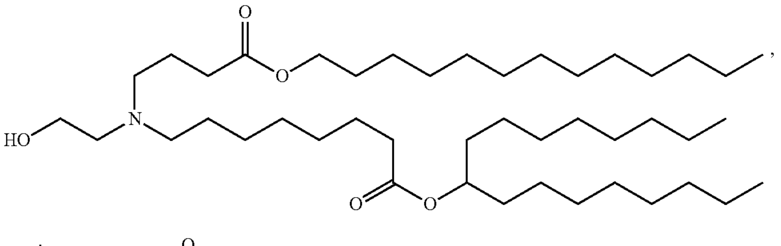

DLIN-MC3-DMA

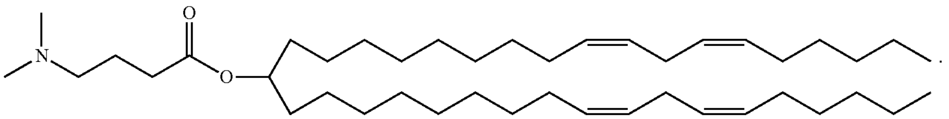

In a more preferred embodiment, the cationic lipid is YK-009.

In one embodiment, the at least one RNA delivery agent further comprises at least one neutral lipid.

In the present disclosure, the neutral lipid refers to an auxiliary lipid that is uncharged or exists in a zwitterionic form at a selected pH value. The neutral lipid may regulate the fluidity of nanoparticles into a lipid bilayer structure and improve efficiency by promoting lipid phase transition, and may also affect target organ specificity.

In one embodiment, the neutral lipid includes one or a combination of at least two of phosphatidylcholine, phosphatidylethanolamine, sphingomyelin, ceramide, sterol, or derivatives thereof.

In one embodiment, the neutral lipid is selected from one or a combination of at least two of the following: 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearoyl-2-oleoyl-sn-glycero-3-phosphoethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, or lysophosphatidylethanolamine (LPE).

In a preferred embodiment, the neutral lipid is DOPE and/or DSPC.

In one embodiment, the at least one RNA delivery agent further comprises a structural lipid.

In the present disclosure, the structural lipid refers to a lipid that enhances the stability of nanoparticles by filling the gaps between lipids.

In one embodiment, the structural lipid is selected from one or a combination of at least two of the following: cholesterol, nonsterol, sitosterol, ergosterol, campesterol, stigmasterol, brassinosterol, tomatine, ursolic acid, α-tocopherol, or corticosteroid.

In a preferred embodiment, the structural lipid is cholesterol.

In one embodiment, the at least one RNA delivery agent further comprises a polymer-conjugated lipid.

In the present disclosure, the polymer-conjugated lipid mainly refers to a lipid modified with polyethylene glycol (PEG). Hydrophilic PEG stabilizes lipid nanoparticles (LNPs), regulates nanoparticle size by limiting lipid fusion, and increases nanoparticle half-life by reducing non-specific interactions with macrophages.

In one embodiment, the polymer-conjugated lipid is selected from one or a combination of at least two of the following: distearoyl phosphatidylethanolamine polyethylene glycol 2000 (DSPE-PEG2000), dimyristoylglycerol-3-methoxypolyethylene glycol 2000 (DMG-PEG2000), or methoxypolyethylene glycol ditetradecylacetamide (ALC-0159).

In one embodiment, the RNA delivery agent comprises a neutral lipid, a structural lipid, and a polymer-conjugated lipid, wherein the molar ratio of the cationic lipid, the neutral lipid, the structural lipid, and the polymer-conjugated lipid is (25 to 75):(5 to 25):(15 to 65):(0.5 to 10), such as (35 to 49):(7.5 to 15):(35 to 55):(1 to 5).

In one embodiment, the pharmaceutical composition further comprises one or at least two cell-penetrating peptides.

The present disclosure provides a kit comprising: (1) the ribose-modified cap analog, or the stereoisomer, the pharmaceutically acceptable salt, or the solvate thereof according to the first aspect of the present disclosure; and (2) a nucleotide triphosphate molecule and an RNA polymerase.

In one embodiment, the kit further comprises one or a combination of at least two of an RNAase inhibitor, an inorganic pyrophosphatase, $Mg^{2+}$, a crowding agent, or a buffer.

The present disclosure may be embodied in other specific forms without departing from the essential attributes of the present disclosure. It should be understood that any and all embodiments of the present disclosure may be combined with technical features in any other embodiment or a plurality of other embodiments to obtain additional embodiments under the premise of no conflict. The present disclosure includes additional embodiments obtained from such combinations.

The embodiments of the present disclosure will be described in detail below in conjunction with examples, but it will be understood by those skilled in the art that the following examples are merely used to illustrate the present disclosure and should not be considered as limiting the scope of the present disclosure. The examples without indication of specific conditions follow the conventional conditions or those recommended by the manufacturer. The reagents or instruments used without indication of manufacturers are all commercially available conventional products.

the Following Abbreviations Represent the Following Reagents:

IBX: 2-iodoxybenzoic acid; $BF_3 \cdot Et_2O$: boron trifluoride diethyl etherate; Allyltrimethylsilane: allyltrimethylsilane; TEA: triethylamine; $Ac_2O$: acetic anhydride; HOAc: acetic acid; conc $H_2SO_4$: concentrated sulfuric acid; BSA: N,O-bis(trimethylsilyl) acetamide; TMSOTf: trimethylsilyl trifluoromethanesulfonate; Toluene: toluene; MeOH: methanol; $Boc_2O$: di-tert-butyl dicarbonate; DIEA: N,N-diisopropylethylamine; DMAP: 4-dimethylaminopyridine; DMSO: dimethyl sulfoxide; HATU: 2-(7-azabenzotriazol-1-yl)-N,N,N',N'-tetramethyluronium hexafluorophosphate; THF: tetrahydrofuran; TBSCl: tert-butyldimethylsilyl chloride; ImH: imidazole; DMF: N,N-dimethylformamide; TBAF: tetrabutylammonium fluoride; TBSOTf: tert-butyldimethylsilyl trifluoromethanesulfonate; NMO: N-methylmorpholine-N-oxide; m-CPBA: m-chloroperoxybenzoic acid; DIAD: diisopropyl azodicarboxylate; NCS: N-chlorosuccinimide; $PO(MeO)_3$: trimethyl phosphate; PySSPy: 2,2'-dithiodipyridine; $PPh_3$: triphenylphosphine; TEAP: triethylamine phosphate; TEAB: triethylamine bicarbonate; MTBE: methyl tert-butyl ether; DCM: dichloromethane; EA: ethyl acetate; DAST: diethylaminosulfur trifluoride; AcSH: thioacetic acid.

Example 1

1. Synthesis of Intermediate INT-I

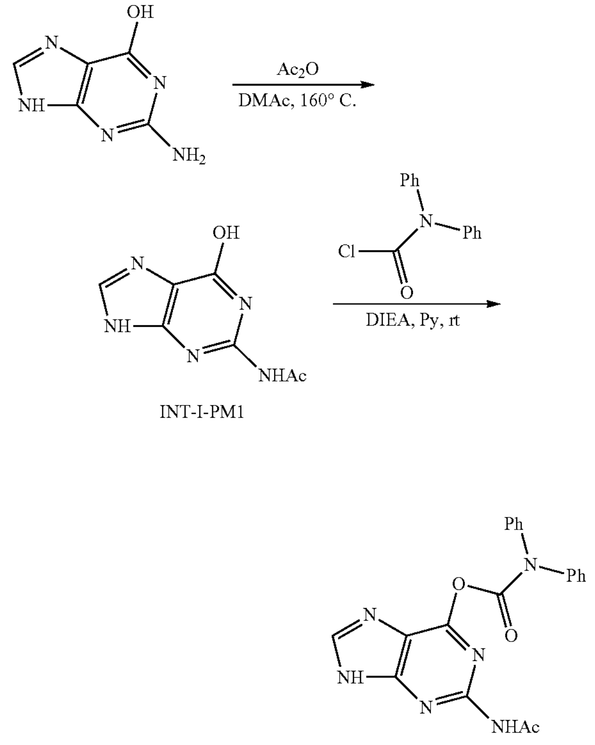

INT-I-PM1

INT-I

Step 1: Synthesis of INT-I-PM1

2-Amino-9H-purin-6-ol (50.0 g, 0.33 mol) was dissolved in N,N-dimethylacetamide (500 mL), and acetic anhydride (100 mL, 1.06 mol) was added thereto. The mixture was heated to 160° C., and stirred and reacted until clarified, indicating that the reaction was complete. The heating was stopped, and the reaction mixture was naturally cooled to room temperature to precipitate a large amount of solid, which was filtered. The filter cake was washed with ethanol until it turned white to obtain INT-I-PM1 (60.0 g, 0.31 mol, 94.1%). $C_7H_7N_5O_2$, MS (ES): m/z ($M+H^+$) 194.1.

Step 2: Synthesis of INT-I

INT-I-PM1 (60.0 g, 0.31 mol) was dissolved in pyridine (200 mL), then N,N-diisopropylethylamine (120.2 g, 0.93 mol) was added thereto, and the mixture was cooled to 0° C. Diphenylcarbamoyl chloride (86.2 g, 0.37 mol) was dissolved in pyridine (100 mL), and the mixture was slowly added dropwise to the above reaction system in an ice bath. After the dropwise addition was completed, the ice bath was removed. The reaction mixture was naturally warmed to room temperature, and stirred and reacted for 3 hours. LCMS monitored that there was no starting material remaining and the reaction was complete. The reaction system was quenched with 100 mL of water, and evaporated to dryness by rotary evaporation under reduced pressure. The residue was added with 800 mL of a mixed solvent of ethanol and water (1:1, v/v), and heated to reflux for 2 hours. The heating was stopped, and the reaction mixture was naturally cooled to room temperature to precipitate a large amount of solid, which was filtered. The filter cake was washed with ethanol to obtain INT-I (59.7 g, 0.15 mol, 49.6%). $C_{20}H_{16}N_6O_3$, MS (ES): m/z ($M+H^+$) 389.1.

2. Synthesis of Intermediate INT-II

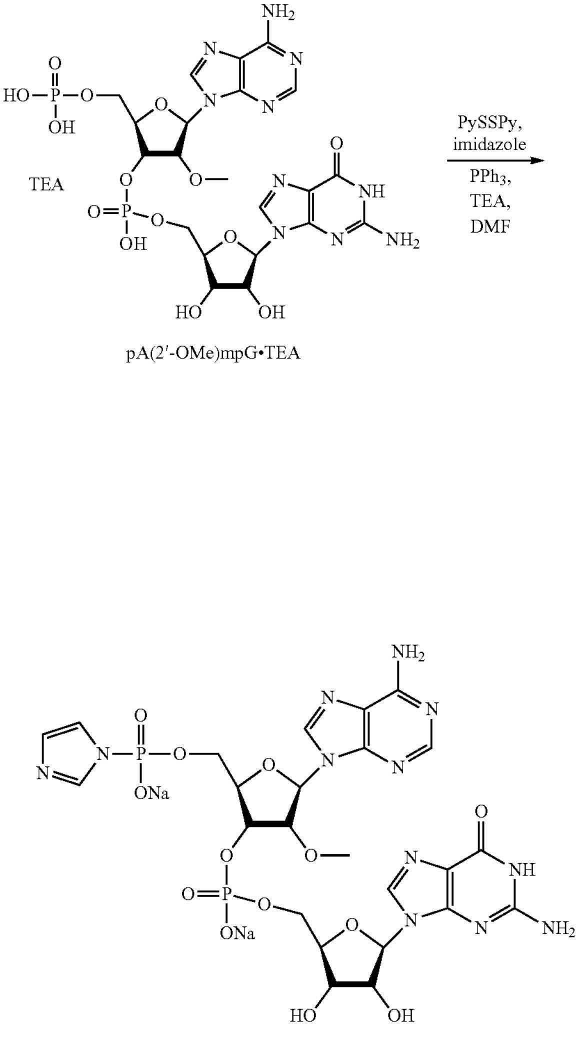

pA(2′-OMe)mpG•TEA

INT-II pA(2'-OMe)mpG·TEA (300.1 mg, 0.37 mmol), imidazole (347.2 mg, 5.10 mmol), dithiodipyridine (1123.6 mg, 5.10 mmol), and triethylamine (516.1 mg, 5.10 mmol) were dissolved in 2.0 mL of ultra-dry N,N-dimethylformamide, then triphenylphosphine (1337.7 mg, 5.10 mmol) was added thereto under nitrogen atmosphere, and the mixture was reacted at 25° C. for 4 hours. After the reaction was completed, the reaction mixture was slowly added to a pre-cooled acetone solution containing sodium iodide (598.1 mg, 3.99 mmol), crystallized at 25° C. for 30 minutes, and centrifuged to obtain INT-II (240.6 mg, 0.30 mmol, yield: 80.9%) as a white solid. $C_{24}H_{30}N_{12}O_{13}P_2$, MS (ES): m/z ($M-H^-$): 755.2.

3. Synthesis of YK-CAP-101
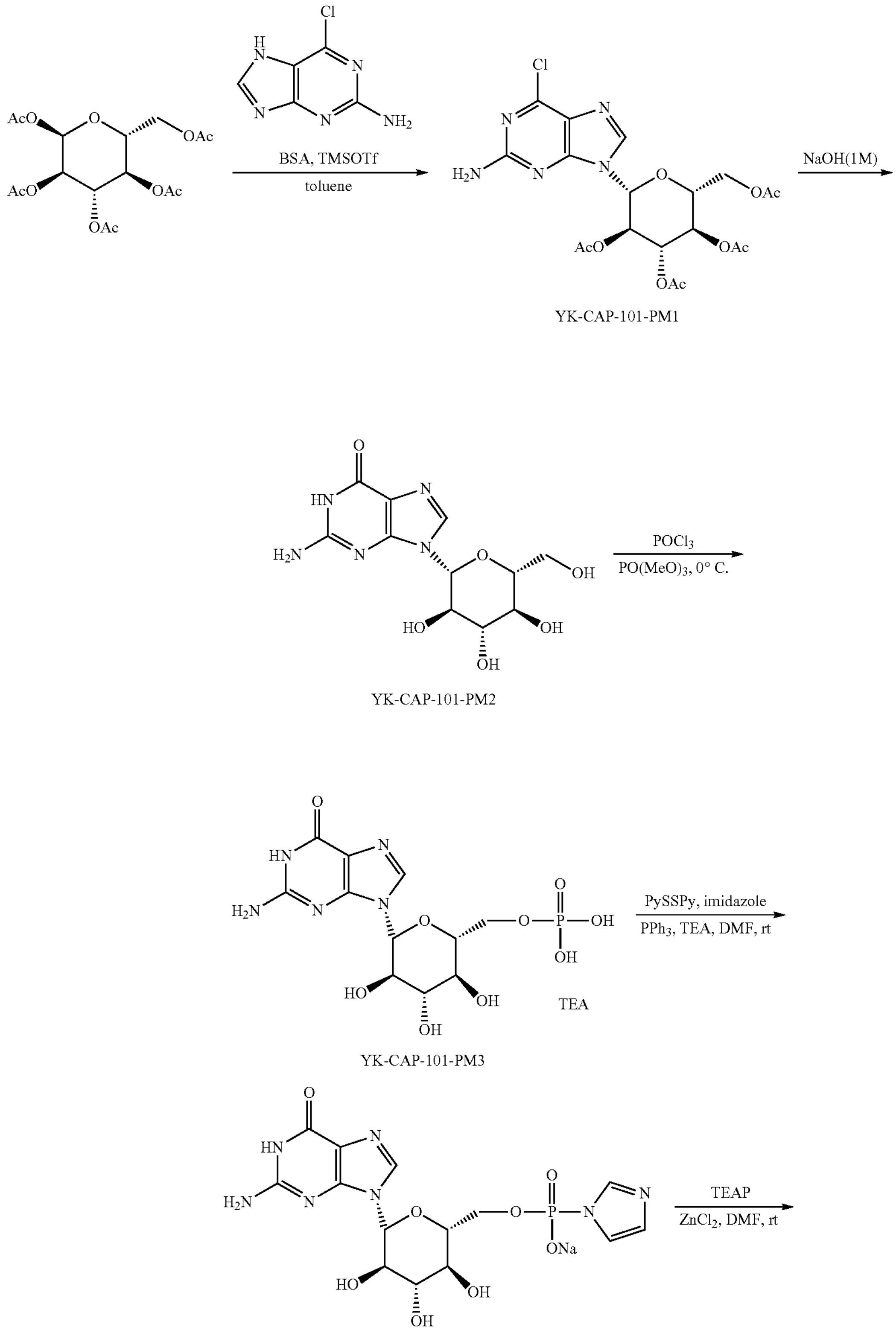
YK-CAP-101-PM1
YK-CAP-101-PM2
YK-CAP-101-PM3
YK-CAP-101-PM4

-continued

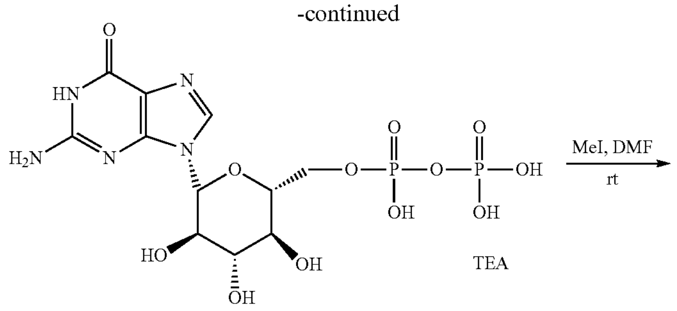

YK-CAP-101-PM5

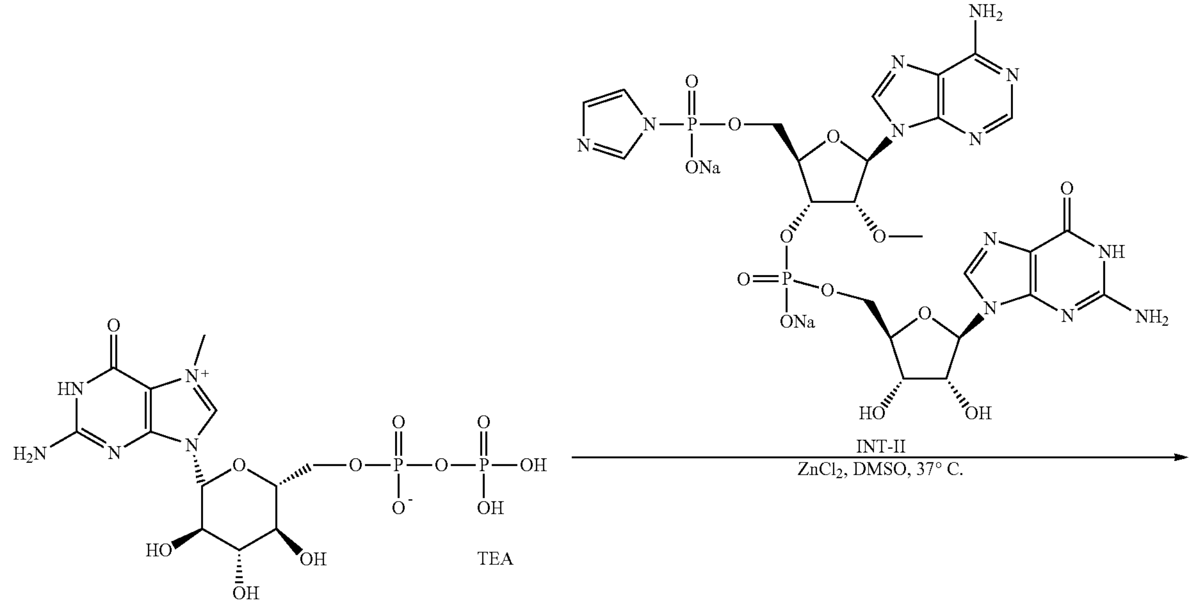

YK-CAP-101-PM6

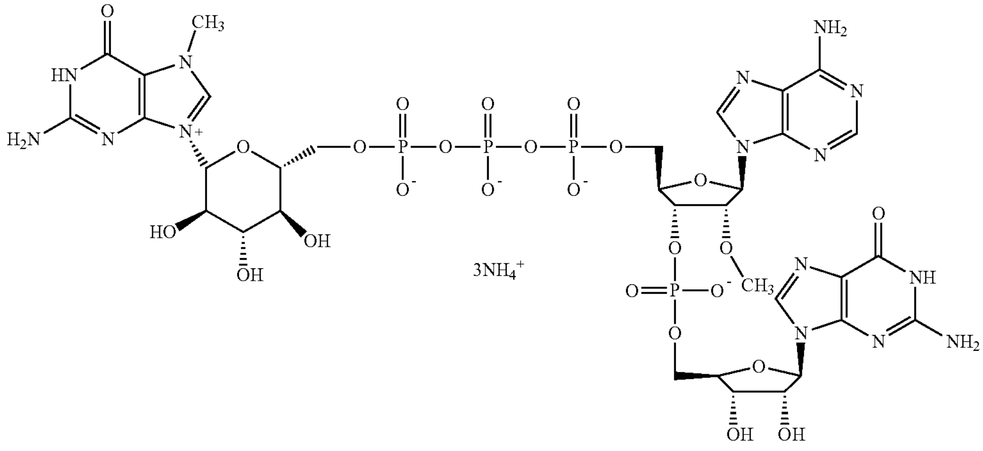

YK-CAP-101

Step 1: Synthesis of YK-CAP-101-PM1

To a 250 mL single-necked flask were added 2-amino-6-chloropurine (6.29 g, 37.09 mmol), toluene (50 mL), and BSA (15.09 g, 74.19 mmol). The system was heated to 80° C., stirred until clarified, and naturally cooled to room temperature. α-Pentaacetylglucose (10.00 g, 25.62 mmol) was dissolved in 20 mL of toluene, and the mixture was added to the system, which was stirred and reacted at room temperature for 5 minutes. TMSOTf (8.24 g, 37.09 mmol) was added thereto at room temperature, and the system was heated to 110° C. and reacted at 110° C. for 3 hours. After the reaction was completed, the system was naturally cooled to room temperature, added with 100 mL of saturated sodium bicarbonate solution and 100 mL of ethyl acetate, stirred for 5 minutes, and filtered through diatomite. The phases were separated, and the aqueous phase was extracted with 100 mL of ethyl acetate. The ethyl acetate phases were combined, washed with 100 mL of saturated brine, dried over anhydrous sodium sulfate, and filtered. The filtrate was evaporated to dryness by rotary evaporation under reduced pressure to obtain a viscous substance, which was purified by silica gel column chromatography (0 to 100% ethyl acetate/n-hexane). The product was collected and concentrated to obtain YK-CAP-101-PM1 (8.40 g, 16.80 mmol, 65.6%). $C_{19}H_{22}ClN_5O_9$, MS (ES): m/z ($M+H^+$) 500.1.

Step 2: Synthesis of YK-CAP-101-PM2

To a 250 mL single-necked flask were added YK-CAP-101-PM1 (8.40 g, 16.80 mmol) and sodium hydroxide aqueous solution (1 M, 40 mL, 40 mmol). The system was heated, and stirred and refluxed for 3 hours. The system was cooled to room temperature and evaporated to dryness by rotary evaporation under reduced pressure. The residue was slurried with 100 mL of (methanol:dichloromethane=1:20) for 10 minutes and filtered to obtain 6.0 g of a brown solid, which was purified by preparative high-pressure liquid chromatography to obtain YK-CAP-101-PM2 (2.13 g, 6.80 mmol, 40.5%). $C_{11}H_{15}N_5O_6$, MS (ES): m/z ($M+H^+$) 314.1.

YK-CAP-101-PM2: $^1H$ NMR (400 MHz, $D_2O$) δ 8.71 (s, 1H), 5.57 (d, J=9.2 Hz, 1H), 3.99 (dd, J=9.2, 9.2 Hz, 1H), 3.86 (dd, J=12.4, 2.0 Hz, 1H), 3.67-3.55 (m, 4H).

Step 3: Synthesis of YK-CAP-101-PM3

YK-CAP-101-PM2 (300 mg, 0.96 mmol) was dissolved in 3 mL of trimethyl phosphate. The mixture was cooled to 0° C. under nitrogen atmosphere, then phosphorus oxychloride (450 mg, 2.93 mmol) was slowly added dropwise thereto, and the mixture was stirred and reacted at 0° C. for about 3 hours. After the reaction was completed, the mixture was added with 5 mL of water, warmed to room temperature, stirred for about 1.5 hours, then washed with dichloromethane (10 mL), and left for phase separation. The upper aqueous phase was collected and concentrated under reduced pressure. The concentrated mixture was diluted with water to 180 mL, and purified by gel column chromatography (eluted with water and 1.5 M TEAB at a ratio of 10:1). The target product peak was collected, concentrated, and lyophilized to obtain YK-CAP-101-PM3 (triethylamine salt, 340 mg, 0.69 mmol, 71.6%) as a white solid. $C_{11}H_{16}N_5O_9P$, MS (ES): m/z ($M-H^-$) 392.1.

Step 4: Synthesis of YK-CAP-101-PM4

YK-CAP-101-PM3 (340 mg, 0.69 mmol), imidazole (706 mg, 10.38 mmol), 2,2'-dithiodipyridine (2287 mg, 10.38 mmol), triethylamine (1050 mg, 10.38 mmol), and triphenylphosphine (2723 mg, 10.38 mmol) were dissolved in 4 mL of dry N,N-dimethylformamide. The mixture was stirred and reacted at room temperature for about 4 hours under nitrogen atmosphere. After the reaction was completed, the reaction mixture was poured into a solution of sodium iodide (1225 mg, 8.17 mmol) in acetone (6 mL), stirred at room temperature for 30 minutes, and centrifuged to obtain a precipitated crude product. The crude product was washed with acetone, and the phases were separated. The lower precipitate was collected and lyophilized to obtain YK-CAP-101-PM4 (sodium salt, 309 mg, 0.66 mmol, 96.2%) as a white solid. $C_{14}H_{18}N_7O_8P$, MS (ES): m/z ($M-H^-$) 442.1.

Step 5: Synthesis of YK-CAP-101-PM5

YK-CAP-101-PM4 (309 mg, 0.66 mmol) and TEAP (458 mg, 2.30 mmol) were dissolved in dry N,N-dimethylformamide (5 mL), then zinc chloride (215 mg, 1.58 mmol) was added thereto, and the mixture was stirred and reacted at room temperature for about 21 hours under nitrogen atmosphere. After the reaction was completed, the system was added with MTBE (10 mL), washed with ultrasonic stirring, allowed to stand, and the supernatant was poured out. The procedure was repeated once. The bottom substance was collected and concentrated under reduced pressure. The residue was dissolved in water (80 mL) until clarified, and purified by gel column chromatography (eluted with water and 1.5 M TEAB at a ratio of 20:1). The target product peak was collected, concentrated, and lyophilized to obtain YK-CAP-101-PM5 (triethylamine salt, 320 mg, 0.56 mmol, 84.4%) as a white solid. $C_{11}H_{17}N_5O_{12}P_2$, MS (ES): m/z ($M-H^-$) 472.0.

Step 6: Synthesis of YK-CAP-101-PM6

YK-CAP-101-PM5 (320 mg, 0.56 mmol) and iodomethane (960 mg, 6.76 mmol) were dissolved in dry N,N-dimethylformamide (4 mL), and the mixture was stirred and reacted in an oil bath at 37° C. for about 23 hours. After the reaction was completed, the system was dissolved in water (5 mL) until clarified, washed with EA (25 mL), and the phases were separated. The lower aqueous phase was collected and concentrated under reduced pressure. The residue was dissolved in water (50 mL) until clarified, and purified by gel column chromatography (eluted with water and 1.5 M TEAB at a ratio of 10:1). The target product peak was collected, concentrated, lyophilized, and further desalted by preparative high performance liquid chromatography (50 mM TEAB and methanol mobile phase system) to obtain YK-CAP-101-PM6 (triethylamine salt, 95 mg, 0.16 mmol, 28.8%) as a white solid. $C_{12}H_{19}N_5O_{12}P_2$, MS (ES): m/z ($M-H^-$) 486.0.

Step 7: Synthesis of YK-CAP-101

YK-CAP-101-PM6 (95 mg, 0.16 mmol) and INT-II (219 mg, 0.27 mmol) were dissolved in dry dimethyl sulfoxide (1.2 mL), then zinc chloride (518 mg, 3.80 mmol) was added thereto, and the mixture was stirred and reacted in an oil bath at 37° C. for about 3 days under nitrogen atmosphere. After the reaction was completed, the mixture was dissolved in 0.25 M EDTA solution until clarified, then added with 1.5 M TEAB to adjust the pH to 6 to 7, and purified by gel column chromatography (eluted with water and 1.5 M TEAB at a ratio of 10:1). The target product peak was collected, concentrated, lyophilized, and further purified by preparative high performance liquid chromatography to obtain the final product YK-CAP-101 (20 mg, 16.30 μmol, 10.2%). $C_{33}H_{45}N_{15}O_{25}P_4$, MS (ES): m/z ($M-H^-$) 1174.2.

$^1H$ NMR (400 MHZ, $D_2O$) δ 8.43 (d, J=1.3 Hz, 1H), 8.38 (s, 1H), 8.06 (d, J=6.0 Hz, 2H), 6.01 (d, J=5.4 Hz, 1H), 5.89 (d, J=2.3 Hz, 1H), 5.81 (d, J=4.5 Hz, 1H), 4.97-4.86 (m, 3H), 4.66 (t, J=4.8 Hz, 1H), 4.52-4.35 (m, 4H), 4.32 (d, J=4.5 Hz, 1H), 4.21 (s, 3H), 4.09 (s, 2H), 3.97 (s, 3H), 3.78 (t, J=7.0 Hz, 1H), 3.43 (s, 4H). $^{31}P$ NMR ($D_2O$, 162 MHz) δ −0.92 (s, 1P), −11.11 (d, J=19.3 Hz, 1P), −11.50 (d, J=17.8 Hz, 1P), −22.23 (t, J=17.8 Hz, 1P).

4. Synthesis of YK-CAP-102
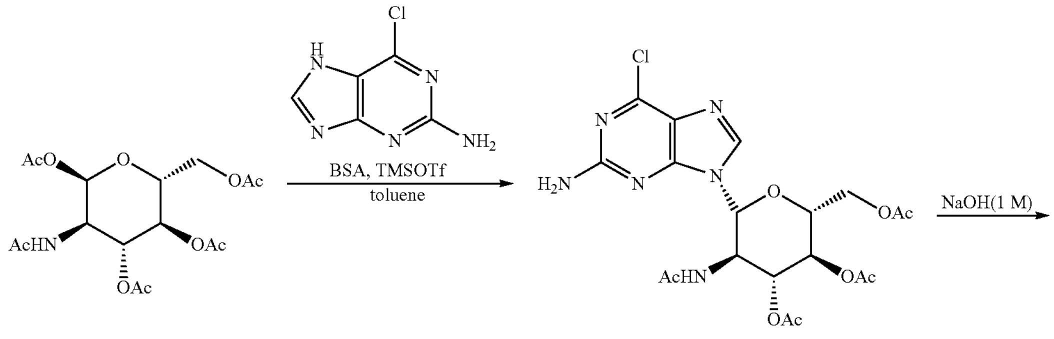
YK-CAP-102-PM1
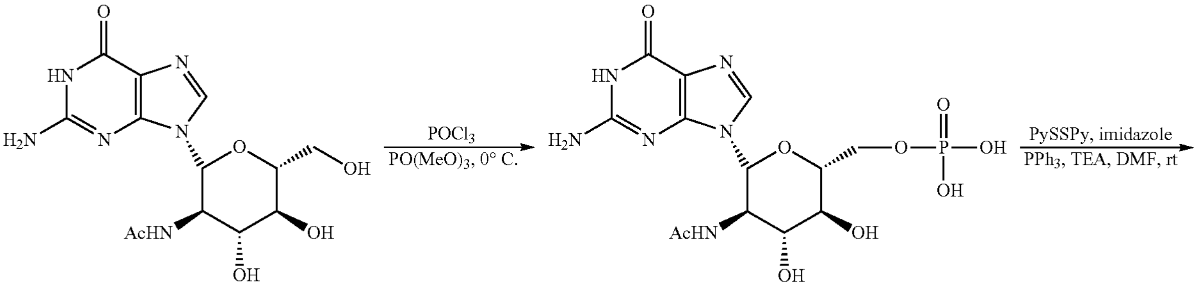
YK-CAP-102-PM2
YK-CAP-102-PM3
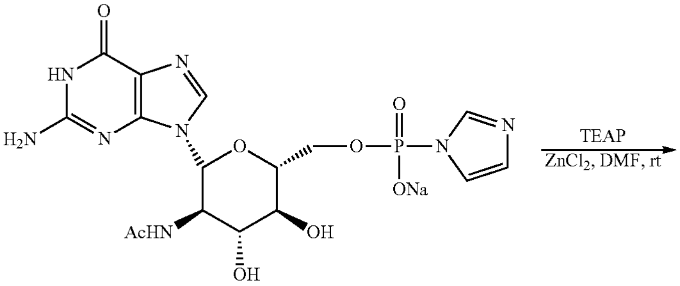
YK-CAP-102-PM4
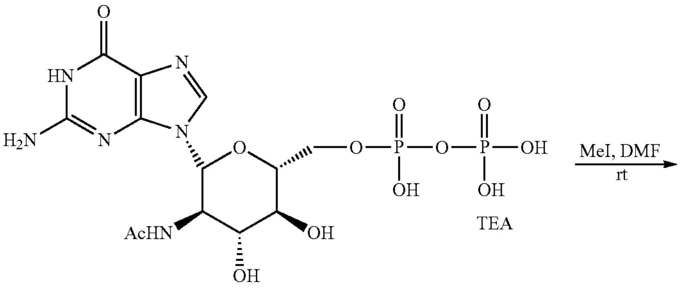
YK-CAP-102-PM5

-continued

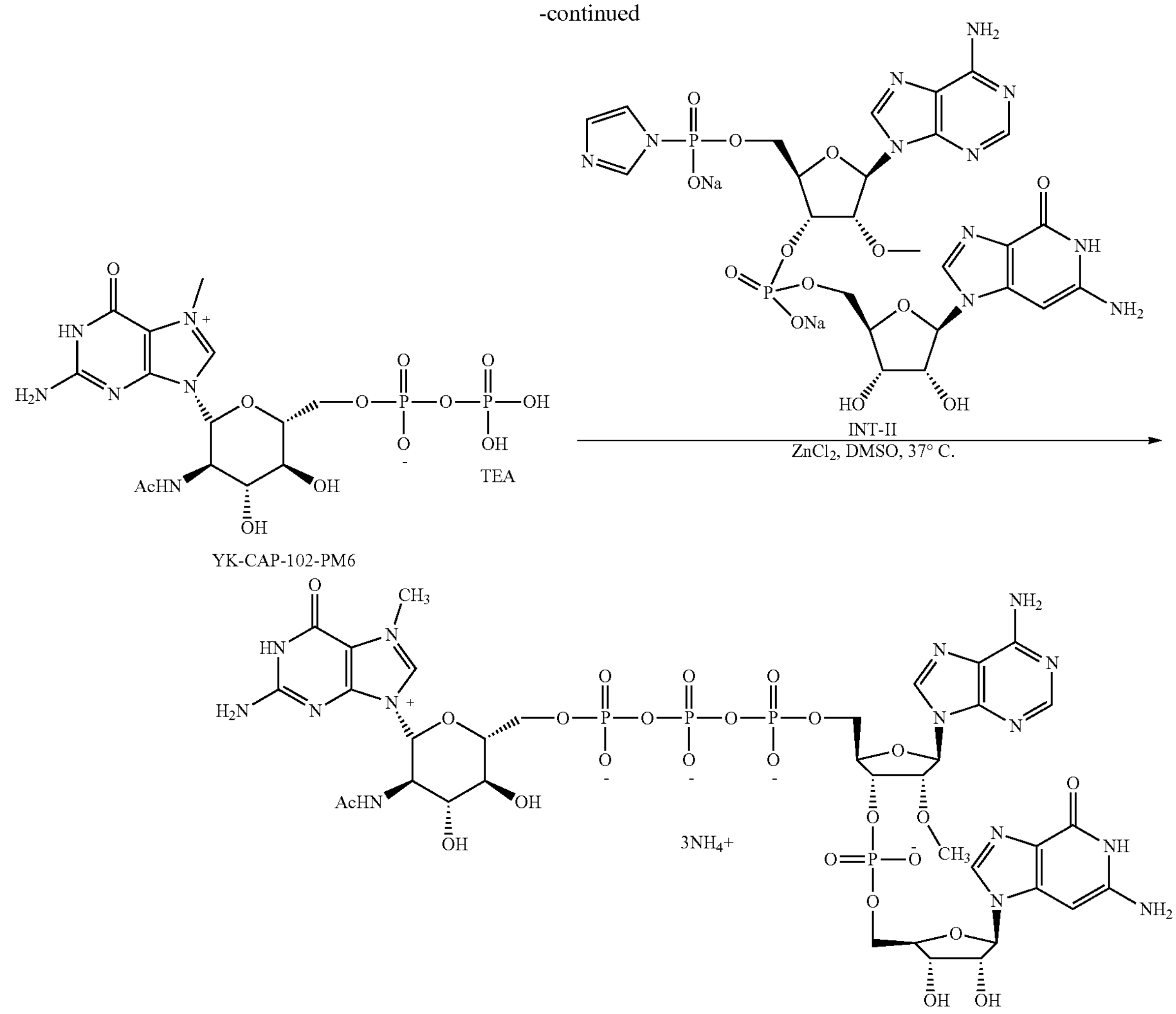

YK-CAP-102-PM6

YK-CAP-102

Step 1: Synthesis of YK-CAP-102-PM1

According to the synthesis method of YK-CAP-101-PM1, α-D-glucosamine pentaacetate (10.0 g, 25.68 mmol) was used as starting material to obtain YK-CAP-102-PM1 (8.79 g, 17.62 mmol, 68.61%). $C_{19}H_{23}ClN_6O_8$, MS (ES): m/z ($M+H^+$) 499.1.

Step 2: Synthesis of YK-CAP-102-PM2

According to the synthesis method of YK-CAP-101-PM2, YK-CAP-102-PM1 (8.79 g, 17.62 mmol) was used as starting material to obtain YK-CAP-102-PM2 (2.37 g, 6.69 mmol, 37.96%). $C_{13}H_{18}N_6O_6$, MS (ES): m/z ($M+H^+$) 355.2.

YK-CAP-102-PM2: $^1H$ NMR (400 MHZ, DMSO-$d_6$) δ 8.41 (s, 1H), 7.97 (d, J=9.2 Hz, 1H), 7.65 (s, 1H), 6.76 (s, 2H), 5.32 (d, J=10.2 Hz, 1H), 4.15 (q, J=9.8 Hz, 1H), 3.67 (d, J=11.9 Hz, 1H), 3.55-3.41 (m, 2H), 3.25 (s, 2H), 1.64 (s, 3H).

Step 3: Synthesis of YK-CAP-102-PM3

According to the synthesis route of YK-CAP-101-PM3, YK-CAP-102-PM2 (500 mg, 1.41 mmol) was used as starting material to obtain YK-CAP-102-PM3 (triethylamine salt, 702 mg, 1.31 mmol, 93.0%). $C_{13}H_{19}NO_9P$, MS (ES): m/z ($M-H^-$) 433.1.

Step 4: Synthesis of Intermediate YK-CAP-102-PM4

According to the synthesis route of YK-CAP-101-PM4, YK-CAP-102-PM3 (702 mg, 1.31 mmol) was used as starting material to obtain YK-CAP-102-PM4 (sodium salt, 521 mg, 1.03 mmol, 78.5%). $C_{16}H_{21}N_8O_8P$, MS (ES): m/z ($M-H^-$) 483.1.

Step 5: Synthesis of Intermediate YK-CAP-102-PM5

According to the synthesis route of YK-CAP-101-PM5, YK-CAP-102-PM4 (521 mg, 1.03 mmol) was used as starting material to obtain YK-CAP-102-PM5 (triethylamine salt, 338 mg, 0.55 mmol, 53.3%). $C_{13}H_{20}N_6O_{12}P_2$, MS (ES): m/z ($M-H^-$) 513.0.

Step 6: Synthesis of Intermediate YK-CAP-102-PM6

According to the synthesis route of YK-CAP-101-PM6, YK-CAP-102-PM5 (338 mg, 0.55 mmol) was used as starting material to obtain YK-CAP-102-PM6 (triethylamine salt, 158 mg, 0.25 mmol, 45.6%). $C_{14}H_{22}N_6O_{12}P_2$, MS (ES): m/z ($M-H^-$) 527.1.

Step 7: Synthesis of YK-CAP-102

According to the synthesis route of YK-CAP-101, YK-CAP-102-PM6 (158 mg, 0.25 mmol) was used as starting material to obtain YK-CAP-102 (23.9 mg, 18.85 μmol, 7.5%). $C_{35}H_{48}N_{16}O_{25}P_4$, MS (ES): m/z ($M-H^-$) 1115.1.

$^1$H NMR (400 MHZ, $D_2O$) δ 8.42 (d, J=1.3 Hz, 1H), 8.38 (s, 1H), 8.04 (d, J=5.8 Hz, 2H), 6.00 (d, J=5.4 Hz, 1H), 5.88 (d, J=2.3 Hz, 1H), 5.81 (d, J=4.4 Hz, 1H), 4.95-4.83 (m, 3H), 4.64 (t, J=4.7 Hz, 1H), 4.53-4.36 (m, 4H), 4.30 (d, J=4.4 Hz, 1H), 4.20 (s, 2H), 4.06 (s, 2H), 3.93 (s, 3H), 3.75 (t, J=7.0 Hz, 3H), 3.62 (s, 3H), 1.67 (s, 3H). $^{31}$P NMR ($D_2O$, 162 MHz) δ−0.92 (s, 1P), −11.21 (d, J=19.2 Hz, 1P), −11.55 (d, J=17.3 Hz, 1P), —23.43 (t, J=17.6 Hz, 1P).

5. Synthesis of YK-CAP-103

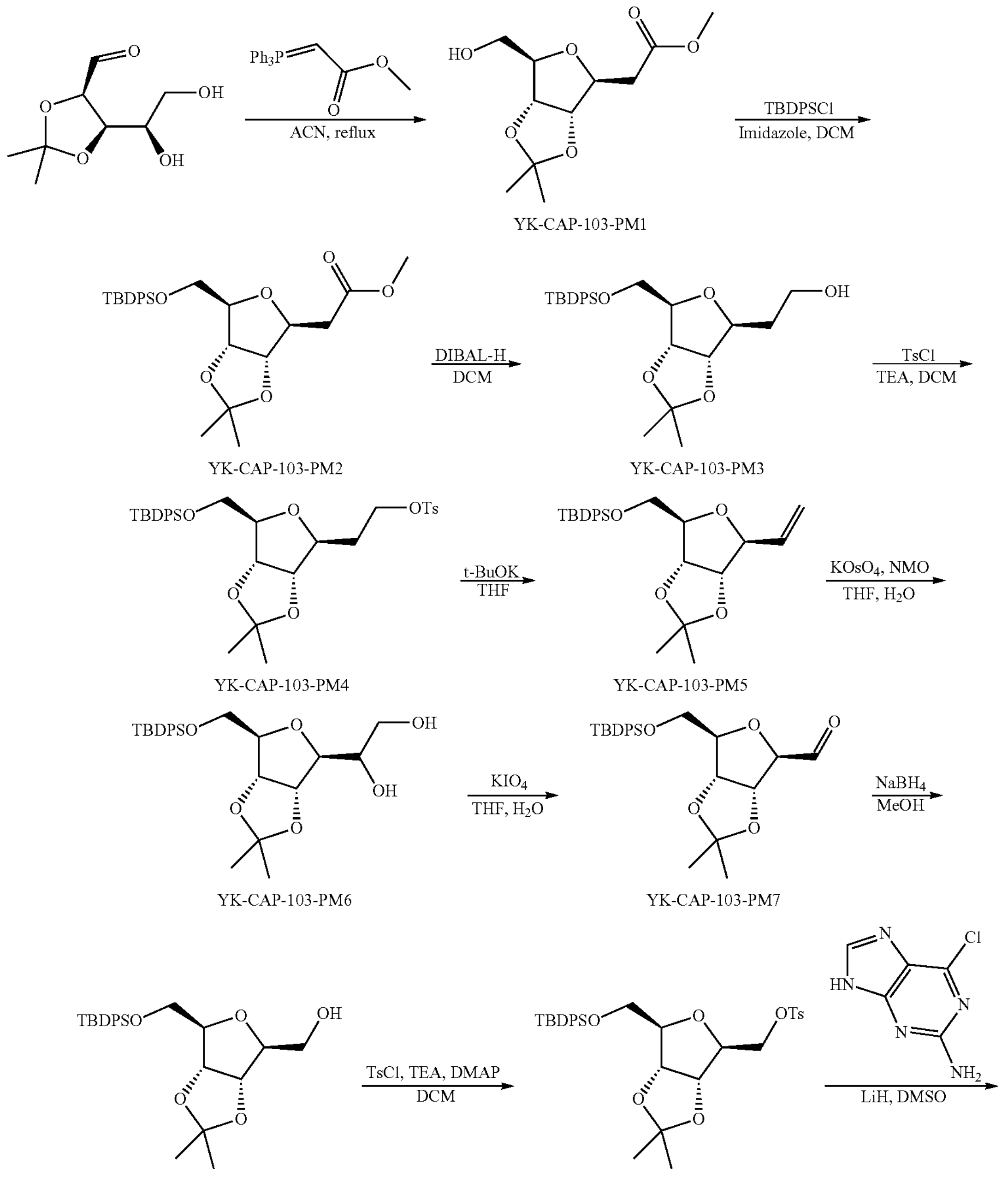

YK-CAP-103-PM1

YK-CAP-103-PM2

YK-CAP-103-PM3

YK-CAP-103-PM4

YK-CAP-103-PM5

YK-CAP-103-PM6

YK-CAP-103-PM7

YK-CAP-103-PM8

YK-CAP-103-PM9

-continued
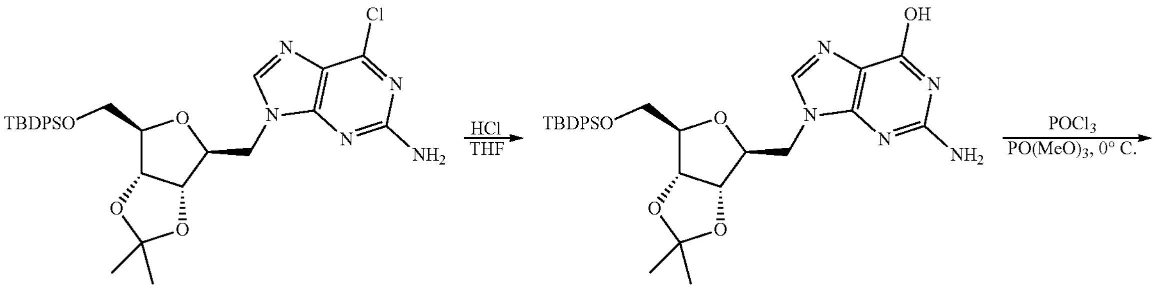
YK-CAP-103-PM10 YK-CAP-103-PM11
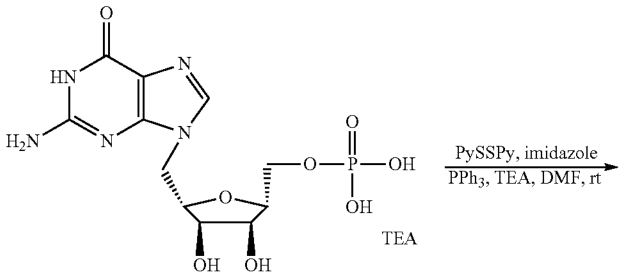
YK-CAP-103-PM12
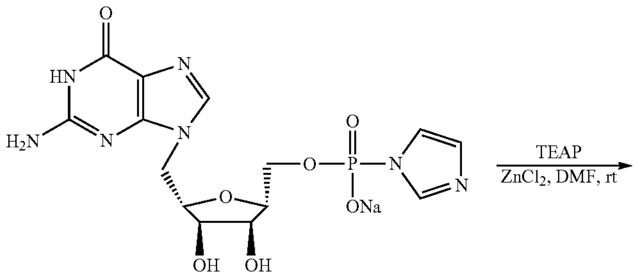
YK-CAP-103-PM13
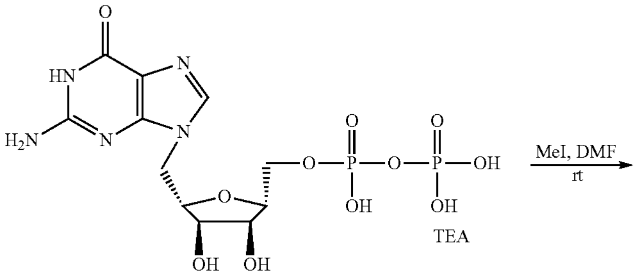
YK-CAP-103-PM14

-continued

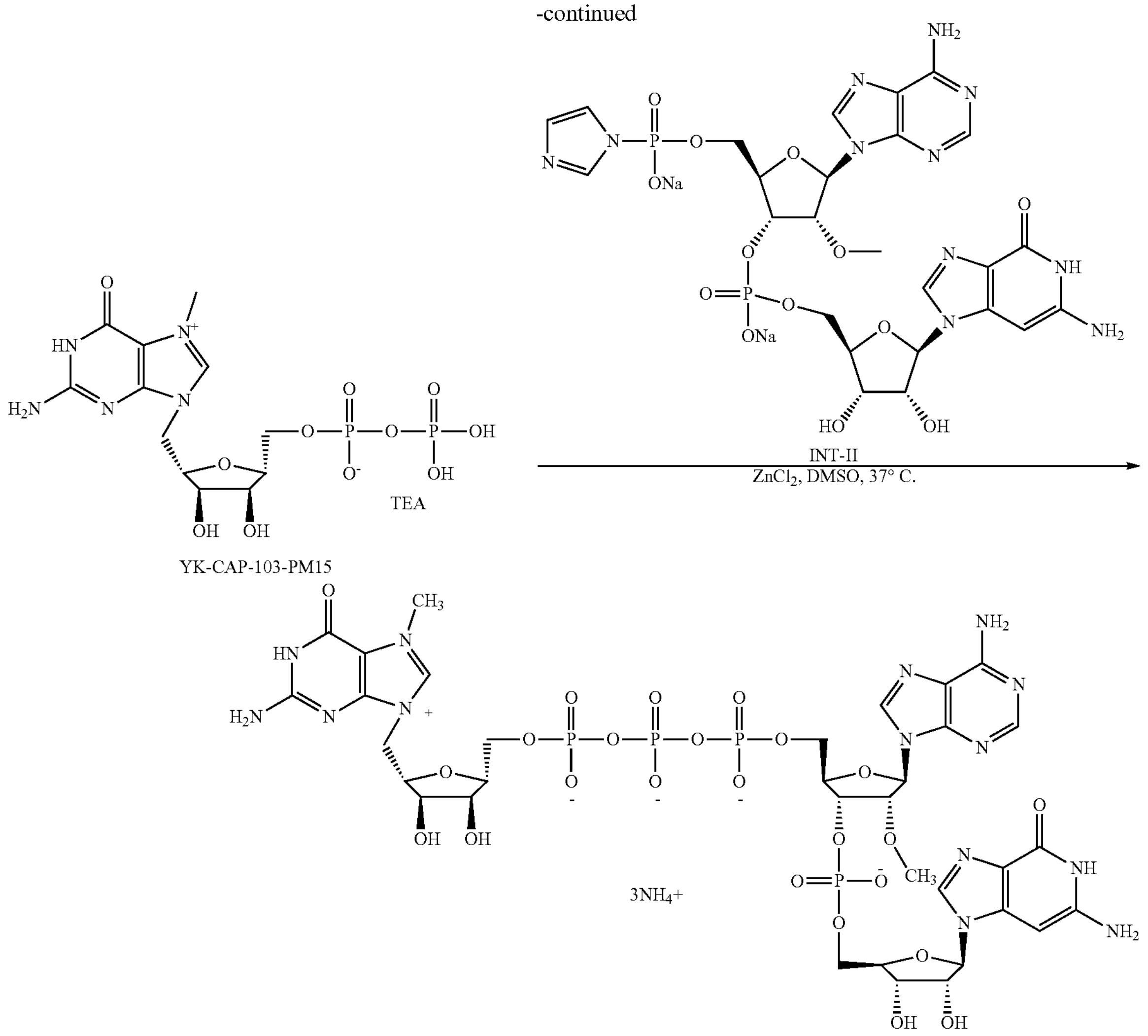

YK-CAP-103-PM15

YK-CAP-103

Step 1: Synthesis of YK-CAP-103-PM1

To a single-necked flask containing acetonitrile (200 mL) were added (4R,5R)-5-((R)-1,2-dihydroxyethyl)-2,2-dimethyl-1,3-dioxolane-4-carbaldehyde (10.00 g, 52.58 mmol) and methyl 2-(triphenyl-5-phosphoranylidene)acetate (21.6 g, 64.60 mmol). The mixture was heated to 90° C., and stirred and reacted at 90° C. for 10 hours. After the reaction was completed, the mixture was diluted with ethyl acetate (300 mL), washed with saturated brine, and the organic phase was dried over anhydrous sodium sulfate. The organic phase was evaporated by rotary evaporation under vacuum to remove the solvent to obtain a yellow oily compound (26.7 g), which was directly used in the next reaction step without purification.

Step 2: Synthesis of YK-CAP-103-PM2

To a single-necked flask containing dichloromethane (200 mL) were sequentially added YK-CAP-103-PM1 (12.8 g, calculated as 25.21 mmol), tert-butyldiphenylchlorosilane (17.2 g, 62.42 mmol), and imidazole (5.31 g, 78.03 mmol), and the mixture was stirred and reacted at room temperature overnight. After the reaction was completed, the mixture was diluted with dichloromethane (100 mL) and washed with saturated brine (200 mL×3). The organic phase was dried over anhydrous sodium sulfate, filtered, and the filtrate was concentrated under vacuum. The residue was purified by silica gel chromatography (0 to 17% ethyl acetate/n-hexane) to obtain YK-CAP-103-PM2 (20.0 g, 41.27 mmol).

Step 3: Synthesis of YK-CAP-103-PM3

YK-CAP-103-PM2 (20.0 g, 41.27 mmol) was dissolved in a single-necked flask containing 150 mL of DCM. The mixture was cooled to −78° C., and a solution of diisobutylaluminum hydride in toluene (1.5 M, 63.2 mL, 94.8 mmol) was slowly added dropwise thereto. After the dropwise addition was completed, the mixture was warmed to room temperature, and stirred and reacted overnight. After the reaction was completed, the mixture was slowly added with 65 mL of methanol in an ice bath, followed by the generation of a white flocculent solid. The mixture was then added with sodium sulfate decahydrate, stirred for 20 minutes, and subjected to suction filtration to remove the solid. The filtrate was evaporated to dryness by rotary evaporation, and then the residue was purified by silica gel chromatography (0 to 30% ethyl acetate/n-hexane) to obtain YK-CAP-103-PM3 (15.00 g, 32.85 mmol, 79.6%).

Step 4: Synthesis of YK-CAP-103-PM4

To a single-necked flask containing dichloromethane (60 mL) were sequentially added YK-CAP-103-PM3 (15.00 g, 32.85 mmol), p-toluenesulfonyl chloride (7.5 g, 39.40 mmol), and triethylamine (5.0 g, 49.30 mmol), and the mixture was stirred and reacted at room temperature overnight. After the reaction was completed, the mixture was diluted with dichloromethane (50 mL) and washed with saturated brine (100 mL×2). The organic phase was dried over anhydrous sodium sulfate, filtered, and the filtrate was concentrated under vacuum. The residue was purified by silica gel chromatography (0 to 20% ethyl acetate/n-hexane) to obtain YK-CAP-103-PM4 (17.00 g, 27.83 mmol, 84.7%).

Step 5: Synthesis of YK-CAP-103-PM5

YK-CAP-103-PM4 (17.00 g, 27.83 mmol) was dissolved in a single-necked flask containing tetrahydrofuran (150 mL), and a solution of potassium tert-butoxide in tetrahydrofuran (1 M, 61.0 mL, 61.0 mmol) was slowly added dropwise thereto at −40° C. After the dropwise addition was completed, the mixture was stirred and reacted at room temperature for 3 hours, diluted with ethyl acetate (200 mL), and washed with saturated brine (150 mL×2). The organic phase was dried over anhydrous sodium sulfate, filtered, and the filtrate was concentrated under vacuum. The residue was purified by silica gel chromatography (0 to 11% ethyl acetate/n-hexane) to obtain YK-CAP-103-PM5 (3.29 g, 7.50 mmol, 27.0%).

Step 6: Synthesis of YK-CAP-103-PM6

YK-CAP-103-PM5 (3.29 g, 7.50 mmol) was dissolved in a mixed solution of tetrahydrofuran (25 mL) and water (5 mL). Potassium osmate dihydrate (140 mg, 0.38 mmol) and N-methylmorpholine-N-oxide (1.05 g, 9.00 mmol) were sequentially added to the above mixed solution. The mixture was heated to 40° C., and stirred and reacted at 40° C. for 6 hours. After the reaction was completed, the mixture was diluted with ethyl acetate (100 mL) and washed with saturated sodium sulfite aqueous solution (80 mL×2). The organic phase was dried over anhydrous sodium sulfate, filtered, and the solvent was removed under vacuum to obtain YK-CAP-103-PM6 (3.48 g, 7.36 mmol, 98.2%).

Step 7: Synthesis of YK-CAP-103-PM7

YK-CAP-103-PM6 (3.48 g, 7.36 mmol) was dissolved in a mixed solution of tetrahydrofuran (25 mL) and water (5 mL). Potassium periodate (2.54 g, 11.04 mmol) was sequentially added to the above mixed solution. The mixture was heated to 40° C., and stirred and reacted at 40° C. for 6 hours. After the reaction was completed, the mixture was diluted with ethyl acetate (100 mL) and washed with saturated sodium sulfite aqueous solution (50 mL×2). The organic phase was dried over anhydrous sodium sulfate, filtered, and the solvent was removed under vacuum to obtain YK-CAP-103-PM7 (3.14 g, 7.13 mmol, 96.9%).

Step 8: Synthesis of YK-CAP-103-PM8

YK-CAP-103-PM7 (5.19 g, 11.78 mmol) was dissolved in a single-necked flask containing methanol (100 mL), then sodium borohydride (0.54 g, 13.18 mmol) was added thereto in batches in an ice bath, and the mixture was stirred and reacted at room temperature for 3 hours. After the reaction was completed, the mixture was diluted with water (150 mL) and extracted with ethyl acetate (150 mL×2). The organic phases were combined, dried over anhydrous sodium sulfate, filtered, and concentrated under vacuum. The residue was purified by silica gel chromatography (0 to 13% ethyl acetate/n-hexane) to obtain YK-CAP-103-PM8 (3.30 g, 7.46 mmol, 63.3%).

Step 9: Synthesis of YK-CAP-103-PM9

According to the synthesis method of YK-CAP-103-PM4, YK-CAP-103-PM8 (3.30 g, 7.46 mmol) was used as starting material to obtain YK-CAP-103-PM9 (3.42 g, 5.73 mmol, 76.8%).

Step 10: Synthesis of YK-CAP-103-PM10

2-Amino-6-chloroguanine (1.17 g, 6.90 mmol) and lithium hydride (55 mg, 6.88 mmol) were dissolved in 30 mL of DMSO, and the mixture was stirred and reacted at 90° C. for 1 hour. A solution of YK-CAP-103-PM9 (3.42 g, 5.73 mmol) in DMSO (15 mL) was then added thereto, and the mixture was stirred and reacted for another 5 hours. After the reaction was completed, the mixture was diluted with water (100 mL) and extracted with dichloromethane (150 mL×2). The organic phases were combined, dried over anhydrous sodium sulfate, filtered, and concentrated under vacuum. The residue was purified by silica gel chromatography (0 to 25% ethyl acetate/dichloromethane) to obtain YK-CAP-103-PM10 (1.90 g, 3.20 mmol, 55.9%). $C_{30}H_{36}ClN_5O_4Si$, MS (ES): m/z ($M+H^+$) 595.2.

Step 11: Synthesis of YK-CAP-103-PM11

YK-CAP-103-PM10 (1.90 g, 3.20 mmol) was dissolved in tetrahydrofuran (40 mL), then 1 M HCl (80 mL) was added thereto, and the mixture was stirred and reacted at 90° C. for 7 hours. After the reaction was completed, the solvent was removed under reduced pressure, and the residue was purified by preparative high-pressure liquid chromatography to obtain compound YK-CAP-103-PM11 (587 mg, 1.97 mmol, 61.7%) as a white solid. $C_{11}H_{15}N_5O_5$, MS (ES): m/z ($M+H^+$) 298.2.

YK-CAP-103-PM11: $^1H$ NMR (400 MHZ, DMSO-$d_6$) δ 10.57 (s, 1H), 7.68 (s, 1H), 6.46 (s, 2H), 5.00-4.53 (m, 2H), 4.17-4.09 (m, 1H), 4.00-3.87 (m, 2H), 3.77-3.61 (m, 3H), 3.46-3.32 (m, 3H).

Step 12: Synthesis of YK-CAP-103-PM12

According to the synthesis route of YK-CAP-101-PM3, YK-CAP-103-PM11 (300 mg, 1.01 mmol) was used as starting material to obtain YK-CAP-103-PM12 (triethylamine salt, 350 mg, 0.73 mmol, 72.5%). $C_{11}H_{16}N_5O_8P$, MS (ES): m/z ($M-H^-$) 376.1.

Step 13: Synthesis of YK-CAP-103-PM13

According to the synthesis route of YK-CAP-101-PM4, YK-CAP-103-PM12 (350 mg, 0.73 mmol) was used as starting material to obtain YK-CAP-103-PM13 (sodium salt, 320 mg, 0.71 mmol, 97.4%). $C_{14}H_{18}N_7O_7P$, MS (ES): m/z ($M-H^-$) 426.1.

Step 14: Synthesis of YK-CAP-103-PM14

According to the synthesis route of YK-CAP-101-PM5, YK-CAP-103-PM13 (320 mg, 0.71 mmol) was used as starting material to obtain YK-CAP-103-PM14 (triethylamine salt, 250 mg, 0.45 mmol, 62.9%). $C_{11}H_{17}N_5O_{11}P_2$, MS (ES): m/z ($M-H^-$) 456.0.

Step 15: Synthesis of YK-CAP-103-PM15

According to the synthesis route of YK-CAP-101-PM6, YK-CAP-103-PM14 (250 mg, 0.45 mmol) was used as starting material to obtain YK-CAP-103-PM15 (triethylamine salt, 90 mg, 0.16 mmol, 34.9%). $C_{12}H_{20}N_5O_{11}P_2$, MS (ES): m/z ($M-H^-$) 470.1.

Step 16: Synthesis of YK-CAP-103

According to the synthesis route of YK-CAP-101, YK-CAP-103-PM15 (90 mg, 0.16 mmol) was used as starting material to obtain YK-CAP-103 (29 mg, 23.95 μmol, 15.0%). $C_{33}H_{45}N_{15}O_{24}P_4$, MS (ES): m/z ($M-H^-$) 1158.2.

$^1H$ NMR (400 MHZ, $D_2O$) δ 8.41 (d, J=1.2 Hz, 1H), 8.33 (d, J=2.3 Hz, 1H), 8.02 (d, J=4.8 Hz, 2H), 6.11 (d, J=5.4 Hz, 1H), 5.91 (d, J=2.4 Hz, 1H), 5.71 (d, J=4.6 Hz, 1H), 5.20-5.03 (m, 2H), 4.91-4.77 (m, 3H), 4.63 (t, J=4.7 Hz, 1H), 4.53-4.35 (m, 4H), 4.26 (d, J=3.1 Hz, 1H), 4.10 (s, 3H), 4.02 (s, 2H), 3.92 (s, 3H), 3.54 (t, J=7.0 Hz, 1H), 3.32 (s, 3H). $^{31}P$ NMR ($D_2O$, 162 MHz) δ–0.91 (s, 1P), –11.22 (d, J=19.4 Hz, 1P), –11.33 (d, J=17.2 Hz, 1P), –24.43 (t, J=17.7 Hz, 1P).

6. Synthesis of YK-CAP-104

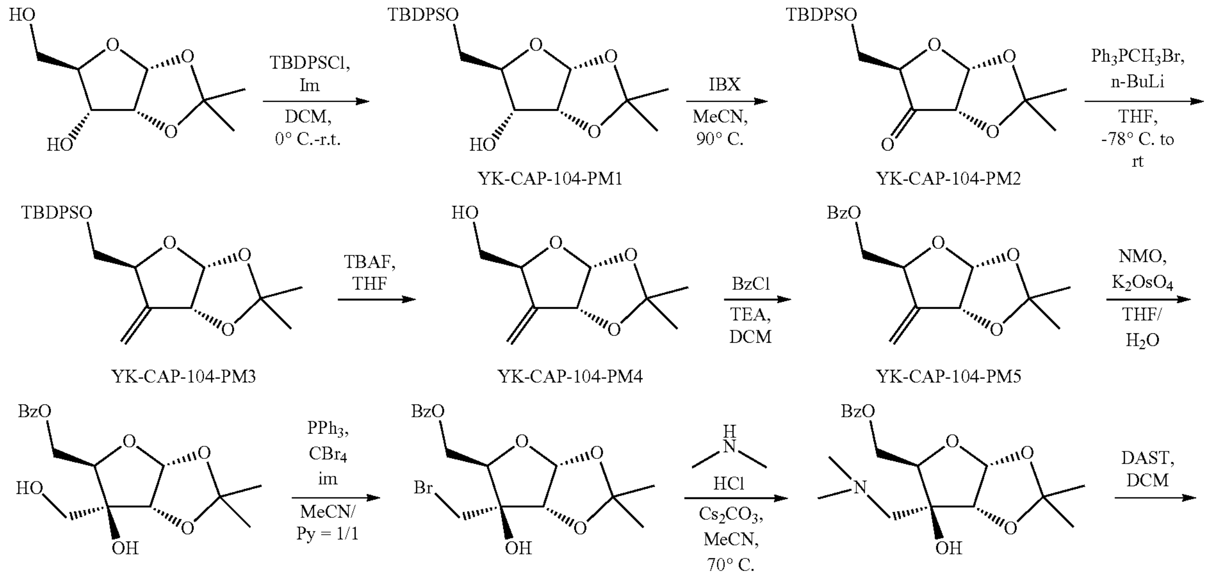

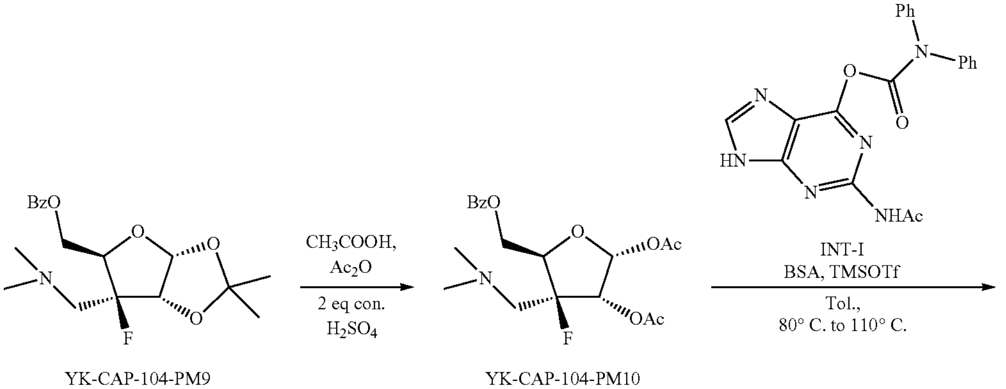

-continued
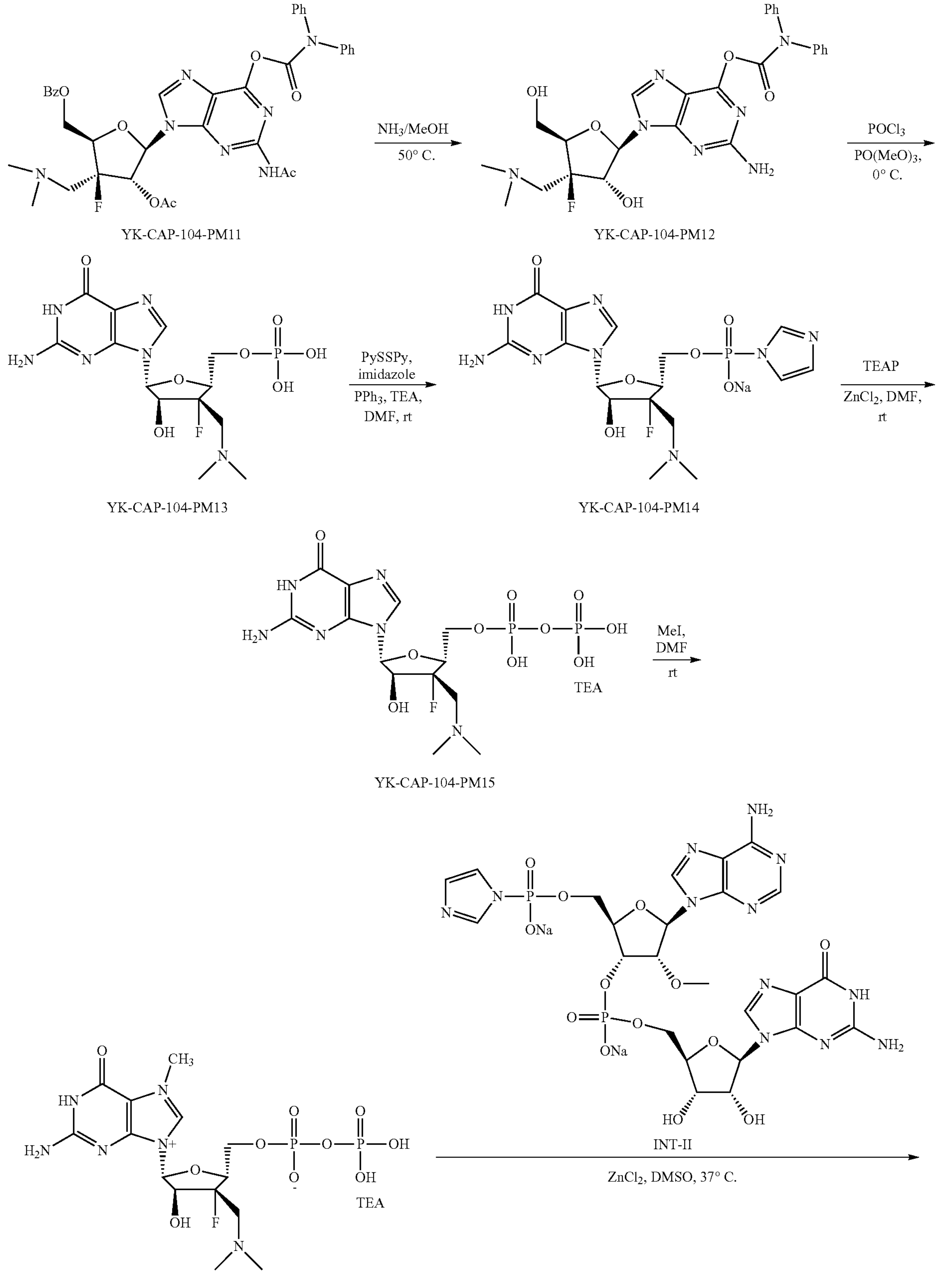
YK-CAP-104-PM11
YK-CAP-104-PM12
YK-CAP-104-PM13
YK-CAP-104-PM14
YK-CAP-104-PM15
INT-II
YK-CAP-104-PM16

-continued

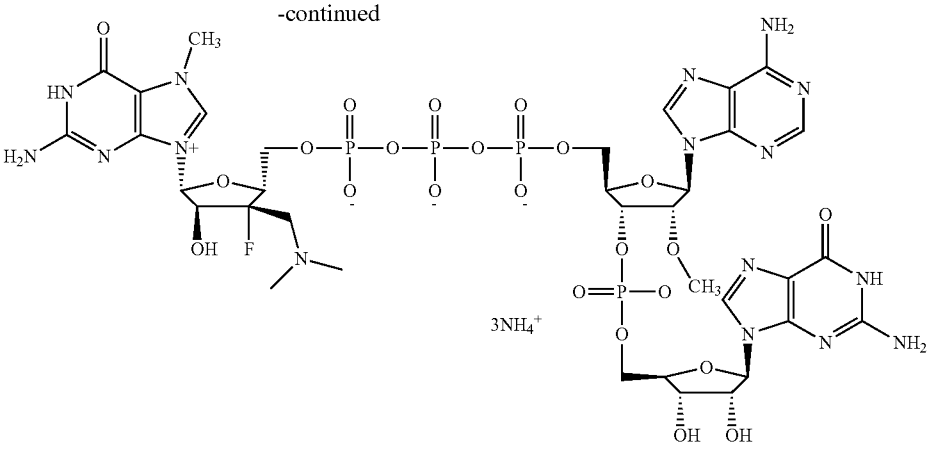

YK-CAP-104

Step 1: Synthesis of YK-CAP-104-PM1

1,2-O-isopropyl-A-D-ribofuranose (20.0 g, 0.11 mol) was dissolved in dichloromethane. Imidazole (11.6 g, 0.17 mol) and TBDPSCl (33.0 g, 0.12 mol) were added to the above system. The mixture was stirred and reacted at room temperature for 15 hours. The reaction mixture was added with saturated sodium bicarbonate solution and extracted with dichloromethane. The dichloromethane phase was then washed once with saturated brine, dried over anhydrous sodium sulfate, filtered, and the filtrate was evaporated to dryness by rotary evaporation under reduced pressure. The residue was subjected to silica gel chromatography (0 to 17% ethyl acetate/n-hexane) to obtain YK-CAP-104-PM1 (33.5 g, 78.16 mmol, 71.1%).

Step 2: Synthesis of YK-CAP-104-PM2

YK-CAP-104-PM1 (33.5 g, 78.16 mmol) was dissolved in acetonitrile, and 2-iodoxybenzoic acid (28.5 g, 101.8 mmol) was added thereto. The mixture was heated to 90° C., and stirred and reacted for 5 hours. The reaction mixture was filtered, and the filtrate was evaporated to dryness by rotary evaporation under reduced pressure to obtain YK-CAP-104-PM2 (32.7 g, 76.66 mmol, 98.1%).

Step 3: Synthesis of YK-CAP-104-PM3

(Bromomethyl)triphenylphosphonium bromide (60.3 g, 138.3 mmol) was dissolved in tetrahydrofuran (400 mL). The mixture was cooled to −78° C., and a 2.5 M solution of n-butyllithium in tetrahydrofuran (76 mL, 190 mmol) was slowly added dropwise thereto. After the dropwise addition was completed, the reaction system was naturally warmed to 0° C., and stirred and reacted for 2 hours. The above reaction system was re-cooled to −78° C., and a solution of YK-CAP-104-PM2 (48.0 g, 112.52 mmol) in tetrahydrofuran (100 mL) was slowly added dropwise thereto. After the dropwise addition was completed, the reaction system was warmed to room temperature, and stirred and reacted overnight. The reaction system was quenched with saturated ammonium chloride solution (200 mL) and extracted with ethyl acetate (300 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 20% ethyl acetate/n-hexane) to obtain YK-CAP-104-PM3 (39.0 g, 91.85 mmol, 81.6%).

Step 4: Synthesis of YK-CAP-104-PM4

YK-CAP-104-PM3 (34.0 g, 80.07 mmol) was dissolved in tetrahydrofuran (200 mL), then tetrabutylammonium fluoride (52.0 g, 198.9 mmol) was added thereto, and the mixture was stirred and reacted at room temperature for 1 hour. The reaction system was added with saturated ammonium chloride aqueous solution and extracted with ethyl acetate (200 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 60% ethyl acetate/n-hexane) to obtain YK-CAP-104-PM4 (13.5 g, 72.50 mmol, 90.5%).

Step 5: Synthesis of YK-CAP-104-PM5

YK-CAP-104-PM4 (13.5 g, 72.50 mmol) was dissolved in dichloromethane (150 mL), and triethylamine (22.0 g, 217.4 mmol) was added thereto. The reaction system was cooled to 0° C., and benzoyl chloride (11.2 g, 79.7 mmol) was slowly added dropwise thereto. The reaction system was naturally warmed to room temperature, and stirred and reacted for 1 hour. After the reaction was completed, the reaction system was quenched with saturated sodium bicarbonate aqueous solution (100 mL) and extracted with dichloromethane (100 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 20% ethyl acetate/n-hexane) to obtain YK-CAP-104-PM5 (19.6 g, 67.51 mmol, 93.1%).

Step 6: Synthesis of YK-CAP-104-PM6

YK-CAP-104-PM5 (18.6 g, 64.07 mmol) was dissolved in a mixed solvent of tetrahydrofuran (160 mL) and water (40 mL). N-methylmorpholine oxide (11.3 g, 96.5 mmol) and potassium osmate dihydrate (2.0 g, 6.4 mmol) were sequentially weighed and added thereto. The mixture was stirred and reacted at room temperature overnight. After the reaction was completed, the reaction system was quenched with saturated sodium sulfite aqueous solution and extracted with ethyl acetate (200 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 60% ethyl acetate/n-hexane) to obtain YK-CAP-104-PM6 (20.5 g, 63.21 mmol, 98.7%).

Step 7: Synthesis of YK-CAP-104-PM7

YK-CAP-104-PM6 (17.7 g, 54.57 mmol) as starting material was dissolved in acetonitrile (140 mL) and pyridine (140 mL). Imidazole (11.1 g, 163.8 mmol), triphenylphosphine (21.5 g, 81.9 mmol), and carbon tetrabromide (27.1 g, 81.9 mmol) were sequentially weighed and added thereto. The above reaction system was heated to 70° C. under nitrogen atmosphere, and stirred and reacted for 6 hours. Thin-layer chromatography (TLC) monitored that the reaction was complete. The reaction mixture was evaporated to dryness by rotary evaporation under vacuum. The residue was purified by silica gel chromatography (0 to 50% ethyl acetate/n-hexane) to obtain YK-CAP-104-PM7 (13.9 g, 35.90 mmol, 65.8%).

Step 8: Synthesis of YK-CAP-104-PM8

YK-CAP-104-PM7 (13.4 g, 34.60 mmol) was dissolved in acetonitrile (120 mL). Potassium carbonate (14.4 g, 104.2 mmol) and dimethylamine hydrochloride (3.4 g, 41.1 mmol) were sequentially added thereto. The above system was heated to 70° C. and reacted for 16 hours. TLC monitored that the reaction was complete. The system was cooled to room temperature, filtered, and the organic phase was evaporated to dryness by rotary evaporation under reduced pressure. The residue was purified by silica gel chromatography (0 to 50% ethyl acetate/n-hexane) to obtain YK-CAP-104-PM8 (8.5 g, 24.18 mmol, 69.9%). $C_{18}H_{25}NO_6$, MS (ES): m/z (M+H$^+$) 352.1.

Step 9: Synthesis of YK-CAP-104-PM9

YK-CAP-104-PM8 (8.5 g, 24.18 mmol) was dissolved in dichloromethane (160 mL). The mixture was cooled to −40° C., and a solution of diethylaminosulfur trifluoride (4.7 g, 29.0 mmol) in dichloromethane (10 mL) was slowly added dropwise thereto. After the dropwise addition was completed, the mixture was slowly warmed to 0° C., and stirred and reacted for 4 hours. TLC monitored that the reaction was complete. The reaction system was quenched with saturated sodium bicarbonate aqueous solution (100 mL) and extracted with dichloromethane (100 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 40% ethyl acetate/n-hexane) to obtain YK-CAP-104-PM9 (5.2 g, 14.71 mmol, 60.8%). $C_{18}H_{24}FNO_5$, MS (ES): m/z (M+H$^+$) 354.2.

Step 10: Synthesis of YK-CAP-104-PM10

YK-CAP-104-PM9 (4.7 g, 13.30 mmol) was dissolved in acetic acid (100 mL), then acetic anhydride (16.4 g, 160.6 mmol) was added thereto, and concentrated sulfuric acid (4.7 g, 26.8 mmol) was slowly added dropwise thereto. After the dropwise addition was completed, the mixture was slowly heated to 40° C., and stirred and reacted for 16 hours.

LCMS monitored that the reaction was complete. The reaction system was quenched with saturated sodium bicarbonate aqueous solution to adjust the pH to neutrality, and extracted with ethyl acetate (200 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 40% ethyl acetate/n-hexane) to obtain YK-CAP-104-PM10 (2.5 g, 6.29 mmol, 47.3%). $C_{19}H_{24}FNO_7$, MS (ES): m/z (M+H$^+$) 398.1.

Step 11: Synthesis of YK-CAP-104-PM11

Intermediate INT-I (2.7 g, 6.9 mmol) was dissolved in 1,2-dichloroethane (50 mL), and N,O-bis(trimethylsilyl) acetamide (2.8 g, 13.8 mmol) was added thereto. The reaction system was heated to 80° C., stirred and reacted for 2 hours, and evaporated to dryness by rotary evaporation under reduced pressure. The residue was dissolved in toluene (30 mL), then a solution of YK-CAP-104-PM10 (2.5 g, 6.29 mmol) in toluene (20 mL) was added thereto, and trimethylsilyl trifluoromethanesulfonate (1.5 g, 6.7 mmol) was slowly added dropwise thereto. The reaction system was heated to 70° C., and stirred and reacted for 2 hours. TLC monitored that the reaction was complete. The reaction system was quenched with saturated sodium bicarbonate aqueous solution and extracted with ethyl acetate (50 mL×3). The organic phases were combined, washed with saturated NaCl aqueous solution, dried over anhydrous sodium sulfate, filtered, and evaporated to dryness by rotary evaporation under reduced pressure. The residue was purified by silica gel chromatography (0 to 70% ethyl acetate/dichloromethane) to obtain YK-CAP-104-PM11 (2.7 g, 3.72 mmol, 59.1%). $C_{37}H_{36}FN_7O_8$, MS (ES): m/z (M+H$^+$) 726.2.

Step 12: Synthesis of YK-CAP-104-PM12

YK-CAP-104-PM11 (2.7 g, 3.72 mmol) was dissolved in a mixed solvent of $NH_3$/MeOH (20 mL) and water (4 mL). The above reaction system was heated to 50° C., and stirred and reacted for 10 hours. LCMS monitored that the reaction was complete. The reaction mixture was evaporated to dryness by rotary evaporation to obtain 2.5 g of a crude product, which was purified by preparative high-pressure liquid chromatography to obtain YK-CAP-104-PM12 (560 mg, 1.64 mmol, 44.0%). $C_{13}H_{19}FN_6O_4$, MS (ES): m/z (M+H$^+$) 343.1.

YK-CAP-104-PM12: $^1$H NMR (400 MHZ, DMSO-d$_6$) δ 9.98 (s, 1H), 7.93 (s, 1H), 6.52 (s, 2H), 5.69 (d, J=6.1 Hz, 1H), 5.51 (s, 1H), 4.97-4.85 (m, 1H), 4.37 (d, J=6.4 Hz, 1H), 4.14 (d, J=4.4 Hz, 1H), 3.77 (d, J=12.1 Hz, 1H), 3.62 (s, 1H), 2.59-2.33 (m, 8H).

Step 13: Synthesis of YK-CAP-104-PM13

According to the synthesis route of YK-CAP-101-PM3, YK-CAP-104-PM12 (560 mg, 1.64 mmol) was used as starting material to obtain YK-CAP-104-PM13 (triethylamine salt, 557 mg, 1.06 mmol, 64.9%). $C_{13}H_{20}FN_6O_7P$, MS (ES): m/z (M−H$^-$) 421.1.

Step 14: Synthesis of YK-CAP-104-PM14

According to the synthesis route of YK-CAP-101-PM4, YK-CAP-104-PM13 (557 mg, 1.06 mmol) was used as starting material to obtain YK-CAP-104-PM14 (sodium salt, 414 mg, 0.84 mmol, 79.0%). $C_{16}H_{23}FN_8O_6P$, MS (ES): m/z (M–H⁻) 471.1.

Step 15: Synthesis of YK-CAP-104-PM15

According to the synthesis route of YK-CAP-101-PM5, YK-CAP-104-PM14 (414 mg, 0.84 mmol) was used as starting material to obtain YK-CAP-104-PM15 (triethylamine salt, 300 mg, 0.50 mmol, 59.2%). $C_{13}H_{21}FN_6O_{10}P_2$, MS (ES): m/z (M–H⁻) 501.1.

Step 16: Synthesis of YK-CAP-104-PM16

According to the synthesis route of YK-CAP-101-PM6, YK-CAP-104-PM15 (300 mg, 0.50 mmol) was used as starting material to obtain YK-CAP-104-PM16 (triethylamine salt, 124 mg, 0.20 mmol, 40.2%). $C_{14}H_{24}FN_6O_{10}P_2$, MS (ES): m/z (M–H⁻) 515.1.

Step 17: Synthesis of YK-CAP-104

According to the synthesis route of YK-CAP-101, YK-CAP-104-PM16 (124 mg, 0.20 mmol) was used as starting material to obtain YK-CAP-104 (ammonium salt, 21 mg, 16.72 μmol, 8.4%). $C_{35}H_{49}FN_{16}O_{23}P_4$, MS (ES): m/z (M–H⁻) 1203.1.

$^1$H NMR (400 MHZ, $D_2O$) δ 8.52 (d, J=1.2 Hz, 1H), 8.44 (d, J=2.2 Hz, 1H), 7.86 (d, J=4.4 Hz, 2H), 6.14 (d, J=5.2 Hz, 1H), 5.94 (d, J=2.4 Hz, 1H), 5.81 (d, J=4.6 Hz, 1H), 4.81-4.67 (m, 3H), 4.63 (t, J=4.6 Hz, 1H), 4.53-4.35 (m, 5H), 4.23 (d, J=3.1 Hz, 1H), 4.19 (s, 3H), 4.12 (s, 2H), 3.78 (s, 3H), 3.32 (t, J=7.0 Hz, 1H), 3.12 (s, 3H), 2.55-2.35 (m, 8H). $^{31}$P NMR ($D_2O$, 162 MHz) δ–0.92 (s, 1P), –11.32 (d, J=20.7 Hz, 1P), –12.33 (d, J=17.5 Hz, 1P), –23.28 (t, J=16.8 Hz, 1P).

7. Synthesis of YK-CAP-105

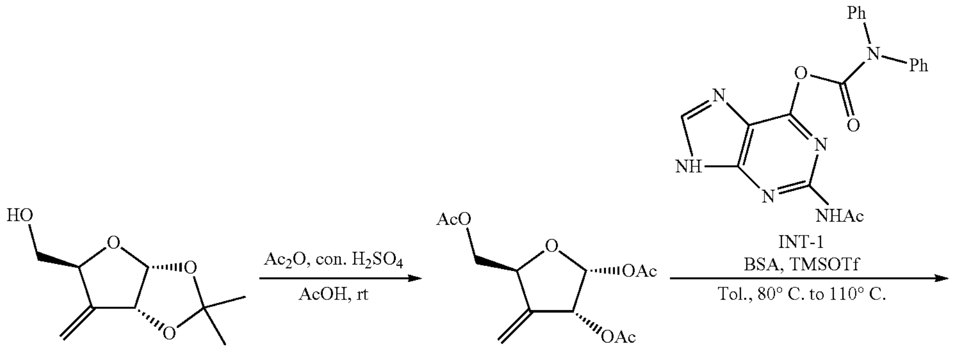

YK-CAP-104-PM4

YK-CAP-105-PM1

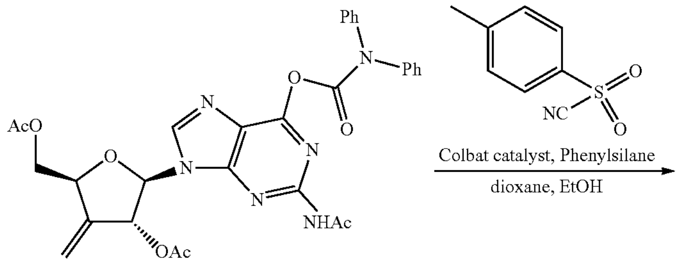

YK-CAP-105-PM2

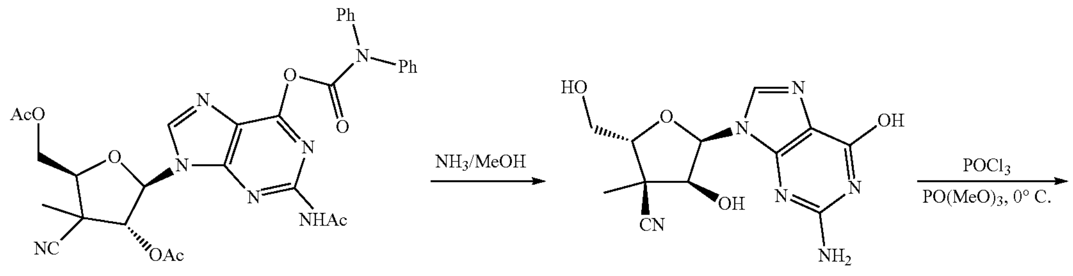

YK-CAP-105-PM3

YK-CAP-105-PM4

-continued
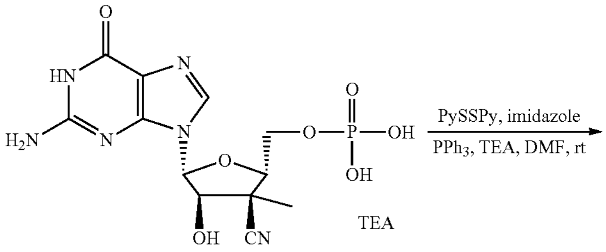
YK-CAP-105-PM5
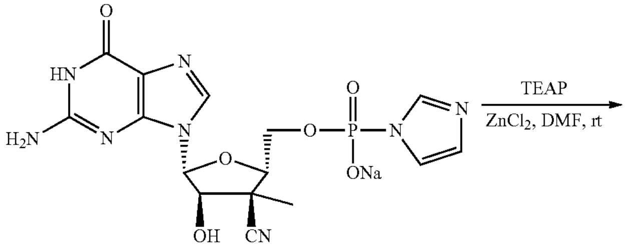
YK-CAP-105-PM6
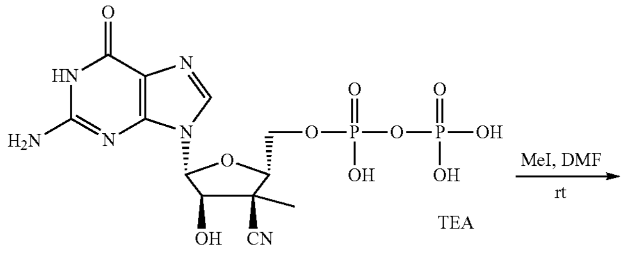
YK-CAP-105-PM7
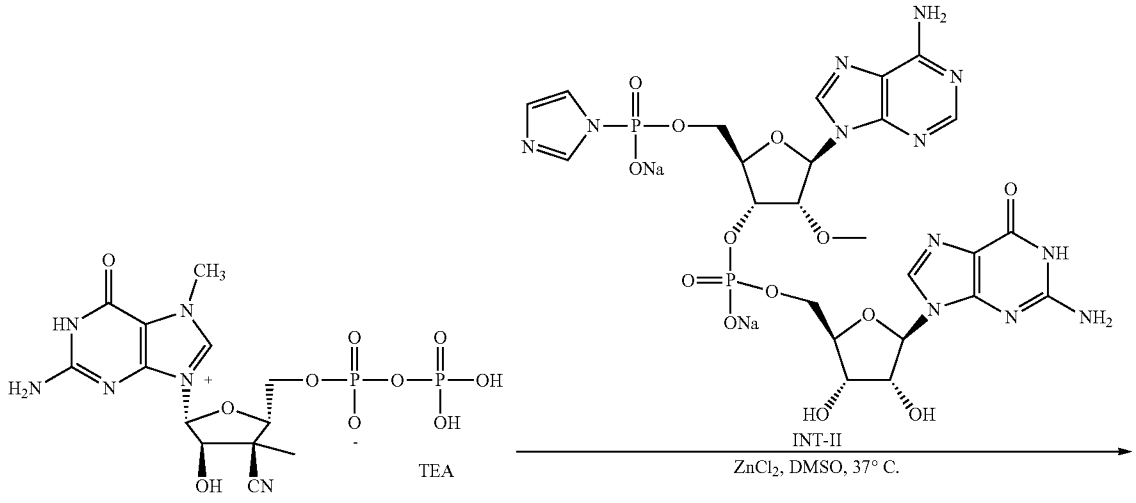
YK-CAP-105-PM8

-continued

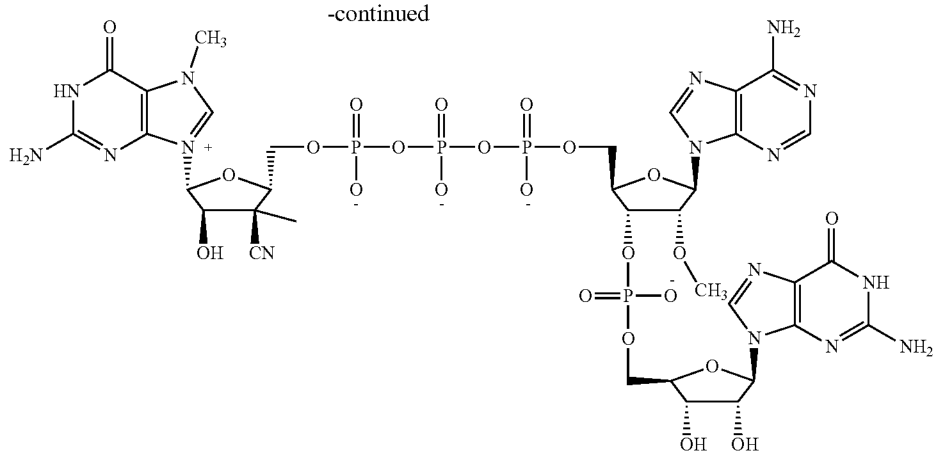

YK-CAP-105

Step 1: Synthesis of YK-CAP-105-PM1

YK-CAP-104-PM4 (5.76 g, 30.93 mmol) was dissolved in acetic acid (8 mL), then acetic anhydride (31.6 g, 310 mmol) and sulfuric acid (500 μL) were added thereto, and the mixture was stirred and reacted at room temperature for 4 hours. After the reaction was completed, the reaction mixture was added with $NaHCO_3$ aqueous solution to adjust the pH to weak acidity, and extracted twice with ethyl acetate. The organic phase was evaporated to dryness by rotary evaporation, and the residue was purified by silica gel chromatography (0 to 80% ethyl acetate/n-hexane) to obtain YK-CAP-105-PM1 (5.9 g, 21.67 mmol, 70.1%).

Step 2: Synthesis of YK-CAP-105-PM2

Intermediate INT-I (9.27 g, 23.87 mmol) and N,O-bis (trimethylsilyl) acetamide (9.72 g, 47.8 mmol) were dissolved in 1,2-dichloroethane (60 mL). The mixture was stirred at 80° C. for 2 hours, and evaporated to dryness by rotary evaporation to remove the solvent. YK-CAP-105-PM1 (5.9 g, 21.67 mmol) was dissolved in toluene (80 mL) and added to the above residue. Trimethylsilyl trifluoromethanesulfonate (5.31 g, 23.9 mmol) was then added thereto, and the mixture was reacted at 70° C. for 2 hours. TLC monitored that the reaction was complete. After filtration, the filtrate was evaporated to dryness by rotary evaporation under reduced pressure. The residue was purified by silica gel column chromatography (0 to 80% ethyl acetate/n-hexane) to obtain YK-CAP-105-PM2 (10.00 g, 16.65 mmol, 76.8%).

Step 3: Synthesis of YK-CAP-105-PM3

YK-CAP-105-PM2 (8.00 g, 13.32 mmol) and [N,N'-(1,1,2,2-tetramethylethane)bis(3,5-di-tert-butylsalicylideneimine)]cobalt (II)(403 mg, 0.67 mmol) were dissolved in 1,4-dioxane (30 mL), then benzenesulfonyl cyanide (72.30 g, 400 mmol) was added thereto, and the mixture was stirred and reacted at room temperature for 5 minutes. Phenylsilane (1.73 g, 16 mmol) was dissolved in anhydrous ethanol (60 mL) and added to the above mixture. The mixture was stirred at room temperature for 3 hours. After the reaction was completed, the reaction mixture was filtered, and extracted twice with water and ethyl acetate. The organic phase was evaporated to dryness by rotary evaporation, and the residue was purified by silica gel chromatography (0 to 70% ethyl acetate/n-hexane) to obtain YK-CAP-105-PM3 (4.50 g, 7.17 mmol, 53.8%).

Step 4: Synthesis of YK-CAP-105-PM4

YK-CAP-105-PM3 (4.50 g, 7.17 mmol) was dissolved in 7 M ammonia/methanol (50 mL), and the mixture was stirred and reacted at 50° C. for 4 hours. After the reaction was completed, the reaction mixture was evaporated to dryness by rotary evaporation to remove the solvent, and the residue was purified by preparative high-pressure liquid chromatography to obtain YK-CAP-105-PM4 (800 mg. 2.61 mmol, 36.4%). $C_{12}H_{14}N_6O_4$, MS (ES): m/z $(M+H^+)$ 307.11.

YK-CAP-105-PM4: $^1H$ NMR (400 MHZ, DMSO-$d_6$) δ 10.66 (s, 1H), 7.97 (s, 1H), 6.54 (d, J=5.2 Hz, 3H), 5.74 (d, J=7.2 Hz, 1H), 5.40 (t, J=4.4 Hz, 1H), 4.62-4.65 (m, 1H), 4.31 (t, J=3.2 Hz, 1H), 3.59-3.69 (m, 2H), 1.53 (s, 3H).

Step 5: Synthesis of YK-CAP-105-PM5

According to the synthesis route of YK-CAP-101-PM3, YK-CAP-105-PM4 (800 mg, 2.61 mmol) was used as starting material to obtain YK-CAP-105-PM5 (triethylamine salt, 994 mg, 2.04 mmol, 78.1%). $C_{12}H_{15}N_6O_7P$, MS (ES): m/z $(M-H^-)$ 385.1.

Step 6: Synthesis of YK-CAP-105-PM6

According to the synthesis route of YK-CAP-101-PM4, YK-CAP-105-PM5 (994 mg, 2.04 mmol) was used as starting material to obtain YK-CAP-105-PM6 (sodium salt, 661 mg, 1.44 mmol, 70.7%). $C_{15}H_{17}N_8O_6P$, MS (ES): m/z $(M-H^-)$ 435.1.

Step 7: Synthesis of YK-CAP-105-PM7

According to the synthesis route of YK-CAP-101-PM5, YK-CAP-105-PM6 (661 mg, 1.44 mmol) was used as starting material to obtain YK-CAP-105-PM7 (triethylamine salt, 612 mg, 1.08 mmol, 74.8%). $C_{12}H_{16}N_6O_{10}P_2$, MS (ES): m/z $(M-H^-)$ 465.0.

Step 8: Synthesis of YK-CAP-105-PM8

According to the synthesis route of YK-CAP-101-PM6, YK-CAP-105-PM7 (612 mg, 1.08 mmol) was used as starting material to obtain YK-CAP-105-PM8 (triethylamine salt, 325 mg, 0.56 mmol, 51.7%). $C_{13}H_{19}N_6O_{10}P_2$, MS (ES): m/z (M−H$^-$) 479.1.

Step 9: Synthesis of YK-CAP-105

According to the synthesis route of YK-CAP-101, YK-CAP-105-PM8 (325 mg, 0.56 mmol) was used as starting material to obtain YK-CAP-105 (16 mg, 13.12 μmol, 2.3%). $C_{34}H_{44}N_{16}O_{23}P_4$, MS (ES): m/z (M−H$^-$) 1267.1.

$^1$H NMR (400 MHz, $D_2O$) δ 8.49 (d, J=1.4 Hz, 1H), 8.44 (d, J=2.5 Hz, 1H), 7.88 (d, J=4.2 Hz, 2H), 6.22 (d, J=4.7 Hz, 1H), 5.93 (d, J=2.4 Hz, 1H), 5.80 (d, J=4.5 Hz, 1H), 4.81-4.66 (m, 3H), 4.62-4.32 (m, 5H), 4.22 (d, J=3.1 Hz, 1H), 4.18 (s, 2H), 4.10 (s, 2H), 3.77 (s, 3H), 3.31 (t, J=6.8 Hz, 1H), 3.11 (s, 3H), 1.53 (s, 3H). $^{31}$P NMR ($D_2O$, 162 MHz) δ −0.90 (s, 1P), −11.33 (d, J=20.2 Hz, 1P), −12.12 (d, J=17.1 Hz, 1P), −22.34 (t, J=16.2 Hz, 1P).

8. Synthesis of YK-CAP-106

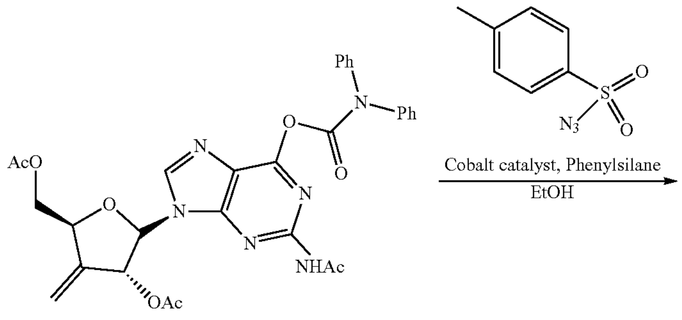

YK-CAP-105-PM2

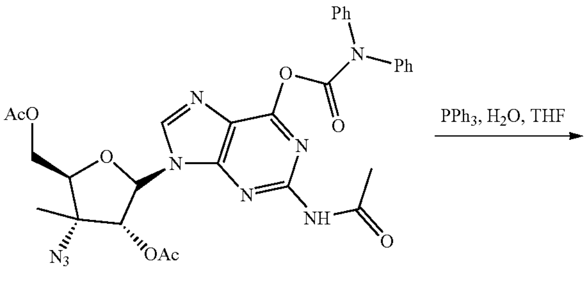

YK-CAP-106-PM1

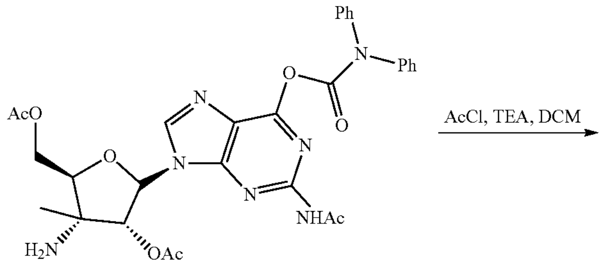

YK-CAP-106-PM2

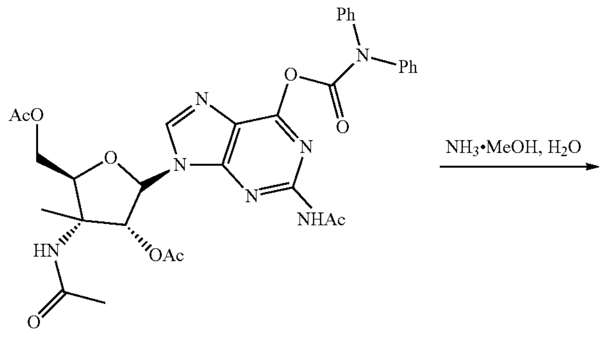

YK-CAP-106-PM3

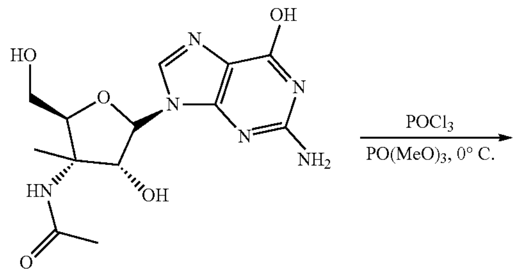

YK-CAP-106-PM4

-continued
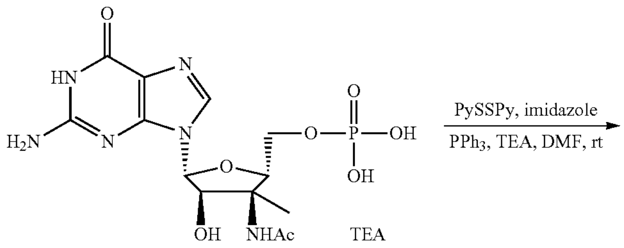
YK-CAP-106-PM5
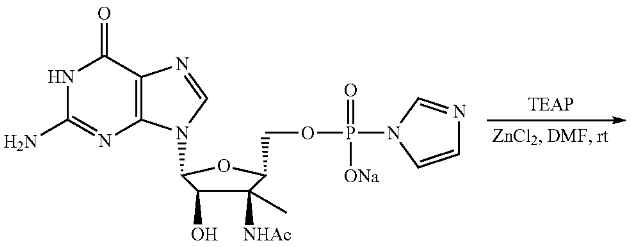
YK-CAP-106-PM6
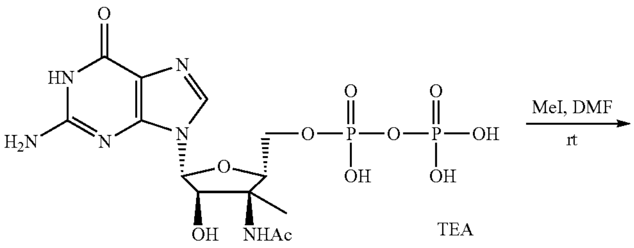
YK-CAP-106-PM7
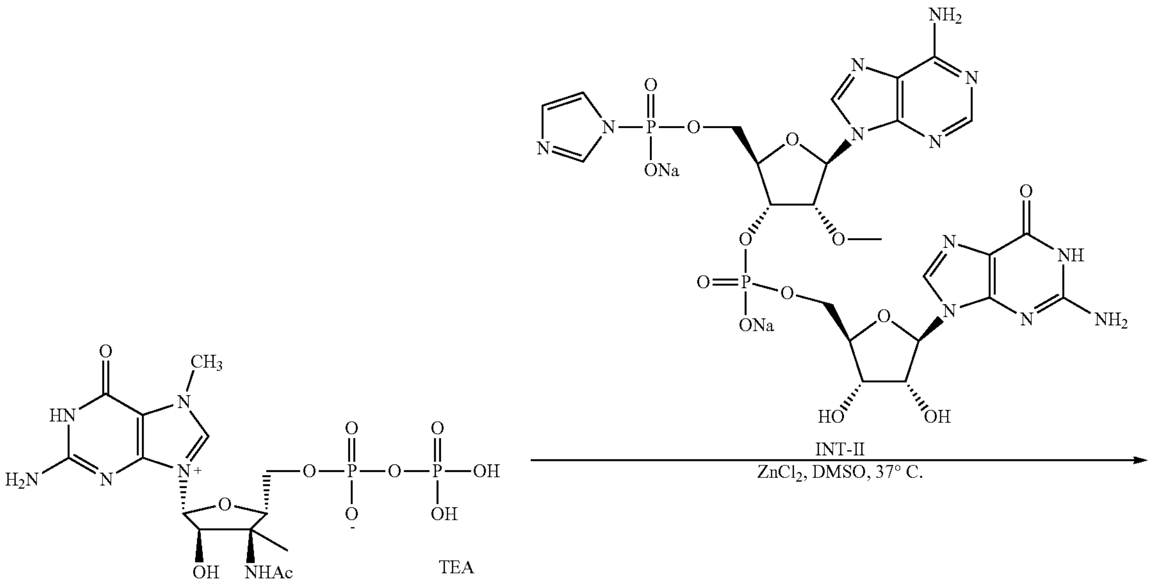
YK-CAP-106-PM8

-continued

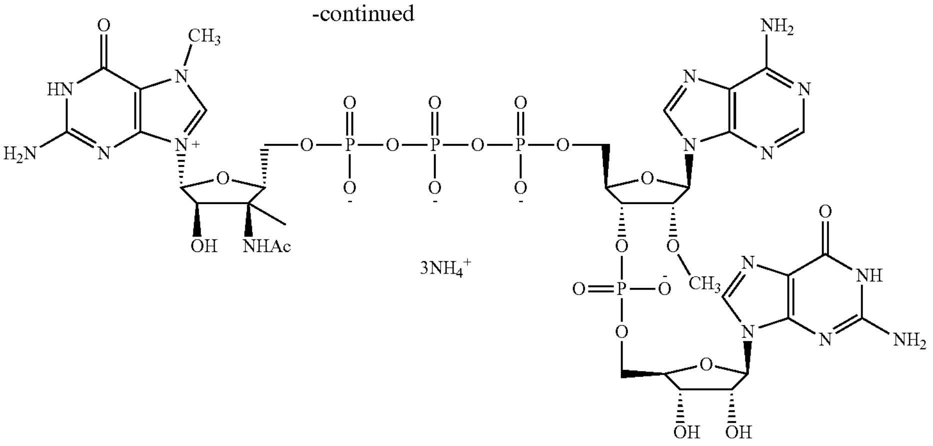

YK-CAP-106

Step 1: Synthesis of YK-CAP-106-PM1

To YK-CAP-105-PM2 (23.00 g, 38.30 mmol) were added p-toluenesulfonyl azide (211.46 g, 1.07 mol) and cobalt catalyst ([N,N'-(1,1,2,2-tetramethylethane)bis(3,5-di-tert-butylsalicylideneimine)]cobalt (II))(696 mg, 1.15 mmol), and the mixture was stirred for 30 minutes under nitrogen atmosphere. A solution of phenylsilane (10.22 g, 45.96 mmol) in anhydrous ethanol (40 mL) was added dropwise thereto at room temperature for 30 minutes. The mixture was stirred and reacted at room temperature for 2 hours. LC-MS monitored that the reaction was complete. The reaction was terminated. The reaction mixture was extracted with EA and saturated NaCl aqueous solution. The phases were separated, and the aqueous phase was back-extracted twice with EA. The organic phases were combined, and evaporated by rotary evaporation to remove the solvent. The crude product was purified by flash column chromatography (EA/PE=0 to 100%) to obtain YK-CAP-106-PM1 (4.90 g, 7.61 mmol, 19.9%). $C_{30}H_{29}N_9O_8$, MS (ES): m/z (M+H$^+$) 644.3.

Step 2: Synthesis of YK-CAP-106-PM2

To YK-CAP-106-PM1 (4.90 g, 7.61 mmol) were added triphenylphosphine (2.78 g, 10.59 mmol), water (4.9 mL), and tetrahydrofuran (49 mL). The mixture was heated to 50° C., and stirred and reacted for 8 hours. LC-MS monitored that the reaction was complete. The reaction was terminated, and the reaction mixture was evaporated by rotary evaporation under reduced pressure to remove the solvent. The crude product was purified by flash column chromatography (MeOH/DCM=0 to 10%) to obtain YK-CAP-106-PM2 (4.22 g, 6.83 mmol, 89.8%). $C_{30}H_{31}N_7O_8$, MS (ES): m/z (M+H$^+$) 618.2.

Step 3: Synthesis of YK-CAP-106-PM3

To YK-CAP-106-PM2 (4.10 g, 6.64 mmol) were added triethylamine (5.04 g, 49.84 mmol) and dichloromethane (82 mL). The mixture was cooled to 0° C., and acetyl chloride (1.68 g, 21.36 mmol) was added dropwise thereto. After the dropwise addition was completed, the mixture was warmed to room temperature and reacted for 24 hours. LC-MS monitored that the reaction was complete. The reaction was terminated. The reaction mixture was poured into ice water and stirred. The phases were separated, and the aqueous phase was back-extracted twice with dichloromethane. The organic phases were combined, and evaporated by rotary evaporation under reduced pressure to remove the solvent. The crude product was purified by flash column chromatography (MeOH/DCM=0 to 10%) to obtain YK-CAP-106-PM3 (2.94 g, 4.46 mmol, 67.1%). $C_{32}H_{33}N_7O_9$, MS (ES): m/z (M+H$^+$) 660.3.

Step 4: Synthesis of YK-CAP-106-PM4

To YK-CAP-106-PM3 (2.94 g, 4.46 mmol) were added 7 M ammonia/methanol solution (29 mL) and water (5.9 mL), and the mixture was stirred and reacted at room temperature for 24 hours. LC-MS monitored that the reaction was complete. The reaction was terminated, and the reaction mixture was evaporated by rotary evaporation under reduced pressure to remove the solvent. The crude product was added with EA, stirred, and subjected to suction filtration to obtain YK-CAP-106-PM4 (1.36 g, 4.02 mmol, 90.1%). $C_{13}H_{18}N_6O_5$, MS (ES): m/z (M+H$^+$) 339.3.

YK-CAP-106-PM4: $^1$H NMR (400 MHZ, MeOD) δ 7.99 (s, 1H), 5.84 (d, 1H), 4.77 (s, 1H), 4.66 (d, 1H), 3.93-3.82 (m, 2H), 2.06 (s, 3H), 1.63 (s, 3H).

Step 5: Synthesis of YK-CAP-106-PM5

According to the synthesis route of YK-CAP-101-PM3, YK-CAP-106-PM4 (500 mg, 1.48 mmol) was used as starting material to obtain YK-CAP-106-PM5 (triethylamine salt, 480 mg, 0.92 mmol, 62.4%). $C_{13}H_{19}N_6O_8P$, MS (ES): m/z (M−H$^-$) 417.2.

Step 6: Synthesis of YK-CAP-106-PM6

According to the synthesis route of YK-CAP-101-PM4, YK-CAP-106-PM5 (480 mg, 0.92 mmol) was used as starting material to obtain YK-CAP-106-PM6 (sodium salt, 410 mg, 0.84 mmol, 90.9%). $C_{16}H_{21}N_8O_7P$, MS (ES): m/z (M−H$^-$) 467.1.

Step 7: Synthesis of YK-CAP-106-PM7

According to the synthesis route of YK-CAP-101-PM5, YK-CAP-106-PM6 (410 mg, 0.84 mmol) was used as starting material to obtain YK-CAP-106-PM7 (triethylamine salt, 331 mg, 0.55 mmol, 65.7%). $C_{13}H_{20}N_6O_{11}P_2$, MS (ES): m/z (M−H$^-$) 497.0.

Step 8: Synthesis of YK-CAP-106-PM8

According to the synthesis route of YK-CAP-101-PM6, YK-CAP-106-PM7 (331 mg, 0.55 mmol) was used as starting material to obtain YK-CAP-106-PM8 (triethylamine salt, 150 mg, 0.24 mmol, 44.5%). $C_{14}H_{22}N_6O_{11}P_2$, MS (ES): m/z (M−H$^-$) 511.1.

Step 9: Synthesis of YK-CAP-106

According to the synthesis route of YK-CAP-101, YK-CAP-106-PM8 (150 mg, 0.24 mmol) was used as starting material to obtain YK-CAP-106 (32 mg, 25.56 μmol, 10.6%). $C_{35}H_{48}N_{16}O_{24}P_4$, MS (ES): m/z (M−H$^-$) 1199.1.

$^1$H NMR (400 MHZ, $D_2O$) δ 8.50 (d, J=1.4 Hz, 1H), 8.44 (d, J=2.2 Hz, 1H), 7.78 (d, J=4.2 Hz, 2H), 6.24 (d, J=4.6 Hz, 1H), 5.94 (d, J=2.3 Hz, 1H), 5.81 (d, J=4.4 Hz, 1H), 4.86-4.76 (m, 3H), 4.61-4.55 (m, 4H), 4.52 (d, J=3.6 Hz, 2H), 4.28 (s, 2H), 4.20 (s, 1H), 3.93-3.82 (m, 5H), 3.23 (t, J=6.7 Hz, 1H), 3.12 (s, 2H), 2.03 (s, 3H), 1.62 (s, 3H). $^{31}$P NMR ($D_2O$, 162 MHz) δ−0.92 (s, 1P), −11.33 (d, J=20.1 Hz, 1P), −12.13 (d, J=16.8 Hz, 1P), −22.11 (t, J=16.4 Hz, 1P).

9. Synthesis of YK-CAP-107

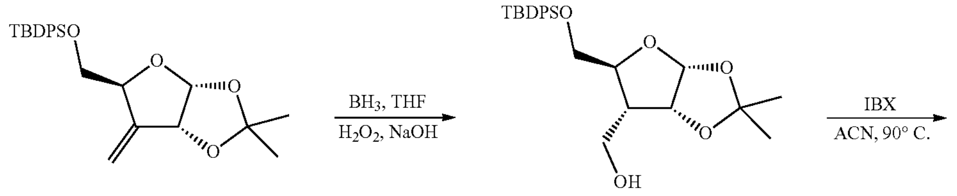

YK-CAP-104-PM3

YK-CAP-107-PM1

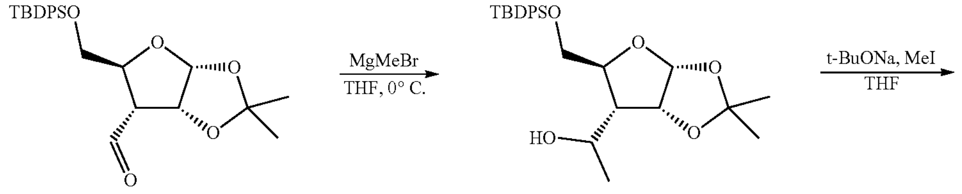

YK-CAP-107-PM2

YK-CAP-107-PM3

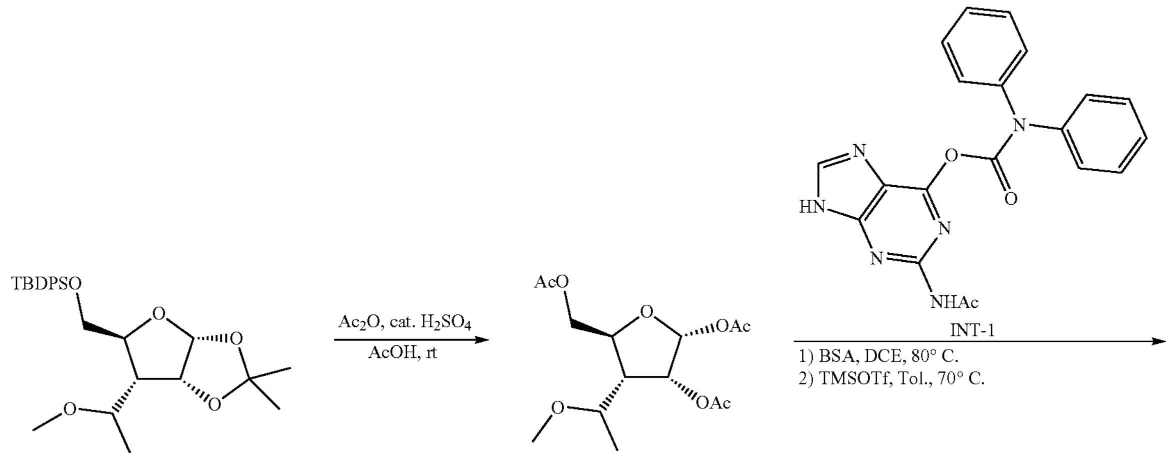

YK-CAP-107-PM4

YK-CAP-107-PM5

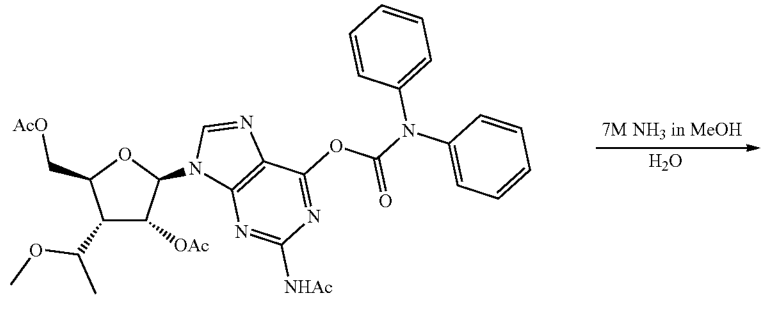

YK-CAP-107-PM6

-continued
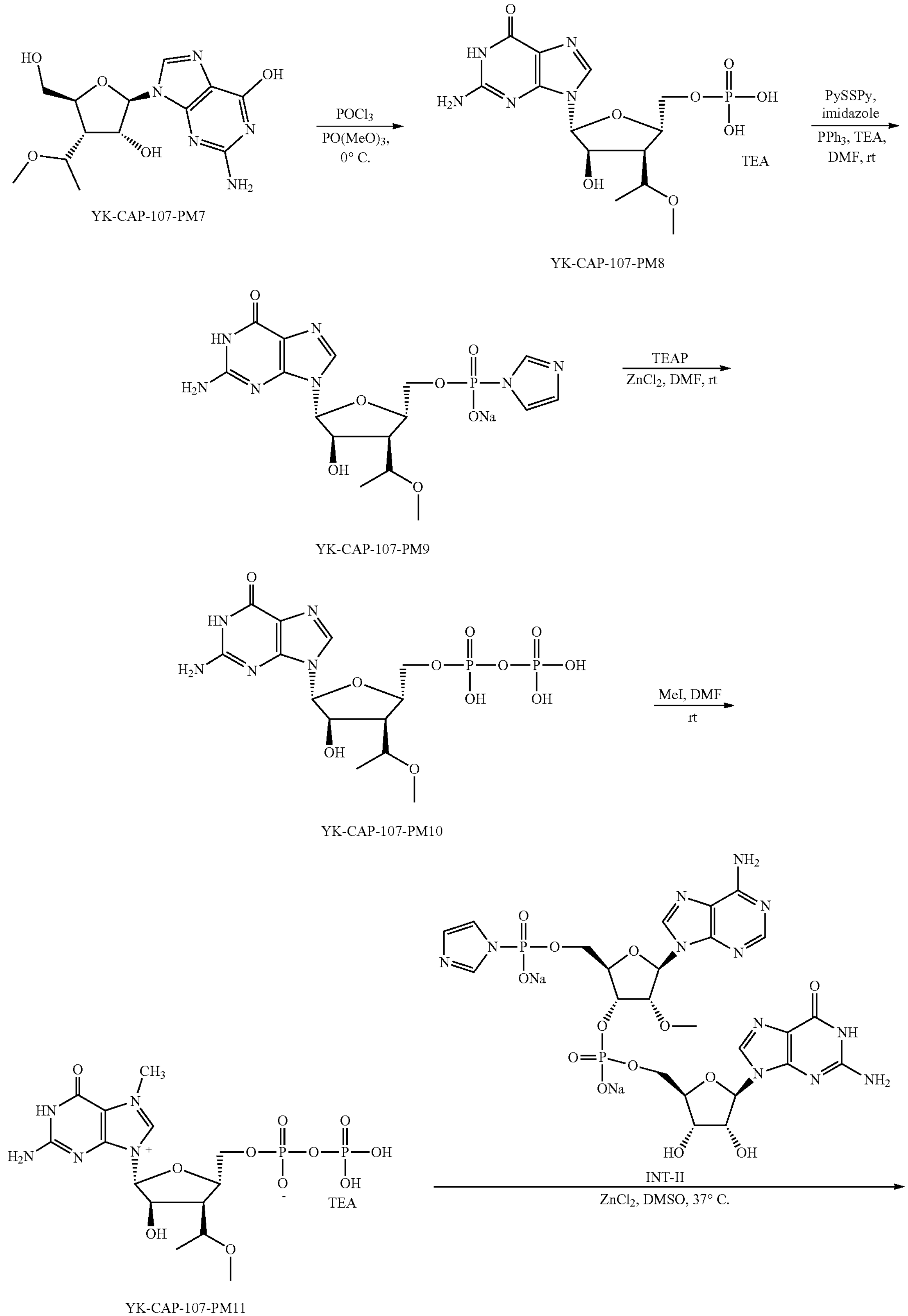
YK-CAP-107-PM7
YK-CAP-107-PM8
YK-CAP-107-PM9
YK-CAP-107-PM10
INT-II
YK-CAP-107-PM11

-continued

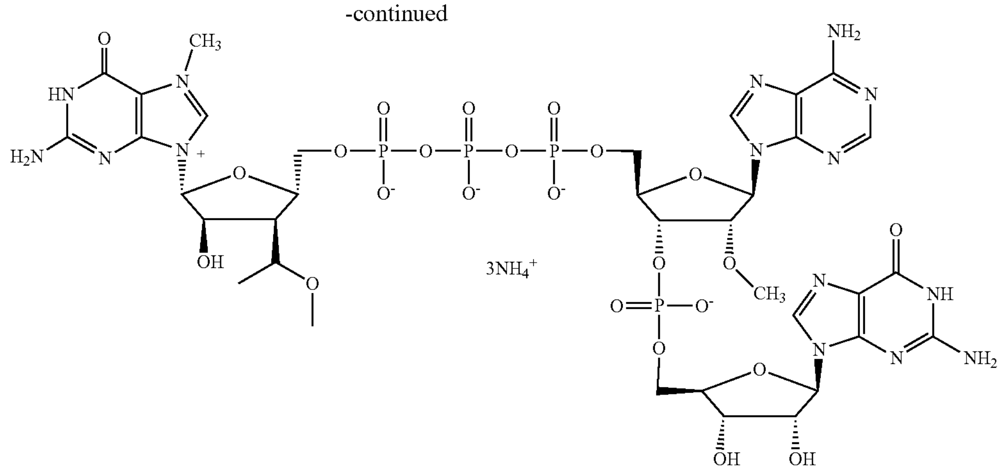

YK-CAP-107

Step 1: Synthesis of YK-CAP-107-PM1

To a three-necked flask was added 1 M solution of borane in tetrahydrofuran (325 mL, 0.325 mol), and a solution of YK-CAP-104-PM3 (60.00 g, 0.14 mol) in tetrahydrofuran (180 mL) was slowly added dropwise thereto at 0° C. After the dropwise addition was completed, the mixture was stirred and reacted at room temperature for 2 hours. THF/$H_2O$ (1:1, 120 mL), 2N NaOH (261 mL), and 30% hydrogen peroxide (271 mL) were then sequentially and slowly added dropwise thereto at 0° C. After the dropwise addition was completed, the mixture was stirred and reacted at room temperature overnight. TLC monitored that the starting material was completely reacted. The reaction was terminated. The reaction mixture was extracted with water. The organic phase was sequentially washed with saturated sodium thiosulfate aqueous solution and saturated brine, dried over anhydrous sodium sulfate, filtered, and evaporated by rotary evaporation to remove the solvent. The crude product was purified by flash column chromatography (PE:EA=0 to 25%) to obtain compound YK-CAP-107-PM1 (48.80 g, 0.11 mol, 78.8%) as a colorless oil.

Step 2: Synthesis of YK-CAP-107-PM2

YK-CAP-107-PM1 (34.20 g, 77.27 mmol) was dissolved in acetonitrile, and 2-iodoxybenzoic acid (28.10 g, 100.5 mmol) was added to the above system. The mixture was heated to 90° C., and stirred and reacted for 5 hours. The reaction mixture was cooled to room temperature, filtered, and the filtrate was evaporated to dryness by rotary evaporation to obtain crude product YK-CAP-107-PM2 (34.50 g) as a light yellow oily liquid, which was directly used in the next step without purification.

Step 3: Synthesis of YK-CAP-107-PM3

YK-CAP-107-PM2 (32.90 g, calculated as 74.67 mmol) was dissolved in tetrahydrofuran. The mixture was cooled to 0° C. under nitrogen atmosphere, and a 1 M solution of methylmagnesium bromide in tetrahydrofuran (97.1 mL, 97.1 mmol) was slowly added dropwise thereto. After the dropwise addition was completed, the mixture was stirred at room temperature for 3 hours. The reaction mixture was cooled to 0° C., quenched with saturated ammonium chloride, and extracted with ethyl acetate. The organic phase was dried, and evaporated to dryness by rotary evaporation. The crude product was purified by flash column chromatography (PE:EA=0 to 41%) to obtain YK-CAP-107-PM3 (16.80 g, 36.79 mmol, 49.3%) as a light yellow oily liquid.

Step 4: Synthesis of YK-CAP-107-PM4

YK-CAP-107-PM3 (16.80 g, 36.79 mmol) was dissolved in THE, and the mixture was cooled to 0° C. under nitrogen atmosphere. A solution of sodium tert-butoxide (11.20 g, 116.7 mmol) in THF was slowly added to the above system. The mixture was stirred and reacted at room temperature for 1.5 hours, and iodomethane (27.60 g, 194.5 mmol) was slowly added dropwise to the above system. After the dropwise addition was completed, the mixture was stirred and reacted for another 3 hours. TLC detected that the reaction was complete. The reaction mixture was quenched with saturated ammonium chloride solution and extracted with ethyl acetate. The organic phase was washed 3 to 5 times with saturated brine, dried, and evaporated to dryness by rotary evaporation. The crude product was purified by flash column chromatography (PE:EA=0 to 12%) to obtain YK-CAP-107-PM4 (13.16 g, 27.96 mmol, 76.0%) as a light yellow oily liquid.

Step 5: Synthesis of YK-CAP-107-PM5

YK-CAP-107-PM4 (13.16 g, 27.96 mmol) was dissolved in glacial acetic acid (130 mL). Acetic anhydride (17.13 g, 167.8 mmol) and concentrated sulfuric acid (0.52 mL) were sequentially added to the above system. The mixture was stirred and reacted at room temperature for 4 hours. The reaction system was diluted with ethyl acetate, washed once with water, and then washed three times with saturated sodium bicarbonate solution. The organic phase was dried, and evaporated to dryness by rotary evaporation to obtain YK-CAP-107-PM5 (11.38 g) as a yellow oily liquid, which was directly used in the next reaction step.

Step 6: Synthesis of YK-CAP-107-PM6

2-Acetamido-9H-purin-6-yldiphenylcarbamate (6.30 g, 16.22 mmol) was dissolved in 1,2-dichloroethane (100 mL), and N,O-bis(trimethylsilyl) acetamide (6.60 g, 32.4 mmol)

was added thereto. The mixture was heated to 80° C., stirred and reacted for 1.5 hours, and subjected to rotary evaporation to remove the reaction solvent. A solution of YK-CAP-107-PM5 (6.00 g, calculated as 18.85 mmol) in toluene (100 mL) and TMSOTf (3.6 g, 16.2 mmol) were then sequentially added thereto at room temperature. The mixture was then heated to 70° C., and stirred and reacted for another 3.5 hours. The reaction system was diluted with ethyl acetate, washed once with saturated sodium bicarbonate solution, filtered to remove the insoluble substance, and the phases of the filtrate were separated. The organic phase was dried, and evaporated to dryness by rotary evaporation. The crude product was purified by flash column chromatography (DCM:EA=0 to 52%) to obtain YK-CAP-107-PM6 (3.20 g, 4.95 mmol, 26.3%) as a yellow solid. $C_{32}H_{34}N_6O_9$, MS (ES): m/z (M+H$^+$) 647.2.

Step 7: Synthesis of YK-CAP-107-PM7

YK-CAP-107-PM6 (3.20 g, 4.95 mmol) was dissolved in 7 M ammonia/methanol solution and water (5:1, 24 mL). The mixture was heated to 50° C., and stirred and reacted for 6 hours. The reaction mixture was evaporated to dryness by rotary evaporation, slurried twice with EA, and subjected to suction filtration to collect the filter cake to obtain YK-CAP-107-PM7 (1.38 g, 4.24 mmol, 85.7%) as a white solid. $C_{13}H_{19}N_5O_5$, MS (ES): m/z (M+H$^+$) 326.2.

YK-CAP-107-PM7: $^1$H NMR (400 MHZ, MeOD) δ 8.07 (s, 1H), 5.82 (d, J=2.6 Hz, 1H), 4.53 (dd, J=6.1, 2.7 Hz, 1H), 4.36 (ddd, J=8.3, 3.9, 2.6 Hz, 1H), 3.95 (dd, J=12.1, 2.4 Hz, 1H), 3.78-3.67 (m, 2H), 3.34 (s, 3H), 2.11 (q, J=7.4 Hz, 1H), 1.23 (d, J=6.1 Hz, 3H).

Step 8: Synthesis of YK-CAP-107-PM8

According to the synthesis route of YK-CAP-101-PM3, YK-CAP-107-PM7 (1.20 g, 3.69 mmol) was used as starting material to obtain YK-CAP-107-PM8 (triethylamine salt, 644 mg, 1.27 mmol, 34.4%). $C_{13}H_{20}N_5O_8P$, MS (ES): m/z (M−H$^-$) 404.1.

Step 9: Synthesis of YK-CAP-107-PM9

According to the synthesis route of YK-CAP-101-PM4, YK-CAP-107-PM8 (644 mg, 1.27 mmol) was used as starting material to obtain YK-CAP-107-PM9 (sodium salt, 549 mg, 1.15 mmol, 90.6%). $C_{16}H_{22}N_7O_7P$, MS (ES): m/z (M−H$^-$) 454.2.

Step 10: Synthesis of YK-CAP-107-PM10

According to the synthesis route of YK-CAP-101-PM5, YK-CAP-107-PM9 (549 mg, 1.15 mmol) was used as starting material to obtain YK-CAP-107-PM10 (triethylamine salt, 531 mg, 0.91 mmol, 78.7%). $C_{13}H_{21}N_5O_{11}P_2$, MS (ES): m/z (M−H$^-$) 484.0.

Step 11: Synthesis of YK-CAP-107-PM11

According to the synthesis route of YK-CAP-101-PM6, YK-CAP-107-PM10 (531 mg, 0.91 mmol) was used as starting material to obtain YK-CAP-107-PM11 (triethylamine salt, 163 mg, 0.27 mmol, 29.8%). $C_{14}H_{23}N_5O_{11}P_2$, MS (ES): m/z (M−H$^-$) 498.1.

Step 12: Synthesis of YK-CAP-107

According to the synthesis route of YK-CAP-101, YK-CAP-107-PM11 (163 mg, 0.27 mmol) was used as starting material to obtain YK-CAP-107 (35 mg, 28.25 μmol, 10.5%). $C_{35}H_{49}N_{15}O_{24}P_4$, MS (ES): m/z (M−H$^-$) 1186.1.

$^1$H NMR (400 MHZ, $D_2O$) δ 8.43 (d, J=1.2 Hz, 1H), 8.34 (d, J=2.1 Hz, 1H), 7.73 (d, J=4.1 Hz, 2H), 6.21 (d, J=4.5 Hz, 1H), 5.74 (d, J=2.3 Hz, 1H), 5.71 (d, J=4.4 Hz, 1H), 4.76-4.61 (m, 3H), 4.51-4.45 (m, 4H), 4.42 (d, J=3.5 Hz, 2H), 4.31 (s, 2H), 4.10 (s, 2H), 3.95-3.92 (m, 1H), 3.90-3.84 (m, 2H), 3.78-3.67 (m, 2H), 3.13 (t, J=6.7 Hz, 1H), 3.34 (s, 3H), 3.10 (s, 2H), 2.07 (q, J=7.4 Hz, 1H), 1.22 (d, J=6.2 Hz, 3H). $^{31}$P NMR ($D_2O$, 161 MHz) δ−0.88 (s, 1P), −11.23 (d, J=20.2 Hz, 1P), −12.22 (d, J=16.6 Hz, 1P), −22.32 (t, J=16.1 Hz, 1P).

10. Synthesis of YK-CAP-108

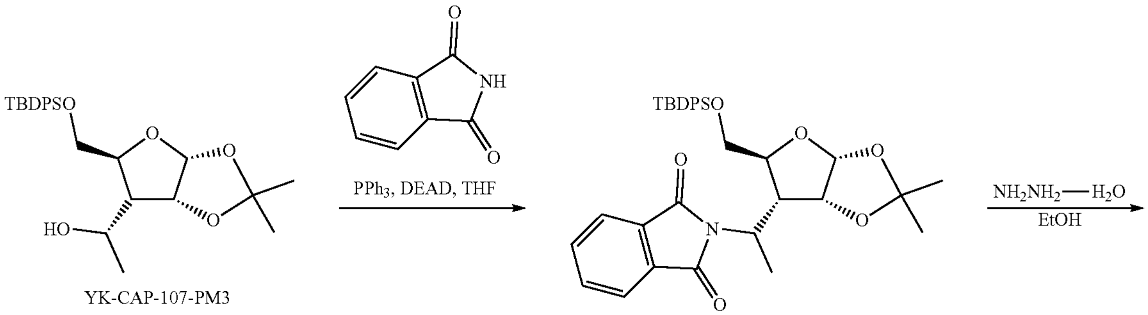

YK-CAP-107-PM3

YK-CAP-108-PM1

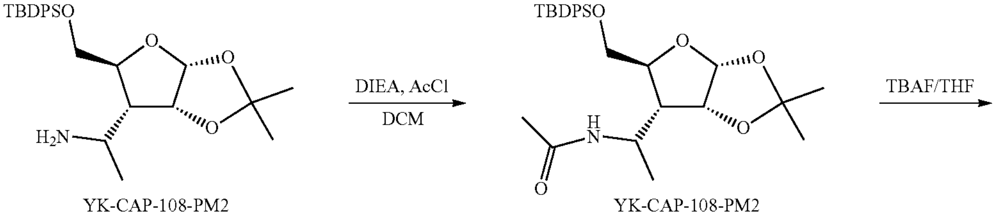

YK-CAP-108-PM2

YK-CAP-108-PM2

-continued
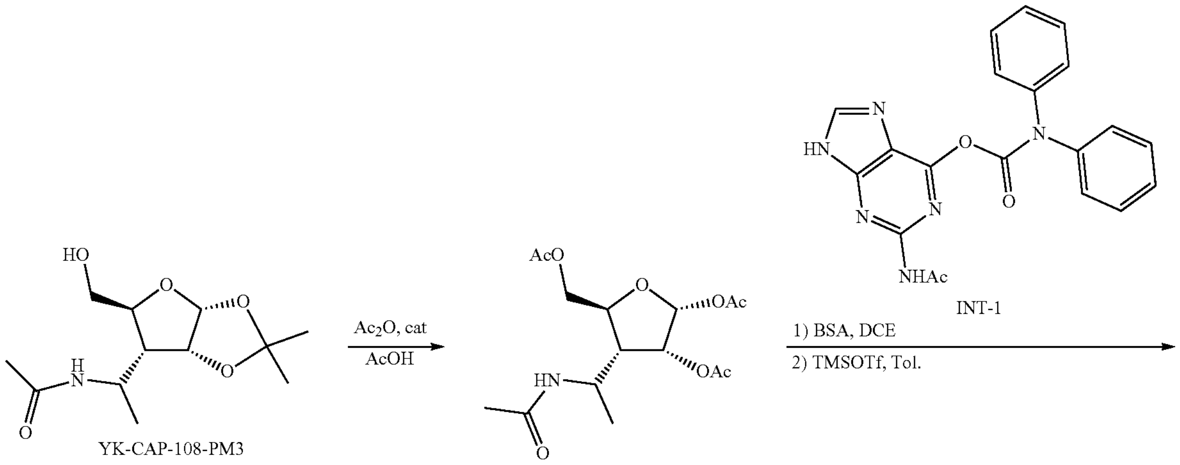
YK-CAP-108-PM3
INT-1
YK-CAP-108-PM4
Chemical Formula: $C_{33}H_{35}N_7O_9$
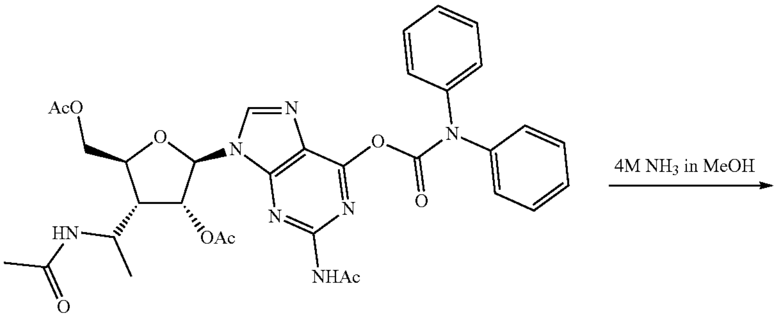
YK-CAP-108-PM5
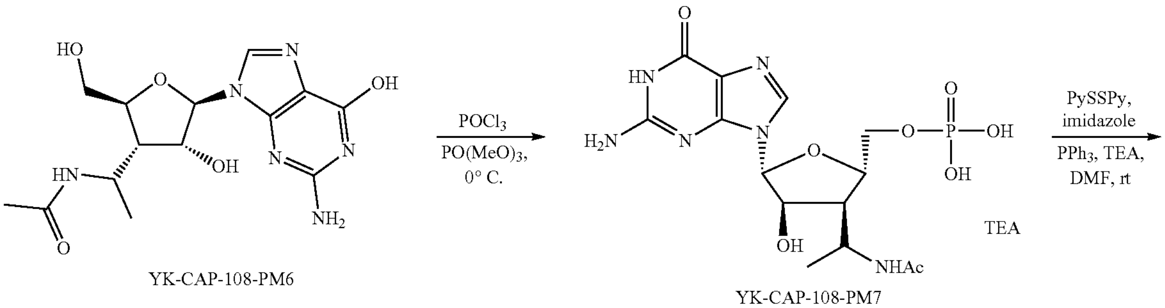
YK-CAP-108-PM6
YK-CAP-108-PM7
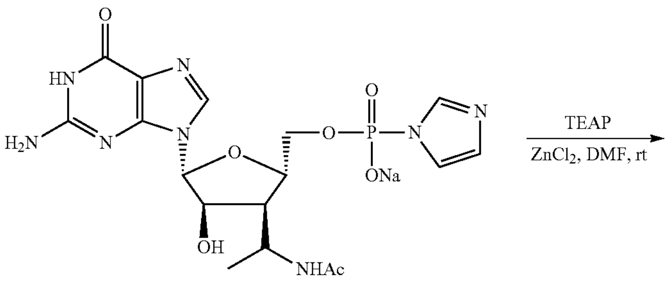
YK-CAP-108-PM8

-continued

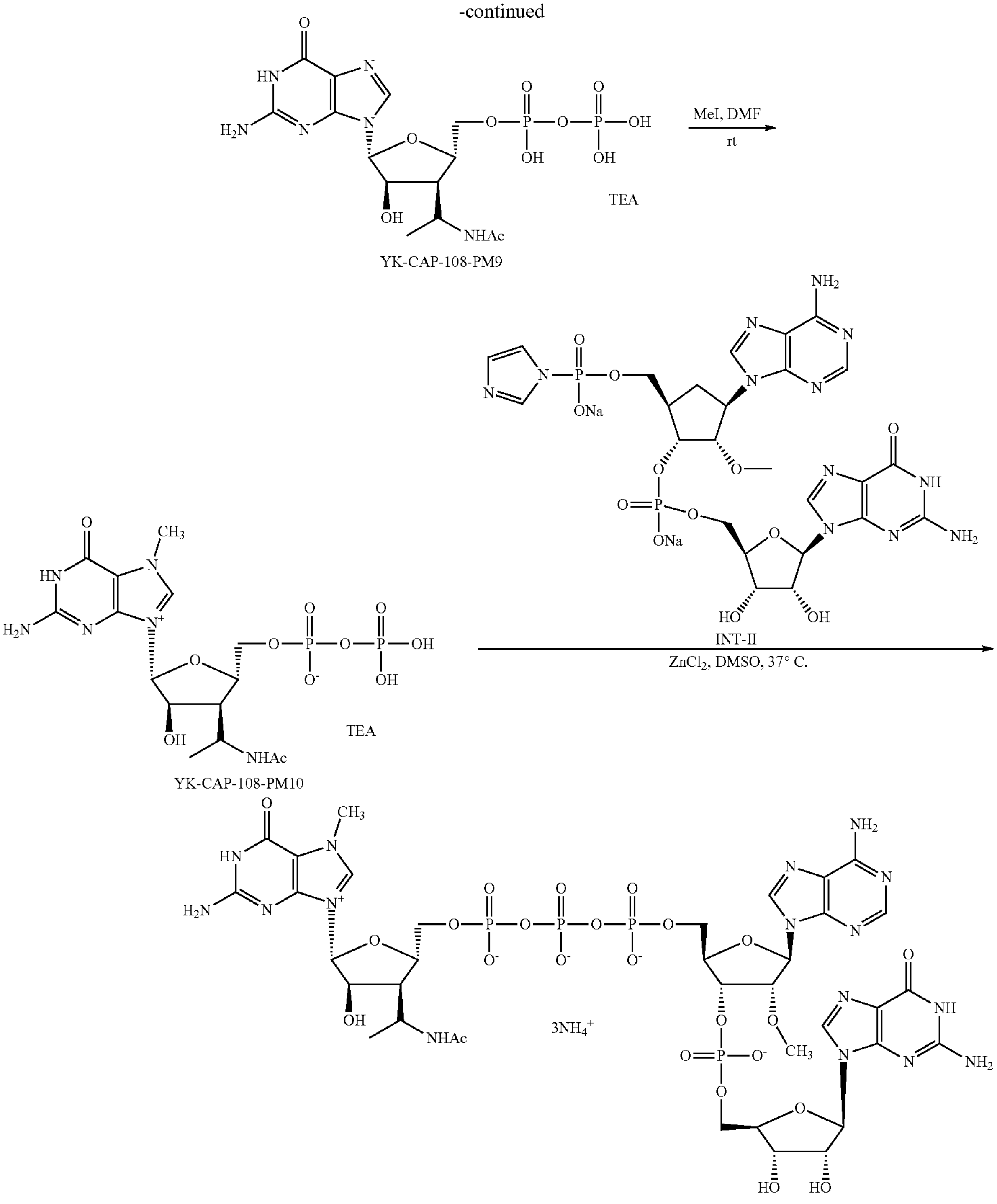

YK-CAP-108-PM9

INT-II

YK-CAP-108-PM10

YK-CAP-108

Step 1: Synthesis of YK-CAP-108-PM1

YK-CAP-107-PM3 (17.5 g, 38.32 mmol) was dissolved in 300 mL of THE, and triphenylphosphine (12.1 g, 46.00 mmol) and phthalimide (6.76 g, 46.00 mmol) were added thereto. The system was cooled to 0° C. under nitrogen atmosphere, and a solution of DEAD (9.3 g, 53.40 mmol) in THF (30 mL) was added dropwise thereto. After the dropwise addition was completed, the mixture was reacted for 3 hours. TLC monitored that the reaction was complete (DCM). After the reaction was completed, the system was added dropwise with 30 mL of purified water at 0° C. to quench the reaction. The reaction mixture was extracted with EA (200 mL×3). The organic phase was sequentially washed with saturated brine (400 mL), dried over anhydrous sodium sulfate, and evaporated to dryness by rotary evaporation. The residue was purified by normal-phase silica gel column chromatography (PE:EA=0 to 40%) to obtain YK-CAP-108-PM1 (18.8 g, 32.09 mmol, 83.8%) as a yellow oil.

Step 2: Synthesis of YK-CAP-108-PM2

YK-CAP-108-PM1 (18.8 g, 32.09 mmol) was dissolved in 200 mL of ethanol, then 85% hydrazine hydrate (37.8 g, 0.64 mol) was added thereto, and the system was heated to 80° C. and reacted for 1 hour. TLC monitored that the reaction was complete (PE/EA=3/1). The reaction was terminated. The system was cooled to room temperature, added with purified water (200 mL) and EA (200 mL), stirred for 10 minutes, and the phases were separated. The aqueous phase was extracted with EA (200 mL×2). The organic phase was sequentially washed with saturated brine (300 mL), dried over anhydrous sodium sulfate, and evaporated to dryness by rotary evaporation to obtain YK-CAP-108-PM2 (14.2 g, 31.16 mmol, 97.1%) as a light yellow oil.

Step 3: Synthesis of YK-CAP-108-PM3

YK-CAP-108-PM2 (14.2 g, 31.16 mmol) was dissolved in 150 mL of DCM, and DIEA (12.1 g, 93.49 mmol) was added thereto. The system was cooled to 0° C. under nitrogen atmosphere, and a solution of acetyl chloride (2.9 g, 37.40 mmol) in DCM (20 mL) was added dropwise thereto. After the dropwise addition was completed, the mixture was reacted at a controlled temperature of 0° C. for 1 hour. TLC monitored that the reaction was complete (PE/EA=3/1). The reaction was terminated. The system was warmed to room temperature, added with 200 mL of saturated sodium bicarbonate solution to quench the reaction, and the phases were separated. The aqueous phase was extracted with DCM (200 mL×2). The organic phase was sequentially washed with saturated brine (300 mL), dried over anhydrous sodium sulfate, and evaporated to dryness by rotary evaporation. The residue was purified by normal-phase silica gel column chromatography (DCM:MeOH=0 to 40%) to obtain YK-CAP-108-PM3 (12.5 g, 25.12 mmol, 80.6%) as a yellow oil.

Step 4: Synthesis of YK-CAP-108-PM4

YK-CAP-108-PM3 (12.5 g, 25.12 mmol) was dissolved in 60 mL of THF. The system was cooled to 0° C. under nitrogen atmosphere, and 1 M TBAF (37.7 mL) was added dropwise thereto. After the dropwise addition was completed, the mixture was warmed to room temperature and reacted for 2 hours. TLC monitored that the reaction was complete (PE/EA=3/1). The reaction was terminated. The reaction mixture was directly evaporated to dryness by rotary evaporation, and the residue was purified by normal-phase silica gel column chromatography (DCM:MeOH=0 to 40%) to obtain YK-CAP-108-PM4 (5.8 g, 22.37 mmol, 89.0%) as a yellow oil.

Step 5: Synthesis of YK-CAP-108-PM5

YK-CAP-108-PM4 (4.5 g, 17.35 mmol) was dissolved in 15 mL of acetic acid, then acetic anhydride (35.4 g, 34.71 mmol) and p-toluenesulfonic acid (1.5 g, 8.67 mmol) were added thereto, and the system was heated to 50° C. The reaction was monitored by TLC. After the reaction was completed, the system was cooled to room temperature, added with 100 mL of purified water and 100 mL of EA, stirred for 10 minutes, and the phases were separated. The aqueous phase was extracted with EA (100 mL×2). The organic phase was sequentially washed with saturated brine (500 mL), dried over anhydrous sodium sulfate, and evaporated to dryness by rotary evaporation. The residue was purified by normal-phase silica gel column chromatography (DCM:MeOH=0 to 40%) to obtain YK-CAP-108-PM5 (5.5 g, 15.94 mmol, 91.8%) as a yellow oil.

Step 6: Synthesis of YK-CAP-108-PM6

Intermediate INT-I (6.8 g, 17.53 mmol) was dissolved in 1,2-dichloroethane (50 mL), and N,O-bis(trimethylsilyl) acetamide (7.1 g, 35.06 mmol) was added thereto. The reaction system was heated to 80° C., stirred and reacted for 2 hours, and evaporated to dryness by rotary evaporation under reduced pressure. The residue was dissolved in toluene (30 mL), then a solution of YK-CAP-108-PM5 (5.5 g, 15.94 mmol) in toluene (20 mL) was added thereto, and trimethylsilyl trifluoromethanesulfonate (3.9 g, 17.53 mmol) was slowly added dropwise thereto. The reaction system was heated to 70° C., and stirred and reacted for 2 hours. TLC monitored that the reaction was complete. The reaction system was quenched with saturated sodium bicarbonate aqueous solution and extracted with ethyl acetate (100 mL×3). The organic phases were combined, washed with saturated NaCl aqueous solution (300 mL), dried over anhydrous sodium sulfate, filtered, and evaporated to dryness by rotary evaporation under reduced pressure. The residue was purified by silica gel chromatography (DCM: MeOH=0 to 100%) to obtain YK-CAP-108-PM6 (3.8 g, 5.64 mmol, 35.4%). $C_{33}H_{35}N_7O_9$, MS (ES): m/z (M+H$^+$) 674.3.

Step 7: Synthesis of YK-CAP-108-PM7

YK-CAP-108-PM6 (3.8 g, 5.64 mmol) was dissolved in a mixed solvent of 4 M $NH_3$/MeOH (40 mL) and water (4 mL), and the mixture was stirred and reacted at room temperature overnight. LCMS monitored that the reaction was complete. The reaction mixture was evaporated to dryness by rotary evaporation, and slurried with EA (100 mL×2) at room temperature to obtain YK-CAP-108-PM7 (1.92 g, 5.45 mmol, 96.6%) as an off-white solid. $C_{14}H_{20}N_6O_5$, MS (ES): m/z (M+H$^+$) 353.1.

YK-CAP-108-PM7: $^1$H NMR (400 MHZ, MeOD) δ 8.02 (s, 1H), 5.71 (d, J=2.5 Hz, 1H), 4.43 (d, J=2.4 Hz, 1H), 4.31-4.20 (m, 1H), 3.93-3.82 (m, 1H), 3.78-3.67 (m, 2H), 2.34-2.25 (m, 1H), 2.06 (s, 3H), 1.63 (s, 3H).

Step 8: Synthesis of YK-CAP-108-PM8

According to the synthesis route of YK-CAP-101-PM3, YK-CAP-108-PM7 (1.50 g, 4.26 mmol) was used as starting material to obtain YK-CAP-108-PM8 (triethylamine salt, 1.11 g, 2.08 mmol, 48.8%). $C_{14}H_{21}N_6O_8P$, MS (ES): m/z (M−H$^-$) 431.1.

Step 9: Synthesis of YK-CAP-108-PM9

According to the synthesis route of YK-CAP-101-PM4, YK-CAP-108-PM8 (1.11 g, 2.08 mmol) was used as starting material to obtain YK-CAP-108-PM9 (sodium salt, 778 mg, 1.54 mmol, 74.2%). $C_{17}H_{23}N_8O_7P$, MS (ES): m/z (M−H$^-$) 481.1.

Step 10: Synthesis of YK-CAP-108-PM10

According to the synthesis route of YK-CAP-101-PM5, YK-CAP-108-PM9 (778 mg, 1.54 mmol) was used as starting material to obtain YK-CAP-108-PM10 (triethylamine salt, 512 mg, 0.83 mmol, 54.2%). $C_{14}H_{22}N_6O_{11}P_2$, MS (ES): m/z ($M-H^-$) 511.0.

Step 11: Synthesis of YK-CAP-108-PM11

According to the synthesis route of YK-CAP-101-PM6, YK-CAP-108-PM10 (512 mg, 0.83 mmol) was used as starting material to obtain YK-CAP-108-PM11 (triethylamine salt, 117 mg, 0.19 mmol, 22.5%). $C_{15}H_{24}N_6O_{11}P_2$, MS (ES): m/z ($M-H^-$) 525.1.

Step 12: Synthesis of YK-CAP-108

According to the synthesis route of YK-CAP-101, YK-CAP-108-PM11 (117 mg, 0.19 mmol) was used as starting material to obtain YK-CAP-108 (18 mg, 14.22 μmol, 7.5%). $C_{36}H_{50}N_{16}O_{24}P_4$, MS (ES): m/z ($M-H^-$) 1213.1.

$^1$H NMR (400 MHZ, $D_2O$) δ 8.43-8.32 (m, 1H), 8.12 (d, J=2.5 Hz, 1H), 7.73-7.54 (m, 2H), 6.22 (d, J=4.5 Hz, 1H), 5.35 (d, J=2.3 Hz, 1H), 5.22-5.11 (m, 1H), 4.72-4.51 (m, 3H), 4.41-4.33 (m, 6H), 4.21 (s, 2H), 4.13 (s, 2H), 3.90-3.84 (m, 3H), 3.13-3.11 (m, 3H), 3.10 (s, 2H), 2.32-2.26 (m, 1H), 2.17 (s, 3H), 1.42 (d, J=6.2 Hz, 3H). $^{31}$P NMR ($D_2O$, 163 MHz) δ−0.87 (s, 1P), −11.21 (d, J=20.1 Hz, 1P), −11.62 (d, J=16.6 Hz, 1P), −21.67 (t, J=17.2 Hz, 1P).

11. Synthesis of YK-CAP-109

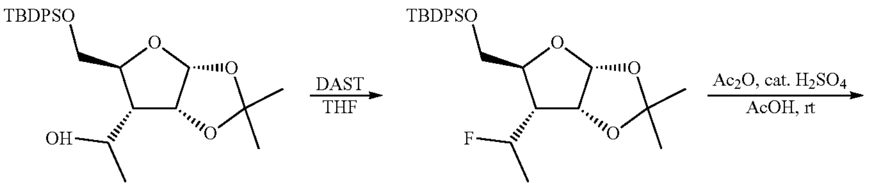

YK-CAP-107-PM3

YK-CAP-109-PM1

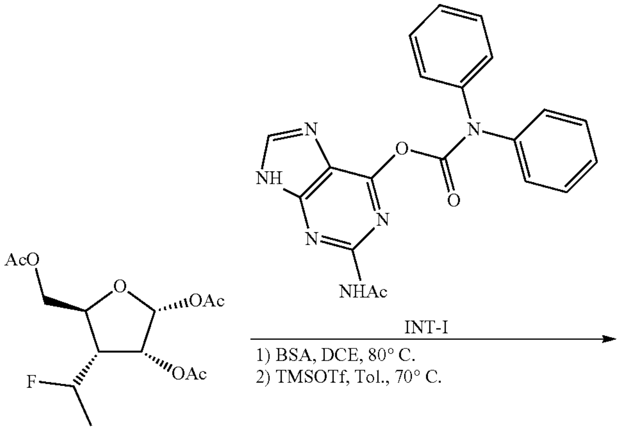

YK-CAP-109-PM2

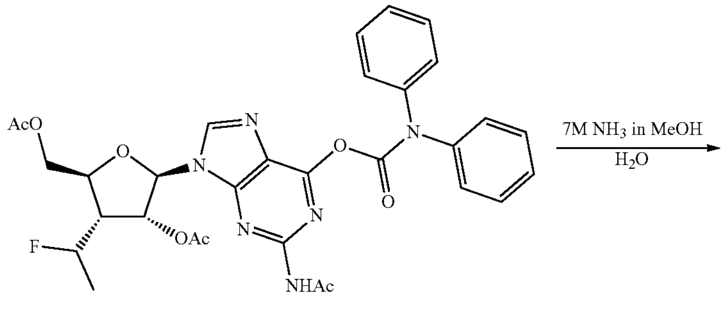

YK-CAP-109-PM3

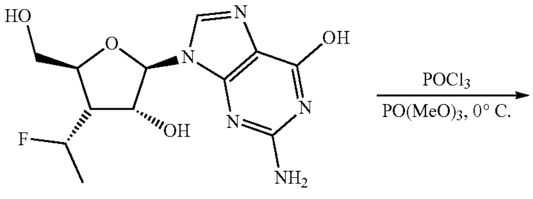

YK-CAP-109-PM4

-continued
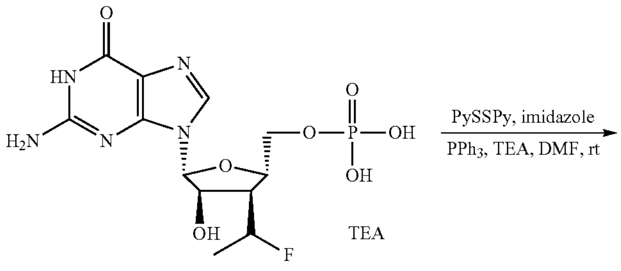
YK-CAP-109-PM5
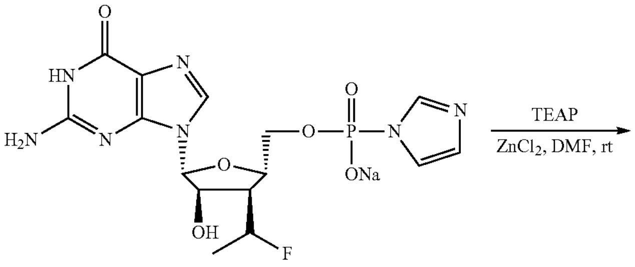
YK-CAP-109-PM6
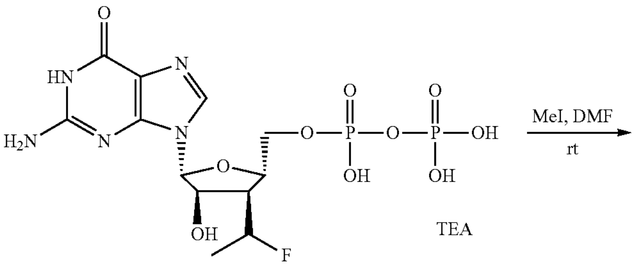
YK-CAP-109-PM7
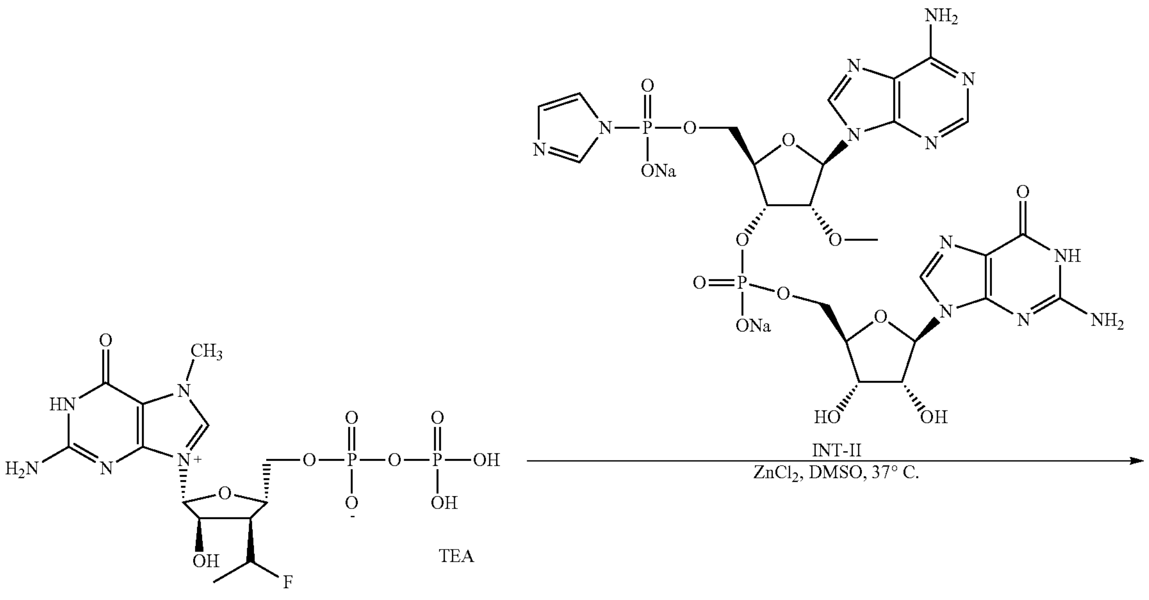
YK-CAP-109-PM8

-continued

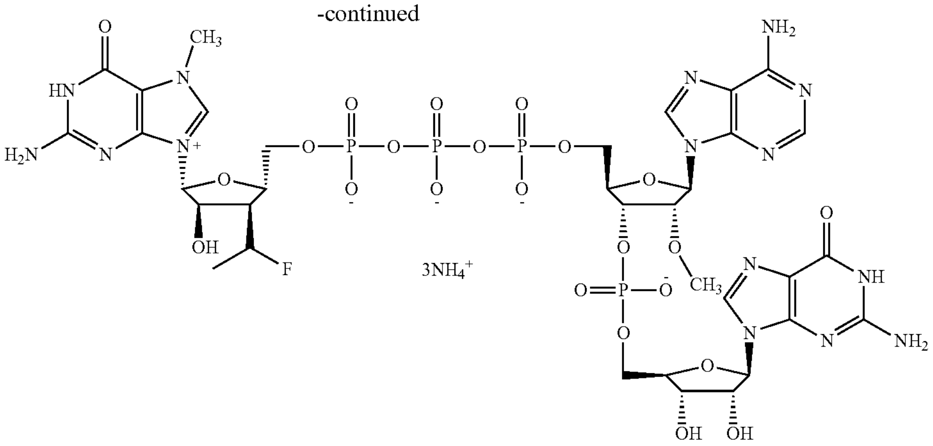

YK-CAP-109

Step 1: Synthesis of YK-CAP-109-PM1

YK-CAP-107-PM3 (10.0 g, 21.90 mmol) was dissolved in dichloromethane. The reaction system was cooled to 0° C., and DAST (7.1 g, 43.80 mmol) was slowly added dropwise thereto. The reaction system was stirred and reacted at 0° C. for 4 hours. The system was slowly added with saturated sodium bicarbonate aqueous solution to quench the reaction, then added with DCM, stirred, and the phases were separated. The organic phase was washed twice with saturated sodium bicarbonate aqueous solution, and the phases were separated. The organic phase was washed two to three times with saturate brine, dried over anhydrous sodium sulfate, filtered, and evaporated to dryness by rotary evaporation. The residue was purified by silica gel column chromatography (0 to 30% ethyl acetate/n-hexane) to obtain YK-CAP-109-PM1 (6.1 g, 13.30 mmol, 60.7%).

Step 2: Synthesis of YK-CAP-109-PM2

YK-CAP-109-PM1 (6.1 g, 13.30 mmol) was dissolved in acetic acid, then acetic anhydride (27.2 g, 266.0 mmol) was added thereto, and concentrated sulfuric acid (280 μL) was slowly added dropwise thereto. After the dropwise addition was completed, the mixture was stirred at room temperature for 16 hours. The reaction mixture was added with 200 mL of water and extracted with ethyl acetate. The organic phase was washed three times with saturated sodium bicarbonate aqueous solution to adjust the pH to alkalinity, then dried, and evaporated to dryness by rotary evaporation to obtain the crude product YK-CAP-109-PM2 (5.80 g) as a yellow oily liquid, which was directly used in the next reaction step.

Step 3: Synthesis of YK-CAP-109-PM3

Intermediate INT-I (6.2 g, 15.96 mmol) was dissolved in 1,2-dichloroethane, and N,O-bis(trimethylsilyl) acetamide (8.1 g, 39.9 mmol) was added thereto. The mixture was heated to 80° C., stirred and reacted for 2 hours, and the reaction solvent was removed under reduced pressure. The mixture was redissolved in toluene, and a solution of YK-CAP-109-PM2 (5.8 g, calculated as 13.30 mmol) in toluene and TMSOTf (4.4 g, 19.9 mmol) were sequentially added thereto at room temperature. The mixture was then heated to 70° C., and stirred and reacted for another 2 hours. The reaction system was diluted with ethyl acetate, washed once with saturated sodium bicarbonate solution, filtered to remove the insoluble substance, and the phases of the filtrate were separated. The organic phase was dried over anhydrous sodium sulfate, and evaporated by rotary evaporation under reduced pressure to remove the solvent. The residue was purified by silica gel column chromatography (0 to 30% ethyl acetate/DCM) to obtain YK-CAP-109-PM3 (3.1 g, 4.88 mmol). $C_{31}H_{31}FN_6O_8$, MS (ES): m/z (M+H$^+$) 635.2.

Step 4: Synthesis of YK-CAP-109-PM4

YK-CAP-109-PM3 (3.1 g, 4.88 mmol) was dissolved in 7 M ammonia/methanol solution and water (5:1), and the mixture was stirred and reacted at room temperature for 16 hours. The reaction mixture was evaporated to dryness by rotary evaporation to remove the solvent, and the crude product was recrystallized with ethyl acetate to obtain YK-CAP-109-PM4 (1.1 g, 3.51 mmol, 71.9%). $C_{12}H_{16}FN_5O_4$, MS (ES): m/z (M+H$^+$) 314.1.

YK-CAP-109-PM4: $^1$H NMR (400 MHZ, DMSO-$d_6$) δ 11.45 (s, 1H), 8.00 (s, 1H), δ 6.40 (s, 2H), 5.73-5.56 (m, 2H), 4.83-4.81 (m, 1H), 4.31-4.29 (m, 1H), 4.17-4.13 (m, 1H), 4.60 (s, 1H), 3.76-3.72 (m, 1H), 3.63-3.50 (m, 1H), 2.34-2.26 (m, 1H), 1.42 (d, J=6.2 Hz, 3H).

Step 5: Synthesis of YK-CAP-109-PM5

Phosphorus oxychloride (1.6 g, 10.5 mmol) was dissolved in 20 mL of trimethyl phosphate. The mixture was cooled to 0° C. under nitrogen atmosphere. The above reaction system was slowly added with YK-CAP-109-PM4 (1.1 g, 3.51 mmol), and stirred and reacted at 0° C. for about 4 hours. After the reaction was completed, the reaction mixture was added with 20 mL of ice water and washed twice with ethyl acetate. The aqueous phase was added with ammonia water to adjust the pH to 3.5, and stored in a refrigerator overnight. The next day, the pH was continuously adjusted to 6.5, and the mixture was diluted to 400 mL for sample loading. The sample was purified by gel column chromatography (eluted with water and 1.5 M TEAB at a ratio of 1:4). The target product peak was collected, concentrated, and lyophilized to obtain YK-CAP-109-PM5 (triethylamine salt, 980 mg, 1.98 mmol, 56.5%) as a white solid. $C_{12}H_{17}FN_5O_7P$, MS (ES): m/z (M−H$^-$) 392.1.

Step 6: Synthesis of YK-CAP-109-PM6

According to the synthesis route of YK-CAP-101-PM4, YK-CAP-109-PM5 (980 mg, 1.98 mmol) was used as starting material to obtain YK-CAP-109-PM6 (sodium salt, 900 mg, 1.93 mmol, 97.6%). $C_{15}H_{19}FN_7O_6P$, MS (ES): m/z (M−$H^-$) 442.1.

Step 7: Synthesis of YK-CAP-109-PM7

According to the synthesis route of YK-CAP-101-PM5, YK-CAP-109-PM6 (900 mg, 1.93 mmol) was used as starting material to obtain YK-CAP-109-PM7 (triethylamine salt, 850 mg, 1.48 mmol, 76.7%). $C_{12}H_{18}FN_5O_{10}P_2$, MS (ES): m/z (M−$H^-$) 472.2.

Step 8: Synthesis of YK-CAP-109-PM8

According to the synthesis route of YK-CAP-101-PM6, YK-CAP-109-PM7 (850 mg, 1.48 mmol) was used as starting material to obtain YK-CAP-109-PM8 (triethylamine salt, 450 mg, 0.76 mmol, 51.7%). $C_{13}H_{20}FN_5O_{10}P_2$, MS (ES): m/z (M−$H^-$) 486.1.

Step 9: Synthesis of YK-CAP-109

According to the synthesis route of YK-CAP-101, YK-CAP-109-PM8 (100 mg, 0.17 mmol) was used as starting material to obtain YK-CAP-109 (35 mg, 28.53 μmol, 16.8%). $C_{34}H_{46}FN_{15}O_{23}P_4$, MS (ES): m/z (M−$H^-$) 1174.2.

$^1$H NMR (400 MHZ, $D_2O$) δ 8.53-8.41 (m, 1H), 8.14 (d, J=2.6 Hz, 1H), 7.63-7.55 (m, 2H), 6.17 (d, J=4.4 Hz, 1H), 5.65 (d, J=2.6 Hz, 1H), 5.32-5.21 (m, 1H), 4.62-4.42 (m, 3H), 4.36-4.33 (m, 4H), 4.22-4.15 (m, 3H), 4.11 (s, 2H), 4.03 (s, 1H), 3.91-3.82 (m, 3H), 3.21-3.15 (m, 3H), 3.11 (s, 2H), 2.31-2.22 (m, 1H), 1.52 (d, J=6.1 Hz, 3H). $^{31}$P NMR ($D_2O$, 163 MHz) δ−0.89 (s, 1P), −11.21 (d, J=20.8 Hz, 1P), −11.74 (d, J=16.6 Hz, 1P), −22.12 (t, J=18.0 Hz, 1P).

12. Synthesis of YK-CAP-110

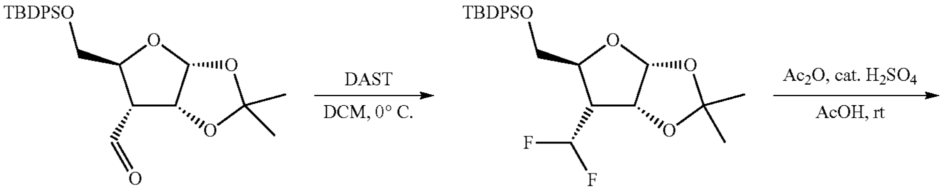

YK-CAP-107-PM2

YK-CAP-110-PM1

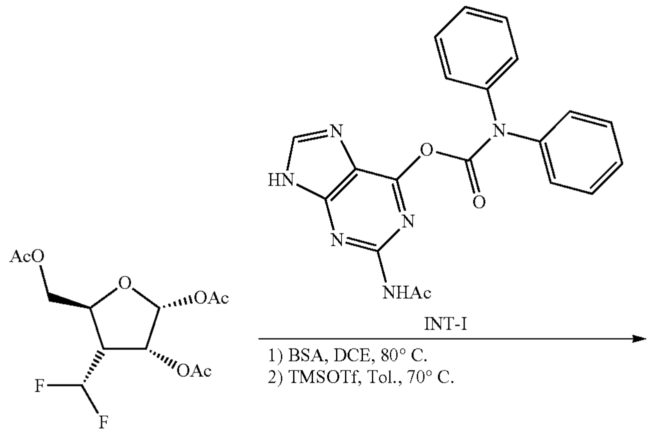

YK-CAP-110-PM2

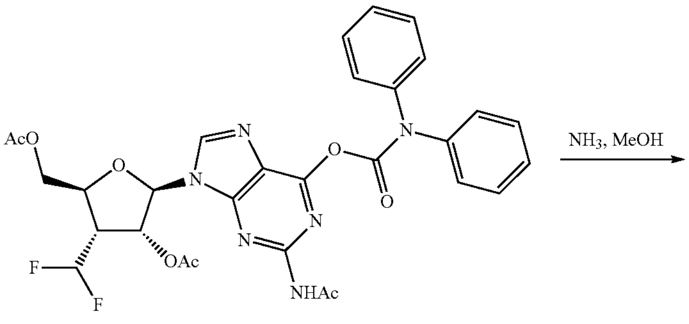

YK-CAP-110-PM3

-continued
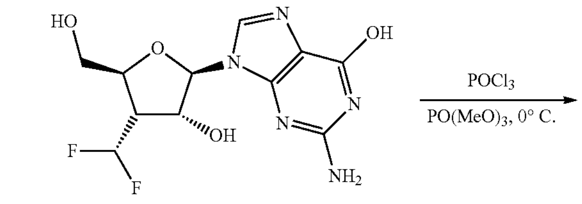
YK-CAP-110-PM4
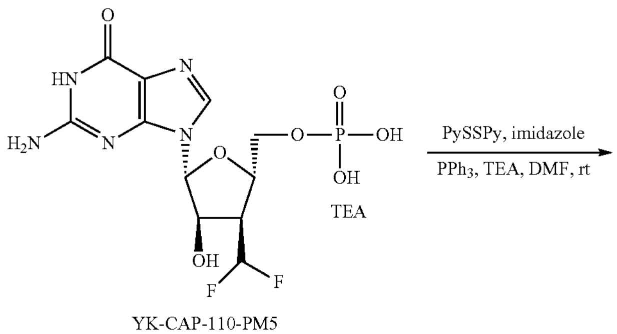
YK-CAP-110-PM5
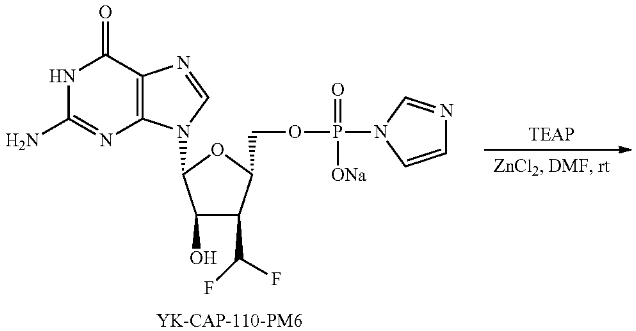
YK-CAP-110-PM6
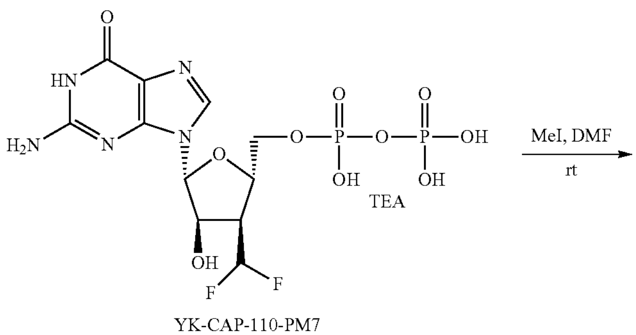
YK-CAP-110-PM7

-continued

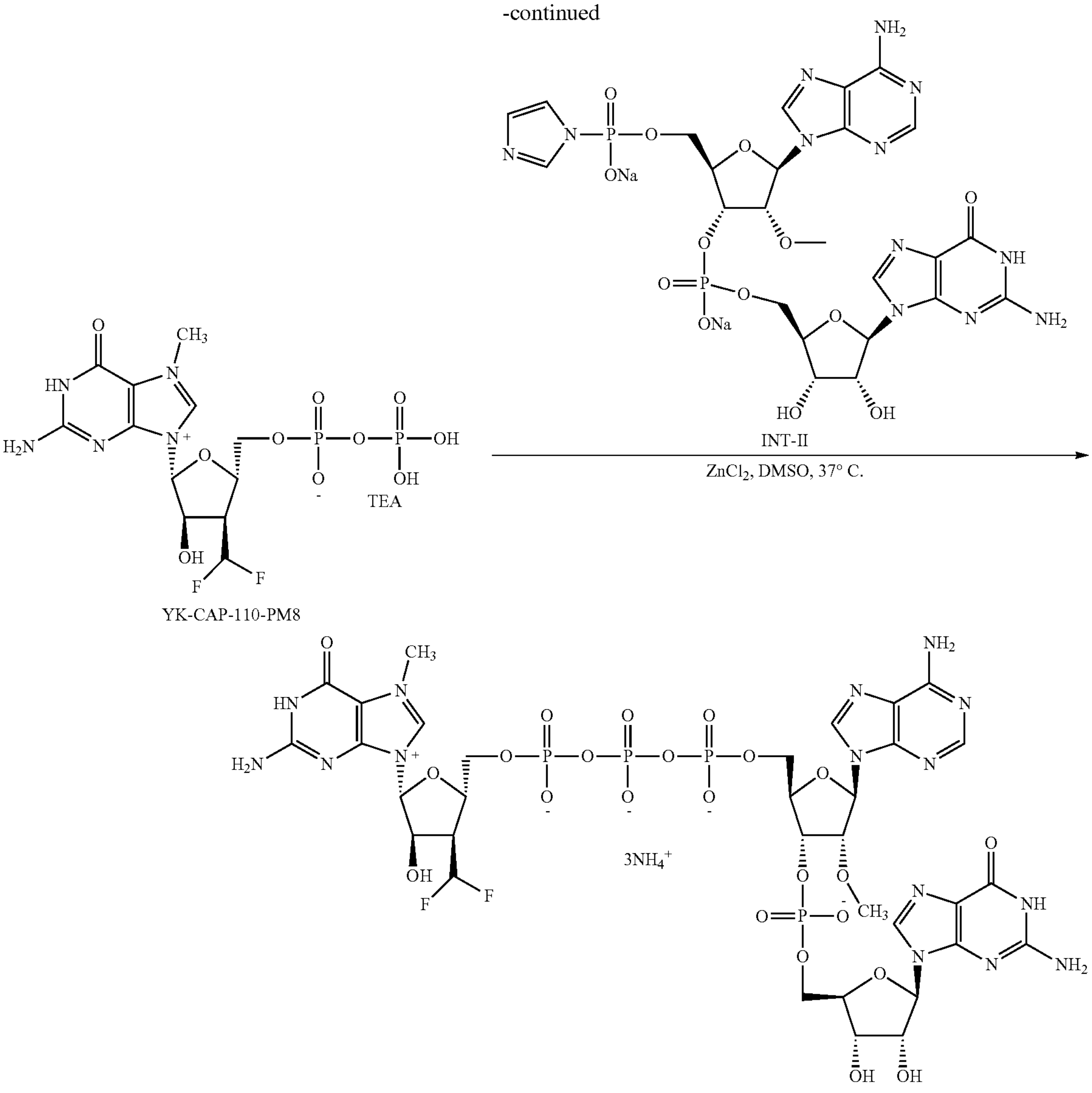

YK-CAP-110-PM8

INT-II

YK-CAP-110

Step 1: Synthesis of YK-CAP-110-PM1

YK-CAP-107-PM2 (14.4 g, 32.68 mmol) was dissolved in dichloromethane. The reaction system was cooled to 0° C., and DAST (16.7 g, 103.5 mmol) was slowly added dropwise thereto. The reaction system was stirred and reacted at 0° C. for 4 hours. The system was slowly added with saturated sodium bicarbonate aqueous solution to quench the reaction, then added with DCM, stirred, and the phases were separated. The organic phase was washed twice with saturated sodium bicarbonate aqueous solution, and the phases were separated. The organic phase was washed two to three times with saturate brine, dried over anhydrous sodium sulfate, filtered, and evaporated to dryness by rotary evaporation. The residue was purified by silica gel column chromatography (0 to 30% ethyl acetate/n-hexane) to obtain YK-CAP-110-PM1 (10.6 g, 22.91 mmol, 70.1%).

Step 2: Synthesis of YK-CAP-110-PM2

YK-CAP-110-PM1 (5.6 g, 12.11 mmol) was dissolved in acetic acid, then acetic anhydride (24.7 g, 242.1 mmol) was added thereto, and concentrated sulfuric acid (280 μL) was slowly added dropwise thereto. After the dropwise addition was completed, the mixture was stirred at room temperature for 16 hours. The reaction mixture was added with 200 mL of water and extracted with ethyl acetate. The organic phase was washed three times with saturated sodium bicarbonate aqueous solution to adjust the pH to alkalinity, then dried, and evaporated to dryness by rotary evaporation to obtain the crude product YK-CAP-110-PM2 (6.0 g) as a yellow oily liquid, which was directly used in the next reaction step.

Step 3: Synthesis of YK-CAP-110-PM3

Intermediate INT-I (5.2 g, 13.4 mmol) was dissolved in 1,2-dichloroethane, and N,O-bis(trimethylsilyl) acetamide (7.4 g, 36.3 mmol) was added thereto. The mixture was heated to 80° C., stirred and reacted for 2 hours, and the reaction solvent was removed under reduced pressure. The mixture was redissolved in toluene, and a solution of YK-CAP-110-PM2 (6.0 g, calculated as 12.11 mmol) in toluene and TMSOTf (3.0 g, 13.4 mmol) were sequentially added thereto at room temperature. The mixture was then heated to 70° C., and stirred and reacted for another 2 hours. The reaction system was diluted with ethyl acetate, washed once with saturated sodium bicarbonate solution, filtered to remove the insoluble substance, and the phases of the filtrate were separated. The organic phase was dried over anhydrous sodium sulfate, and evaporated by rotary evaporation under reduced pressure to remove the solvent. The residue was purified by silica gel column chromatography (0 to 30% ethyl acetate/DCM) to obtain YK-CAP-110-PM3 (3.5 g, 5.48 mmol). $C_{30}H_{28}F_2N_6O_8$, MS (ES): m/z (M+H$^+$) 639.1.

Step 4: Synthesis of YK-CAP-110-PM4

YK-CAP-110-PM3 (3.5 g, 5.48 mmol) was dissolved in 4 M ammonia/methanol solution and water (5:1), and the mixture was stirred and reacted at room temperature for 16 hours. The reaction mixture was evaporated to dryness by rotary evaporation to remove the solvent, and the crude product was recrystallized with ethyl acetate to obtain YK-CAP-110-PM4 (1.3 g, 4.10 mmol, 74.7%). $C_{11}H_{13}F_2N_5O_4$, MS (ES): m/z (M+H$^+$) 318.1.

YK-CAP-110-PM4: $^1$H NMR (400 MHZ, DMSO-d$_6$) δ 10.56 (s, 1H), 8.00 (s, 1H), δ 6.40 (s, 2H), 5.71-5.56 (m, 2H), 4.86-4.83 (m, 1H), 4.36-4.32 (m, 1H), 4.19-4.15 (m, 1H), 4.62 (s, 1H), 3.75-3.73 (m, 1H), 3.62-3.49 (m, 1H), 3.27-3.22 (m, 1H).

Step 5: Synthesis of YK-CAP-110-PM5

Phosphorus oxychloride (1.9 g, 12.3 mmol) was dissolved in 20 mL of trimethyl phosphate. The mixture was cooled to 0° C. under nitrogen atmosphere, and YK-CAP-110-PM4 (1.3 g, 4.10 mmol) was slowly added to the above reaction system. The mixture was stirred and reacted at 0° C. for about 4 hours. After the reaction was completed, the reaction mixture was added with 20 mL of ice water and washed twice with ethyl acetate. The aqueous phase was added with ammonia water to adjust the pH to 3.5, and stored in a refrigerator overnight. The next day, the pH was continuously adjusted to 6.5, and the mixture was diluted to 400 mL for sample loading. The sample was purified by gel column chromatography (eluted with water and 1.5 M TEAB at a ratio of 1:5). The target product peak was collected, concentrated, and lyophilized to obtain YK-CAP-110-PM5 (triethylamine salt, 1.1 g, 2.21 mmol, 53.8%) as a white solid. $C_{11}H_{14}F_2N_5O_7P$, MS (ES): m/z (M−H$^-$) 396.1.

Step 6: Synthesis of YK-CAP-110-PM6

According to the synthesis route of YK-CAP-101-PM4, YK-CAP-110-PM5 (1.1 g, 2.21 mmol) was used as starting material to obtain YK-CAP-110-PM6 (sodium salt, 1.0 g, 2.13 mmol, 96.4%). $C_{14}H_{16}F_2N_7O_6P$, MS (ES): m/z (M−H$^-$) 446.1.

Step 7: Synthesis of YK-CAP-110-PM7

According to the synthesis route of YK-CAP-101-PM5, YK-CAP-110-PM6 (1.0 g, 2.13 mmol) was used as starting material to obtain YK-CAP-110-PM7 (triethylamine salt, 900 mg, 1.56 mmol, 73.1%). $C_{11}H_{15}F_2N_5O_{10}P_2$, MS (ES): m/z (M−H$^-$) 476.1.

Step 8: Synthesis of YK-CAP-110-PM8

According to the synthesis route of YK-CAP-101-PM6, YK-CAP-110-PM7 (900 mg, 1.56 mmol) was used as starting material to obtain YK-CAP-110-PM8 (triethylamine salt, 500 mg, 0.84 mmol, 54.1%). $C_{12}H_{17}F_2N_5O_{10}P_2$, MS (ES): m/z (M−H$^-$) 490.2.

Step 9: Synthesis of YK-CAP-110

According to the synthesis route of YK-CAP-101, YK-CAP-110-PM8 (100 mg, 0.17 mmol) was used as starting material to obtain YK-CAP-110 (25 mg, 22.03 μmol, 13.0%). $C_{33}H_{43}F_2N_{15}O_{23}P_4$, MS (ES): m/z (M−H$^-$) 1178.1.

$^1$H NMR (400 MHZ, D$_2$O) δ 8.43 (d, J=1.5 Hz, 1H), 8.36 (d, J=2.6 Hz, 1H), 8.12 (d, J=4.6 Hz, 2H), 6.10 (d, J=5.4 Hz, 1H), 5.88 (d, J=2.2 Hz, 1H), 5.61 (d, J=4.4 Hz, 1H), 4.90-4.88 (m, 3H), 4.85-4.82 (m, 1H), 4.62 (t, J=4.7 Hz, 1H), 4.51-4.38 (m, 4H), 4.23 (d, J=3.0 Hz, 1H), 4.12 (s, 2H), 4.04 (s, 2H), 3.93 (s, 3H), 3.64 (t, J=7.0 Hz, 1H), 3.41 (s, 3H), 3.28-3.22 (m, 1H). $^{31}$P NMR (D$_2$O, 162 MHz) δ−0.93 (s, 1P), −11.17 (d, J=19.2 Hz, 1P), −11.35 (d, J=17.1 Hz, 1P), −24.38 (t, J=17.6 Hz, 1P).

13. Synthesis of YK-CAP-111

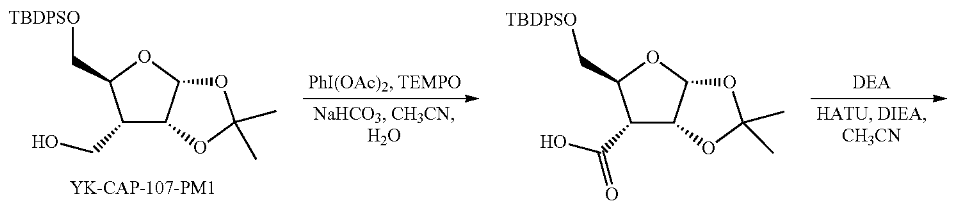

YK-CAP-107-PM1

YK-CAP-111-PM1

-continued
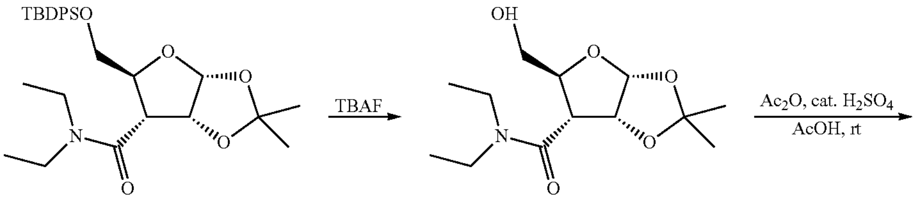
YK-CAP-111-PM2 YK-CAP-111-PM3
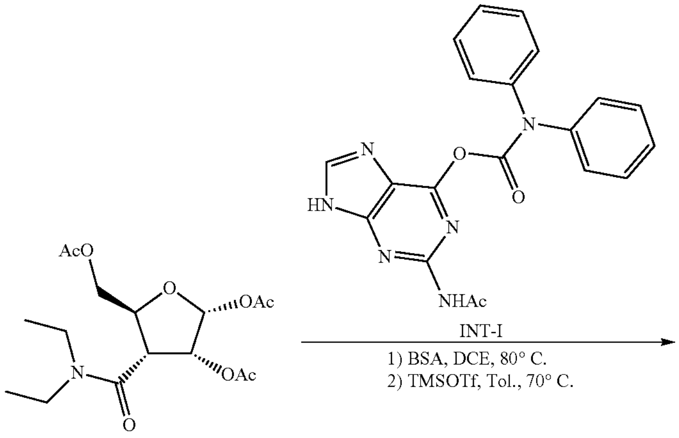
YK-CAP-111-PM4
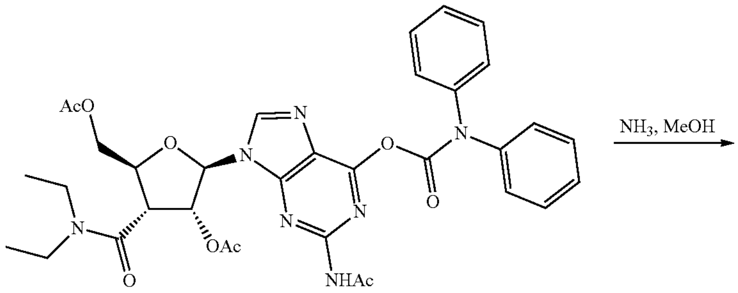
YK-CAP-111-PM5
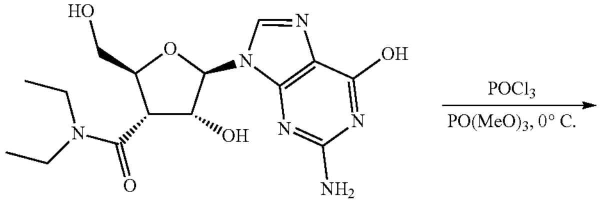
YK-CAP-111-PM6
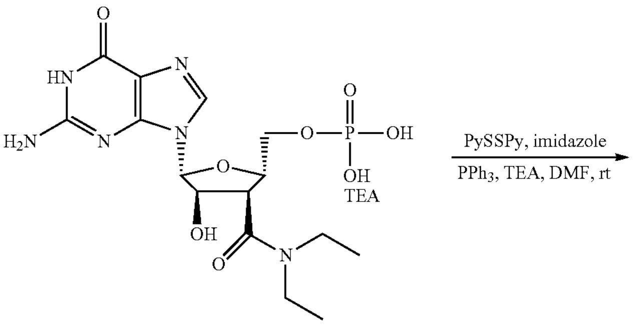
YK-CAP-111-PM7

-continued
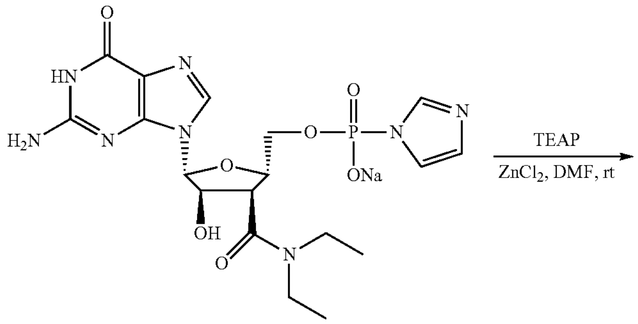
YK-CAP-111-PM8
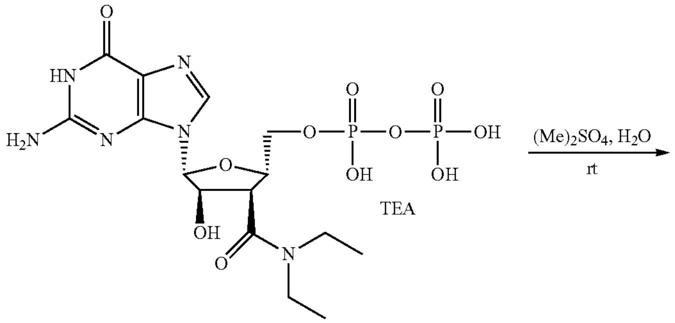
YK-CAP-111-PM9
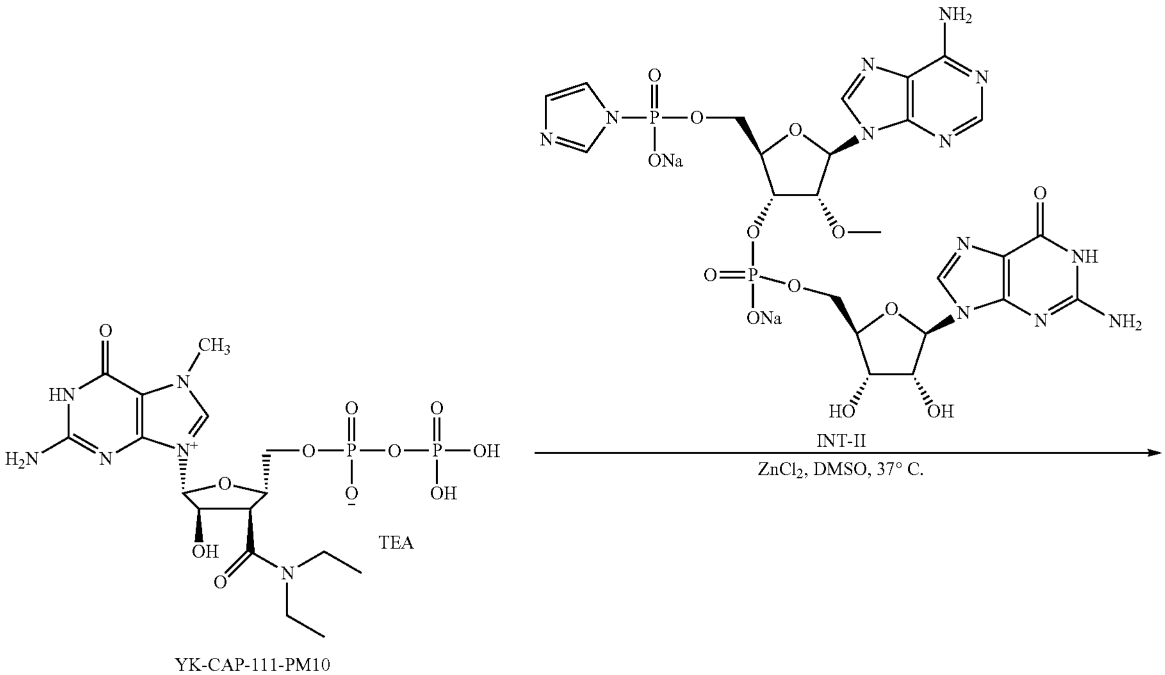
YK-CAP-111-PM10

-continued

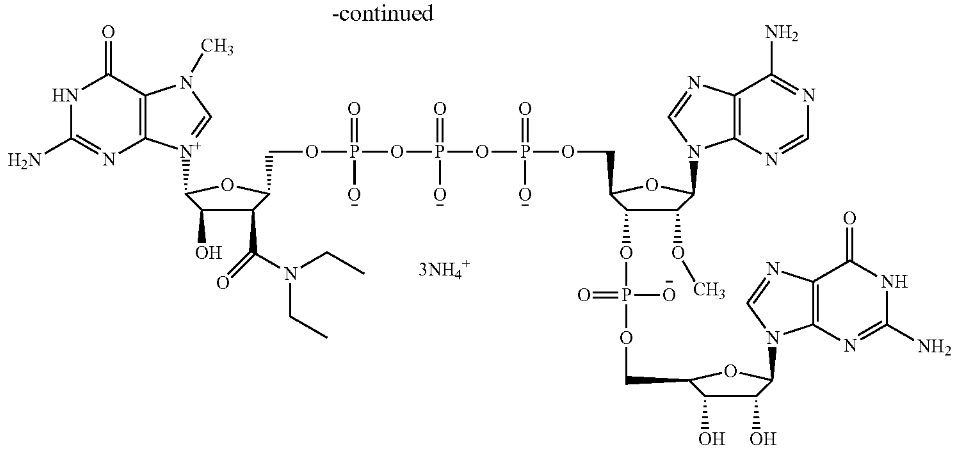

YK-CAP-111

Step 1: Synthesis of YK-CAP-111-PM1

YK-CAP-107-PM1 (35.0 g, 79.07 mmol) was dissolved in acetonitrile and water (1:1, 280 mL), then (diacetoxyiodo) benzene (53.5 g, 166.03 mmol), sodium bicarbonate (9.96 g, 118.56 mmol), and TEMPO (1.85 g, 11.85 mmol) were sequentially added thereto in an ice bath, and the mixture was reacted at room temperature for 2 hours. TLC monitored that the starting material was completely reacted. The reaction was terminated. The reaction mixture was quenched with saturated sodium thiosulfite aqueous solution, extracted with EA, and the phases were separated. The organic phase was dried over anhydrous sodium sulfate, filtered, and evaporated by rotary evaporation to remove the solvent to obtain the crude product YK-CAP-111-PM1 (68.0 g) as a brown oil, which was directly used in the next reaction step without purification.

Step 2: Synthesis of YK-CAP-111-PM2

YK-CAP-111-PM1 (34.0 g, calculated as 39.54 mmol) was dissolved in acetonitrile, and the mixture was cooled to 0° C. DIEA (14.0 g, 108.33 mmol) and HATU (17.86 g, 46.97 mmol) were added thereto. The mixture was stirred for 20 minutes, and then diethylamine (6.6 g, 90.24 mmol) was added thereto. The mixture was warmed to room temperature, and stirred and reacted for 4 hours. The reaction mixture was concentrated under reduced pressure, and the residue was purified by silica gel column chromatography (0 to 20% ethyl acetate/n-hexane) to obtain YK-CAP-111-PM2 (17.5 g, 34.20 mmol, 86.5%).

Step 3: Synthesis of YK-CAP-111-PM3

YK-CAP-111-PM2 (17.5 g, 34.20 mmol) was dissolved in tetrahydrofuran, then TBAF (13.4 g, 51.25 mmol) was added thereto, and the mixture was stirred and reacted at room temperature for 2 hours. The reaction mixture was evaporated to dryness by rotary evaporation, and the residue was purified by silica gel column chromatography (0 to 90% ethyl acetate/n-hexane) to obtain YK-CAP-111-PM3 (8.9 g, 32.56 mmol, 95.2%).

Step 4: Synthesis of YK-CAP-111-PM4

YK-CAP-111-PM3 (4.0 g, 14.63 mmol) was dissolved in acetic acid, then sulfuric acid (300 μL) was added thereto, and the mixture was stirred at room temperature for 30 minutes. Acetic anhydride (30.0 g, 293.86 mmol) was then added thereto. The mixture was stirred at room temperature for 18 hours. The reaction mixture was added with 200 mL of water and extracted with ethyl acetate. The organic phase was washed three times with saturated sodium bicarbonate aqueous solution to adjust the pH to alkalinity, then dried, and evaporated to dryness by rotary evaporation to obtain the crude product YK-CAP-111-PM4 (3.19 g) as a yellow oily liquid, which was directly used in the next reaction step.

Step 5: Synthesis of YK-CAP-111-PM5

Intermediate INT-I (3.79 g, 9.76 mmol) was dissolved in 1,2-dichloroethane, and N,O-bis(trimethylsilyl) acetamide (5.42 g, 26.64 mmol) was added thereto. The mixture was heated to 80° C., stirred and reacted for 2 hours, and the reaction solvent was removed under reduced pressure. A solution of YK-CAP-111-PM4 (3.19 g) in toluene and TMSOTf (2.96 g, 13.32 mmol) were sequentially added thereto at room temperature. The mixture was then heated to 70° C., and stirred and reacted for another 2 hours. The reaction system was diluted with ethyl acetate, washed once with saturated sodium bicarbonate solution, filtered to remove the insoluble substance, and the phases of the filtrate were separated. The organic phase was dried over anhydrous sodium sulfate, and evaporated by rotary evaporation under reduced pressure to remove the solvent. The residue was purified by silica gel column chromatography (0 to 60% ethyl acetate/DCM) to obtain YK-CAP-111-PM5 (2.20 g, 3.20 mmol).

Step 6: Synthesis of YK-CAP-111-PM6

YK-CAP-111-PM5 (2.20 g, 3.20 mmol) was dissolved in 4 M ammonia/methanol solution and water (5:1), and the mixture was stirred and reacted at room temperature for 16 hours. The reaction mixture was evaporated to dryness by rotary evaporation to remove the solvent, and the crude product was recrystallized with ethyl acetate to obtain YK-CAP-111-PM6 (890 mg, 2.43 mmol, 75.9%). $C_{15}H_{22}N_6O_5$, MS (ES): m/z $(M+H^+)$ 367.1.

YK-CAP-111-PM6: $^1H$ NMR (400 MHZ, DMSO-$d_6$) δ 11.40 (s, 1H), 8.31 (s, 1H), 6.38 (s, 2H), 6.16 (d, J=4.3 Hz, 1H), 5.38-5.41 (m, 1H), 4.84-4.91 (m, 1H), 4.28-4.31 (m,

1H), 3.98-4.02 (m, 1H), 3.45-3.49 (m, 2H), 3.33-3.21 (q, J=4.1 Hz, 4H), 2.65-2.62 (m, 1H), 1.17-1.15 (t, J=4.1 Hz, 6H).

Step 7: Synthesis of YK-CAP-111-PM7

Phosphorus oxychloride (1.3 g, 8.48 mmol) was dissolved in 15 mL of trimethyl phosphate. The mixture was cooled to 0° C. under nitrogen atmosphere, and YK-CAP-111-PM6 (880 mg, 2.42 mmol) was slowly added to the above reaction system. The mixture was stirred and reacted at 0° C. for about 4 hours. After the reaction was completed, the reaction mixture was added with 20 mL of ice water and washed twice with ethyl acetate. The aqueous phase was added with ammonia water to adjust the pH to 3.5, and refrigerated overnight. The pH was continuously adjusted to 6.5, and the mixture was diluted to 400 mL for sample loading. The sample was purified by gel column chromatography (eluted with water and 1.5 M TEAB at a ratio of 5:1). The target product peak was collected, concentrated, and lyophilized to obtain YK-CAP-111-PM7 (triethylamine salt, 900 mg, 1.64 mmol, 68.5%) as a white solid. $C_{15}H_{23}N_6O_8P$, MS (ES): m/z (M−H$^-$) 445.1.

Step 8: Synthesis of YK-CAP-111-PM8

According to the synthesis route of YK-CAP-101-PM4, YK-CAP-111-PM7 (900 mg, 1.64 mmol) was used as starting material to obtain YK-CAP-111-PM8 (sodium salt, 730 mg, 1.41 mmol, 85.7%). $C_{18}H_{25}N_8O_7P$, MS (ES): m/z (M−H$^-$) 495.1.

Step 9: Synthesis of YK-CAP-111-PM9

According to the synthesis route of YK-CAP-101-PM5, YK-CAP-111-PM8 (720 mg, 1.39 mmol) was used as starting material to obtain YK-CAP-111-PM9 (triethylamine salt, 750 mg, 1.20 mmol, 86.1%). $C_{15}H_{24}N_6O_{11}P_2$, MS (ES): m/z (M−H$^-$) 525.1.

Step 10: Synthesis of YK-CAP-111-PM10

YK-CAP-111-PM9 (400 mg, 0.64 mmol) was dissolved in $H_2O$ (20 mL), and the mixture was added with glacial acetic acid to adjust the pH to 4.0. Dimethyl sulfate (800 μL, 8.45 mmol) was added thereto within 30 minutes. The reaction system was added with NaOH aqueous solution (0.1 M) to maintain the pH between 3.8 and 4.1, and stirred at room temperature for 5 hours. After the reaction was completed, the reaction mixture was extracted twice with dichloromethane. The pH of the aqueous phase was adjusted to 6.5, and the volume was fixed to 400 mL. The residue was purified by gel column chromatography (eluted with water and 1 M TEAB at a ratio of 3:2). The target product peak was collected, concentrated, and lyophilized to obtain YK-CAP-111-PM10 (triethylamine salt, 350 mg, 0.55 mmol, 85.6%) as a white solid. $C_{16}H_{26}N_6O_{11}P_2$, MS (ES): m/z (M−H$^-$) 539.1.

Step 11: Synthesis of YK-CAP-111

According to the synthesis route of YK-CAP-101, YK-CAP-111-PM10 (100 mg, 0.16 mmol) was used as starting material to obtain YK-CAP-111 (ammonium salt, 50 mg, 39.07 μmol, 25.1%). $C_{37}H_{52}N_{16}O_{24}P_4$, MS (ES): m/z (M−H$^-$) 1127.2.

$^1$H NMR (400 MHZ, $D_2O$) δ 8.43 (d, J=1.3 Hz, 1H), 8.35 (s, 1H), 8.06 (d, J=6.0 Hz, 2H), 6.01 (d, J=5.4 Hz, 1H), 5.86 (d, J=2.3 Hz, 1H), 5.82 (d, J=4.5 Hz, 1H), 4.97-4.84 (m, 3H), 4.66 (t, J=4.8 Hz, 1H), 4.51-4.35 (m, 4H), 4.32 (d, J=4.5 Hz, 1H), 4.21 (s, 2H), 4.09 (s, 2H), 3.97 (s, 3H), 3.72 (t, J=7.0 Hz, 1H), 3.35-3.21 (d, J=4.1 Hz, 4H), 3.04 (s, 3H), 1.94-1.87 (m, 1H), 1.21-1.14 (t, J=4.1 Hz, 6H). $^{31}$P NMR ($D_2O$, 162 MHz) δ−0.92 (s, 1P), −11.15 (d, J=19.2 Hz, 1P), −11.62 (d, J=17.1 Hz, 1P), −23.46 (t, J=17.5 Hz, 1P).

14. Synthesis of YK-CAP-112

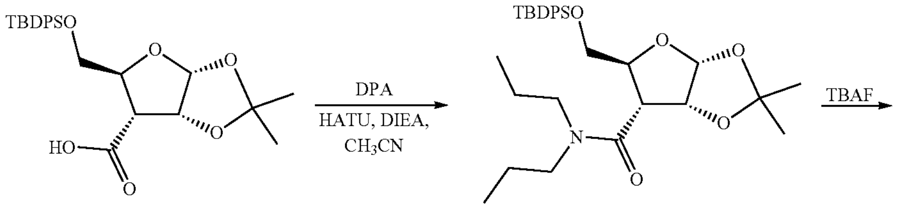

YK-CAP-111-PM1

YK-CAP-112-PM1

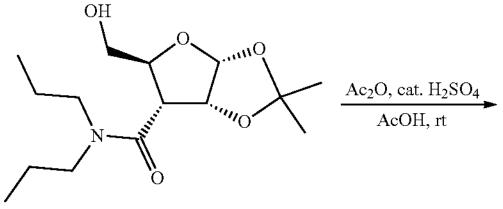

YK-CAP-112-PM2

-continued
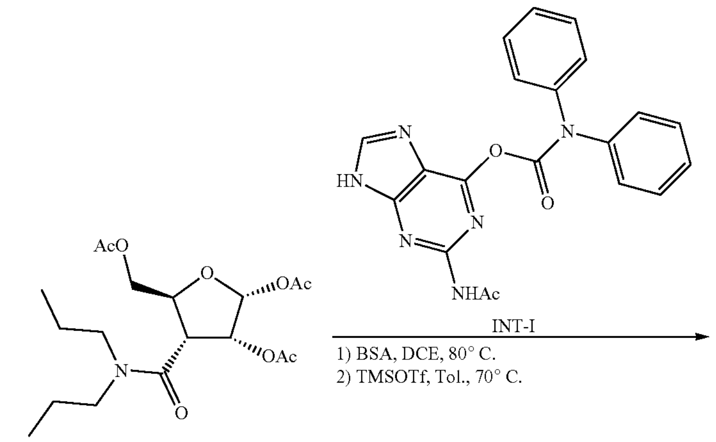
YK-CAP-112-PM3
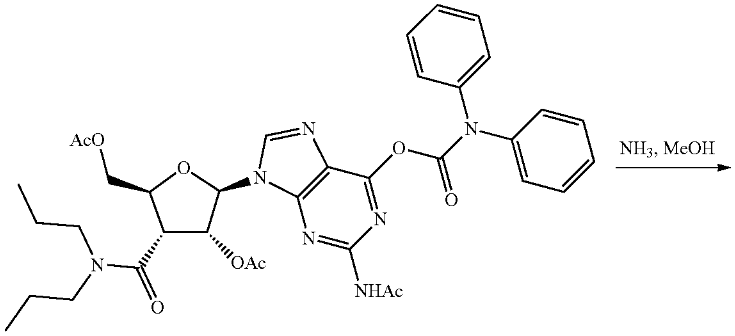
YK-CAP-112-PM4
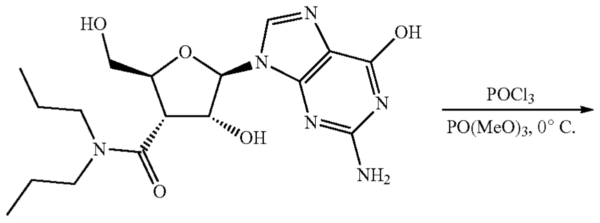
YK-CAP-112-PM5
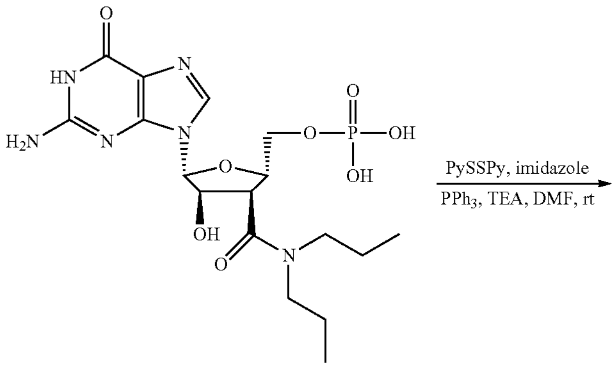
YK-CAP-112-PM6

-continued
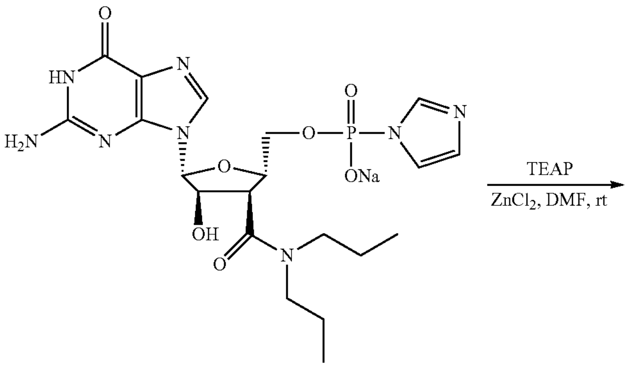
YK-CAP-112-PM7
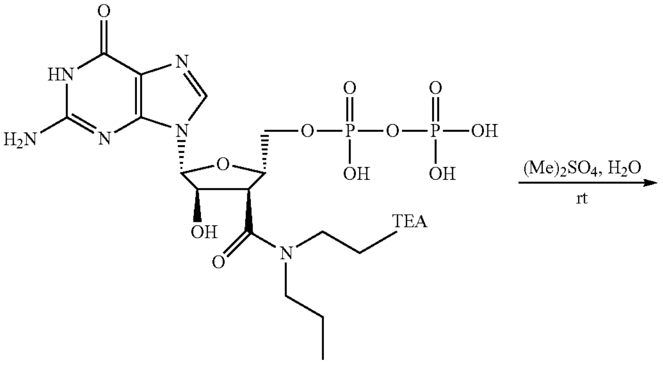
YK-CAP-112-PM8
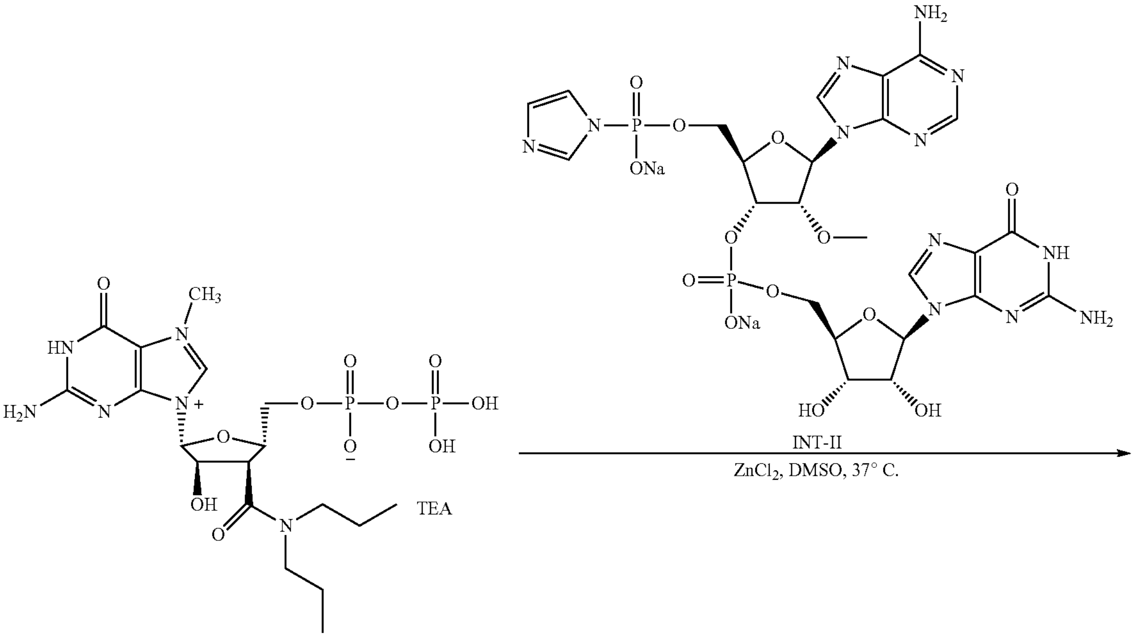
YK-CAP-112-PM9

-continued

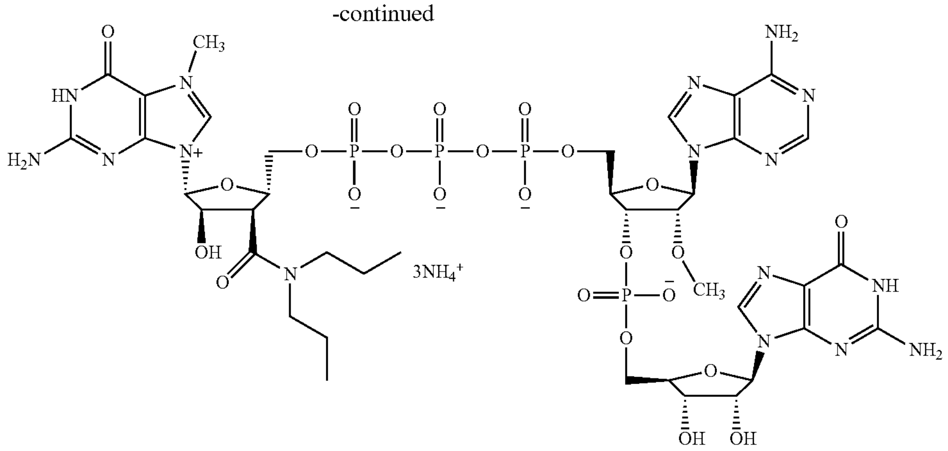

YK-CAP-112

Step 1: Synthesis of YK-CAP-112-PM1

According to the synthesis route of YK-CAP-111-PM2, YK-CAP-111-PM1 (10.0 g, 21.90 mmol) and dipropylamine (5.5 g, 54.35 mmol) were used as starting materials to obtain YK-CAP-112-PM1 (11.0 g, 20.38 mmol, 93.1%).

Step 2: Synthesis of YK-CAP-112-PM2

According to the synthesis route of YK-CAP-111-PM3, YK-CAP-112-PM1 (11.0 g, 20.38 mmol) was used as starting material to obtain YK-CAP-112-PM2 (6.0 g, 19.91 mmol, 97.7%).

Step 3: Synthesis of YK-CAP-112-PM3

According to the synthesis route of YK-CAP-111-PM4, YK-CAP-112-PM2 (6.0 g, 19.91 mmol) was used as starting material to obtain the crude product YK-CAP-112-PM3 (5.1 g) as a yellow oily liquid, which was directly used in the next reaction step.

Step 4: Synthesis of YK-CAP-112-PM4

According to the synthesis route of YK-CAP-111-PM5, YK-CAP-112-PM3 (5.1 g) was used as starting material to obtain YK-CAP-112-PM4 (3.9 g, 5.45 mmol). $C_{36}H_{41}N_7O_9$, MS (ES): m/z $(M+H^+)$ 716.3.

Step 5: Synthesis of YK-CAP-112-PM5

According to the synthesis route of YK-CAP-111-PM6, YK-CAP-112-PM4 (3.9 g, 5.45 mmol) was used as starting material to obtain YK-CAP-112-PM5 (1.7 g, 4.31 mmol, 79.1%). $C_{17}H_{26}N_6O_5$, MS (ES): m/z $(M+H^+)$ 395.2.

YK-CAP-112-PM5: $^1$H NMR (400 MHZ, DMSO-$d_6$) δ 11.37 (s, 1H), 8.41 (s, 1H), 6.28 (s, 2H), 6.19 (d, J=4.1, 1H), 5.46 (s, 1H), 5.01 (s, 1H), 4.25-4.28 (m, 1H), 3.99-4.01 (m, 1H), 3.41-3.43 (m, 2H), 3.21-3.24 (m, 4H), 2.56-2.58 (m, 1H), 1.57-1.54 (m, 4H), 0.87 (t, J=1.8 Hz, 6H).

Step 6: Synthesis of YK-CAP-112-PM6

According to the synthesis route of YK-CAP-111-PM7, YK-CAP-112-PM5 (1.7 g, 4.31 mmol) was used as starting material to obtain YK-CAP-112-PM6 (triethylamine salt, 1.80 g, 3.13 mmol, 72.6%). $C_{17}H_{27}N_6O_8P$, MS (ES): m/z $(M-H^-)$ 473.1.

Step 7: Synthesis of YK-CAP-112-PM7

According to the synthesis route of YK-CAP-101-PM4, YK-CAP-112-PM6 (1.8 g, 3.13 mmol) was used as starting material to obtain YK-CAP-112-PM7 (sodium salt, 1.47 g, 2.69 mmol, 86.0%). $C_{20}H_{29}N_8O_7P$, MS (ES): m/z $(M-H^-)$ 523.1.

Step 8: Synthesis of YK-CAP-112-PM8

According to the synthesis route of YK-CAP-101-PM5, YK-CAP-112-PM7 (1.47 g, 2.69 mmol) was used as starting material to obtain YK-CAP-112-PM8 (triethylamine salt, 1.30 g, 1.98 mmol, 73.7%). $C_{17}H_{28}N_6O_{11}P_2$, MS (ES): m/z $(M-H^-)$ 553.1.

Step 9: Synthesis of YK-CAP-112-PM9

According to the synthesis route of YK-CAP-111-PM10, YK-CAP-112-PM8 (600 mg, 0.92 mmol) was used as starting material to obtain YK-CAP-112-PM9 (triethylamine salt, 200 mg, 0.30 mmol, 32.6%). $C_{18}H_{30}N_6O_{11}P_2$, MS (ES): m/z $(M-H^-)$ 567.1.

Step 10: Synthesis of YK-CAP-112

According to the synthesis route of YK-CAP-101, YK-CAP-112-PM9 (200 mg, 0.30 mmol) was used as starting material to obtain YK-CAP-112 (ammonium salt, 50 mg, 38.23 μmol, 12.8%). $C_{39}H_{56}N_{16}O_{24}P_4$, MS (ES): m/z $(M-H^-)$ 1255.2.

$^1$H NMR (400 MHZ, $D_2O$) δ 8.43 (d, J=1.3 Hz, 1H), 8.34 (s, 1H), 8.11 (d, J=6.1 Hz, 2H), 6.05 (d, J=5.3 Hz, 1H), 5.87 (d, J=2.3 Hz, 1H), 5.81 (d, J=4.4 Hz, 1H), 4.91-4.82 (m, 2H), 4.64 (t, J=4.7 Hz, 1H), 4.48-4.37 (m, 5H), 4.30 (d, J=4.6 Hz, 1H), 4.22 (s, 2H), 4.11 (s, 2H), 3.96 (s, 3H), 3.72 (t, J=7.0 Hz, 1H), 3.33-3.26 (t, J=4.1 Hz, 4H), 3.11 (s, 3H), 2.22-2.14 (m, 1H), 1.58-1.54 (m, 4H), 0.87 (t, J=1.8 Hz, 6H). $^{31}$P NMR ($D_2O$, 162 MHz) δ−0.94 (s, 1P), −11.22 (d, J=19.1 Hz, 1P), −11.52 (d, J=17.2 Hz, 1P), −23.11 (t, J=17.3 Hz, 1P).

15. Synthesis of YK-CAP-113
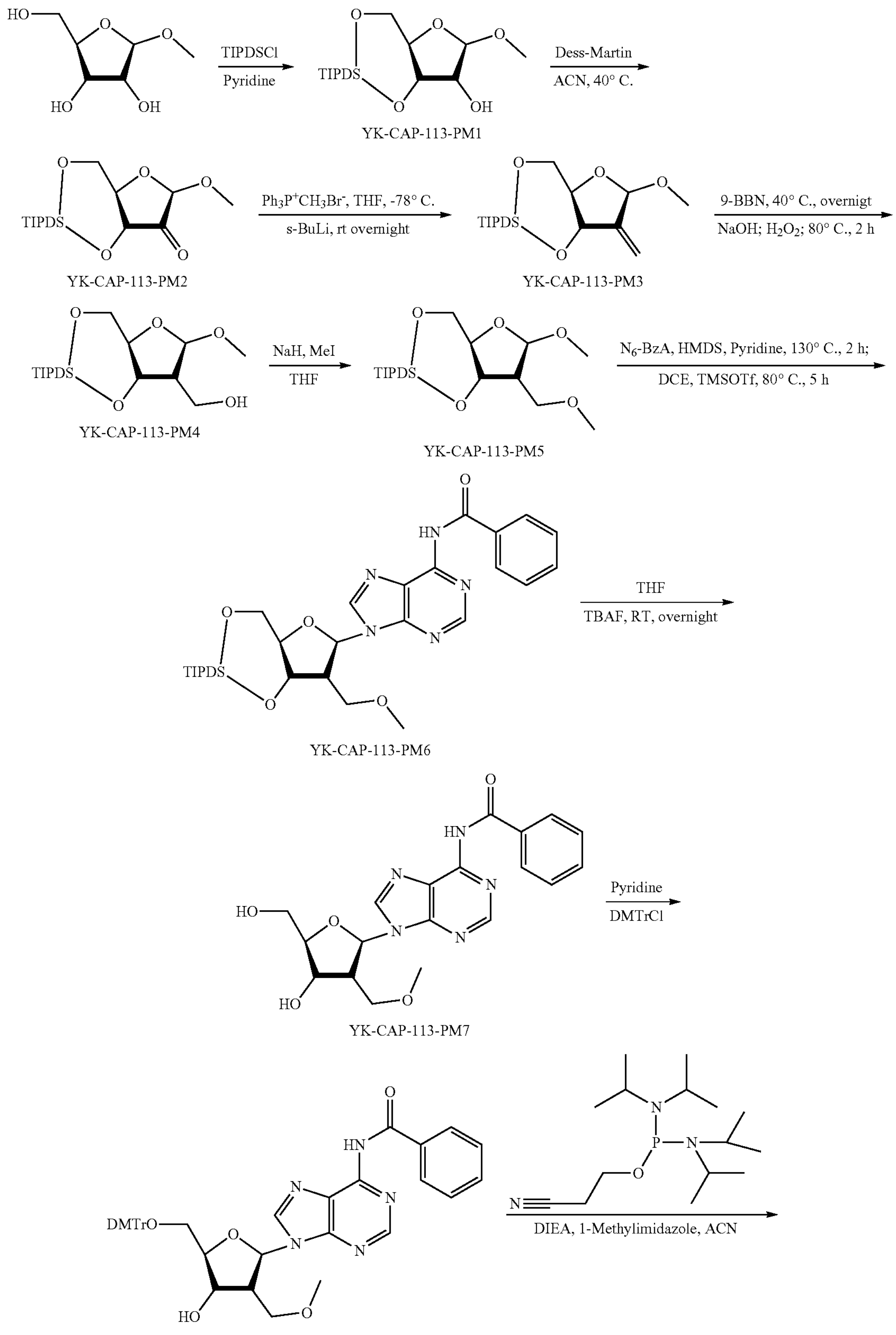
YK-CAP-113-PM1
YK-CAP-113-PM2
YK-CAP-113-PM3
YK-CAP-113-PM4
YK-CAP-113-PM5
YK-CAP-113-PM6
YK-CAP-113-PM7
YK-CAP-113-PM8

-continued
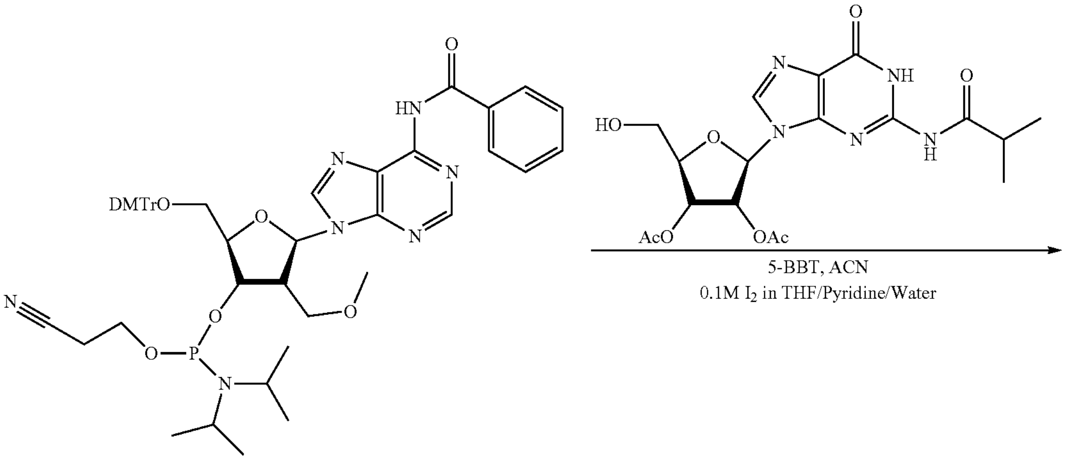
YK-CAP-113-PM9
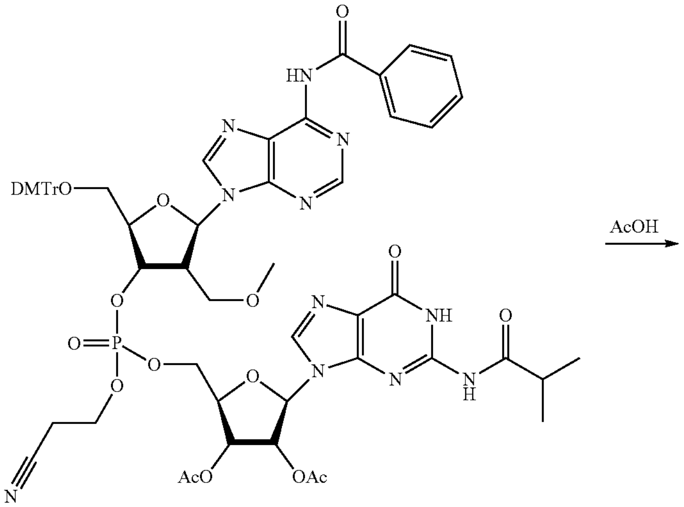
YK-CAP-113-PM10
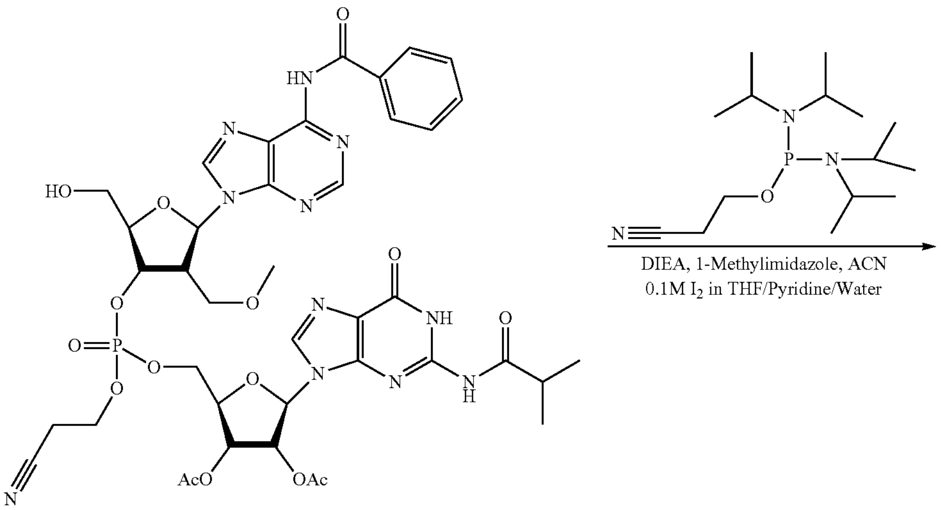
YK-CAP-113-PM11

-continued

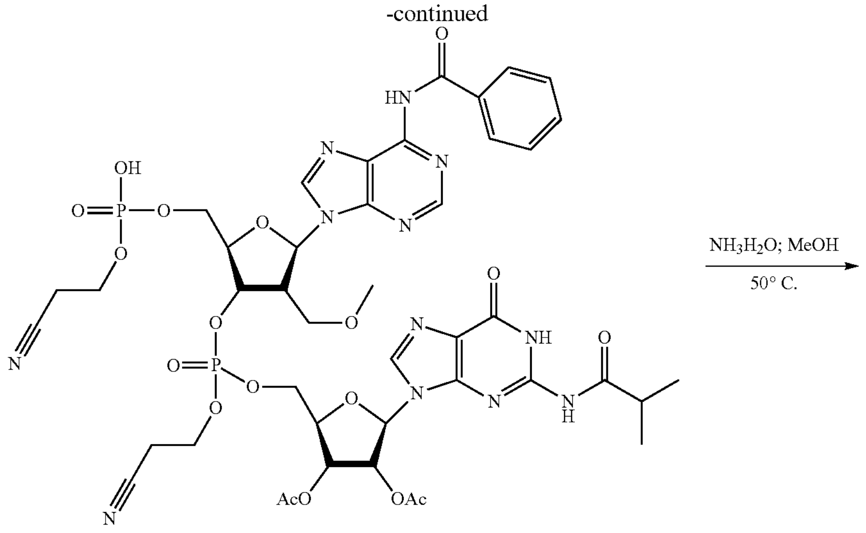

YK-CAP-113-PM12

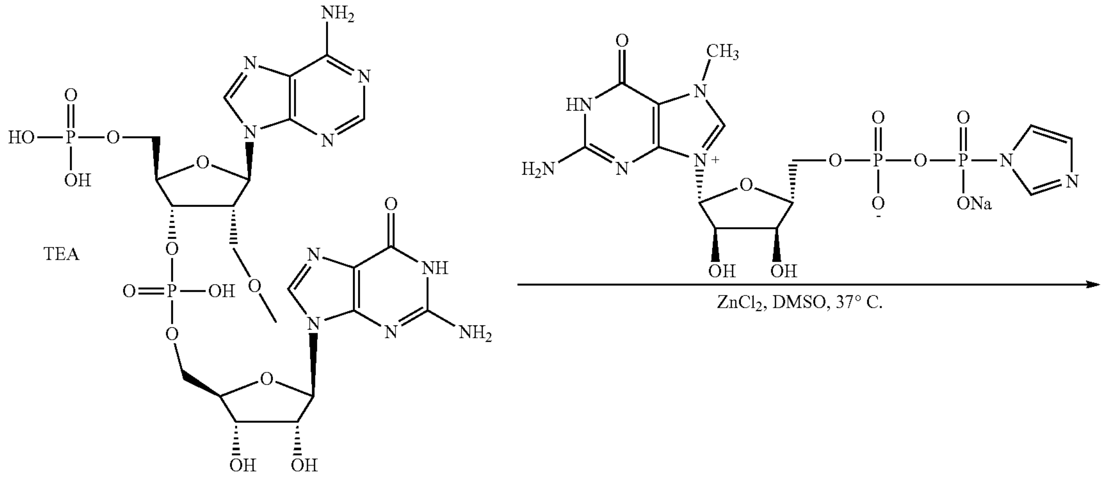

YK-CAP-113-PM13

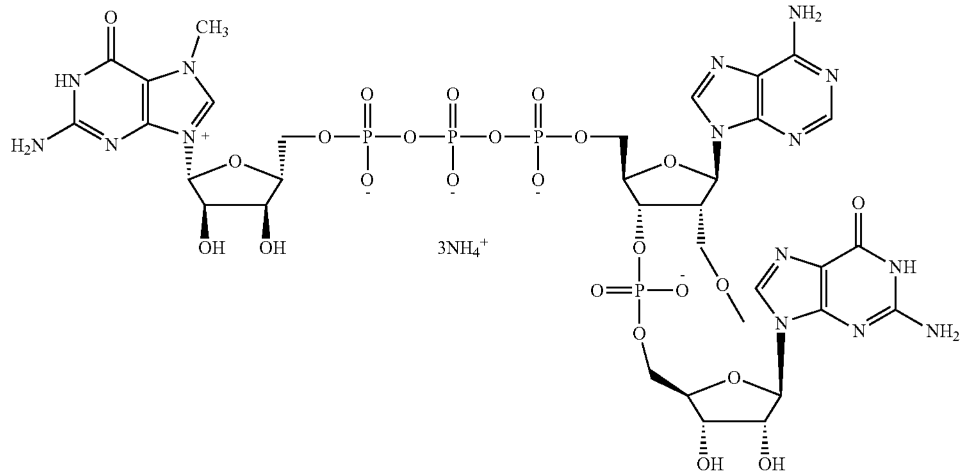

YK-CAP-113

Step 1: Synthesis of YK-CAP-113-PM1

Methyl-beta-D-ribofuranoside (100.0 g, 0.61 mol) was dissolved in 1 L of anhydrous pyridine, and TIPDSCl (230.6 g, 0.73 mol) was added dropwise thereto in an ice-water bath. After the dropwise addition was completed, the mixture was warmed to room temperature, and stirred and reacted for 12 hours. The reaction mixture was concentrated under reduced pressure to remove a large amount of solvent, and the residue was purified by silica gel column chromatography (0 to 30% ethyl acetate/n-hexane) to obtain YK-CAP-113-PM1 (212.2 g, 0.52 mol, 85.7%).

Step 2: Synthesis of YK-CAP-113-PM2

YK-CAP-113-PM1 (212.2 g, 0.52 mol) was dissolved in 2 L of acetonitrile, and Dess-Martin periodinane (485.1 g, 1.14 mol) was added thereto. The mixture was heated to 40° C., and stirred and reacted for 12 hours. The reaction mixture was cooled to room temperature, filtered, and the filtrate was evaporated to dryness by rotary evaporation under reduced pressure to obtain YK-CAP-113-PM2 (208.8 g, 0.52 mol, 98.9%).

Step 3: Synthesis of YK-CAP-113-PM3

(Bromomethyl)triphenylphosphonium bromide (408.7 g, 1.14 mol) was dissolved in tetrahydrofuran (3000 mL). The mixture was cooled to −78° C., and a 2.5 M solution of n-butyllithium in tetrahydrofuran (456 mL, 1.14 mol) was slowly added dropwise thereto. After the dropwise addition was completed, the reaction system was naturally warmed to 0° C., and stirred and reacted for 2 hours. The above reaction system was re-cooled to −78° C., and a solution of YK-CAP-113-PM2 (208.8 g, 0.52 mol) in tetrahydrofuran (400 mL) was slowly added dropwise thereto. After the dropwise addition was completed, the reaction system was warmed to room temperature, and stirred and reacted overnight. The reaction system was quenched with saturated ammonium chloride solution (2000 mL) and extracted with ethyl acetate (2000 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 20% ethyl acetate/n-hexane) to obtain YK-CAP-113-PM3 (108.8 g, 0.27 mol, 52.4%).

Step 4: Synthesis of YK-CAP-113-PM4

To a three-necked flask was added a 1 M solution of 9-BBN in tetrahydrofuran (540 mL, 0.54 mmol), and the mixture was cooled to 0° C. under nitrogen atmosphere. A solution of YK-CAP-113-PM3 (108.8 g, 0.27 mol) in tetrahydrofuran was slowly added dropwise to the above system. After the dropwise addition was completed, the mixture was stirred and reacted at room temperature for 2 hours. The reaction system was re-cooled to 0° C., and water/tetrahydrofuran (1:1)(540 mL), 2N sodium hydroxide solution (540 mL), and 30% hydrogen peroxide (460 mL) were sequentially and slowly added thereto. After the addition was completed, the reaction system was warmed to room temperature, and stirred and reacted for another 3 hours. The reaction system was diluted with ethyl acetate, and the phases were separated. The aqueous phase was back-extracted once with ethyl acetate. The organic phases were combined, dried, filtered, and the filtrate was evaporated to dryness by rotary evaporation under reduced pressure. The residue was purified by silica gel column chromatography (0 to 17% ethyl acetate/n-hexane) to obtain YK-CAP-113-PM4 (98.0 g, 0.23 mol, 86.2%).

Step 5: Synthesis of YK-CAP-113-PM5

YK-CAP-113-PM4 (20.0 g, 47.54 mmol) and sodium hydride (1369 mg, 57.04 mmol) were dissolved in dry tetrahydrofuran (100 mL), and the mixture was cooled to 0° C. Iodomethane (13.5 g, 95.11 mmol) was then added dropwise thereto under nitrogen atmosphere, and the mixture was stirred and reacted for about 5 hours. After the reaction was completed, the system was quenched with water (10 mL) and extracted with EA (200 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 20% ethyl acetate/n-hexane) to obtain YK-CAP-113-PM5 (17.8 g, 40.95 mmol, 86.1%).

Step 6: Synthesis of YK-CAP-113-PM6

Benzoyladenosine (39.2 g, 163.85 mmol) was dissolved in hexamethyldisilazane (500 mL), and a catalytic amount of ammonium sulfate was added thereto. The mixture was heated to 130° C. under nitrogen atmosphere, stirred for 12 hours, and evaporated to dryness by rotary evaporation to remove the solvent. YK-CAP-113-PM5 (17.8 g, 40.95 mmol) was dissolved in 1,2-dichloroethane (300 mL) and added to the above residue. Trimethylsilyl trifluoromethanesulfonate (10.1 g, 48.97 mmol) was then added thereto, and the mixture was reacted at 80° C. for 5 hours. TLC monitored that the reaction was complete. After filtration, the filtrate was evaporated to dryness by rotary evaporation under reduced pressure. The residue was purified by silica gel column chromatography (0 to 80% ethyl acetate/n-hexane) to obtain YK-CAP-113-PM6 (14.5 g, 22.59 mmol, 55.2%). $C_{31}H_{47}N_5O_6Si_2$, MS (ES): m/z ($M+H^+$) 642.3.

Step 7: Synthesis of YK-CAP-113-PM7

YK-CAP-113-PM6 (14.5 g, 22.59 mmol) was dissolved in tetrahydrofuran (100 mL), then tetrabutylammonium fluoride (23.6 g, 90.26 mmol) was added thereto, and the mixture was stirred and reacted at room temperature for 1 hour. The reaction system was added with saturated ammonium chloride aqueous solution and extracted with ethyl acetate (200 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 60% ethyl acetate/n-hexane) to obtain YK-CAP-113-PM7 (7.5 g, 18.78 mmol, 83.1%). $C_{19}H_{21}N_5O_5$, MS (ES): m/z ($M+H^+$) 400.2.

Step 8: Synthesis of YK-CAP-113-PM8

YK-CAP-113-PM7 (7.5 g, 18.78 mmol) was dissolved in pyridine (50 mL), then 4,4'-dimethoxytrityl chloride (10.2 g, 30.10 mmol) was added thereto at room temperature, and the mixture was stirred and reacted at room temperature for 3 hours. TLC monitored that the reaction was complete. The reaction mixture was quenched with 10 mL of methanol, stirred for 10 minutes, and subjected to rotary evaporation until no solvent was evaporated to obtain a crude product. The crude product was purified by flash column chromatography to obtain YK-CAP-113-PM8 (8.8 g, 12.54 mmol, 66.8%). $C_{40}H_{39}N_5O_7$, MS (ES): m/z ($M+H^+$) 702.3.

Step 9: Synthesis of YK-CAP-113-PM9

YK-CAP-113-PM8 (8.8 g, 12.54 mmol) was dissolved in acetonitrile (100 mL), then N-methylimidazole (1.1 g, 13.40 mmol) and bis(diisopropylamino)(2-cyanoethoxy)phosphine (11.3 g, 37.49 mmol) were sequentially added thereto, and the mixture was stirred and reacted for 6 hours under nitrogen atmosphere. TLC monitored that the reaction was complete. The reaction mixture was diluted with ethyl acetate. The organic phase was washed with saturated sodium bicarbonate aqueous solution, and the phases were separated. The organic phase was washed once with water, and the phases were separated. The aqueous phases were combined and back-extracted once with ethyl acetate. The organic phases were combined, dried over anhydrous sodium sulfate, and filtered. The organic phase was subjected to rotary evaporation under reduced pressure until no solvent was evaporated to obtain a crude product. The crude product was purified by flash column chromatography. The product fraction was evaporated to remove the solvent, then dissolved in ethyl acetate, added dropwise with ice-cold n-hexane, and stirred for 10 minutes. The residue was filtered to obtain YK-CAP-113-PM9 (8.1 g, 8.98 mmol, 71.6%). $C_{49}H_{56}N_7O_8P$, MS (ES): m/z (M−H$^-$) 900.4.

Step 10: Synthesis of YK-CAP-113-PM10

YK-CAP-113-PM9 (4.0 g, 4.43 mmol), N-isobutyryl-2', 3'-acetylguanosine (2.0 g, 4.57 mmol), and tetrazole (3.1 g, 44.25 mmol) were dissolved in acetonitrile (50 mL), and the mixture was stirred and reacted at room temperature for 3 hours under nitrogen atmosphere. The above reaction mixture was added with 0.1 M iodine solution (53 mL), stirred and reacted for another 1 hour, diluted with 200 mL of brine, and extracted with dichloromethane (200 mL×3). The organic phases were combined, dried over anhydrous sodium sulfate, filtered, and evaporated to dryness by rotary evaporation. The organic phase was subjected to rotary evaporation under reduced pressure until no solvent was evaporated to obtain YK-CAP-113-PM10 (5.2 g, 4.15 mmol, 93.5%). $C_{61}H_{64}N_{11}O_{17}P$, MS (ES): m/z (M−H$^-$) 1252.4.

Step 11: Synthesis of YK-CAP-113-PM11

YK-CAP-113-PM10 (5.2 g, 4.15 mmol) was dissolved in 80% acetic acid aqueous solution (20 mL), and the mixture was stirred and reacted at room temperature for 2 hours under nitrogen atmosphere. The reaction system was concentrated under reduced pressure to remove acetic acid, and subjected to rotary evaporation until no solvent was evaporated to obtain a crude product. The crude product was purified by flash column chromatography to obtain YK-CAP-113-PM11 (3.0 g, 3.15 mmol, 76.0%). $C_{40}H_{46}N_{11}O_{15}P$, MS (ES): m/z (M−H$^-$) 950.3.

Step 12: Synthesis of YK-CAP-113-PM12

YK-CAP-113-PM11 (3.0 g, 3.15 mmol) was dissolved in acetonitrile (30 mL), then N-methylimidazole (0.5 g, 6.09 mmol) and bis(diisopropylamino)(2-cyanoethoxy)phosphine (2.8 g, 9.29 mmol) were sequentially added thereto, and the mixture was stirred and reacted for 2 hours under nitrogen atmosphere. The above reaction mixture was added with 0.1 M iodine solution (40 mL), stirred and reacted for another 1 hour, diluted with 200 mL of brine, and extracted with dichloromethane (200 mL×3). The organic phases were combined, dried over anhydrous sodium sulfate, filtered, and evaporated to dryness by rotary evaporation. The organic phase was subjected to rotary evaporation under reduced pressure until no solvent was evaporated to obtain YK-CAP-113-PM12 (1.8 g, 1.66 mmol, 52.6%). $C_{43}H_{50}N_{12}O_{18}P_2$, MS (ES): m/z (M−H$^-$) 1083.3.

Step 13: Synthesis of YK-CAP-113-PM13

YK-CAP-113-PM12 (1.8 g, 1.66 mmol) was dissolved in a mixed solution of ammonia water (10 mL) and methanol (5 mL). The mixture was heated to 50° C. under nitrogen atmosphere, and stirred and reacted for 24 hours. The reaction system was concentrated under reduced pressure to remove the solvent, and subjected to rotary evaporation until no solvent was evaporated to obtain a crude product. The crude product was dissolved in water (50 mL) until clarified, and purified by gel column chromatography (eluted with water and 1.5 M TEAB at a ratio of 10:1). The target product peak was collected, concentrated, lyophilized, and further desalted by preparative high performance liquid chromatography (50 mM TEAB and methanol mobile phase system) to obtain YK-CAP-113-PM13 (triethylamine salt, 660 mg, 0.80 mmol, 48.4%) as a white solid. $C_{22}H_{30}N_{10}O_{14}P_2$, MS (ES): m/z (M−H$^-$) 719.1.

Step 14: Synthesis of YK-CAP-113

According to the synthesis method of YK-CAP-101, YK-CAP-113-PM11 (150 mg, 0.18 mmol) and Im-m7GDP (193 mg, 0.36 mmol) were used as starting materials to obtain YK-CAP-113 (ammonium salt, 40 mg, 33.04 μmol, 18.1%). $C_{33}H_{45}N_{15}O_{24}P_4$, MS (ES): m/z (M−H$^-$) 1158.2. $^1$H NMR (400 MHZ, $D_2O$) δ 8.44 (d, J=1.3 Hz, 1H), 8.33 (s, 1H), 8.08 (d, J=6.0 Hz, 2H), 6.02 (d, J=5.4 Hz, 1H), 5.90 (d, J=2.3 Hz, 1H), 5.82 (d, J=4.4 Hz, 1H), 4.95-4.82 (m, 3H), 4.63 (t, J=4.5 Hz, 1H), 4.53-4.31 (m, 4H), 4.26 (d, J=4.5 Hz, 1H), 4.21 (s, 3H), 4.09 (s, 1H), 3.76 (t, J=7.0 Hz, 1H), 3.43 (s, 3H), 3.35 (s, 3H), 3.21-3.11 (m, 2H), 2.42-2.35 (m, 1H). $^{31}$P NMR ($D_2O$, 162 MHz) δ−0.94 (s, 1P), −11.34 (d, J=19.2 Hz, 1P), −11.82 (d, J=17.3 Hz, 1P), −23.11 (t, J=17.3 Hz, 1P).

16. Synthesis of YK-CAP-114

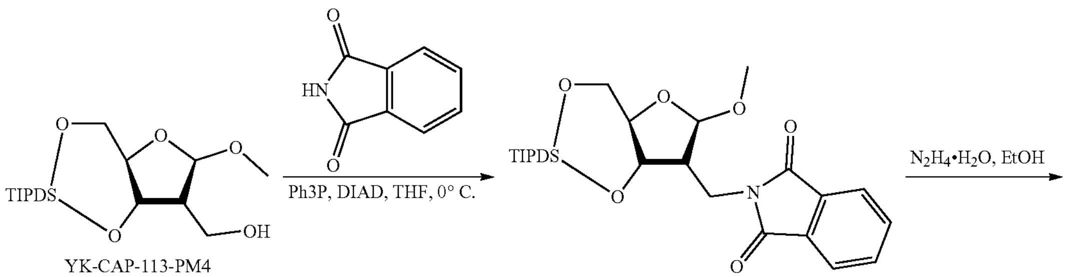

YK-CAP-113-PM4

YK-CAP-114-PM1

-continued
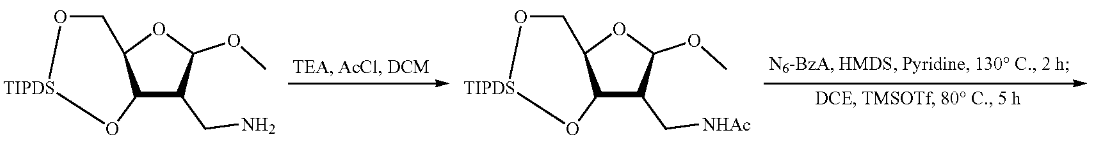
YK-CAP-114-PM2 YK-CAP-114-PM3
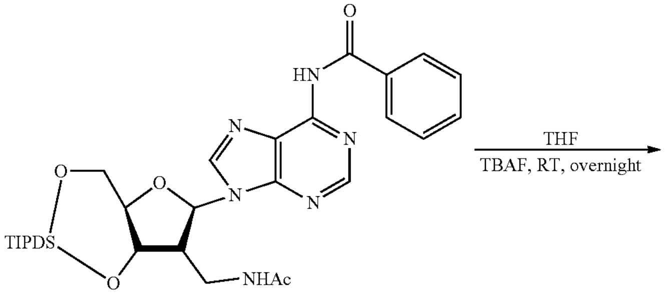
YK-CAP-114-PM4
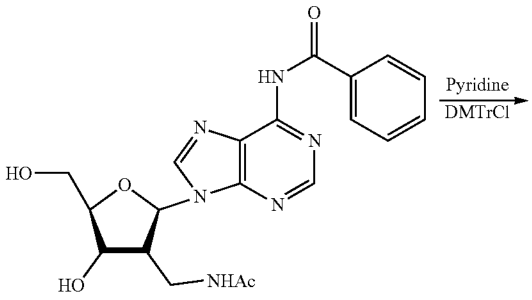
YK-CAP-114-PM5
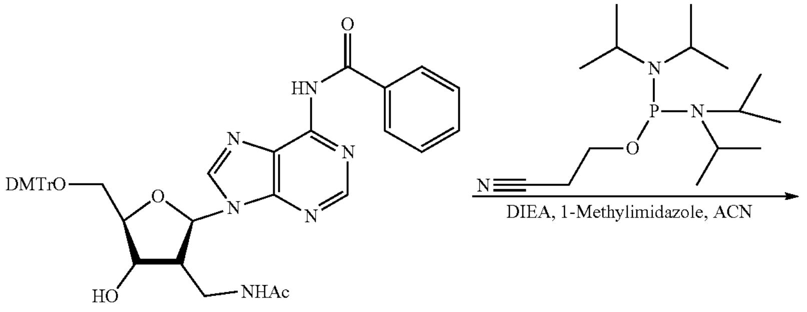
YK-CAP-114-PM6
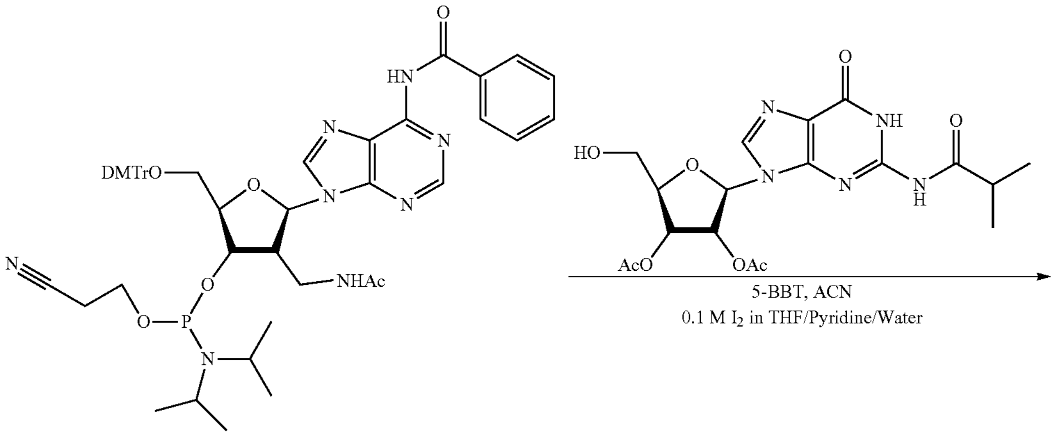
YK-CAP-114-PM7

-continued
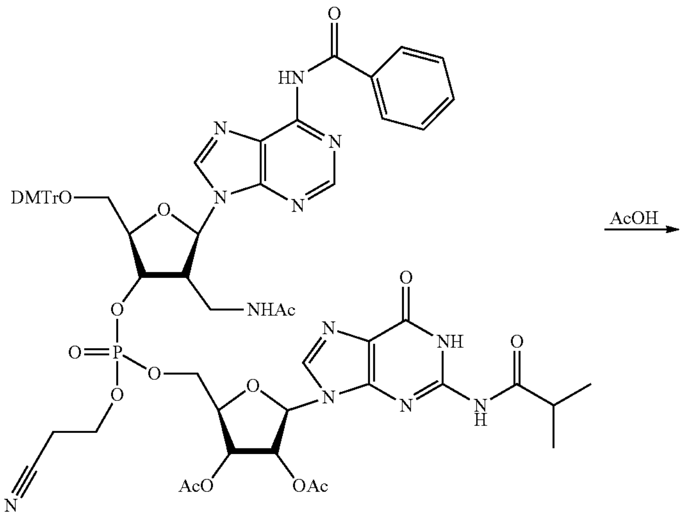
YK-CAP-114-PM8
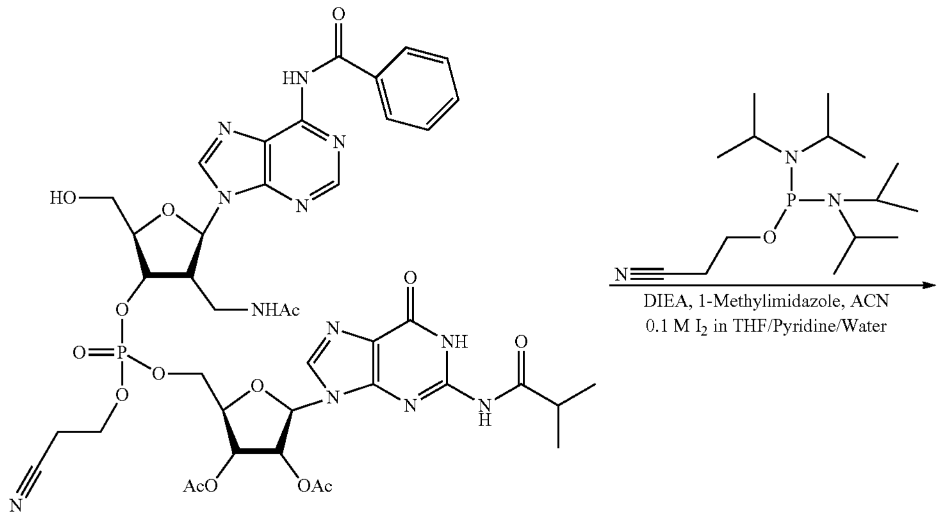
YK-CAP-114-PM9
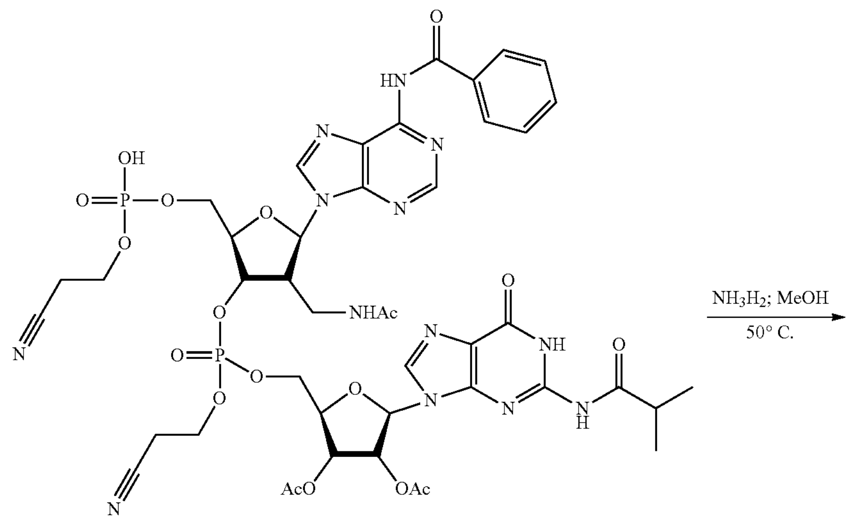
YK-CAP-114-PM10

-continued

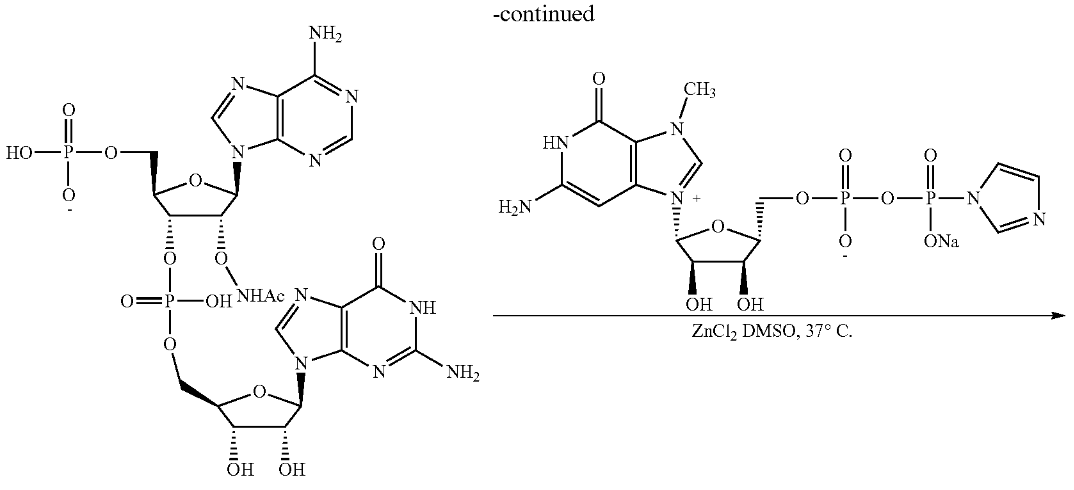

YK-CAP-114-PM11

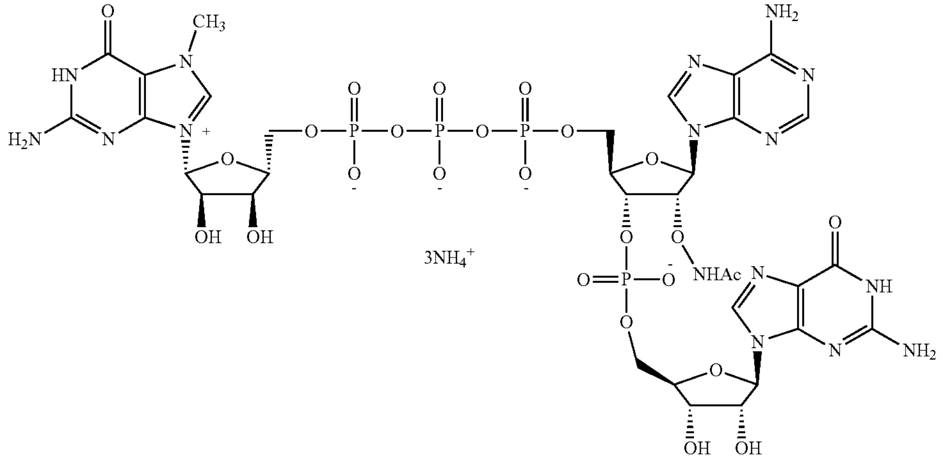

YK-CAP-114

Step 1: Synthesis of YK-CAP-114-PM1

YK-CAP-113-PM4 (13.3 g, 31.61 mmol), phthalimide (5.6 g, 38.06 mmol), triphenylphosphine (16.6 g, 63.29 mmol), and DIAD (7.7 g, 38.08 mmol) were dissolved in dry tetrahydrofuran (150 mL). The mixture was cooled to 0° C., and stirred and reacted for about 5 hours under nitrogen atmosphere. After the reaction was completed, the system was quenched with water (10 mL) and extracted with EA (200 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 20% ethyl acetate/n-hexane) to obtain YK-CAP-114-PM1 (15.9 g, 28.92 mmol, 91.5%). $C_{27}H_{43}NO_7Si_2$, MS (ES): m/z ($M+H^+$) 550.3.

Step 2: Synthesis of YK-CAP-114-PM2

YK-CAP-114-PM1 (15.9 g, 28.92 mmol) was dissolved in 300 mL of ethanol, and 50 mL of hydrazine hydrate was added thereto. The mixture was heated to 80° C., and stirred and reacted for 12 hours. After the reaction was completed, the system was quenched with water (10 mL) and extracted with EA (200 mL×3). The organic phases were combined, washed with saturated NaCl aqueous solution, dried over anhydrous sodium sulfate, filtered, and evaporated to dryness by rotary evaporation to obtain YK-CAP-114-PM2 (12.0 g, 28.59 mmol, 98.9%). $C_{19}H_{41}NO_5Si_2$, MS (ES): m/z ($M+H^+$) 420.3.

Step 3: Synthesis of YK-CAP-114-PM3

YK-CAP-114-PM2 (12.0 g, 28.59 mmol) and triethylamine (5.9 g, 58.31 mmol) were dissolved in dichloromethane (150 mL). The mixture was cooled to 0° C., and acetyl chloride (3.3 g, 42.04 mmol) was slowly added dropwise thereto. After the dropwise addition was completed, the reaction system was maintained at 0° C., and stirred and reacted for 3 hours. After the reaction was completed, the system was quenched with water (20 mL) and extracted with DCM (200 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 20% ethyl acetate/n-hexane) to obtain YK-CAP-114-PM3 (12.2 g, 26.42 mmol, 92.4%). $C_{21}H_{43}NO_6Si_2$, MS (ES): m/z ($M+H^+$) 462.3.

Step 4: Synthesis of YK-CAP-114-PM4

According to the synthesis method of YK-CAP-113-PM6, YK-CAP-114-PM3 (12.2 g, 26.42 mmol) was used as starting material to obtain YK-CAP-114-PM4 (8.5 g, 12.71 mmol, 48.1%). $C_{32}H_{48}N_{606}Si_{2}$, MS (ES): m/z ($M+H^{+}$) 669.3.

Step 5: Synthesis of YK-CAP-114-PM5

According to the synthesis method of YK-CAP-113-PM7, YK-CAP-114-PM4 (8.5 g, 12.71 mmol) was used as starting material to obtain YK-CAP-114-PM5 (4.4 g, 10.32 mmol, 81.2%). $C_{20}H_{22}N_{6}O_{5}$, MS (ES): m/z ($M+H^{+}$) 427.2.

Step 6: Synthesis of YK-CAP-114-PM6

According to the synthesis method of YK-CAP-113-PM8, YK-CAP-114-PM5 (4.4 g, 10.32 mmol) was used as starting material to obtain YK-CAP-114-PM6 (5.5 g, 7.55 mmol, 73.1%). $C_{41}H_{40}N_{6}O_{7}$, MS (ES): m/z ($M+H^{+}$) 729.3.

Step 7: Synthesis of YK-CAP-114-PM7

According to the synthesis method of YK-CAP-113-PM9, YK-CAP-114-PM6 (5.5 g, 7.55 mmol) was used as starting material to obtain YK-CAP-114-PM7 (5.0 g, 5.38 mmol, 71.3%). $C_{50}H_{57}N_{8}O_{8}P$, MS (ES): m/z ($M-H^{-}$) 927.4.

Step 8: Synthesis of YK-CAP-114-PM8

According to the synthesis method of YK-CAP-113-PM10, YK-CAP-114-PM7 (5.0 g, 5.38 mmol) was used as starting material to obtain YK-CAP-114-PM8 (5.7 g, 4.45 mmol, 82.7%). $C_{62}H_{65}N_{12}O_{17}P$, MS (ES): m/z ($M-H^{-}$) 1279.4.

Step 9: Synthesis of YK-CAP-114-PM9

According to the synthesis method of YK-CAP-113-PM11, YK-CAP-114-PM8 (5.7 g, 4.45 mmol) was used as starting material to obtain YK-CAP-114-PM9 (3.5 g, 3.58 mmol, 80.4%). $C_{41}H_{47}N_{12}O_{15}P$, MS (ES): m/z ($M-H^{-}$) 977.3.

Step 10: Synthesis of YK-CAP-114-PM10

According to the synthesis method of YK-CAP-113-PM12, YK-CAP-114-PM9 (3.5 g, 3.58 mmol) was used as starting material to obtain YK-CAP-114-PM10 (2.0 g, 1.80 mmol, 50.3%). $C_{44}H_{51}N_{13}O_{18}P_{2}$, MS (ES): m/z ($M-H^{-}$) 1110.3.

Step 11: Synthesis of YK-CAP-114-PM11

According to the synthesis method of YK-CAP-113-PM13, YK-CAP-114-PM10 (2.0 g, 1.80 mmol) was used as starting material to obtain YK-CAP-114-PM11 (triethylamine salt, 800 mg, 0.94 mmol, 52.4%). $C_{23}H_{31}N_{11}O_{14}P_{2}$, MS (ES): m/z ($M-H^{-}$) 746.2.

Step 12: Synthesis of YK-CAP-114

According to the synthesis method of YK-CAP-113, YK-CAP-114-PM11 (150 mg, 0.18 mmol) was used as starting material to obtain YK-CAP-114 (ammonium salt, 26 mg, 21.01 μmol, 11.9%). $C_{34}H_{46}N_{16}O_{24}P_{4}$, MS (ES): m/z ($M-H^{-}$) 1185.2.

$^{1}H$ NMR (400 MHZ, $D_2O$) δ 8.42 (d, J=1.4 Hz, 1H), 8.32 (s, 1H), 8.11 (d, J=6.0 Hz, 2H), 6.12 (d, J=5.4 Hz, 1H), 5.92 (d, J=2.3 Hz, 1H), 5.84 (d, J=4.3 Hz, 1H), 4.92-4.86 (m, 3H), 4.61 (t, J=4.5 Hz, 1H), 4.52-4.33 (m, 4H), 4.21 (d, J=4.5 Hz, 1H), 4.16 (s, 3H), 4.03 (s, 1H), 3.72 (t, J=6.3 Hz, 1H), 3.42 (s, 3H), 3.32-3.23 (m, 2H), 2.42-2.32 (m, 1H), 1.88 (s, 3H). $^{31}P$ NMR ($D_2O$, 162 MHz) δ-0.88 (s, 1P), -11.12 (d, J=19.1 Hz, 1P), -12.21 (d, J=17.2 Hz, 1P), -23.55 (t, J=17.1 Hz, 1P).

17. Synthesis of YK-CAP-115

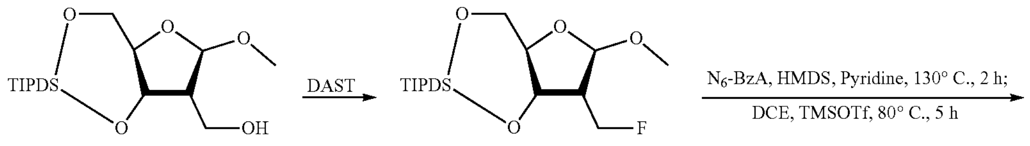

YK-CAP-113-PM4 YK-CAP-115-PM1

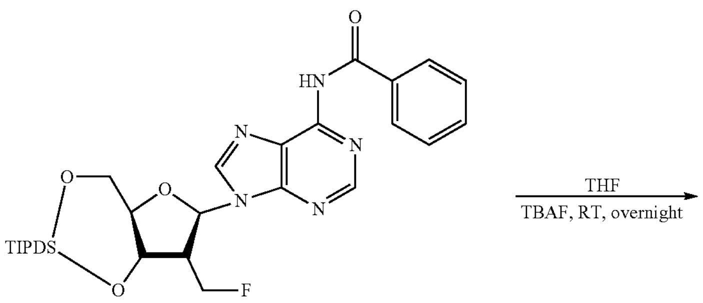

YK-CAP-115-PM2

-continued
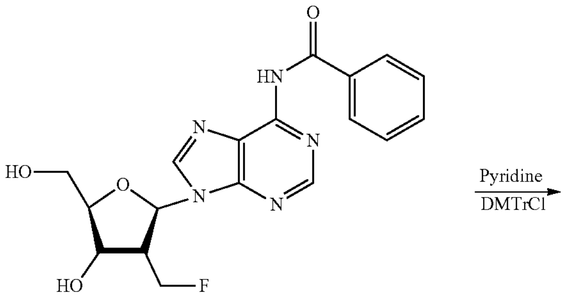
YK-CAP-115-PM3
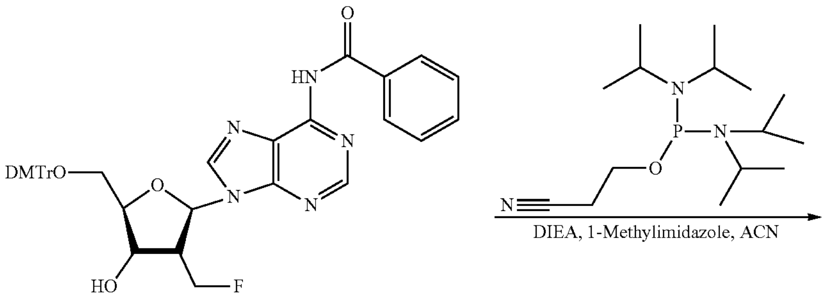
YK-CAP-115-PM4
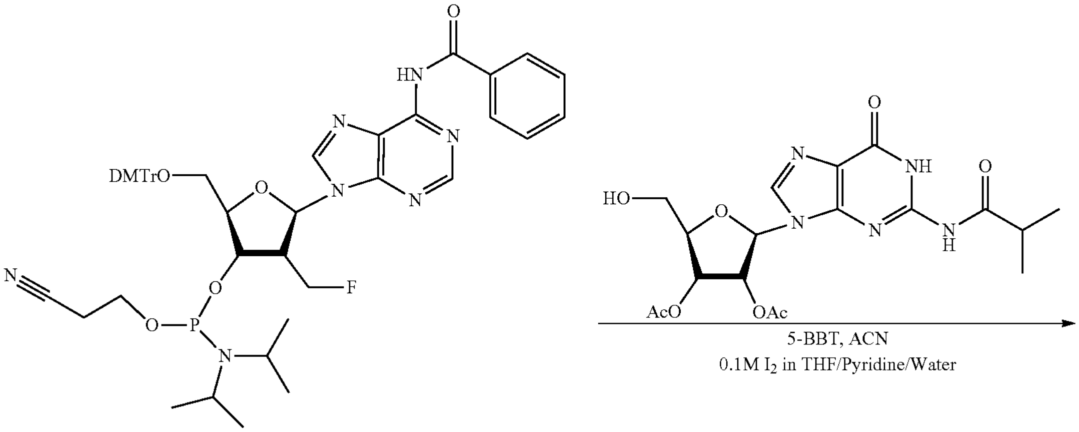
YK-CAP-115-PM5
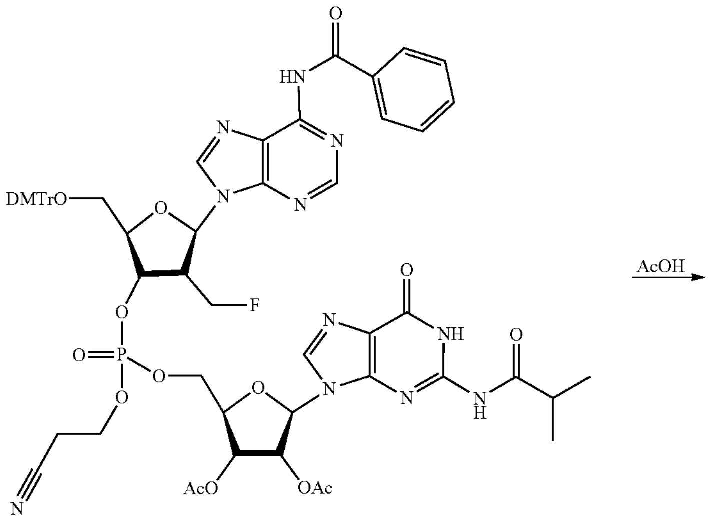
YK-CAP-115-PM6

-continued
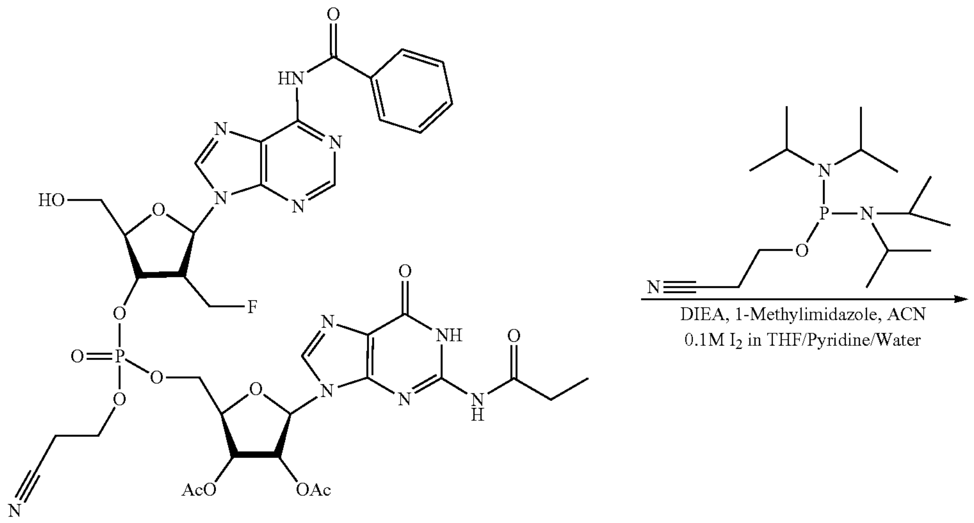
YK-CAP-115-PM7
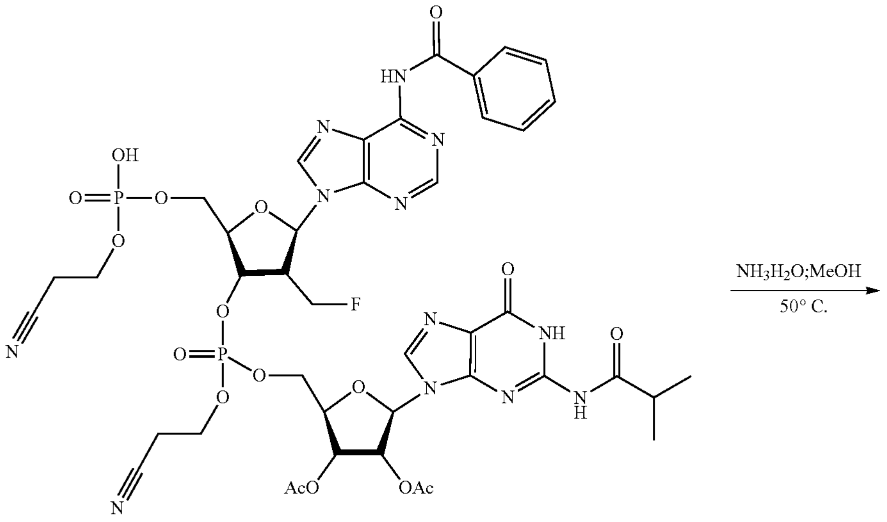
YK-CAP-115-PM8
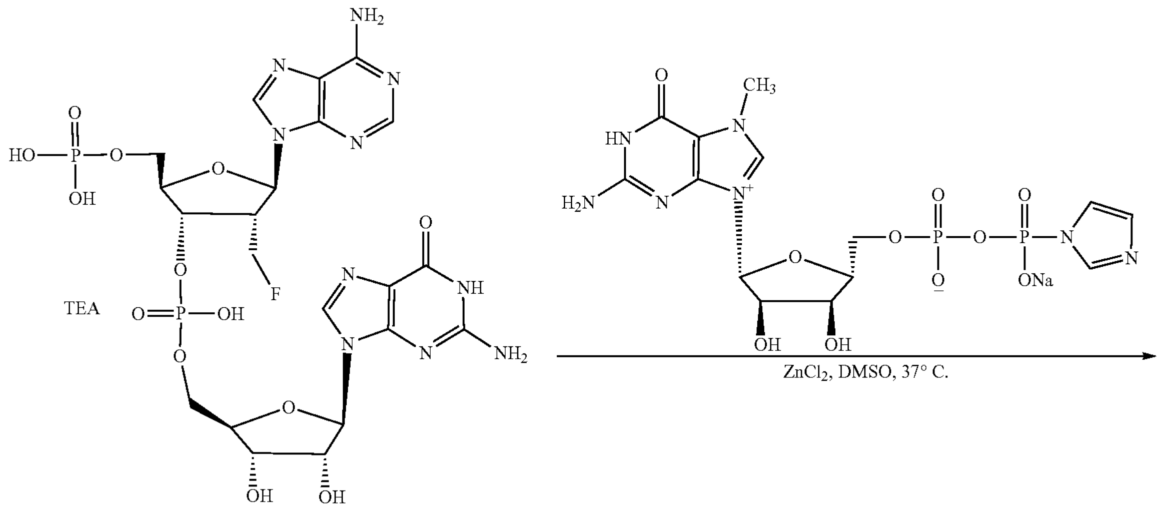
YK-CAP-115-PM9

-continued

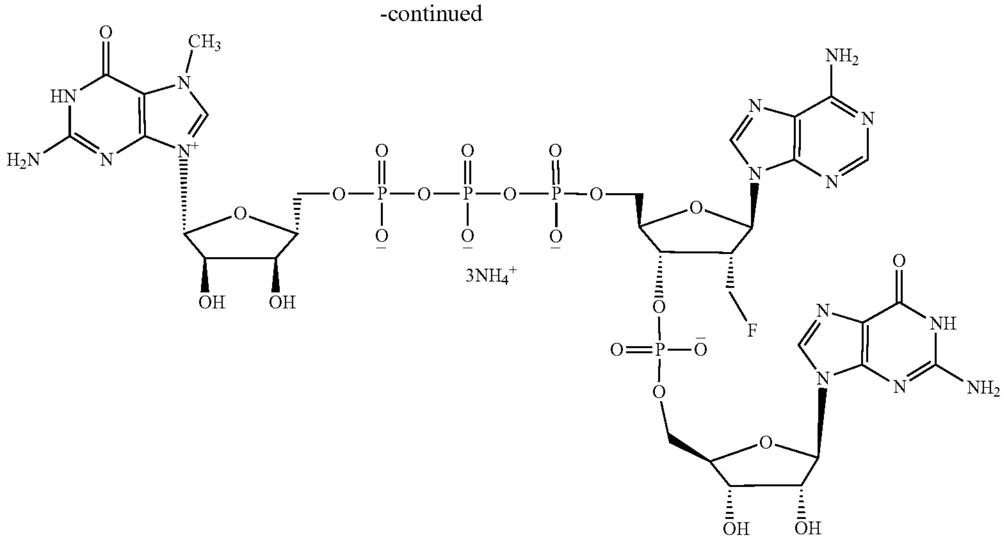

YK-CAP-115

Step 1: Synthesis of YK-CAP-115-PM1

YK-CAP-113-PM4 (20.0 g, 47.54 mmol) was dissolved in dichloromethane (200 mL). The mixture was cooled to −40° C., and a solution of diethylaminosulfur trifluoride (9.2 g, 57.08 mmol) in dichloromethane (20 mL) was slowly added dropwise thereto. After the dropwise addition was completed, the mixture was slowly warmed to 0° C., and stirred and reacted for 4 hours. TLC monitored that the reaction was complete. The reaction system was quenched with saturated sodium bicarbonate aqueous solution (100 mL) and extracted with dichloromethane (200 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 40% ethyl acetate/n-hexane) to obtain YK-CAP-115-PM1 (11.2 g, 26.50 mmol, 55.7%).

Step 2: Synthesis of YK-CAP-115-PM2

According to the synthesis method of YK-CAP-113-PM6, YK-CAP-115-PM1 (11.2 g, 26.50 mmol) was used as starting material to obtain YK-CAP-115-PM2 (8.6 g, 13.65 mmol, 51.5%). $C_{30}H_{44}FN_5O_5Si_2$, MS (ES): m/z (M+H$^+$) 630.3.

Step 3: Synthesis of YK-CAP-115-PM3

According to the synthesis method of YK-CAP-113-PM7, YK-CAP-115-PM2 (8.6 g, 13.65 mmol) was used as starting material to obtain YK-CAP-115-PM3 (4.8 g, 12.39 mmol, 90.8%). $C_{18}H_{18}FN_5O_4$, MS (ES): m/z (M−H$^-$) 388.1.

Step 4: Synthesis of YK-CAP-115-PM4

According to the synthesis method of YK-CAP-113-PM8, YK-CAP-115-PM3 (4.8 g, 12.39 mmol) was used as starting material to obtain YK-CAP-115-PM4 (5.6 g, 8.12 mmol, 65.5%). $C_{39}H_{36}FN_5O_6$, MS (ES): m/z (M−H$^-$) 690.3.

Step 5: Synthesis of YK-CAP-115-PM5

According to the synthesis method of YK-CAP-113-PM9, YK-CAP-115-PM4 (5.6 g, 8.12 mmol) was used as starting material to obtain YK-CAP-115-PM5 (5.0 g, 5.62 mmol, 69.2%). $C_{48}H_{53}FN_7O_7P$, MS (ES): m/z (M−H$^-$) 888.4.

Step 6: Synthesis of YK-CAP-115-PM6

According to the synthesis method of YK-CAP-113-PM10, YK-CAP-115-PM5 (5.0 g, 5.62 mmol) was used as starting material to obtain YK-CAP-115-PM6 (4.9 g, 3.94 mmol, 70.2%). $C_{60}H_{61}FN_{11}O_{16}P$, MS (ES): m/z (M−H$^-$) 1240.4.

Step 7: Synthesis of YK-CAP-115-PM7

According to the synthesis method of YK-CAP-113-PM11, YK-CAP-115-PM6 (4.9 g, 3.94 mmol) was used as starting material to obtain YK-CAP-115-PM7 (2.3 g, 2.45 mmol, 62.0%). $C_{39}H_{43}FN_{11}O_{14}P$, MS (ES): m/z (M−H$^-$) 938.3.

Step 8: Synthesis of YK-CAP-115-PM8

According to the synthesis method of YK-CAP-113-PM12, YK-CAP-115-PM7 (2.3 g, 2.45 mmol) was used as starting material to obtain YK-CAP-115-PM8 (2.0 g, 1.86 mmol, 76.2%). $C_{42}H_{47}FN_{12}O_{17}P_2$, MS (ES): m/z (M−H$^-$) 1071.3.

Step 9: Synthesis of YK-CAP-115-PM9

According to the synthesis method of YK-CAP-113-PM13, YK-CAP-115-PM8 (2.0 g, 1.86 mmol) was used as starting material to obtain YK-CAP-115-PM9 (triethylamine salt, 720 mg, 0.89 mmol, 47.7%). $C_{21}H_{27}FN_{10}O_{13}P_2$, MS (ES): m/z (M−H$^-$) 707.1.

Step 10: Synthesis of YK-CAP-115

According to the synthesis method of YK-CAP-113, YK-CAP-115-PM9 (150 mg, 0.19 mmol) was used as starting material to obtain YK-CAP-115 (ammonium salt, 31 mg, 25.86 μmol, 14.0%). $C_{32}H_{42}FN_{15}O_{23}P_4$, MS (ES): m/z (M−H$^-$) 1146.1.

$^1H$ NMR (400 MHZ, $D_2O$) δ 8.44 (d, J=1.4 Hz, 1H), 8.32 (s, 1H), 8.12 (d, J=6.0 Hz, 2H), 6.12 (d, J=5.2 Hz, 1H), 5.95 (d, J=2.2 Hz, 1H), 5.82 (d, J=4.2 Hz, 1H), 4.95-4.82 (m, 3H), 4.80-4.73 (m, 2H), 4.53 (t, J=4.5 Hz, 1H), 4.41-4.34 (m, 4H), 4.21 (d, J=4.1 Hz, 1H), 4.13 (s, 3H), 4.04 (s, 1H), 3.61 (t, J=6.3 Hz, 1H), 3.42 (s, 3H), 2.92-2.81 (m, 1H). 31P NMR ($D_2O$, 162 MHz) δ−0.86 (s, 1P), −11.62 (d, J=19.1 Hz, 1P), −12.41 (d, J=17.2 Hz, 1P), −22.42 (t, J=17.0 Hz, 1P).
18. Synthesis of YK-CAP-116
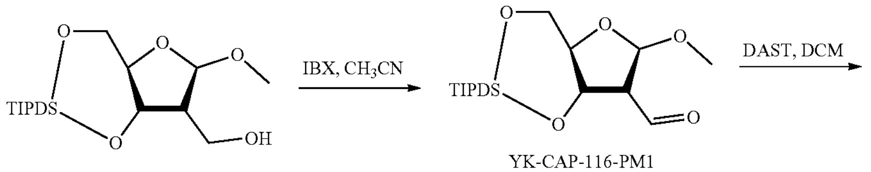
YK-CAP-113-PM4
YK-CAP-116-PM1
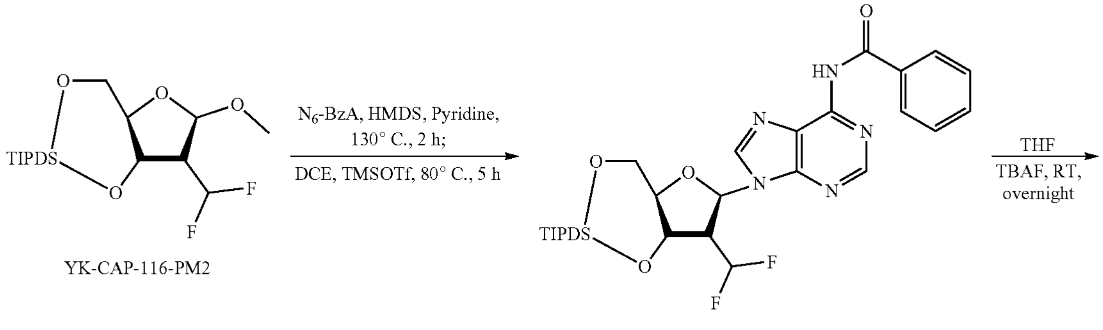
YK-CAP-116-PM2
YK-CAP-116-PM3
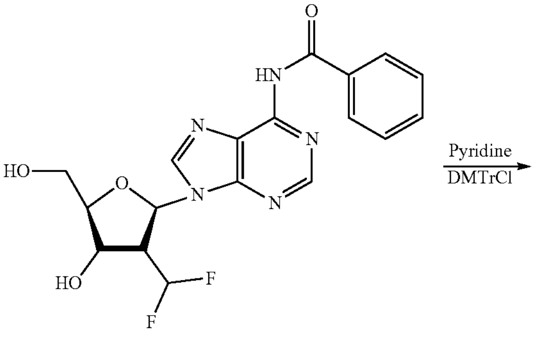
YK-CAP-116-PM4
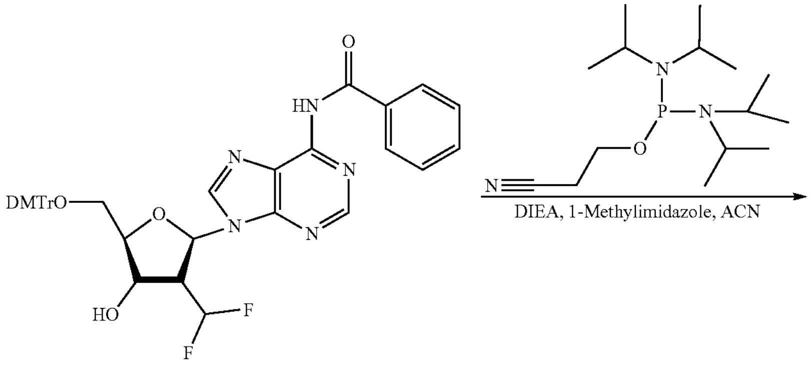
YK-CAP-116-PM5

-continued
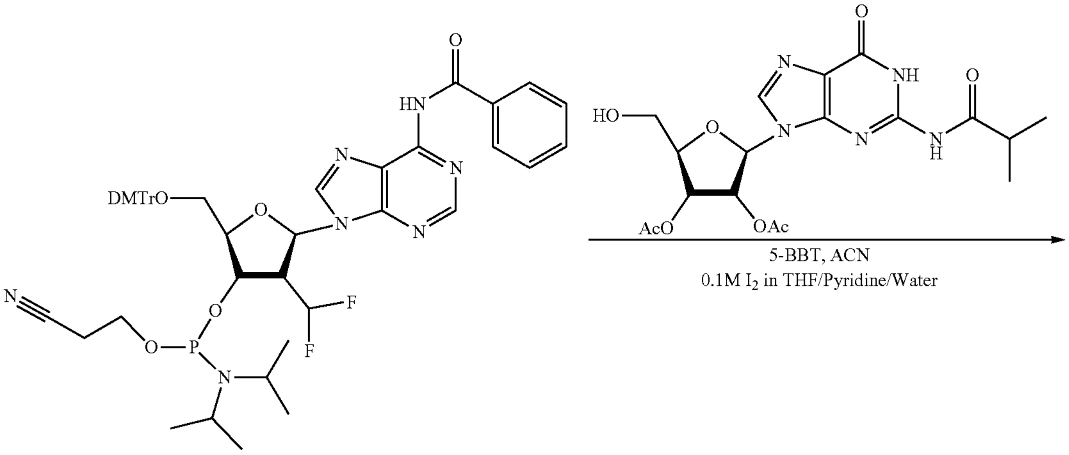
YK-CAP-116-PM6
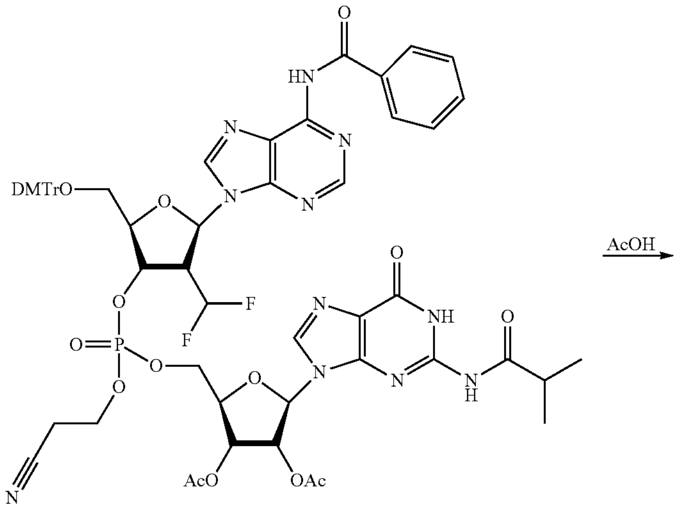
YK-CAP-116-PM7
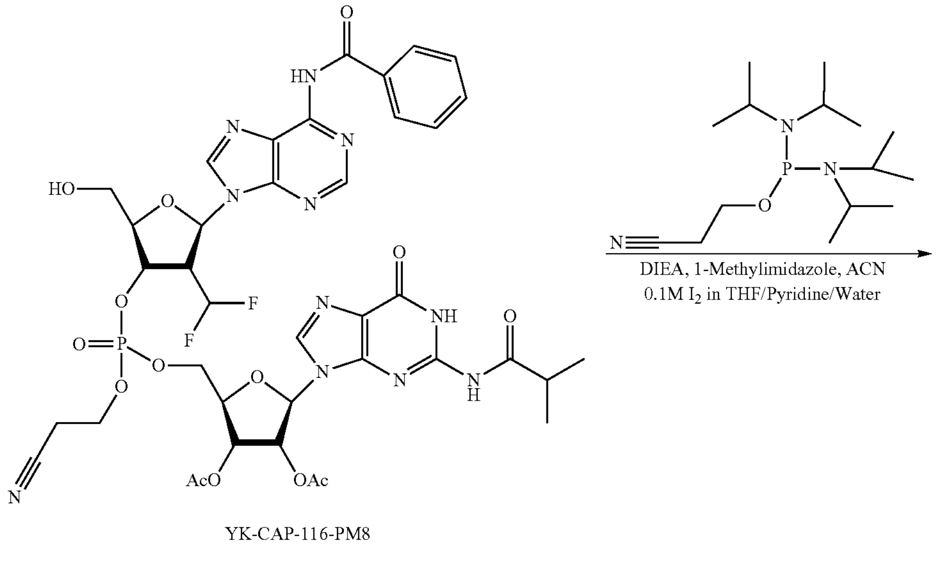
YK-CAP-116-PM8

-continued
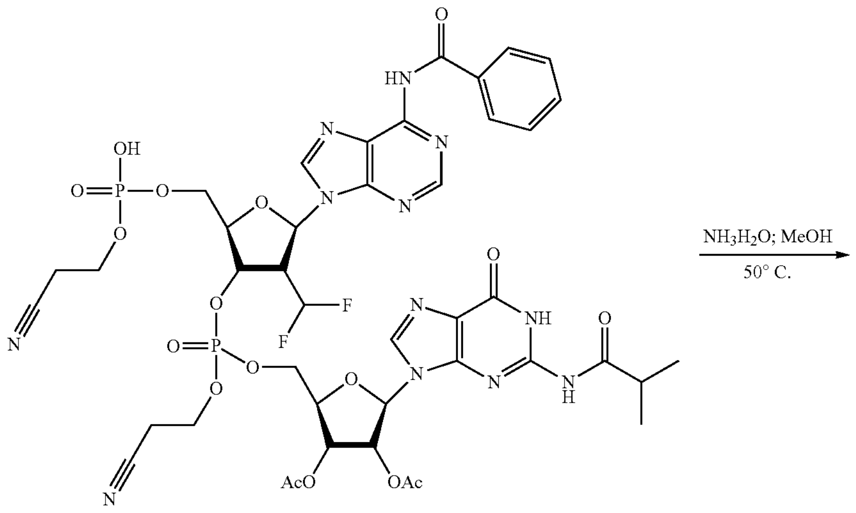
YK-CAP-116-PM9
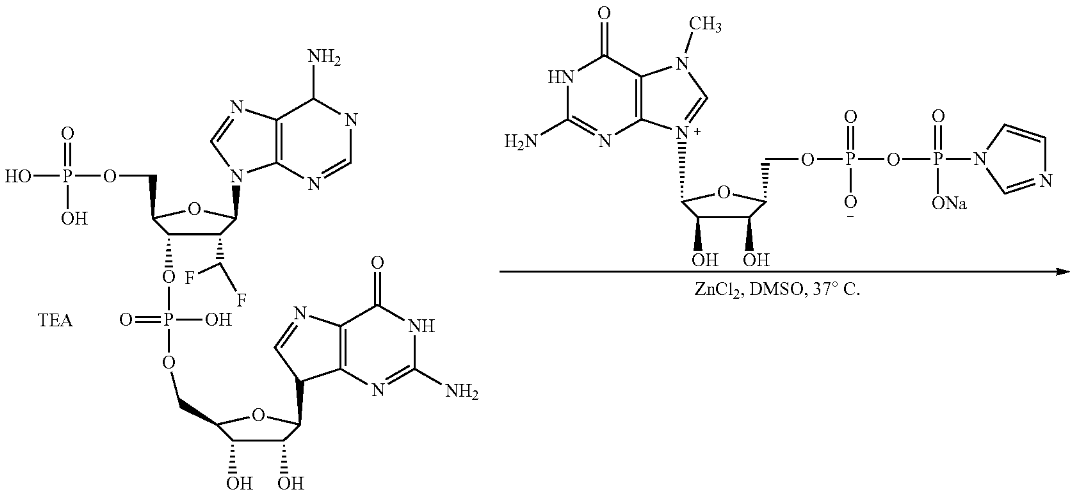
YK-CAP-116-PM10
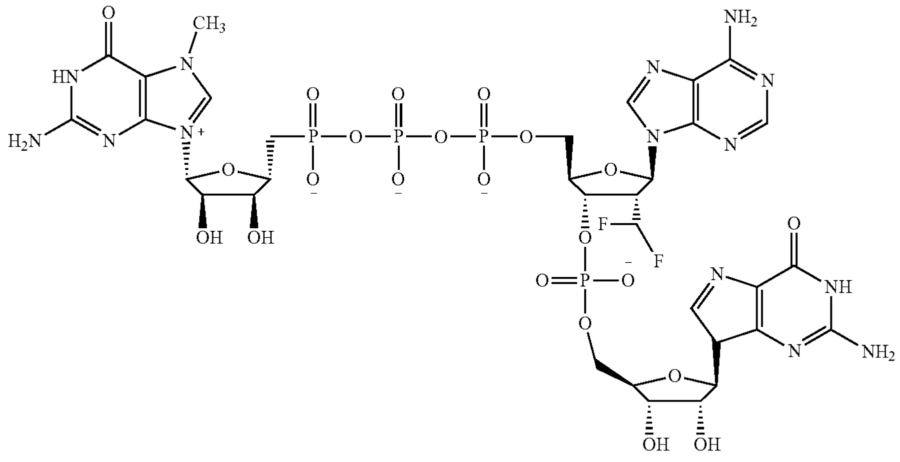
YK-CAP-116

Step 1: Synthesis of YK-CAP-116-PM1

YK-CAP-113-PM4 (20.0 g, 47.54 mmol) was dissolved in acetonitrile (200 mL), and 2-iodoxybenzoic acid (16.0 g, 57.14 mmol) was added thereto. The mixture was heated to 90° C., and stirred and reacted for 4 hours. The reaction mixture was cooled to room temperature, filtered, and the filtrate was evaporated to dryness by rotary evaporation under reduced pressure to obtain YK-CAP-116-PM1 (18.4 g, 43.95 mmol, 92.4%).

Step 2: Synthesis of YK-CAP-116-PM2

YK-CAP-116-PM1 (18.4 g, 43.95 mmol) was dissolved in dichloromethane (200 mL). The reaction system was cooled to −40° C., and a solution of diethylaminosulfur trifluoride (21.3 g, 132.14 mmol) in dichloromethane (40 mL) was slowly added dropwise thereto. After the dropwise addition was completed, the reaction system was slowly warmed to 0° C., and stirred and reacted for 4 hours. TLC monitored that the reaction was complete. The reaction system was quenched with saturated sodium bicarbonate aqueous solution (200 mL) and extracted with dichloromethane (300 mL×3). The organic phases were combined, washed with saturated NaCl aqueous solution, dried over anhydrous sodium sulfate, filtered, and evaporated to dryness by rotary evaporation. The residue was purified by silica gel chromatography (0 to 40% ethyl acetate/n-hexane) to obtain YK-CAP-116-PM2 (12.8 g, 29.05 mmol, 66.1%).

Step 3: Synthesis of YK-CAP-116-PM3

According to the synthesis method of YK-CAP-113-PM6, YK-CAP-116-PM2 (12.8 g, 29.05 mmol) was used as starting material to obtain YK-CAP-116-PM3 (9.6 g, 14.82 mmol, 51.0%). $C_{30}H_{43}F_2N_5O_5Si_2$, MS (ES): m/z (M+H$^+$) 648.3.

Step 4: Synthesis of YK-CAP-116-PM4

According to the synthesis method of YK-CAP-113-PM7, YK-CAP-116-PM3 (9.6 g, 14.82 mmol) was used as starting material to obtain YK-CAP-116-PM4 (5.2 g, 12.83 mmol, 86.6%). $C_{18}H_{17}F_2N_5O_4$, MS (ES): m/z (M+H$^+$) 406.1.

Step 5: Synthesis of YK-CAP-116-PM5

According to the synthesis method of YK-CAP-113-PM8, YK-CAP-116-PM4 (5.2 g, 12.83 mmol) was used as starting material to obtain YK-CAP-116-PM5 (6.4 g, 9.04 mmol, 70.5%). $C_{39}H_{35}F_2N_5O_6$, MS (ES): m/z (M+H$^+$) 708.3.

Step 6: Synthesis of YK-CAP-116-PM6

According to the synthesis method of YK-CAP-113-PM9, YK-CAP-116-PM5 (6.4 g, 9.04 mmol) was used as starting material to obtain YK-CAP-116-PM6 (5.5 g, 6.06 mmol, 67.0%). $C_{48}H_{52}F_2N_7O_7P$, MS (ES): m/z (M−H$^-$) 906.4.

Step 7: Synthesis of YK-CAP-116-PM7

According to the synthesis method of YK-CAP-113-PM10, YK-CAP-116-PM6 (5.5 g, 6.06 mmol) was used as starting material to obtain YK-CAP-116-PM7 (5.3 g, 4.21 mmol, 69.4%). $C_{60}H_{60}F_2N_{11}O_{16}P$, MS (ES): m/z (M−H$^-$) 1258.4.

Step 8: Synthesis of YK-CAP-116-PM8

According to the synthesis method of YK-CAP-113-PM11, YK-CAP-116-PM7 (5.3 g, 4.21 mmol) was used as starting material to obtain YK-CAP-116-PM8 (2.8 g, 2.92 mmol, 69.5%). $C_{39}H_{42}F_2N_{11}O_{14}P$, MS (ES): m/z (M−H$^-$) 956.3.

Step 9: Synthesis of YK-CAP-116-PM9

According to the synthesis method of YK-CAP-113-PM12, YK-CAP-116-PM8 (2.8 g, 2.92 mmol) was used as starting material to obtain YK-CAP-116-PM9 (2.2 g, 2.02 mmol, 69.0%). $C_{42}H_{46}F_2N_{12}O_{17}P_2$, MS (ES): m/z (M−H$^-$) 1089.3.

Step 10: Synthesis of YK-CAP-116-PM10

According to the synthesis method of YK-CAP-113-PM13, YK-CAP-116-PM9 (2.2 g, 2.02 mmol) was used as starting material to obtain YK-CAP-116-PM10 (triethylamine salt, 580 mg, 0.70 mmol, 34.7%). $C_{21}H_{26}F_2N_{10}O_{13}P_2$, MS (ES): m/z (M−H$^-$) 725.1.

Step 11: Synthesis of YK-CAP-116

According to the synthesis method of YK-CAP-113, YK-CAP-116-PM10 (150 mg, 0.18 mmol) was used as starting material to obtain YK-CAP-116 (ammonium salt, 17 mg, 13.97 μmol, 7.7%). $C_{32}H_{41}F_2N_{15}O_{23}P_4$, MS (ES): m/z (M−H$^-$) 1164.1.

$^1$H NMR (400 MHZ, $D_2O$) δ 8.52 (d, J=1.4 Hz, 1H), 8.45 (s, 1H), 8.25 (d, J=6.0 Hz, 2H), 6.29 (d, J=5.2 Hz, 1H), 6.11 (d, J=2.1 Hz, 1H), 5.89 (d, J=4.2 Hz, 1H), 4.91-4.81 (m, 3H), 4.59 (t, J=4.6 Hz, 1H), 4.42-4.31 (m, 4H), 4.25 (d, J=4.1 Hz, 1H), 4.11 (s, 2H), 4.02 (s, 1H), 3.86-3.73 (m, 2H), 3.63 (t, J=6.3 Hz, 1H), 3.43 (s, 3H), 2.41-2.27 (m, 1H). $^{31}$P NMR ($D_2O$, 162 MHz) δ −0.82 (s, 1P), −11.65 (d, J=19.1 Hz, 1P), −12.27 (d, J=17.8 Hz, 1P), −23.88 (t, J=17.3 Hz, 1P).

19. Synthesis of YK-CAP-117

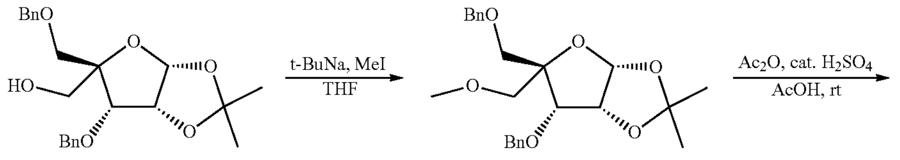

YK-CAP-117-PM1

-continued
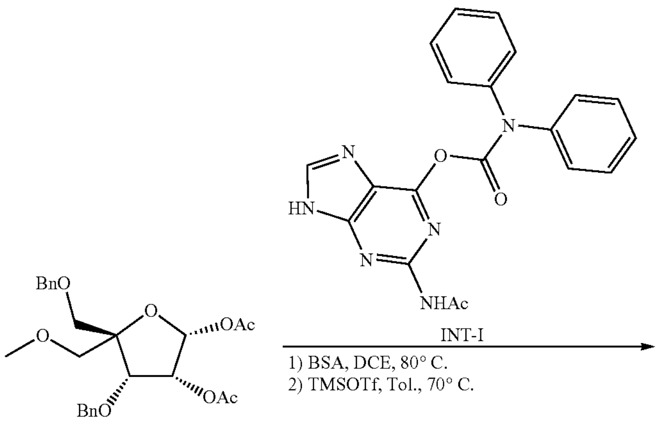
YK-CAP-117-PM2
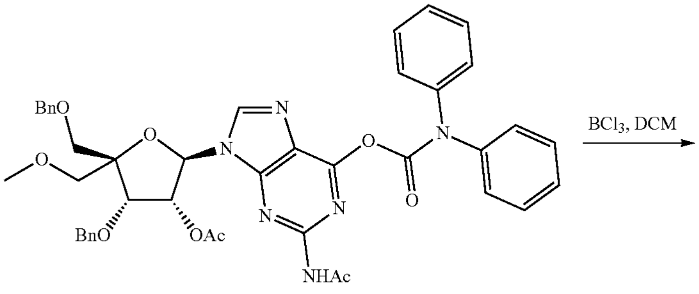
YK-CAP-117-PM3
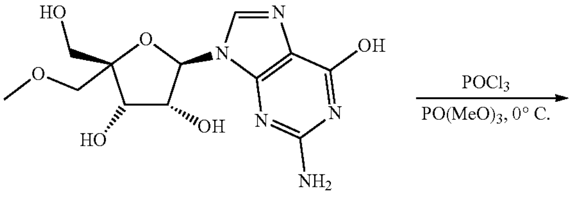
YK-CAP-117-PM4
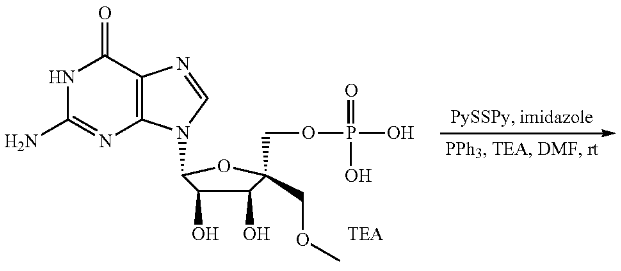
YK-CAP-117-PM5
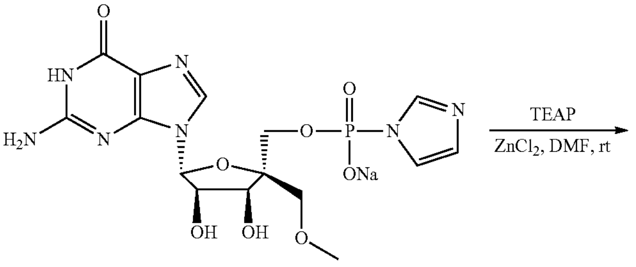
YK-CAP-117-PM6

-continued
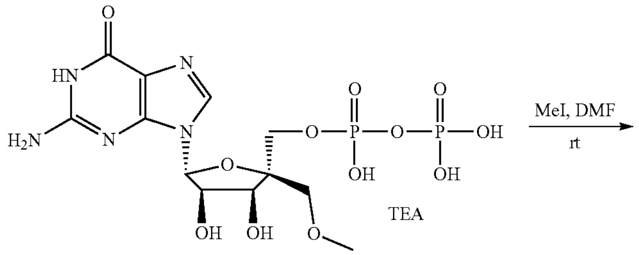
YK-CAP-117-PM7
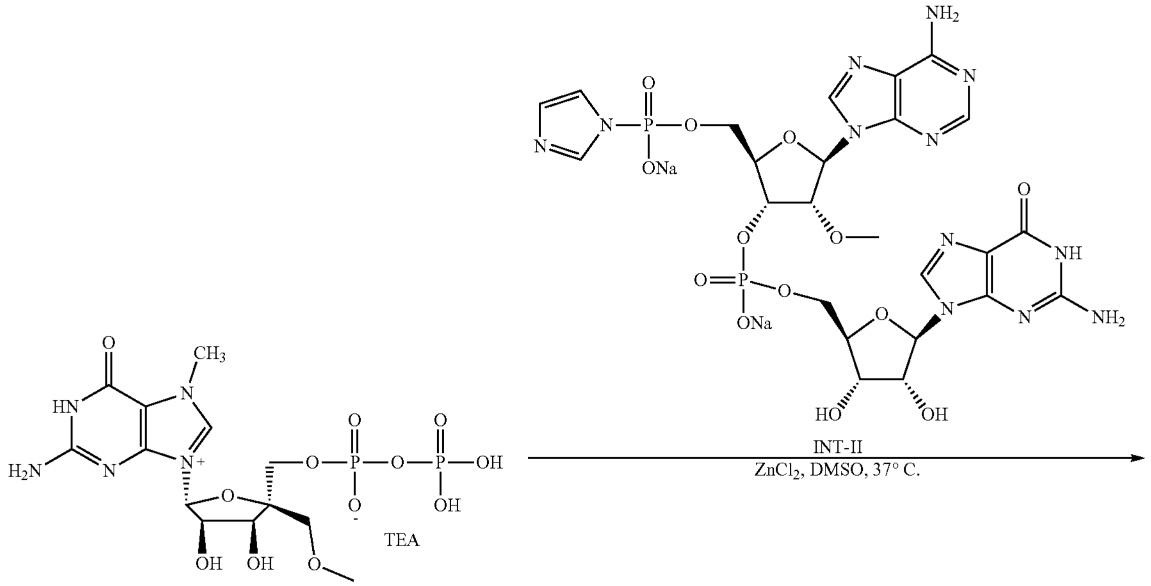
YK-CAP-117-PM8
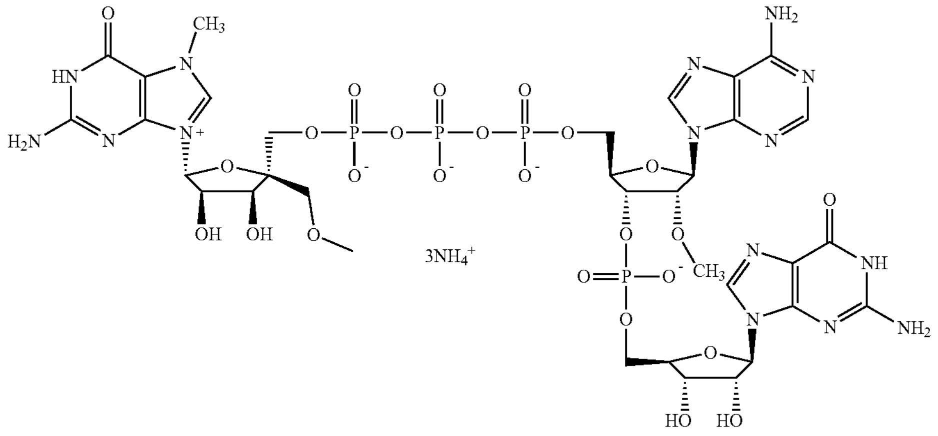
YK-CAP-117

Step 1: Synthesis of YK-CAP-117-PM1

According to the synthesis route of YK-CAP-107-PM4, 3-O-benzyl-4-C-benzyloxymethyl-1,2-O-isopropylidene-A-D-ribofuranose (10.00 g, 24.97 mmol) was used as starting material to obtain YK-CAP-117-PM1 (8.62 g, 20.80 mmol, 83.3%).

Step 2: Synthesis of YK-CAP-117-PM2

YK-CAP-117-PM1 (8.62 g, 20.80 mmol) was dissolved in acetic acid, then acetic anhydride (21.23 g, 207.95 mmol) was added thereto, and concentrated sulfuric acid (380 μL) was slowly added dropwise thereto. After the dropwise addition was completed, the mixture was stirred at room temperature for 16 hours. The reaction mixture was added with 300 mL of water and extracted with ethyl acetate. The organic phase was washed three times with saturated sodium bicarbonate aqueous solution to adjust the pH to alkalinity, then dried, and evaporated to dryness by rotary evaporation. The residue was purified by silica gel chromatography (0 to 40% ethyl acetate/n-hexane) to obtain YK-CAP-117-PM2 (8.13 g, 17.73 mmol, 85.3%) as a yellow oily liquid.

Step 3: Synthesis of YK-CAP-117-PM3

According to the synthesis route of YK-CAP-104-PM11, YK-CAP-117-PM2 (8.13 g, 17.73 mmol) was used as starting material to obtain YK-CAP-117-PM3 (6.24 g, 7.93 mmol, 44.7%). $C_{43}H_{42}N_6O_9$, MS (ES): m/z (M+H$^+$) 787.3.

Step 4: Synthesis of YK-CAP-117-PM4

YK-CAP-117-PM3 (6.24 g, 7.93 mmol) was dissolved in dichloromethane (200 mL). The above reaction system was cooled to −40° C. under nitrogen atmosphere, and a 1 M solution of boron trichloride (79.3 mL, 79.30 mmol) in dichloromethane was slowly added dropwise thereto. After the dropwise addition was completed, the reaction system was slowly warmed to 0° C. and stirred at the same temperature for 3 hours. TLC showed that the reaction was complete. The reaction system was re-cooled to −40° C., quenched with methanol, evaporated to dryness by rotary evaporation, left at room temperature for 24 hours, added dropwise with DCM to precipitate a solid, and filtered to obtain a brown crude product, which was purified by preparative HPLC to obtain YK-CAP-117-PM4 (1.19 g, 3.64 mmol, 45.8%). $C_{12}H_{17}N_6O_5$, MS (ES): m/z (M+H$^+$) 328.1.

YK-CAP-117-PM4: $^1$H NMR (400 MHZ, MeOD) δ 8.15 (s, 1H), 4.51 (s, 1H), 4.41 (s, 1H), 4.21-4.17 (m, 1H), 3.81 (s, 2H), 3.44-3.31 (m, 2H), 2.97 (s, 3H).

Step 5: Synthesis of YK-CAP-117-PM5

According to the synthesis route of YK-CAP-101-PM3, YK-CAP-117-PM4 (1.19 g, 3.64 mmol) was used as starting material to obtain YK-CAP-117-PM5 (triethylamine salt, 1.23 g, 2.42 mmol, 66.5%). $C_{12}H_{18}N_5O_9P$, MS (ES): m/z (M−H$^-$) 406.1.

Step 6: Synthesis of YK-CAP-117-PM6

According to the synthesis route of YK-CAP-101-PM4, YK-CAP-117-PM5 (1.23 g, 2.42 mmol) was used as starting material to obtain YK-CAP-117-PM6 (sodium salt, 993 mg, 2.07 mmol, 85.6%). $C_{15}H_{20}N_7O_9P$, MS (ES): m/z (M−H$^-$) 456.1.

Step 7: Synthesis of YK-CAP-117-PM7

According to the synthesis route of YK-CAP-101-PM5, YK-CAP-117-PM6 (993 mg, 2.07 mmol) was used as starting material to obtain YK-CAP-117-PM7 (triethylamine salt, 794 mg, 1.35 mmol, 65.1%). $C_{12}H_{19}N_5O_{12}P_2$, MS (ES): m/z (M−H$^-$) 486.1.

Step 8: Synthesis of YK-CAP-117-PM8

According to the synthesis route of YK-CAP-101-PM6, YK-CAP-117-PM7 (794 mg, 1.35 mmol) was used as starting material to obtain YK-CAP-117-PM8 (triethylamine salt, 520 mg, 0.86 mmol, 64.0%). $C_{13}H_{21}N_5O_{12}P_2$, MS (ES): m/z (M−H$^-$) 500.1.

Step 9: Synthesis of YK-CAP-117

According to the synthesis route of YK-CAP-101, YK-CAP-117-PM8 (150 mg, 0.25 mmol) was used as starting material to obtain YK-CAP-117 (ammonium salt, 26 mg, 20.95 μmol, 8.4%). $C_{34}H_{47}N_{15}O_{25}P_4$, MS (ES): m/z (M−H$^-$) 1188.1.

$^1$H NMR (400 MHZ, $D_2O$) δ 8.44 (d, J=1.5 Hz, 1H), 8.26 (d, J=2.5 Hz, 2H), 8.15 (d, J=4.5 Hz, 1H), 6.31 (d, J=5.2 Hz, 1H), 5.72 (d, J=2.4 Hz, 1H), 5.51 (d, J=4.6 Hz, 1H), 4.90-4.86 (m, 3H), 4.60 (t, J=4.7 Hz, 1H), 4.50-4.38 (m, 5H), 4.22 (d, J=2.9 Hz, 1H), 4.13 (s, 2H), 4.05 (s, 2H), 3.92 (s, 3H), 3.54 (t, J=7.0 Hz, 2H), 3.44-3.31 (m, 3H), 2.97 (s, 3H). $^{31}$P NMR ($D_2O$, 162 MHz) δ−0.91 (s, 1P), −11.22 (d, J=19.1 Hz, 1P), −11.32 (d, J=16.4 Hz, 1P), −22.12 (t, J=17.4 Hz, 1P).

20. Synthesis of YK-CAP-118

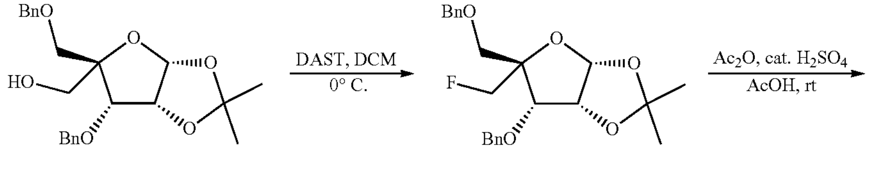

YK-CAP-118-PM1

-continued
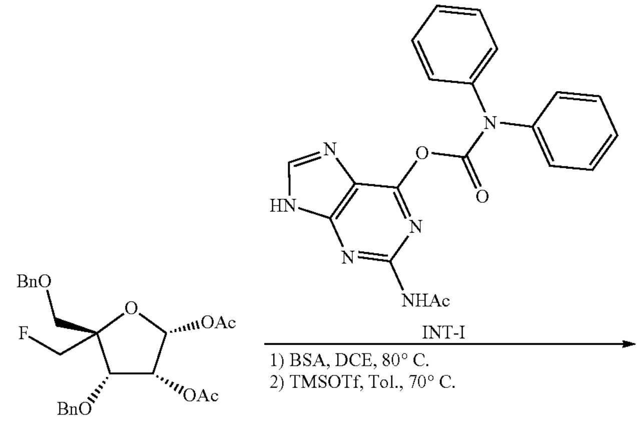
YK-CAP-118-PM2
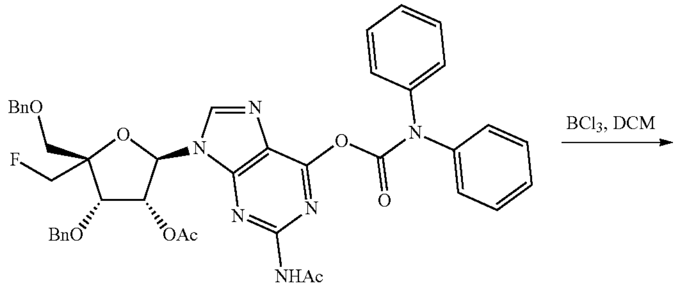
YK-CAP-118-PM3
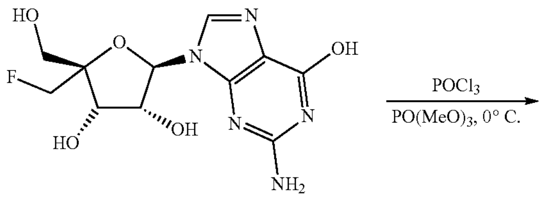
YK-CAP-118-PM4
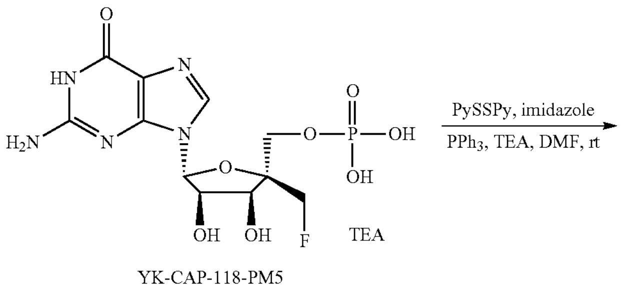
YK-CAP-118-PM5
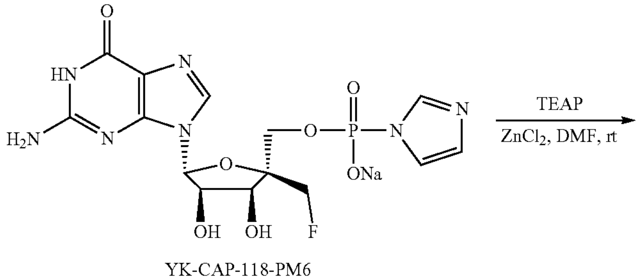
YK-CAP-118-PM6

-continued

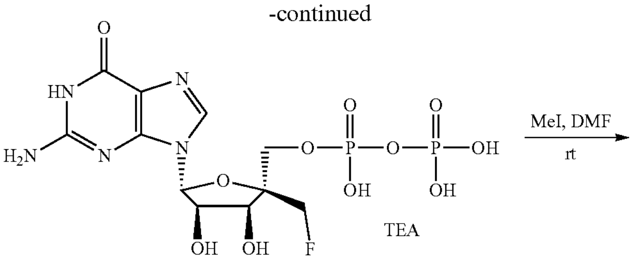

YK-CAP-118-PM7

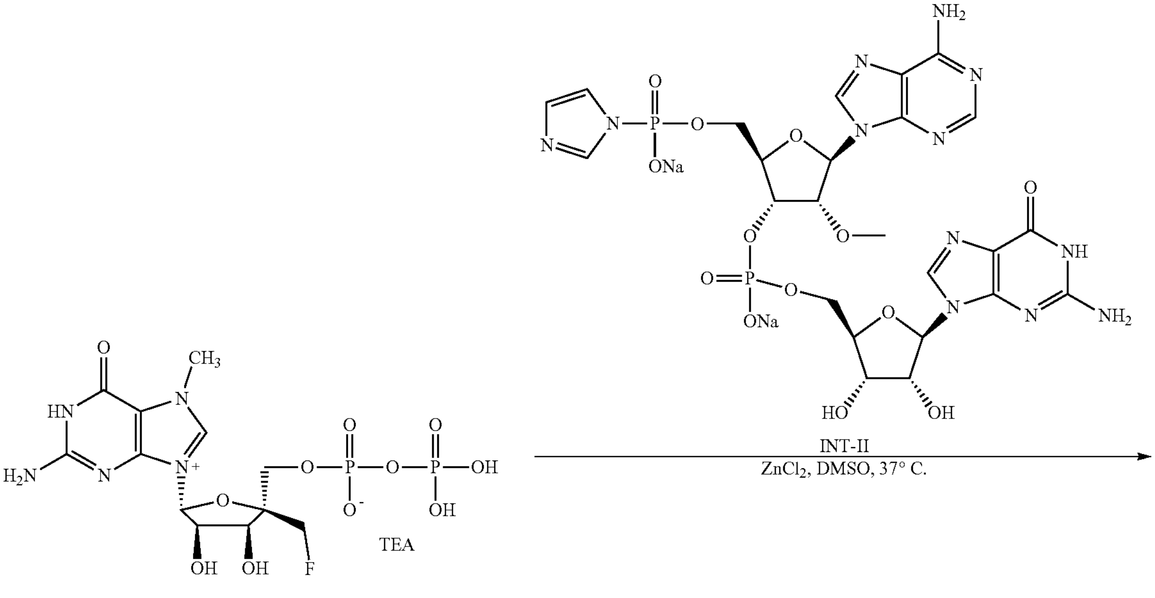

YK-CAP-118-PM8

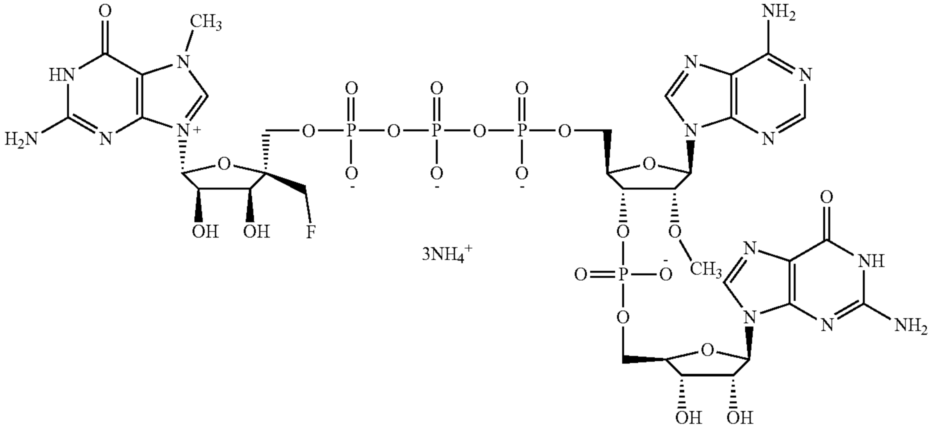

YK-CAP-118

Step 1: Synthesis of YK-CAP-118-PM1

According to the synthesis route of YK-CAP-109-PM1, 3-O-benzyl-4-C-benzyloxymethyl-1,2-O-isopropylidene-A-D-ribofuranose (10.00 g, 24.97 mmol) was used as starting material to obtain YK-CAP-118-PM1 (9.11 g, 22.64 mmol, 90.6%).

Step 2: Synthesis of YK-CAP-118-PM2

According to the synthesis route of YK-CAP-117-PM2, YK-CAP-118-PM1 (9.11 g, 22.64 mmol) was used as starting material to obtain YK-CAP-118-PM2 (7.18 g, 16.08 mmol, 71.0%).

Step 3: Synthesis of YK-CAP-118-PM3

According to the synthesis route of YK-CAP-104-PM11, YK-CAP-118-PM2 (7.18 g, 16.08 mmol) was used as starting material to obtain YK-CAP-118-PM3 (6.64 g, 8.57 mmol, 53.3%). $C_{42}H_{39}FN_6O_8$, MS (ES): m/z (M+H$^+$) 775.3.

Step 4: Synthesis of YK-CAP-118-PM4

According to the synthesis route of YK-CAP-117-PM4, YK-CAP-118-PM3 (6.64 g, 8.57 mmol) was used as starting material to obtain YK-CAP-118-PM4 (2.31 g, 7.33 mmol, 85.5%). $C_{11}H_{14}FN_5O_5$, MS (ES): m/z (M+H$^+$) 316.1.

YK-CAP-118-PM4: $^1$H NMR (400 MHZ, MeOD) δ 8.12 (s, 1H), 4.51 (s, 1H), 4.40 (s, 1H), 4.27-4.22 (m, 1H), 3.88 (s, 2H), 3.72-3.62 (m, 2H).

Step 5: Synthesis of YK-CAP-118-PM5

According to the synthesis route of YK-CAP-101-PM3, YK-CAP-118-PM4 (1.30 g, 4.12 mmol) was used as starting material to obtain YK-CAP-118-PM5 (triethylamine salt, 1.15 g, 2.32 mmol, 56.2%). $C_{11}H_{15}FN_5O_8P$, MS (ES): m/z (M–H$^-$) 394.1.

Step 6: Synthesis of YK-CAP-118-PM6

According to the synthesis route of YK-CAP-101-PM4, YK-CAP-118-PM5 (1.15 g, 2.32 mmol) was used as starting material to obtain YK-CAP-118-PM6 (sodium salt, 870 mg, 1.86 mmol, 80.4%). $C_{14}H_{17}FN_7O_7P$, MS (ES): m/z (M–H$^-$) 444.1.

Step 7: Synthesis of YK-CAP-118-PM7

According to the synthesis route of YK-CAP-101-PM5, YK-CAP-118-PM6 (870 mg, 1.86 mmol) was used as starting material to obtain YK-CAP-118-PM7 (triethylamine salt, 664 mg, 1.15 mmol, 61.9%). $C_{11}H_{16}FN_5O_{11}P_2$, MS (ES): m/z (M–H$^-$) 474.1.

Step 8: Synthesis of YK-CAP-118-PM8

According to the synthesis route of YK-CAP-101-PM6, YK-CAP-118-PM7 (664 mg, 1.15 mmol) was used as starting material to obtain YK-CAP-118-PM8 (triethylamine salt, 419 mg, 0.71 mmol, 61.6%). $C_{12}H_{18}FN_5O_{11}P_2$, MS (ES): m/z (M–H$^-$) 488.1.

Step 9: Synthesis of YK-CAP-118

According to the synthesis route of YK-CAP-101, YK-CAP-118-PM8 (150 mg, 0.25 mmol) was used as starting material to obtain YK-CAP-118 (ammonium salt, 33 mg, 26.86 μmol, 10.7%). $C_{33}H_{44}FN_{15}O_{24}P_4$, MS (ES): m/z (M–H$^-$) 1176.1.

$^1$H NMR (400 MHZ, $D_2O$) δ 8.37 (d, J=1.2 Hz, 1H), 8.33-8.21 (m, 1H), 8.14 (d, J=4.5 Hz, 2H), 6.33 (d, J=5.1 Hz, 1H), 5.61 (d, J=2.3 Hz, 1H), 5.45 (d, J=4.6 Hz, 1H), 4.92-4.83 (m, 3H), 4.63-4.55 (m, 2H), 4.50-4.38 (m, 4H), 4.31 (d, J=2.9 Hz, 1H), 4.11 (s, 2H), 4.01 (s, 2H), 3.90-3.76 (m, 3H), 3.52 (t, J=7.0 Hz, 2H), 3.46-3.34 (m, 3H). $^{31}$P NMR ($D_2O$, 162 MHz) δ–0.90 (s, 1P), –11.23 (d, J=19.1 Hz, 1P), –11.59 (d, J=16.0 Hz, 1P), –22.33 (t, J=17.2 Hz, 1P).

21. Synthesis of YK-CAP-119

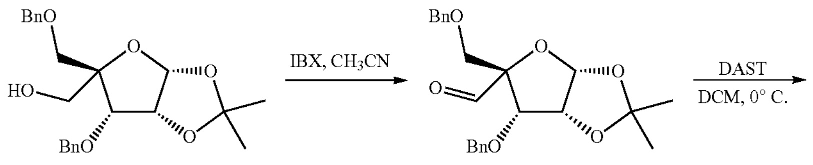

YK-CAP-119-PM1

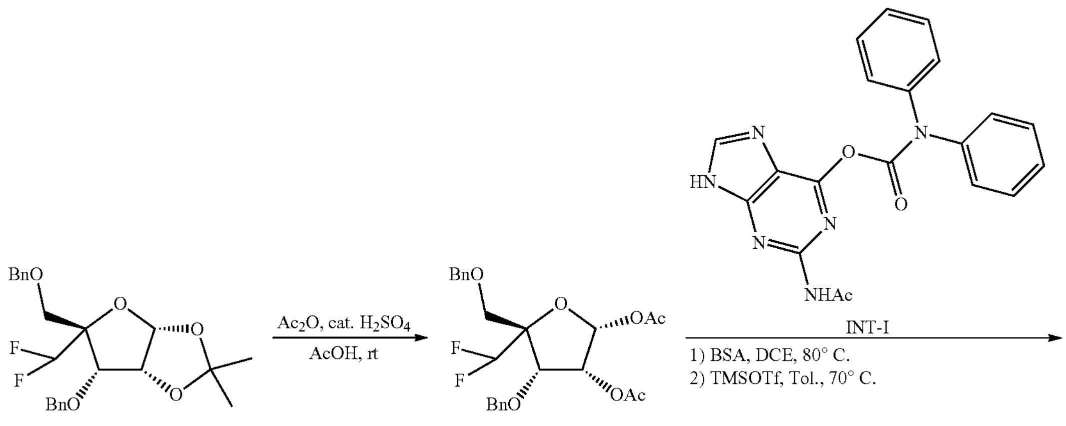

YK-CAP-119-PM2

YK-CAP-119-PM3

-continued
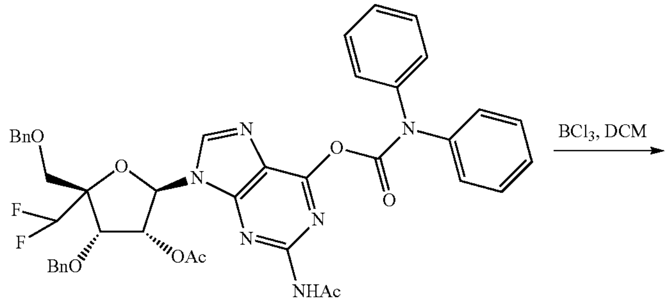
YK-CAP-119-PM4
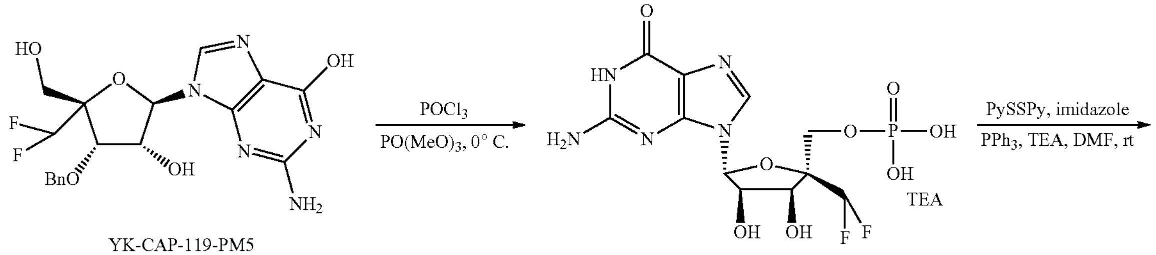
YK-CAP-119-PM5
YK-CAP-119-PM6
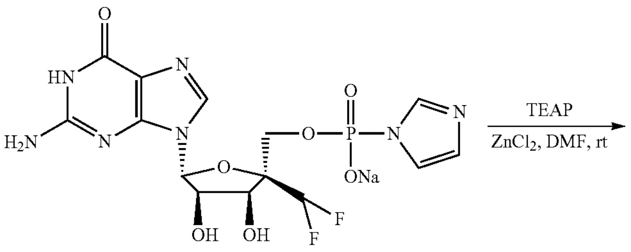
YK-CAP-119-PM7
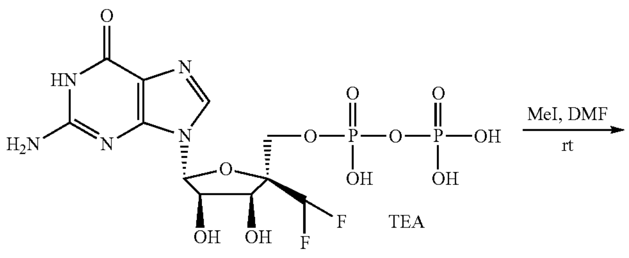
YK-CAP-119-PM8

-continued

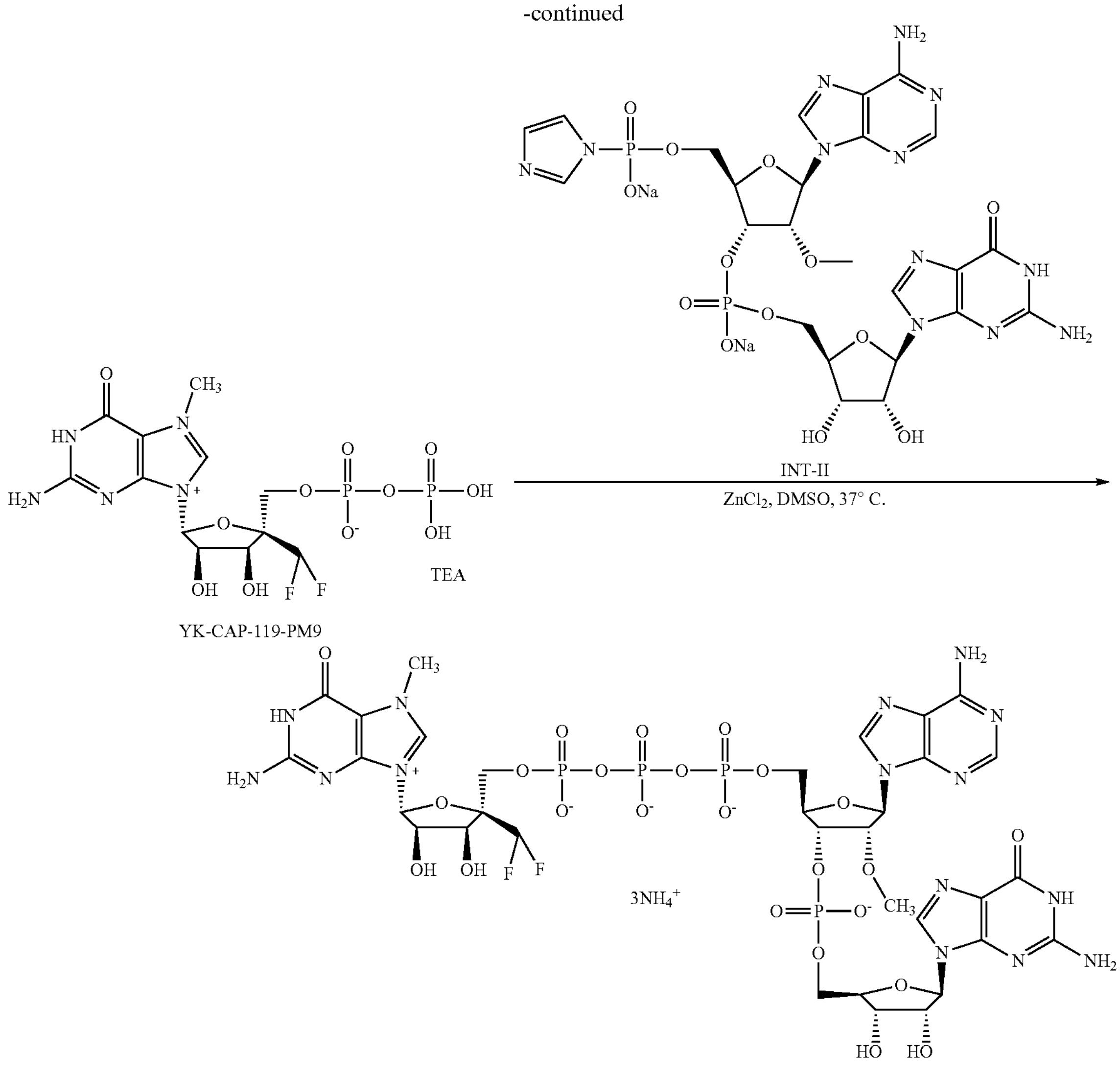

YK-CAP-119-PM9

YK-CAP-119

Step 1: Synthesis of YK-CAP-119-PM1

3-O-benzyl-4-C-benzyloxymethyl-1,2-O-isopropylidene-A-D-ribofuranose (10.0 g, 24.97 mmol) was dissolved in 50 mL of acetonitrile, and 2-iodoxybenzoic acid (10.49 g, 37.46 mmol) was added thereto. The mixture was heated to 70° C., and stirred and reacted for 2 hours. TLC monitored that the reaction was complete. The reaction was terminated. The reaction mixture was cooled to room temperature, then filtered through diatomite, and the filter cake was rinsed with acetonitrile (50 mL). The filtrate was evaporated to dryness by rotary evaporation under reduced pressure and dried under vacuum to obtain YK-CAP-119-PM1 (10.21 g) as a light yellow liquid, which was directly used in the next step (the yield was calculated as 100%).

Step 2: Synthesis of YK-CAP-119-PM2

According to the synthesis route of YK-CAP-110-PM1, YK-CAP-119-PM1 (10.21 g, calculated as 24.97 mmol) was used as starting material to obtain YK-CAP-119-PM2 (8.16 g, 19.41 mmol, 77.7%).

Step 3: Synthesis of YK-CAP-119-PM3

According to the synthesis route of YK-CAP-117-PM2, YK-CAP-119-PM2 (8.16 g, 19.41 mmol) was used as starting material to obtain YK-CAP-119-PM3 (6.55 g, 14.10 mmol, 72.7%).

Step 4: Synthesis of YK-CAP-119-PM4

According to the synthesis route of YK-CAP-104-PM11, YK-CAP-119-PM3 (6.55 g, 14.10 mmol) was used as starting material to obtain YK-CAP-119-PM4 (5.77 g, 7.28 mmol, 51.6%). $C_{42}H_{38}F_2N_6O_8$, MS (ES): m/z $(M+H^+)$ 793.3.

Step 5: Synthesis of YK-CAP-119-PM5

According to the synthesis route of YK-CAP-117-PM4, YK-CAP-119-PM4 (5.77 g, 7.28 mmol) was used as starting material to obtain YK-CAP-119-PM5 (2.16 g, 6.48 mmol, 89.0%). $C_{11}H_{13}F_2N_5O_5$, MS (ES): m/z $(M+H^+)$ 334.1.

YK-CAP-119-PM5: $^{1}$H NMR (400 MHZ, MeOD) δ 8.24 (s, 1H), 4.77 (s, 1H), 4.56 (s, 1H), 4.51 (s, 1H), 4.27-4.22 (m, 1H), 3.72-3.62 (m, 2H).

Step 6: Synthesis of YK-CAP-119-PM6

According to the synthesis route of YK-CAP-101-PM3, YK-CAP-119-PM5 (1.50 g, 4.50 mmol) was used as starting material to obtain YK-CAP-119-PM6 (triethylamine salt, 1.29 g, 2.51 mmol, 55.7%). $C_{11}H_{14}F_2N_5O_8P$, MS (ES): m/z (M−H$^-$) 412.1.

Step 7: Synthesis of YK-CAP-119-PM7

According to the synthesis route of YK-CAP-101-PM4, YK-CAP-119-PM6 (1.29 g, 2.51 mmol) was used as starting material to obtain YK-CAP-119-PM7 (sodium salt, 991 mg, 2.04 mmol, 81.4%). $C_{14}H_{16}F_2N_7O_7P$, MS (ES): m/z (M−H$^-$) 462.1.

Step 8: Synthesis of YK-CAP-119-PM8

According to the synthesis route of YK-CAP-101-PM5, YK-CAP-119-PM7 (991 mg, 2.04 mmol) was used as starting material to obtain YK-CAP-119-PM8 (triethylamine salt, 774 mg, 1.30 mmol, 63.8%). $C_{11}H_{15}F_2N_5O_{11}P_2$, MS (ES): m/z (M−H$^-$) 492.0.

Step 9: Synthesis of YK-CAP-119-PM9

According to the synthesis route of YK-CAP-101-PM6, YK-CAP-119-PM8 (774 mg, 1.30 mmol) was used as starting material to obtain YK-CAP-119-PM9 (triethylamine salt, 533 mg, 0.88 mmol, 67.3%). $C_{12}H_{17}F_2N_5O_{11}P_2$, MS (ES): m/z (M−H$^-$) 506.1.

Step 10: Synthesis of YK-CAP-119

According to the synthesis route of YK-CAP-101, YK-CAP-119-PM9 (150 mg, 0.25 mmol) was used as starting material to obtain YK-CAP-119 (ammonium salt, 32 mg, 25.67 μmol, 10.3%). $C_{33}H_{43}F_2N_{15}O_{24}P_4$, MS (ES): m/z (M−H$^-$) 1194.1.

$^{1}$H NMR (400 MHZ, $D_2O$) δ 8.35 (d, J=1.2 Hz, 1H), 8.30-8.19 (m, 1H), 8.12 (d, J=4.4 Hz, 2H), 6.25 (d, J=5.2 Hz, 1H), 5.65 (d, J=2.2 Hz, 1H), 5.27 (d, J=4.5 Hz, 1H), 4.93-4.88 (m, 3H), 4.83-4.79 (s, 1H), 4.66-4.57 (m, 2H), 4.51-4.42 (m, 5H), 4.22 (d, J=2.9 Hz, 1H), 4.04 (s, 2H), 3.88-3.75 (m, 3H), 3.42 (t, J=7.0 Hz, 1H), 3.36-3.31 (m, 3H). $^{31}$P NMR ($D_2O$, 162 MHz) δ−0.93 (s, 1P), −12.13 (d, J=19.1 Hz, 1P), −13.31 (d, J=16.1 Hz, 1P), −24.57 (t, J=17.4 Hz, 1P).

22. Synthesis of Compound 5227

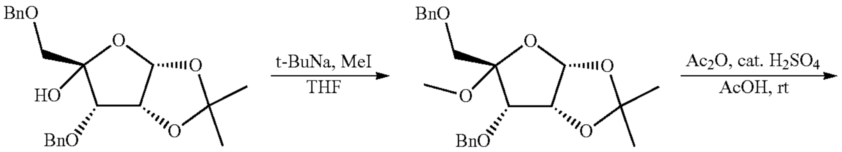

5227-S 5227-PM1

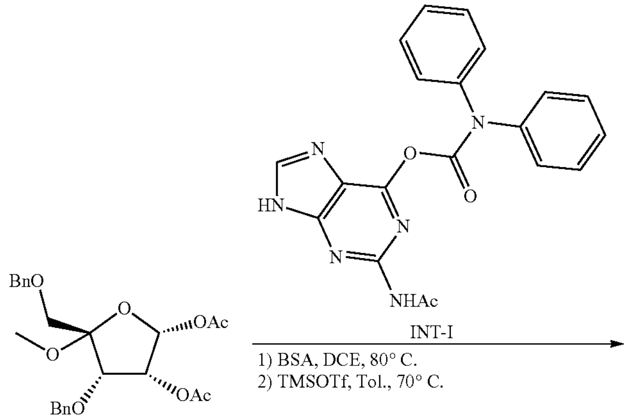

5227-PM2

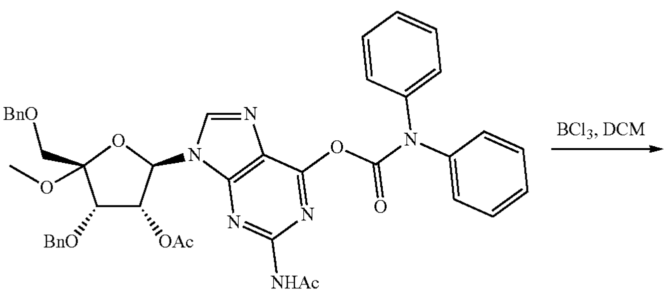

5227-PM3

-continued
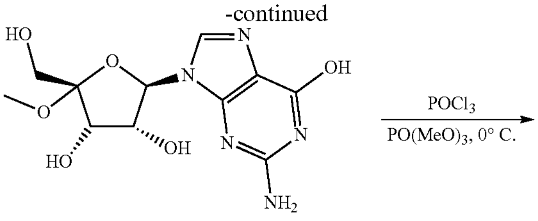
5227-PM4
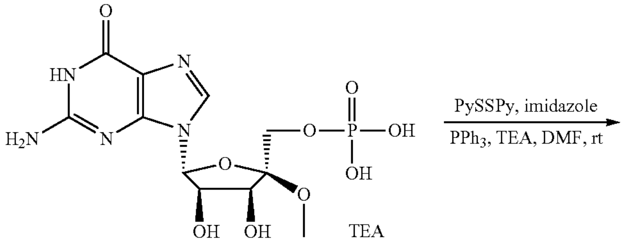
5227-PM5
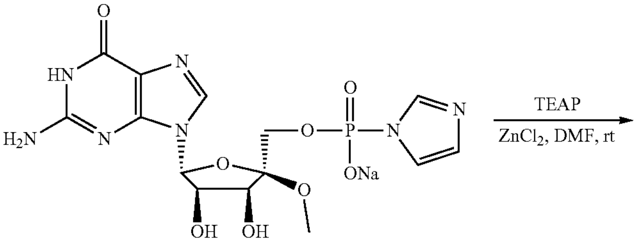
5227-PM6
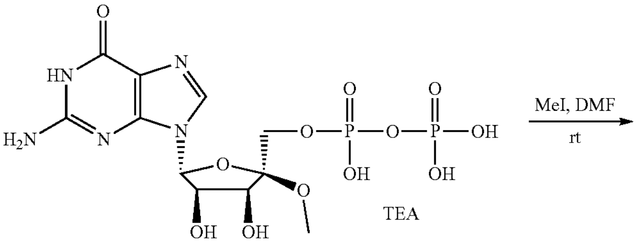
5227-PM7
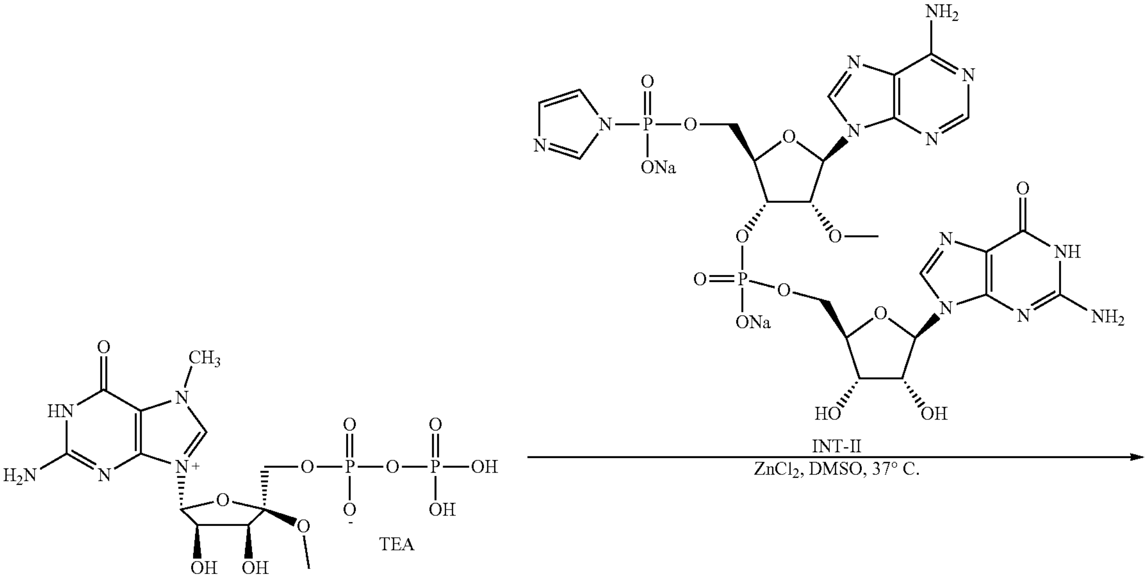
5227-PM8

-continued
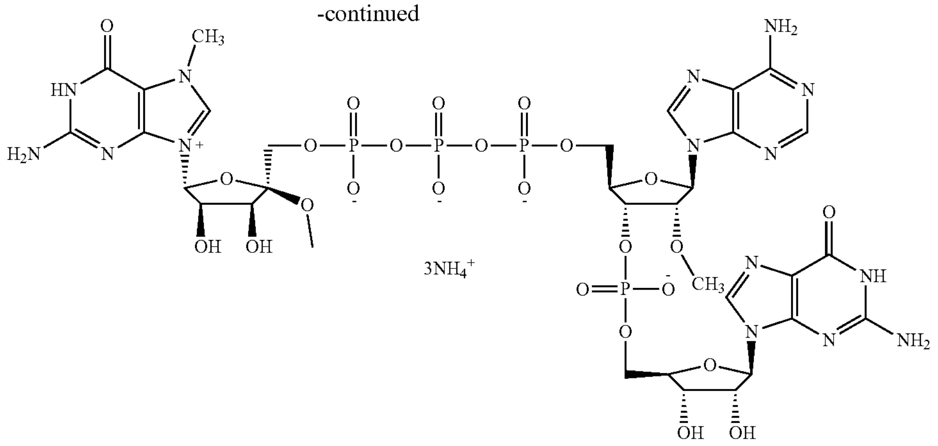
5227
According to the synthesis method of YK-CAP-117, 5227-S was used as starting material to obtain 35 mg of compound 5227.
23. Synthesis of CAP-2'O-ethyl
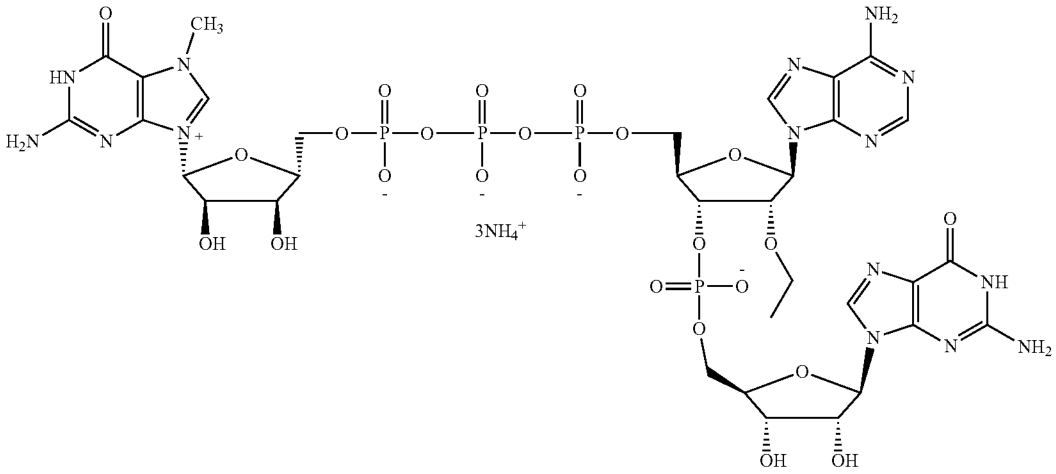
CAP-2'O-ethyl
According to the method in WO2023025073A1, 47 mg of CAP-2'O-ethyl was obtained.

Example 2: In Vitro Transcription Yield of mRNA and Capping Rate

I. Structural Differences in Cap Analogs

TABLE 1

| Structures of cap analogs | | |
|---|---|---|
| Name | Structure | Remark |
| YK-CAP-101 | 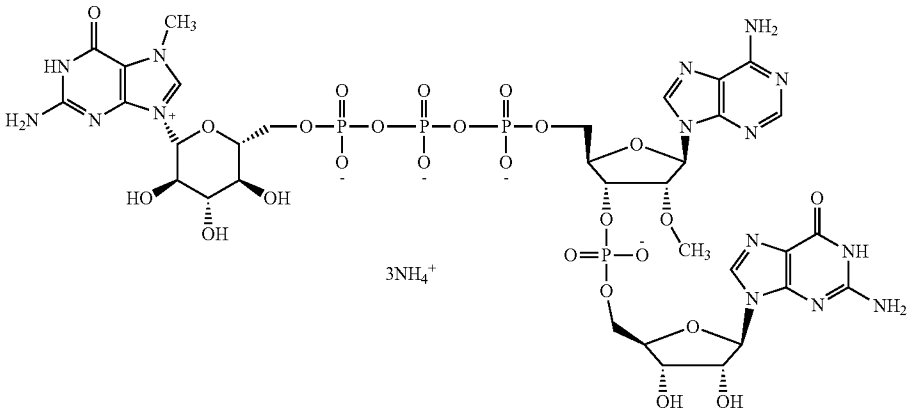 YK-CAP-101 | Structure designed in the present disclosure, synthesized in Example 1 |
| YK-CAP-102 | 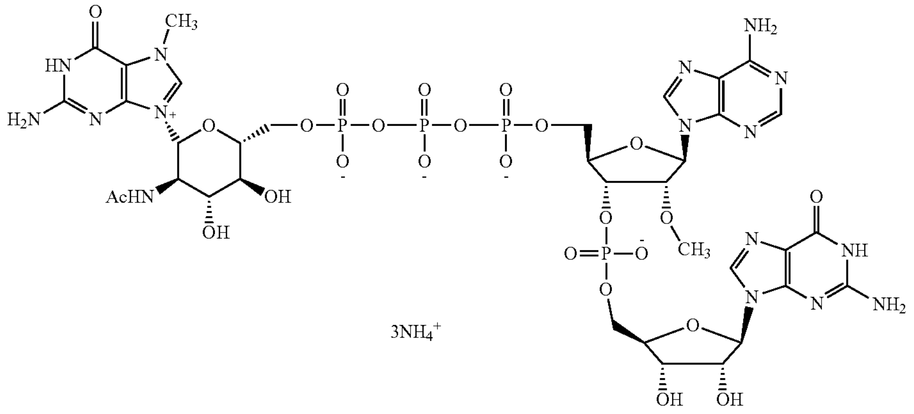 YK-CAP-102 | Structure designed in the present disclosure, synthesized in Example 1 |
| YK-CAP-103 | 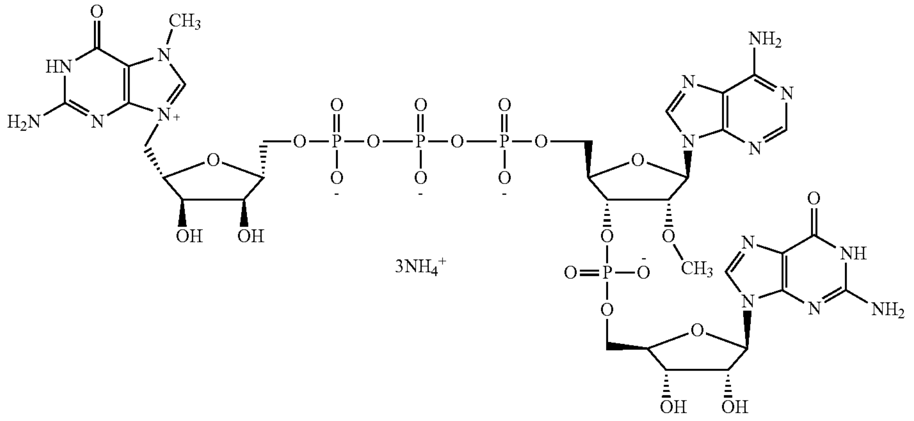 YK-CAP-103 | Structure designed in the present disclosure, synthesized in Example 1 |

TABLE 1-continued
| Structures of cap analogs | | |
|---|---|---|
| Name | Structure | Remark |
| YK-CAP-104 | 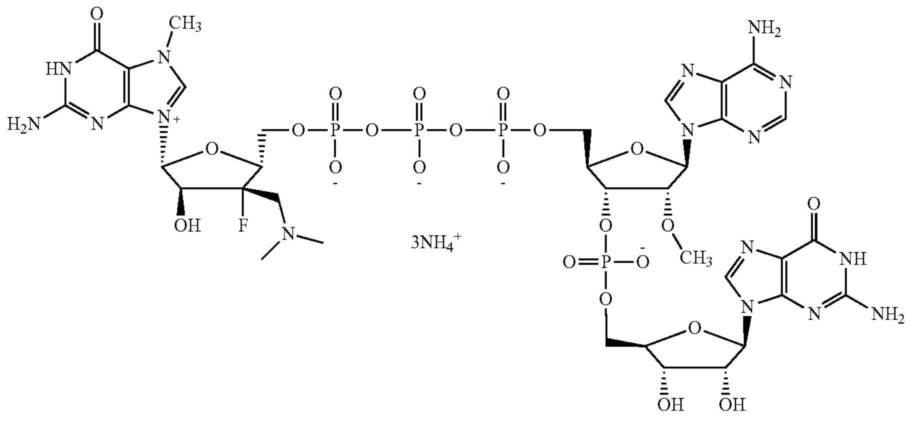 YK-CAP-104 | Structure designed in the present disclosure, synthesized in Example 1 |
| YK-CAP-105 | 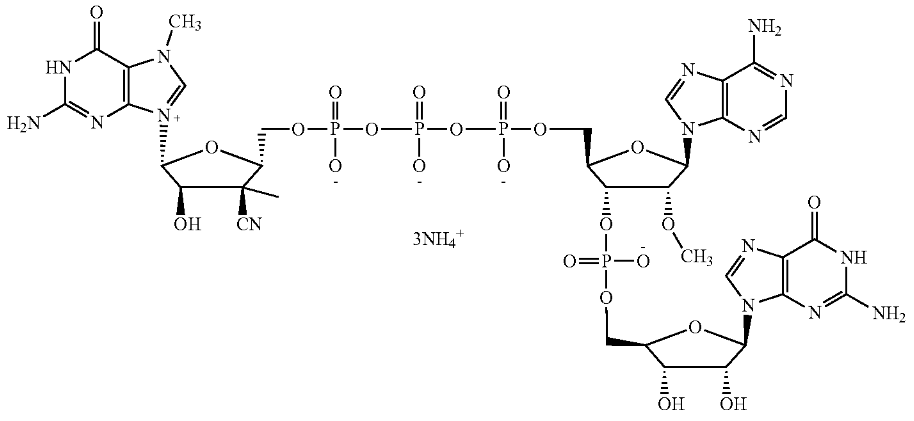 YK-CAP-105 | Structure designed in the present disclosure, synthesized in Example 1 |
| YK-CAP-106 | 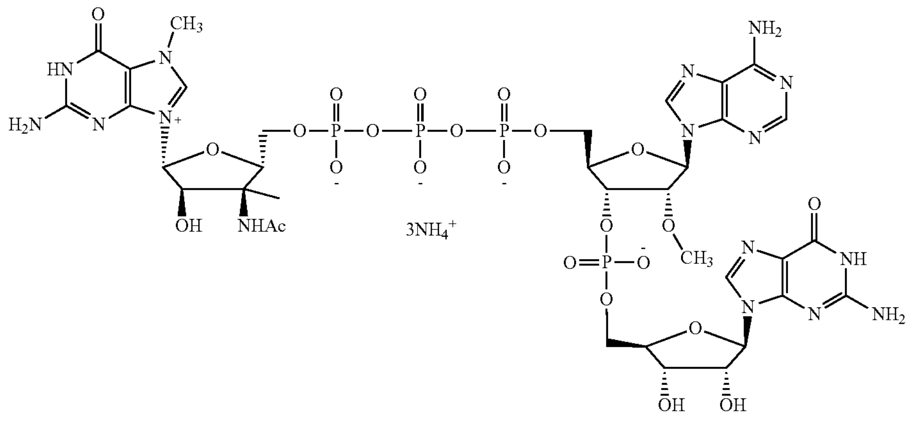 YK-CAP-106 | Structure designed in the present disclosure, synthesized in Example 1 |

TABLE 1-continued
| Structures of cap analogs | | |
|---|---|---|
| Name | Structure | Remark |
| YK-CAP-107 | 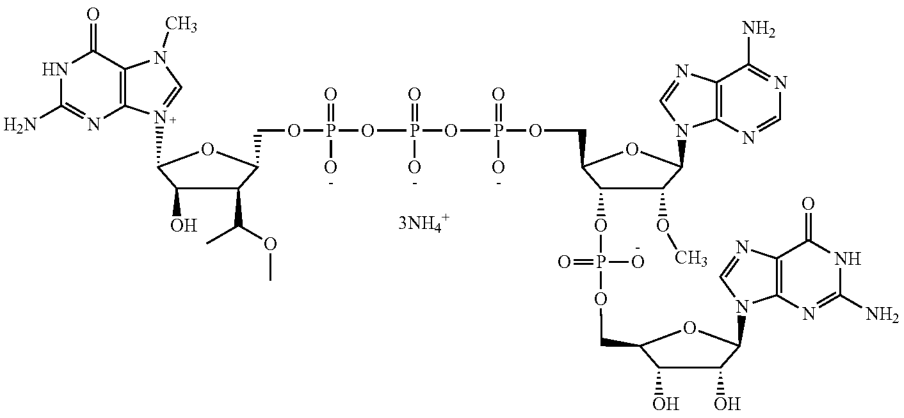 YK-CAP-107 | Structure designed in the present disclosure, synthesized in Example 1 |
| YK-CAP-108 | 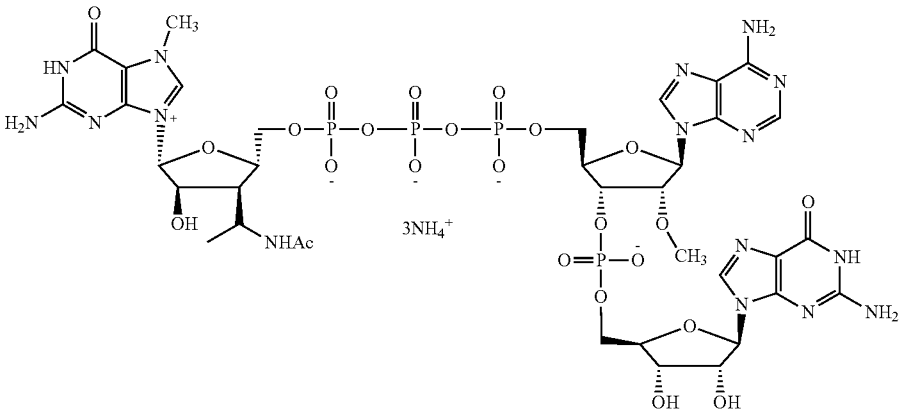 YK-CAP-108 | Structure designed in the present disclosure, synthesized in Example 1 |
| YK-CAP-109 | 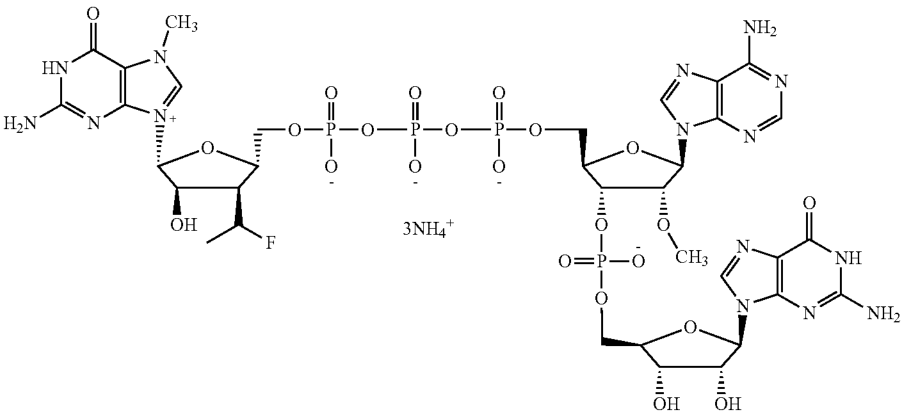 YK-CAP-109 | Structure designed in the present disclosure, synthesized in Example 1 |

TABLE 1-continued
| Structures of cap analogs | | |
|---|---|---|
| Name | Structure | Remark |
| YK-CAP-110 | 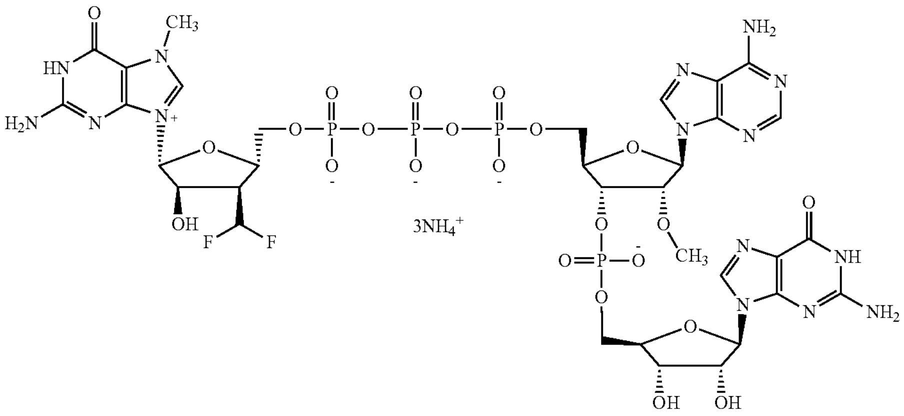 YK-CAP-110 | Structure designed in the present disclosure, synthesized in Example 1 |
| YK-CAP-111 | 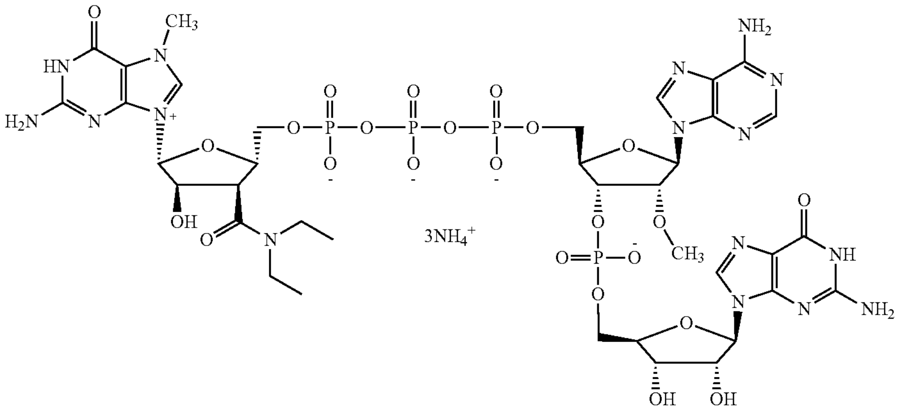 YK-CAP-111 | Structure designed in the present disclosure, synthesized in Example 1 |
| YK-CAP-112 | 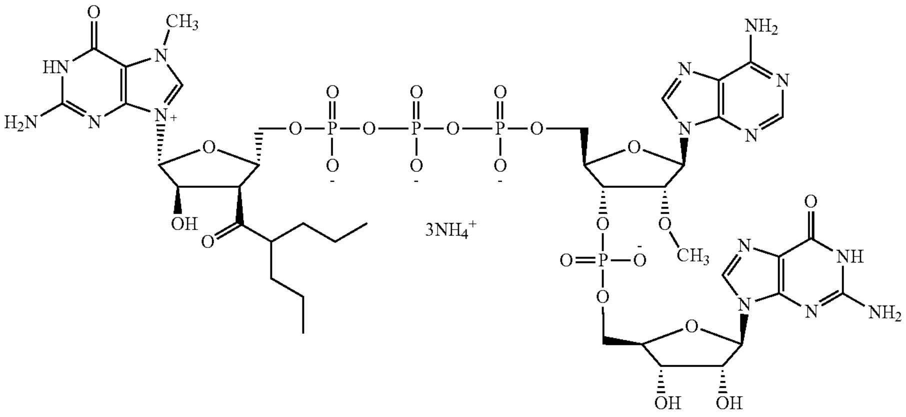 YK-CAP-112 | Structure designed in the present disclosure, synthesized in Example 1 |

TABLE 1-continued
| Structures of cap analogs | | |
|---|---|---|
| Name | Structure | Remark |
| YK-CAP-113 | 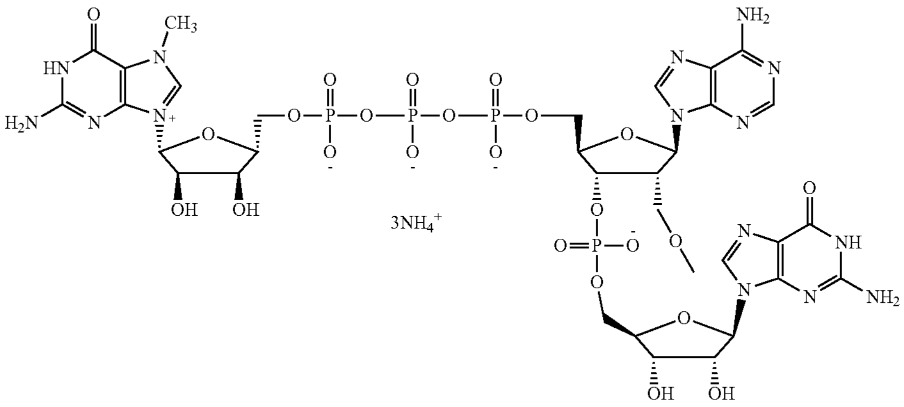 YK-CAP-113 | Structure designed in the present disclosure, synthesized in Example 1 |
| YK-CAP-114 | 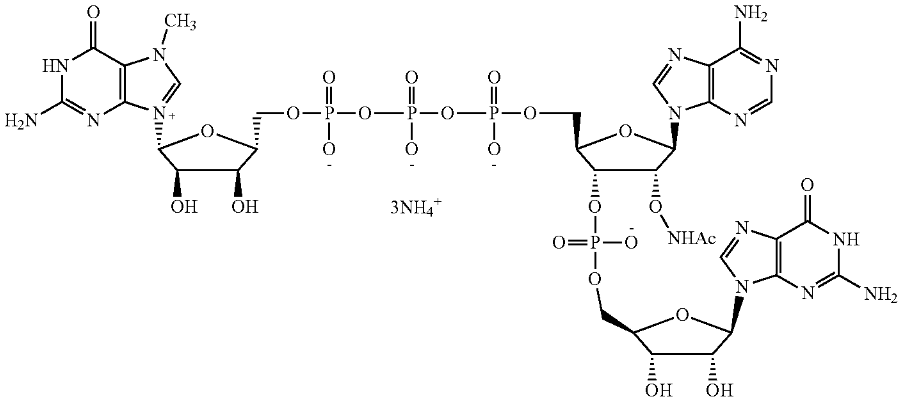 YK-CAP-114 | Structure designed in the present disclosure, synthesized in Example 1 |
| YK-CAP-115 | 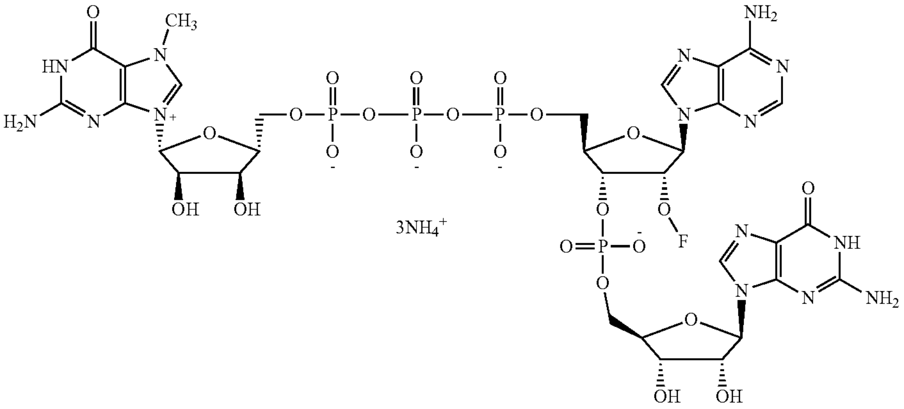 YK-CAP-115 | Structure designed in the present disclosure, synthesized in Example 1 |

TABLE 1-continued
| Structures of cap analogs | | |
|---|---|---|
| Name | Structure | Remark |
| YK-CAP-116 | 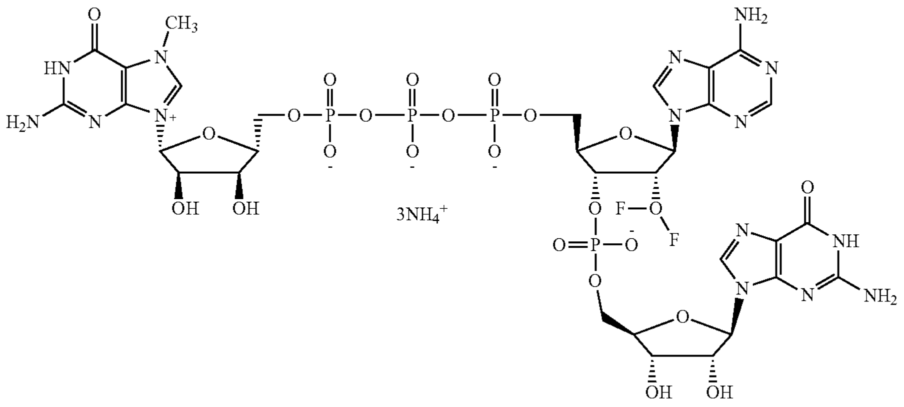 YK-CAP-116 | Structure designed in the present disclosure, synthesized in Example 1 |
| YK-CAP-117 | 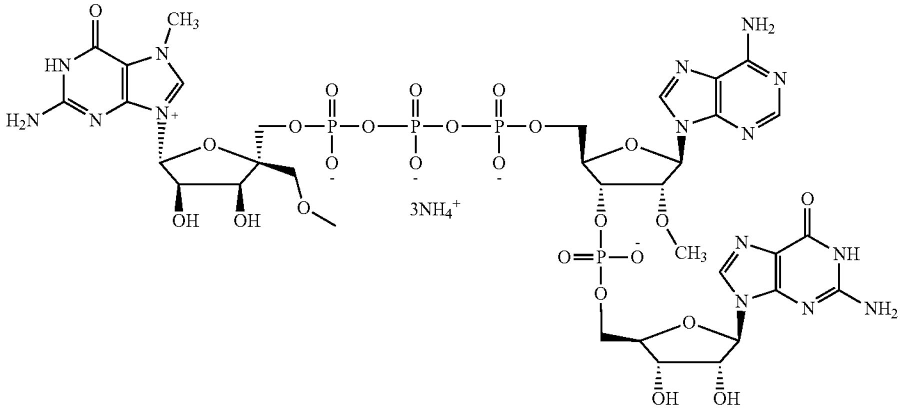 YK-CAP-117 | Structure designed in the present disclosure, synthesized in Example 1 |
| YK-CAP-118 | 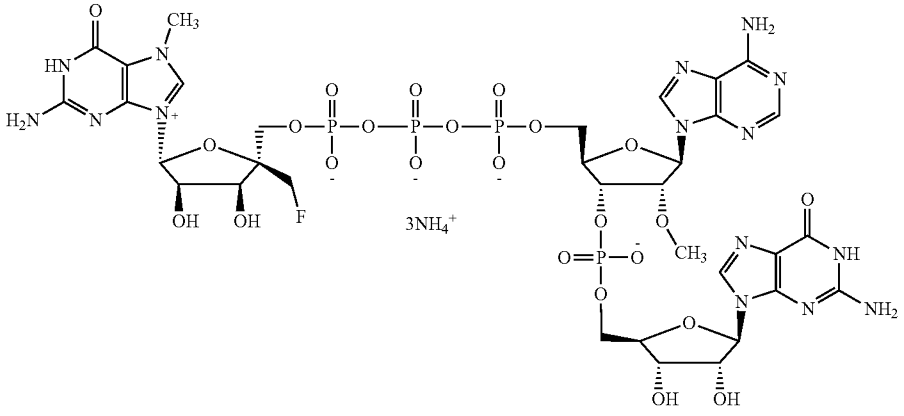 YK-CAP-118 | Structure designed in the present disclosure, synthesized in Example 1 |

TABLE 1-continued
| Structures of cap analogs | | |
|---|---|---|
| Name | Structure | Remark |
| YK-CAP-119 | 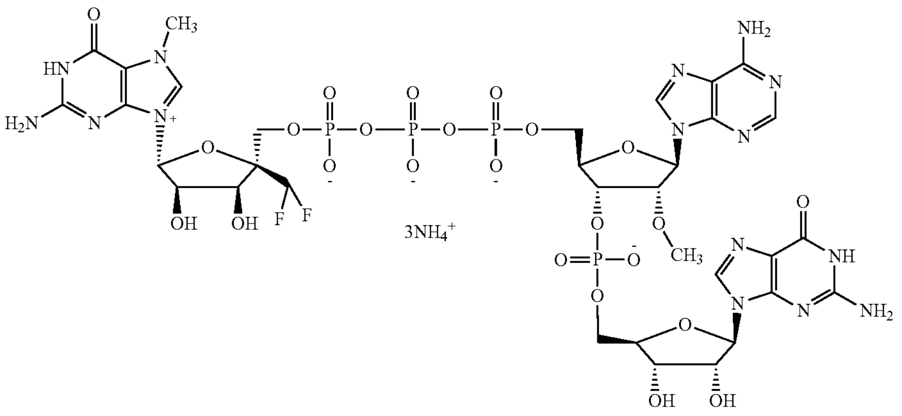 YK-CAP-119 | Structure designed in the present disclosure, synthesized in Example 1 |
| 5227 | 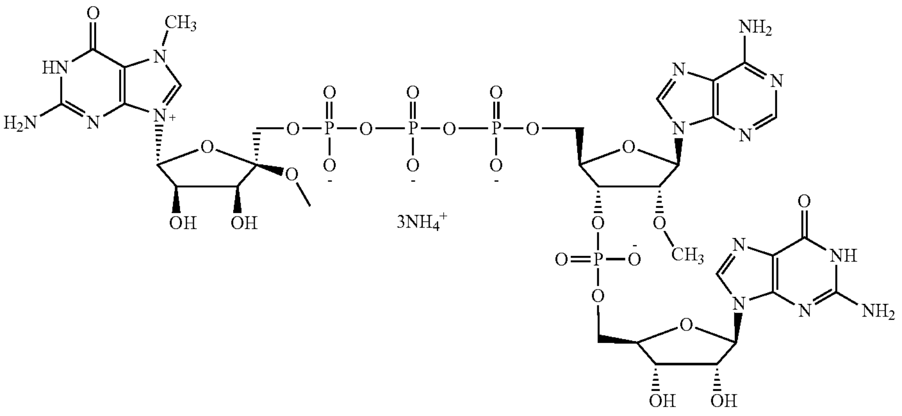 5227 | Synthesized in Example 1, compound 5227 on page 124 of specification of WO2022051677-A1 |
| CAP-2'O-ethyl | 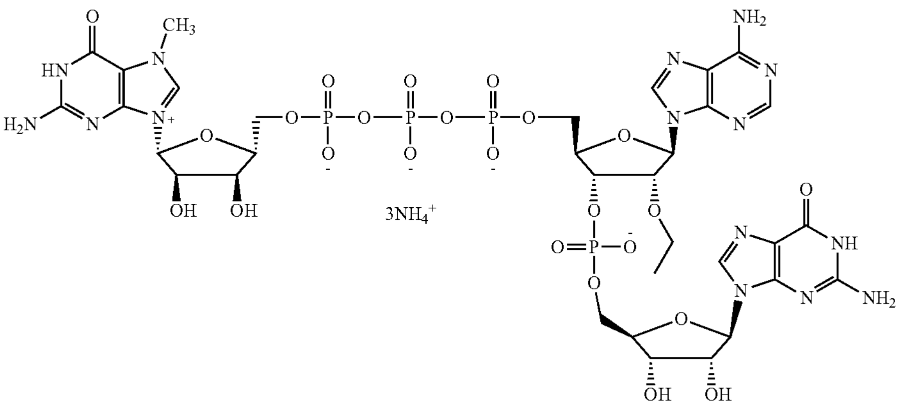 CAP-2'O-ethyl | Synthesized in Example 1, Table 6 on page 27 of specification of WO2023025073-A1 |

TABLE 1-continued
| Structures of cap analogs | | |
|---|---|---|
| Name | Structure | Remark |
| N-7113 | 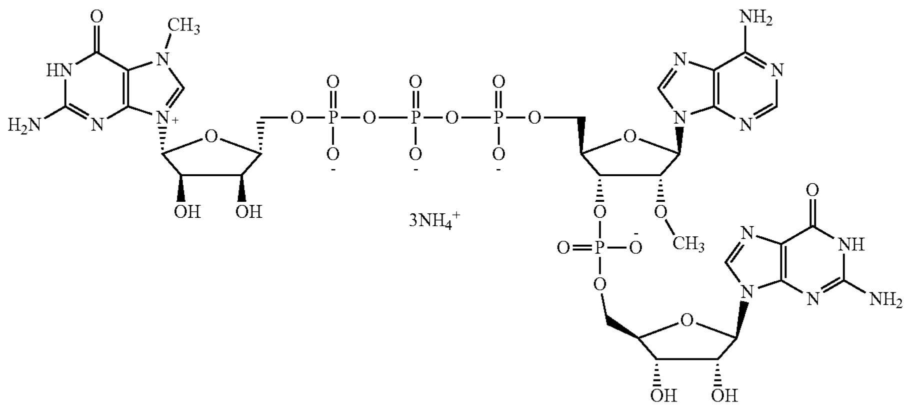 N7113 | Purchased from Jiangsu Synthgene Biotechnology Co., Ltd., compound described in claim 15 on page 2 of CN116751827B |
| Compound 14 | 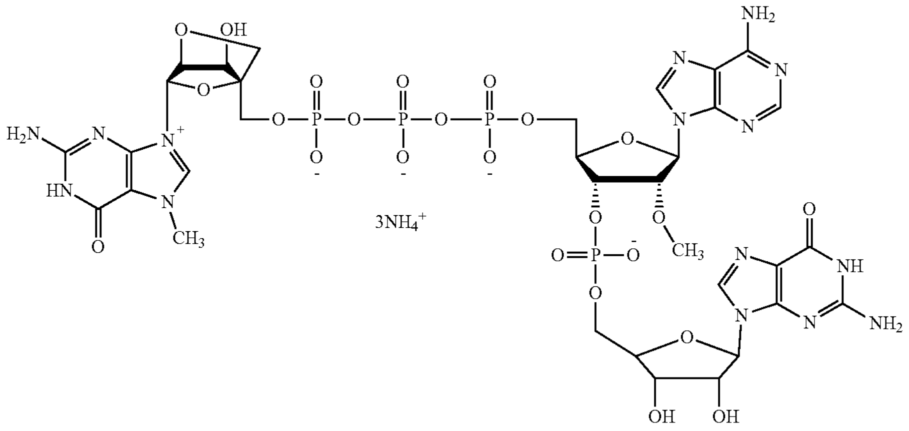 | Purchased from Jiangsu Synthgene Biotechnology Co., Ltd., compound 14 on page 90 of CN115803333A |
| HN3002 | 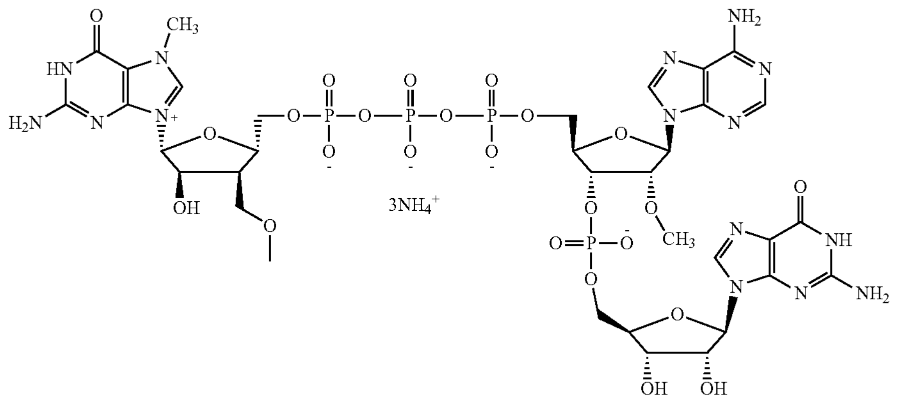 HN3002 | Purchased from Guangzhou Henovcom Bioscience Co., Ltd., compound 3 on page 9 of CN115260264B |

TABLE 1-continued

| Structures of cap analogs | | |
|---|---|---|
| Name | Structure | Remark |
| m6A | 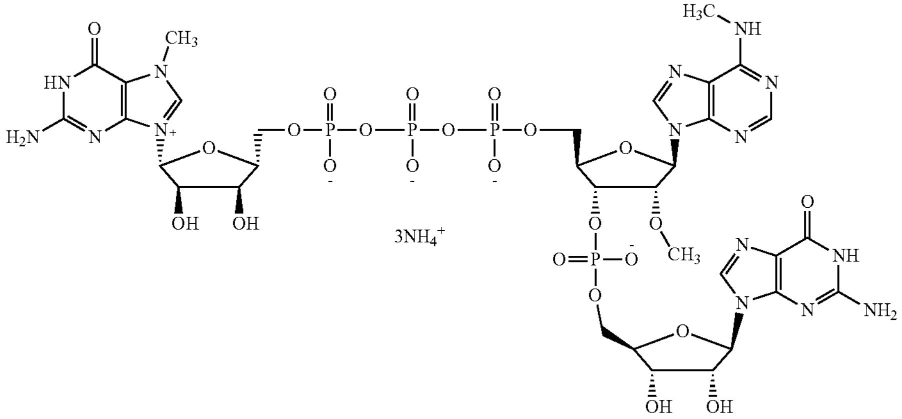 m6A | Purchased from Jiangsu Synthgene Biotechnology Co., Ltd., compound 31 on page 21 of WO2023/147352A1 |

As can be seen from Table 1, the chemical structures of compounds YK-CAP-101 to 119 in the present disclosure have some similarities and some significant differences compared to the mRNA cap analogs disclosed in the prior art as shown below:

1. The first sugar ring of compounds YK-CAP-101 and YK-CAP-102 in the present disclosure is a 6-membered ring, while the first sugar ring of N7113 is a 5-membered ring. The other structures are exactly identical.
2. The group attached to the first sugar ring and guanine of compound YK-CAP-103 in the present disclosure is different from that of N7113, i.e., there is one more methylene group at the C1 position. The other structures are exactly identical.
3. The first sugar ring of compounds YK-CAP-104 to 106 in the present disclosure has two substituents at the C3 position, which is different from N7113, i.e., the C3-substituents of N7113 are hydroxyl and hydrogen; the C3-substituents of YK-CAP-104 are dimethylaminomethyl and fluorine, respectively; the C3-substituents of YK-CAP-105 are cyano and methyl, respectively; the C3-substituents of YK-CAP-106 are acetamido and methyl, respectively. The other structures are exactly identical.
4. The substituents at the C3 position of the first sugar ring of compounds YK-CAP-107 to 112 in the present disclosure are different from those of N7113 and HN3002, i.e., the C3-substituents of N7113 and HN3002 are hydroxyl and methoxymethyl; the C3-substituents of YK-CAP-107 to 112 are 1-methoxyethyl, 1-acetamidoethyl, 1-fluoroethyl, difluoromethyl, N,N-diacetamido, and N,N-dipropionamido, respectively. The other structures are exactly identical.
5. The substituents at the C2 position of the second sugar ring of compounds YK-CAP-113 to 116 in the present disclosure are different from those of N7113 and CAP-2'O-ethyl, i.e., the C2-substituents of N7113 and CAP-2'O-ethyl are methoxy and ethoxy; the C2-substituents of YK-CAP-113 to 116 are methoxymethyl, acetamidomethyl, 1-fluoromethyl, and difluoromethyl, respectively. The other structures are exactly identical.
6. The substituents at the C4 position of the first sugar ring of compounds YK-CAP-117 to 119 in the present disclosure are different from those of N7113 and 5227, i.e., the C4-substituents of N7113 and 5227 are hydrogen and methoxy; the C4-substituents of YK-CAP-117 to 119 are methoxymethyl, 1-fluoromethyl, and difluoromethyl, respectively. The other structures are exactly identical.
7. Compounds YK-CAP-101 to 119 in the present disclosure differ greatly in structure from compound 14 and m6A, specifically, the first sugar ring of compound 14 is a locked nucleic acid sugar ring, i.e., there is a methylene bridge between 2'-O and C4'; the second base of m6A, adenine, is methylated.

II. Measurement of In Vitro Transcription Yield of mRNA and Capping Rate

1. Experimental Methods (1) Capping synthesis using cap analogs

The plasmid was first linearized with plasmid linearizing enzyme, and then the linearized plasmid was purified.

(2) In vitro transcription and synthesis of mRNA

YK-CAP-101 to 119, compound 5227, and CAP-2'O-ethyl synthesized in Example 1 were respectively used as cap analogs. The reaction system is shown in Table 2:

TABLE 2

| In vitro transcription reaction system | |
|---|---|
| System | Amount |
| T7 RNA polymerase | 50 U |
| 10X buffer | 2 μL |
| 100mMATP | 1 μL |
| 100mMGTP | 1 μL |
| 100mMCTP | 1 μL |
| 100mMUTP | 1 μL |
| 100 mM cap analog | 1 μL |
| Nuclease inhibitor | 20 U |
| Inorganic pyrophosphatase | 0.05 U |

TABLE 2-continued

| In vitro transcription reaction system | |
|---|---|
| System | Amount |
| Sterile enzyme-free water | Supplemented to 20 μL |
| DNA template | 1 μg |

During the experiment, the volume of materials required for the system was first calculated, and then sample addition was conducted. The system was first added with sterile enzyme-free water, followed by the sequential addition of 10× buffer, NTPs, and cap analogs, mixed well, and gently centrifuged. Nuclease inhibitors, inorganic pyrophosphatase, T7RNA polymerase, and linearized DNA templates were then added thereto. The system was mixed well, gently centrifuged, and incubated at 37° C. After 2 hours of incubation, the system was added with 1 U of DNase I and incubated at 37° C. for another 30 minutes. The mRNA precipitate was then washed with 75% ethanol, and after the ethanol was briefly evaporated to dryness, the mRNA was redissolved in sterile enzyme-free water.

(3) The transcription product was purified, and the in vitro transcription yield of mRNA was recorded.

(4) The obtained mRNA was subjected to an annealing reaction with a probe.

The annealing reaction was performed in a PCR instrument: 95° C. for 5 minutes; 65° C. for 2 minutes; 55° C. for 2 minutes; 40° C. for 2 minutes; 22° C. for 2 minutes.

(5) Magnetic bead pretreatment and probe binding: 100 μL of magnetic beads was placed on a magnetic frame for pretreatment. The magnetic bead solution was added with 120 μL of sample and incubated at room temperature for 30 minutes with slow mixing.

(6) mRNA splicing and obtaining the mRNA 5' single-strand sequence bound to the probe The mixture was added with 20 μL of RNase H (5 U/μL) and incubated at 37° C. for 3 hours with mixing every half hour. After incubation, the magnetic beads were washed and then added with 100 μL of 75% methanol heated to 80° C. The mixture was heated to 80° C. on a heating plate, held for 3 minutes, then placed on a magnetic frame to aspirate the supernatant, and dried at room temperature for 45 minutes to a volume of 10 μL using a centrifugal evaporator. The sample was then resuspended in 50 μL of 100 μM EDTA/1% MeOH and ready for LC-MS analysis to determine the capping of RNA in the transcription reaction. Since there is a significant difference in molecular weight between capped and uncapped bases, the capping rate of mRNA transcription initiated by different cap analogs can be determined based on the difference in molecular mass.

2. Experimental Results

The measurement results of the in vitro transcription yield of mRNA and capping rate show that the ribose-modified cap analogs of the present disclosure have a significant difference in the in vitro transcription yield of mRNA and capping rate. Compared to the ribose-modified cap analogs in the prior art, the ribose-modified cap analogs of the present disclosure show a significant increase in both in vitro transcription yield of mRNA and capping rate.

The specific in vitro transcription yield of mRNA and capping rate are shown in Table 3.

TABLE 3

In vitro transcription yield of mRNA and capping rate

| Name | Yield per unit template (μg) | Increase relative to 5227 (%) | Capping rate (%) | Increase relative to 5227 (%) |
|---|---|---|---|---|
| YK-CAP-101 | 32.5 | −75.8 | 42.8 | −40.5 |
| YK-CAP-102 | 44.1 | −67.1 | 30.2 | −58.0 |
| YK-CAP-103 | 88.0 | −34.4 | 71.1 | −1.1 |
| YK-CAP-104 | 73.2 | −45.5 | 77.2 | 7.4 |
| YK-CAP-105 | 82.3 | −38.7 | 69.3 | −3.6 |
| YK-CAP-106 | 155.5 | 15.9 | 95.3 | 32.5 |
| YK-CAP-107 | 170.7 | 27.2 | 97.3 | 35.3 |
| YK-CAP-108 | 151.8 | 13.1 | 95.8 | 33.2 |
| YK-CAP-109 | 168.1 | 25.3 | 95.2 | 32.4 |
| YK-CAP-110 | 172.1 | 28.2 | 97.4 | 35.5 |
| YK-CAP-111 | 173.5 | 29.3 | 98.1 | 36.4 |
| YK-CAP-112 | 169.2 | 26.1 | 95.2 | 32.4 |
| YK-CAP-113 | 166.1 | 23.8 | 95.2 | 32.4 |
| YK-CAP-114 | 161.2 | 20.1 | 95.2 | 32.4 |
| YK-CAP-115 | 158.1 | 17.8 | 95.7 | 33.1 |
| YK-CAP-116 | 159.4 | 18.8 | 96.4 | 34.1 |
| YK-CAP-117 | 153.2 | 14.2 | 95.1 | 32.3 |
| YK-CAP-118 | 172.2 | 28.3 | 97.2 | 35.2 |
| YK-CAP-119 | 154.2 | 14.9 | 96.3 | 33.9 |
| Compound 14 | 123.2 | −8.2 | 78.3 | 8.9 |
| 5227 | 134.2 | 0 | 71.9 | 0 |

1) The ribose-modified cap analogs of the present disclosure show a significant difference in the in vitro transcription yield of mRNA and capping rate. YK-CAP-106 to 119 have significantly higher in vitro transcription yield of mRNA and capping rate than those of YK-CAP-101 to 105. YK-CAP-111 has the highest transcription yield and capping rate, with the transcription yield being 5.3 times that of YK-CAP-101 (the lowest) and the capping rate being 3.2 times that of YK-CAP-102 (the lowest).

As can be seen from Table 3, all the ribose-modified cap analogs of the present disclosure are capable of transcribing mRNA. There is a significant difference in the mRNA transcription activity among different ribose-modified cap analogs. YK-CAP-106 to 119 have very high in vitro transcription yield of mRNA, all exceeding 150 μg. Specifically, YK-CAP-107, YK-CAP-110, YK-CAP-111, YK-CAP-117, and YK-CAP-118 have a yield of 170.7 μg, 172.1 μg, 173.5 μg, 153.2 μg, and 172.2 μg, respectively, with YK-CAP-111 having the highest yield of 173.5 μg (as shown in FIG. 1). YK-CAP-101 has the lowest in vitro transcription yield of mRNA, which is only 32.5 μg. YK-CAP-102 to 105 also have a very low yield of 44.1 μg, 88.0 μg, 73.2 μg, and 82.3 μg, respectively. The transcription yield of YK-CAP-111 is 5.3 times, 3.9 times, 2.0 times, 2.4 times, and 2.1 times that of YK-CAP-101 to 105, respectively, showing a significant increase.

YK-CAP-106 to 119 have very high capping rate, all exceeding 95%. Specifically, YK-CAP-107, YK-CAP-110, YK-CAP-111, YK-CAP-117, and YK-CAP-118 have a capping rate of 97.3%, 97.4%, 98.1%, 95.1%, and 97.2%, respectively, with YK-CAP-111 having the highest capping rate of 98.1%.

Figure 2:
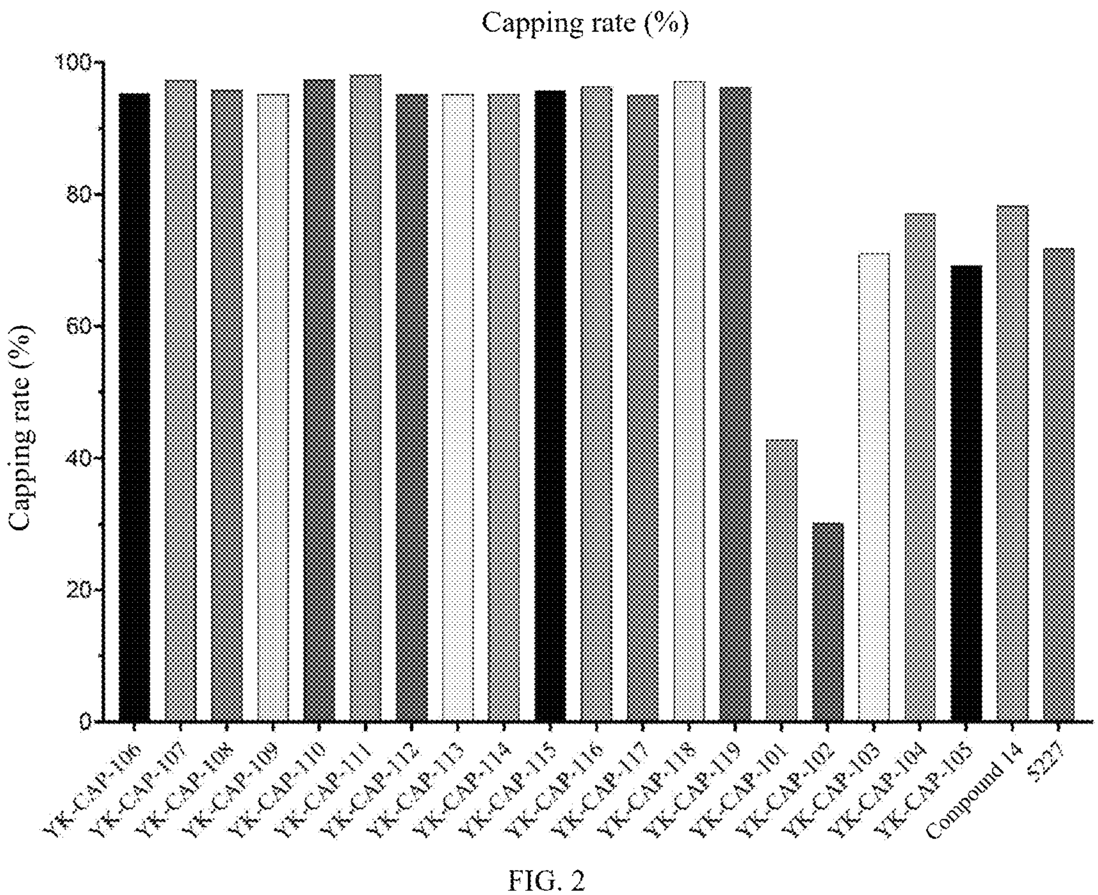
FIG. 2 is a graph showing the results of capping rate of mRNA transcription initiated by YK-CAP-106, YK-CAP-107, YK-CAP-108, YK-CAP-109, YK-CAP-110, YK-CAP-111, YK-CAP-112, YK-CAP-113, YK-CAP-114, YK-CAP-115, YK-CAP-116, YK-CAP-117, YK-CAP-118, YK-CAP-119, YK-CAP-101, YK-CAP-102, YK-CAP-103, YK-CAP-104, YK-CAP-105, compound 14, and 5227 as cap analogs.

YK-CAP-102 has the lowest capping rate, which is only 30.2%. YK-CAP-101 and YK-CAP-103 to 105 also have a very low capping rate of 42.8%, 71.1%, 77.2%, and 69.3%, respectively. The capping rate of YK-CAP-111 is 2.3 times, 3.2 times, 1.4 times, 1.3 times, and 1.4 times higher than that of YK-CAP-101 to 105, respectively, showing a significant increase (as shown in FIG. 2).

2) Compared to the ribose-modified cap analogs in the prior art, the ribose-modified cap analogs of the present disclosure show a significant increase in both in vitro transcription yield of mRNA and capping rate. For example, the transcription yield of YK-CAP-111 is 40.8% higher than that of compound 14, and the capping rate of YK-CAP-111 is 36.4% higher than that of 5227.

The in vitro transcription yield of mRNA and capping rate of compound 14 are 123.2 μg and 78.3%, respectively. The in vitro transcription yield of mRNA and capping rate of YK-CAP-111 in the present disclosure are 40.8% and 25.3% higher than those of compound 14, respectively, showing a significant increase.

The in vitro transcription yield of mRNA and capping rate of 5227 are 134.2 μg and 71.9%, respectively. The in vitro transcription yield of mRNA and capping rate of YK-CAP-111 in the present disclosure are 29.3% and 36.4% higher than those of 5227, respectively, showing a significant increase.

3) The ribose-modified cap analogs with similar structures vary greatly in the in vitro transcription yield of mRNA and capping rate, making it impossible to predict the in vitro transcription yield of mRNA and capping rate based on structure.

The ribose-modified cap analogs YK-CAP-117 to 119 designed in the present disclosure have structures that are very similar. This series of compounds is also very similar in structure to 5227, but they vary greatly in the in vitro transcription yield of mRNA and capping rate.

For example, compounds YK-CAP-117 to 119 in the present disclosure differ from 5227 only in the substituent at the C4 position of the first sugar ring, i.e., the C4-substituent of 5227 is methoxy; the C4-substituents of YK-CAP-117 to 119 are methoxymethyl, 1-fluoromethyl, and difluoromethyl, respectively. The other structures are exactly identical. However, the in vitro transcription yield of mRNA of YK-CAP-117 to 119 is 14.2%, 28.3% and 14.9% higher than that of 5227, respectively, and the capping rate of YK-CAP-117 to 119 is 32.3%, 35.2%, and 33.9% higher than that of 5227, respectively, showing a significant increase.

It can be seen that ribose-modified cap analogs with similar structures do not necessarily have similar mRNA transcription activities and capping rates. On the contrary, there may be a huge difference.

As can be seen from the in vitro transcription yield of mRNA and capping rate, the ribose-modified cap analogs YK-CAP-106 to 119 in the present disclosure show a significant increase in both in vitro transcription yield of mRNA and capping rate compared to both YK-CAP-101 to 105 in the present disclosure and compounds 14 and 5227 in the prior art, which demonstrates that the ribose modification of YK-CAP-106 to 119 shows excellent resistance to reverse transcription during in vitro transcription of mRNA and can greatly enhance the binding ability of the cap structure to the capping enzyme, thereby increasing the capping rate of mRNA transcription.

Example 3: Preparation and Characterization of Lipid Nanoparticles

1. Experimental Methods

Cationic lipid YK-009 (Beijing Youcare Kechuang Pharmaceutical Technology Co., Ltd.), DSPC (AVT (Shanghai) Pharmaceutical Technology Co., Ltd.), cholesterol (AVT (Shanghai) Pharmaceutical Technology Co., Ltd.), and DMG-PEG2000 were dissolved in ethanol at a molar ratio of 49:10:39.5:1.5, and the mRNA was diluted in 50 mM citrate buffer (pH=4). The ethanol lipid solution was mixed with the Fluc-mRNA aqueous solution prepared from different cap structures at a volume ratio of 1:3 using a microfluidic device at a flow rate of 10 mL/min to prepare LNPs at a weight ratio of total lipid to mRNA of approximately 15:1.

The resulting liposomes were diluted to 10-fold volume with PBS, and then ultrafiltered with a 300 KDa ultrafiltration tube to remove ethanol. The volume was then fixed to a certain volume with PBS. Finally, the LNPs were filtered through a 0.2 μm sterile filter to obtain an LNP preparation encapsulating Fluc-mRNA using YK-009/DSPC/cholesterol/DMG-PEG2000 (at a molar ratio of 49:10:39.5:1.5).

The particle size and polydispersity index (PDI) were determined by dynamic light scattering using a Malvern laser particle size analyzer. 10 μL of the liposome solution was taken, diluted to 1 mL with RNase-free deionized water, and added to a sample pool. Each sample was measured in triplicate. The measurement conditions were: a scattering angle of 90° and a temperature of 25° C. The encapsulation efficiency of LNPs was determined using the Quant-iT RiboGreen RNA Quantification Kit (Thermo Fisher Scientific, UK) according to the manufacturer's instructions.

2. Experimental Results

The specific characterization data for lipid nanoparticles are shown in Table 4.

TABLE 4

Characterization of lipid nanoparticles

| Name | Particle size (nm) | PDI | EE (%) |
|---|---|---|---|
| YK-CAP-101 | 75.45 | 0.043 | 93.4 |
| YK-CAP-102 | 73.22 | 0.055 | 95.3 |
| YK-CAP-103 | 67.24 | 0.053 | 94.7 |
| YK-CAP-104 | 69.24 | 0.047 | 95.7 |
| YK-CAP-105 | 77.22 | 0.063 | 95.7 |
| YK-CAP-106 | 68.24 | 0.048 | 97.1 |
| YK-CAP-107 | 78.42 | 0.053 | 96.3 |
| YK-CAP-108 | 83.13 | 0.023 | 96.4 |
| YK-CAP-109 | 86.35 | 0.035 | 97.2 |
| YK-CAP-110 | 69.64 | 0.033 | 97.7 |
| YK-CAP-111 | 78.33 | 0.053 | 95.1 |
| YK-CAP-112 | 83.24 | 0.056 | 93.5 |
| YK-CAP-113 | 79.34 | 0.043 | 96.1 |
| YK-CAP-114 | 66.36 | 0.049 | 94.3 |
| YK-CAP-115 | 68.35 | 0.034 | 95.3 |
| YK-CAP-116 | 74.24 | 0.063 | 98.3 |
| YK-CAP-117 | 72.56 | 0.044 | 94.3 |
| YK-CAP-118 | 75.84 | 0.055 | 97.2 |
| YK-CAP-119 | 82.45 | 0.057 | 94.6 |
| 5227 | 83.34 | 0.028 | 94.9 |
| CAP-2'O-ethyl | 81.34 | 0.035 | 96.3 |
| N-7113 | 87.45 | 0.078 | 96.1 |
| Compound 14 | 79.35 | 0.073 | 94.2 |
| HN3002 | 75.35 | 0.058 | 95.1 |
| m6A | 75.76 | 0.047 | 93.8 |

As can be seen from Table 4, good lipid nanoparticles can be prepared from the Fluc-mRNA transcribed using the cap analogs YK-CAP-101 to 119 in the present disclosure and the cap analogs 5227, CAP-2'O-ethyl, N-7113, compound 14, HN3002, and m6A disclosed in the prior art. All lipid nanoparticles have a particle size between 66 and 88 nm, a PDI value between 0.023 and 0.078, and an encapsulation efficiency of 90% or more.

Example 4: Translation Efficiency of Different Capped Luciferase mRNAs

1. Experimental Methods (1) HEK293T cells were cultured in DMEM medium containing 10% FBS and penicillin/streptomycin at 37° C. with 5% $CO_2$.

(2)Cells in the culture dish were digested and counted, then spread in a 96-well plate at 10,000 cells per well, and cultured overnight until the cells adhered to the wall.

(3) When the cell density reached approximately 80%, transfection was performed by adding 0.5 μg of mRNA sample and Lipofectamine MessengerMAX Transfection Reagent (Invitrogen) per well according to the manufacturer's instructions.

(4) After the transfected cells were cultured at 37° C. with 5% $CO_2$ for 24 hours, the growth medium was removed from the cells to be tested, and the cells were rinsed with PBS. After centrifugation to remove PBS, 50 μL of 1× lysis buffer was added. The cells and all liquid were transferred to a microcentrifuge tube and centrifuged.

(5) 20 μL of sample was taken and added to 100 μL of Dual-Lumi™ II Luciferase Assay Reagent pre-equilibrated to room temperature, and mixed appropriately.

(6) The mixture was incubated at room temperature (approximately 25° C.) for 5 minutes to stabilize the luminescence signal. Chemiluminescence was detected using a multifunctional microplate reader with a function for detecting chemiluminescence, and the data were recorded.

2. Experimental Results

The relative fluorescence readings of capped mRNAs are shown in Table 5. The relative fluorescence intensity is proportional to the translation efficiency of mRNA.

TABLE 5

Relative fluorescence readings of capped mRNAs

| Name | Relative fluorescence intensity | Multiple of m6A |
|---|---|---|
| YK-CAP-101 | 0.22 | 0.6 |
| YK-CAP-102 | 0.34 | 0.9 |
| YK-CAP-103 | 0.77 | 2.0 |
| YK-CAP-104 | 0.81 | 2.1 |
| YK-CAP-105 | 0.72 | 1.9 |
| YK-CAP-106 | 1.53 | 4.0 |
| YK-CAP-107 | 1.62 | 4.3 |
| YK-CAP-108 | 1.43 | 3.8 |
| YK-CAP-109 | 1.53 | 4.0 |
| YK-CAP-110 | 1.95 | 5.1 |
| YK-CAP-111 | 2.12 | 5.6 |
| YK-CAP-112 | 1.74 | 4.6 |
| YK-CAP-113 | 1.63 | 4.3 |
| YK-CAP-114 | 1.45 | 3.8 |
| YK-CAP-115 | 1.69 | 4.4 |
| YK-CAP-116 | 1.39 | 3.7 |
| YK-CAP-117 | 1.82 | 4.8 |
| YK-CAP-118 | 1.65 | 4.3 |
| YK-CAP-119 | 1.45 | 3.8 |
| 5227 | 0.82 | 2.2 |
| CAP-2'O-ethyl | 1.13 | 3.0 |
| N-7113 | 1.00 | 2.6 |
| Compound 14 | 1.12 | 2.9 |
| HN3002 | 1.13 | 3.0 |
| m6A | 0.38 | 1.0 |

1) The ribose-modified cap analogs of the present disclosure show a significant difference in translation efficiency of mRNA. YK-CAP-106 to 119 have significantly higher translation efficiency than that of YK-CAP-101 to 105. YK-CAP-111 has the highest translation efficiency, which is 9.6 times that of YK-CAP-101 (the lowest).

As can be seen from Table 5, the ribose-modified cap analogs of the present disclosure show a significant difference in relative fluorescence intensity (corresponding to the translation efficiency of mRNA). YK-CAP-106 to YK-CAP-119 have high relative fluorescence intensity (between 1.4 and 2.2). Specifically, YK-CAP-107, YK-CAP-110, YK-CAP-111, YK-CAP-117, and YK-CAP-118 have a relative fluorescence intensity of 1.62, 1.95, 2.12, 1.82, and 1.65, respectively, with YK-CAP-111 having the highest relative fluorescence intensity of 2.12, followed by YK-CAP-110 with a relative fluorescence intensity of 1.95.

Figure 3:
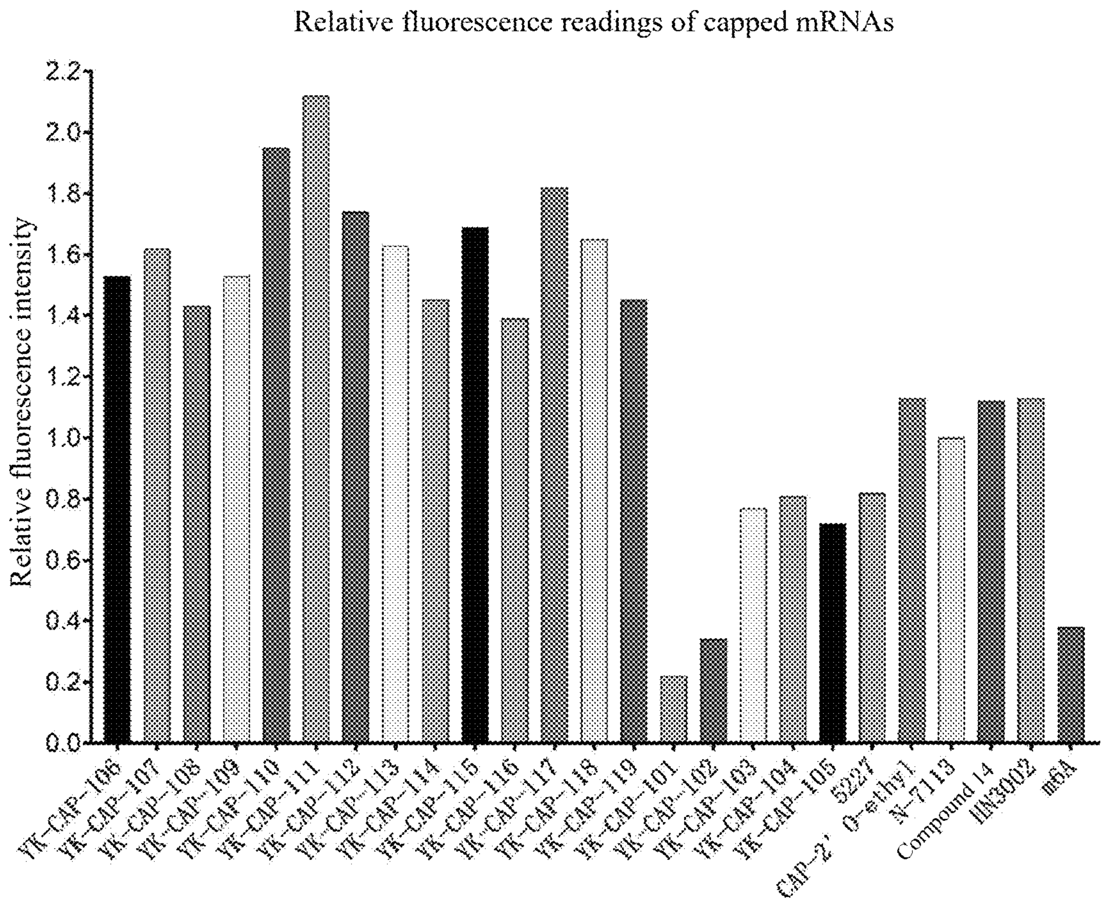
FIG. 3 is a graph showing the results of capped mRNA relative fluorescence intensity assay using YK-CAP-106, YK-CAP-107, YK-CAP-108, YK-CAP-109, YK-CAP-110, YK-CAP-111, YK-CAP-112, YK-CAP-113, YK-CAP-114, YK-CAP-115, YK-CAP-116, YK-CAP-117, YK-CAP-118, YK-CAP-119, YK-CAP-101, YK-CAP-102, YK-CAP-103, YK-CAP-104, YK-CAP-105, 5227, CAP-2'O-ethyl, N-7113, compound 14, HN3002, and m6A as cap analogs.

YK-CAP-101 has the lowest relative fluorescence intensity, which is only 0.22. YK-CAP-102 to YK-CAP-105 also have a very low relative fluorescence intensity of 0.34, 0.77, 0.81, and 0.72, respectively. The relative fluorescence intensity of YK-CAP-111 is 9.6 times, 6.2 times, 2.8 times, 2.6 times, and 2.9 times that of YK-CAP-101 to YK-CAP-105, respectively, while the relative fluorescence intensity of YK-CAP-110 is 8.9 times, 5.7 times, 2.5 times, 2.4 times, and 2.7 times that of YK-CAP-101 to YK-CAP-105, respectively (as shown in FIG. 3).

2)Compared to the ribose-modified cap analogs in the prior art, the ribose-modified cap analogs of the present disclosure show a significant increase in the translation efficiency of mRNA. For example, the translation efficiency of YK-CAP-111 is 5.6 times that of m6A.

N-7113, HN3002, compound 14, and m6A have a relative fluorescence intensity (corresponding to the translation efficiency of mRNA) of 1.00, 1.12, 1.13, and 0.38, respectively. The relative fluorescence intensity of YK-CAP-111 in the present disclosure is 2.1 times, 1.9 times, 1.9 times, and 5.6 times that of N-7113, HN3002, compound 14, and m6A, respectively, while the relative fluorescence intensity of YK-CAP-110 in the present disclosure is 1.9 times, 1.7 times, 1.7 times, and 5.1 times that of N-7113, HN3002, compound 14, and m6A, respectively.

3) The ribose-modified cap analogs with similar structures vary greatly in the translation efficiency of mRNA, making it impossible to predict the translation efficiency of mRNA.

The ribose-modified cap analogs YK-CAP-117 to 119 designed in the present disclosure have structures that are very similar. This series of compounds is also very similar in structure to 5227, but they vary greatly in the translation efficiency of mRNA. For example, compounds YK-CAP-117 to 119 in the present disclosure differ from 5227 only in the substituent at the C4 position of the first sugar ring, i.e., the C4-substituent of 5227 is methoxy; the C4-substituents of YK-CAP-117 to 119 are methoxymethyl, 1-fluoromethyl, and difluoromethyl, respectively. The other structures are exactly identical. However, the translation efficiency of mRNA of YK-CAP-117 to 119 is 2.2 times, 2.0 times, and 1.8 times that of 5227, respectively, showing a significant increase.

Similarly, the ribose-modified cap analogs YK-CAP-113 to 116 designed in the present disclosure have structures that are very similar. This series of compounds is also very similar in structure to CAP-2'O-ethyl, but they vary greatly in the translation efficiency of mRNA. For example, compounds YK-CAP-113 to 116 in the present disclosure differ from CAP-2'O-ethyl only in the substituent at the C2 position of the second sugar ring, i.e., the C2-substituent of CAP-2'O-ethyl is ethoxy; the C2-substituents of YK-CAP-113 to 116 are methoxymethyl, acetamidomethyl, 1-fluoromethyl, and difluoromethyl, respectively. The other structures are exactly identical. However, the translation efficiency of mRNA of YK-CAP-113 to 116 is 1.4 times, 1.3 times, 1.5 times, and 1.2 times that of CAP-2'O-ethyl, respectively, showing a significant increase.

It can be seen that ribose-modified cap analogs with similar structures do not necessarily have similar translation efficiency of luciferase mRNA. On the contrary, there may be a huge difference.

As can be seen from the translation efficiency of different capped luciferase mRNAs, the ribose-modified cap analogs in the present disclosure, including YK-CAP-106 to 119, show a significant increase in the translation efficiency of mRNA compared to both ribose-modified cap analogs with similar structures (including YK-CAP-101 to 105 in the present disclosure as well as 5227, CAP-2'O-ethyl, N-7113, and HN3002) and ribose-modified cap analogs with vastly different structures (including compound 14 and m6A). It suggests that the modified ribose of YK-CAP-106 to 119 binds more readily to the cap-binding protein (EIF4E), which improves the translation efficiency of the target mRNA. Moreover, ribose-modified cap analogs with similar structures do not necessarily have similar translation efficiency of luciferase mRNA. On the contrary, there may be a huge difference.

Example 5: Decapping Enzyme Stability Test

1. Experimental Methods

30 μmol of RNA purified by polyacrylamide gel electrophoresis (PAGE) was subjected to an enzymatic reaction with 50 U of mRNA decapping enzyme (New England Biolabs) and 1×MDE buffer at 37° C. for 45 minutes. The enzymatic reactants were subjected to PAGE and stained with SYBR Green II (Lonza), followed by observation of the post-electrophoresis gel image on a Typhoon FLA 7000 (GE Healthcare) instrument. The electrophoresis band intensity ratio of RNA capping to RNA decapping was counted using ImageQuant (GE Healthcare) software, and the decapping rate of the decapping enzyme was calculated.

2. Experimental Results

TABLE 6

Decapping rate after treatment with decapping enzyme

| Name | Decapping rate (%) of DCP2 enzyme | Decrease relative to N-7113 (%) |
|---|---|---|
| YK-CAP-101 | 32.4 | 11.4 |
| YK-CAP-102 | 41.2 | 2.6 |
| YK-CAP-103 | 36.5 | 7.3 |
| YK-CAP-104 | 46.1 | −2.3 |
| YK-CAP-105 | 33.9 | 9.9 |
| YK-CAP-106 | 17.3 | 26.5 |
| YK-CAP-107 | 11.5 | 32.3 |
| YK-CAP-108 | 16.3 | 27.5 |
| YK-CAP-109 | 17.3 | 26.5 |
| YK-CAP-110 | 10.2 | 33.6 |
| YK-CAP-111 | 11.5 | 32.3 |
| YK-CAP-112 | 11.9 | 31.9 |
| YK-CAP-113 | 15.3 | 28.5 |
| YK-CAP-114 | 14.2 | 29.6 |
| YK-CAP-115 | 15.3 | 28.5 |
| YK-CAP-116 | 14.3 | 29.5 |
| YK-CAP-117 | 9.8 | 34.0 |
| YK-CAP-118 | 11.9 | 31.9 |
| YK-CAP-119 | 11.4 | 32.4 |
| 5227 | 23.2 | 20.6 |
| CAP-2'O-ethyl | 28.3 | 15.5 |
| N-7113 | 43.8 | 0.0 |
| Compound 14 | 26.8 | 17.0 |
| HN3002 | 23.3 | 20.5 |
| m6A | 33.8 | 10.0 |

1) The ribose-modified cap analogs of the present disclosure show a significant difference in decapping rate. YK-CAP-106 to 119 have a significantly lower decapping rate than that of YK-CAP-101 to 105. YK-CAP-117 has the lowest decapping rate, which is 36.3% lower than that of YK-CAP-104 (the highest).

As can be seen from the data in Table 6, the ribose-modified cap analogs YK-CAP-101 to 119 in the present disclosure vary greatly in the decapping rate. YK-CAP-106 to 119 all have very low decapping rates. Specifically, YK-CAP-107, YK-CAP-110, YK-CAP-111, YK-CAP-117, and YK-CAP-118 have a decapping rate of 11.5%, 10.2%, 11.5%, 9.8%, and 11.9%, respectively, with YK-CAP-117 having the lowest decapping rate of only 9.8%, followed by YK-CAP-110 with a decapping rate of 10.2%.

Figure 4:
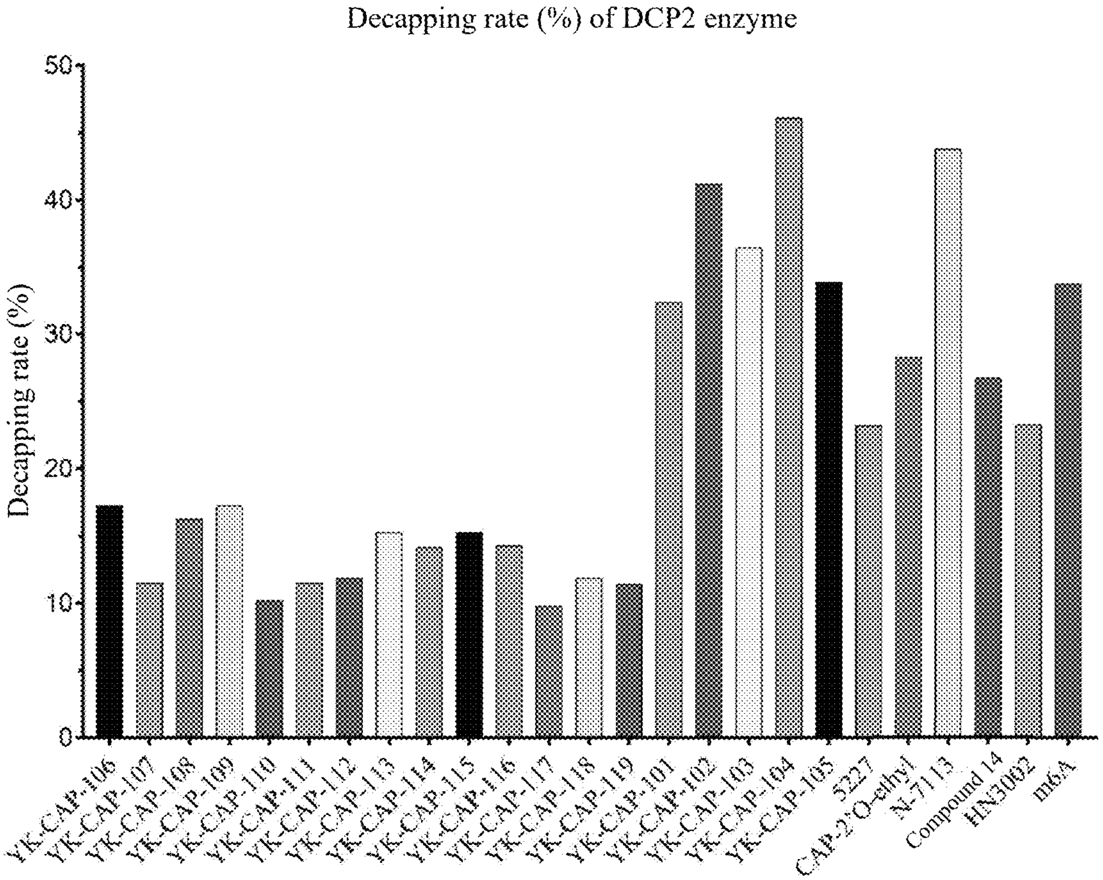
FIG. 4 is a graph showing the results of decapping rate of DCP2 enzyme using YK-CAP-106, YK-CAP-107, YK-CAP-108, YK-CAP-109, YK-CAP-110, YK-CAP-111, YK-CAP-112, YK-CAP-113, YK-CAP-114, YK-CAP-115, YK-CAP-116, YK-CAP-117, YK-CAP-118, YK-CAP-119, YK-CAP-101, YK-CAP-102, YK-CAP-103, YK-CAP-104, YK-CAP-105, 5227, CAP-2'O-ethyl, N-7113, compound 14, HN3002, and m6A as cap analogs.

YK-CAP-104 has the highest decapping rate, which is 46.1%. YK-CAP-101, YK-CAP-102, YK-CAP-103, and YK-CAP-105 also have a high decapping rate of 32.4%, 41.2%, 36.5%, and 33.9%, respectively. The decapping rate of YK-CAP-117 is 22.6%, 31.4%, 26.7%, 36.3%, and 24.1% lower than that of YK-CAP-101 to 105, respectively, while the decapping rate of YK-CAP-110 is 22.2%, 31.0%, 26.3%, 35.9%, and 23.7% lower than that of YK-CAP-101 to 105 (as shown in FIG. 4).

2) Compared to the ribose-modified cap analogs with similar or vastly different structures in the prior art, the ribose-modified cap analogs of the present disclosure show a significant decrease in the decapping rate. For example, the decapping rate of YK-CAP-117 is 34.0% lower than that of N-7113.

N-7113, compound 14, HN3002, and m6A have a decapping rate of 43.8%, 26.8%, 23.3%, and 33.8%, respectively. The decapping rate of YK-CAP-117 in the present disclosure is 34.0%, 17.0%, 13.5%, and 24.0% lower than that of N-7113, compound 14, HN3002, and m6A, respectively, while the decapping rate of YK-CAP-110 is 33.6%, 16.6%, 13.1%, and 23.6% lower than that of N-7113, compound 14, HN3002, and m6A, respectively.

3) The ribose-modified cap analogs with similar structures vary greatly in the decapping rate, making it impossible to predict the decapping rate based on structure.

The ribose-modified cap analogs YK-CAP-117 to 119 designed in the present disclosure have structures that are very similar. This series of compounds is also very similar in structure to 5227, but they vary greatly in the mRNA decapping rate. For example, compounds YK-CAP-117 to 119 in the present disclosure differ from 5227 only in the substituent at the C4 position of the first sugar ring, i.e., the C4-substituent of 5227 is methoxy; the C4-substituents of YK-CAP-117 to 119 are methoxymethyl, 1-fluoromethyl, and difluoromethyl, respectively. The other structures are exactly identical. However, the mRNA decapping rate of YK-CAP-117 to 119 is 13.4%, 11.3%, and 11.8% lower than that of 5227, respectively, showing a significant decrease.

Similarly, the ribose-modified cap analogs YK-CAP-113 to 116 designed in the present disclosure have structures that are very similar. This series of compounds is also very similar in structure to CAP-2'O-ethyl, but they vary greatly in the mRNA decapping rate. For example, compounds YK-CAP-113 to 116 in the present disclosure differ from CAP-2'O-ethyl only in the substituent at the C2 position of the second sugar ring, i.e., the C2-substituent of CAP-2'O-ethyl is ethoxy; the C2-substituents of YK-CAP-113 to 116 are methoxymethyl, acetamidomethyl, 1-fluoromethyl, and difluoromethyl, respectively. The other structures are exactly identical. However, the mRNA decapping rate of YK-CAP-113 to 116 is 13.0%, 14.1%, 13.0%, and 14.0% lower than that of CAP-2'O-ethyl, respectively, showing a significant decrease.

It can be seen that ribose-modified cap analogs with similar structures do not necessarily have similar decapping rates. On the contrary, there may be a huge difference.

As can be seen from the decapping rate of DCP2 enzyme, the ribose-modified cap analogs in the present disclosure, including YK-CAP-106 to 119, show a significant decrease in the decapping rate of DCP2 enzyme compared to both ribose-modified cap analogs with similar structures (including YK-CAP-101 to 105 in the present disclosure as well as 5227, CAP-2'O-ethyl, N-7113, and HN3002 in the prior art) and ribose-modified cap analogs with vastly different structures (including compound 14 and m6A). Moreover, ribose-modified cap analogs with similar structures do not necessarily have similar decapping rates. On the contrary, there may be a huge difference.

Example 6: Animal Experiments

1. Experimental Methods

The LNP preparation containing 5 μg of cap analog-transcribed Fluc-mRNA was intramuscularly injected into female BALB/C mice aged 4 to 6 weeks and weighing 17 to 19 g. At specific time points after administration (6 hours, 12 hours, 24 hours, 48 hours, 96 hours, and 168 hours), the mice were intraperitoneally injected with fluorescence imaging substrate. The mice were then allowed to move freely for 5 minutes, followed by detection of the total radiation intensity of the protein expressed by LNP-carrying mRNA in the mice using an IVIS Spectrum small-animal in vivo imaging system (corresponding to the amount of protein expression).

2. Experimental Results

The test results are shown in Table 7. In the in vivo imaging experiments in mice, the multiple of the total radiation intensity for each group of mice relative to the m6A group is shown in Table 8 (where the total radiation intensity is represented as the given value×$10^8$ p/s).

TABLE 7

Experimental data of in vivo imaging in mice

| Name | Total radiation intensity (×108 p/s) | | | | | |
|---|---|---|---|---|---|---|
| | 6 h | 12 h | 24 h | 48 h | 96 h | 168 h |
| YK-CAP-101 | 1.81 | 0.96 | 0.36 | 0.19 | 0.04 | 0.02 |
| YK-CAP-106 | 5.88 | 6.85 | 1.76 | 0.53 | 0.11 | 0.03 |
| YK-CAP-107 | 8.09 | 6.87 | 1.92 | 0.60 | 0.11 | 0.03 |
| YK-CAP-108 | 6.42 | 6.03 | 1.70 | 1.04 | 0.19 | 0.02 |
| YK-CAP-109 | 6.04 | 5.84 | 1.85 | 0.54 | 0.14 | 0.03 |
| YK-CAP-110 | 9.52 | 10.55 | 3.04 | 2.30 | 0.27 | 0.04 |
| YK-CAP-111 | 8.61 | 9.34 | 2.75 | 1.95 | 0.27 | 0.03 |
| YK-CAP-112 | 8.90 | 7.48 | 2.44 | 1.43 | 0.30 | 0.03 |
| YK-CAP-113 | 6.07 | 7.63 | 2.02 | 1.29 | 0.31 | 0.04 |
| YK-CAP-114 | 8.89 | 5.76 | 2.31 | 1.51 | 0.29 | 0.03 |
| YK-CAP-115 | 6.20 | 5.42 | 1.85 | 1.21 | 0.25 | 0.02 |
| YK-CAP-116 | 9.13 | 6.54 | 1.98 | 1.45 | 0.27 | 0.03 |
| YK-CAP-117 | 8.99 | 8.00 | 2.08 | 1.73 | 0.35 | 0.02 |
| YK-CAP-118 | 7.06 | 6.28 | 2.03 | 1.33 | 0.35 | 0.02 |
| YK-CAP-119 | 7.47 | 6.65 | 2.15 | 1.26 | 0.25 | 0.02 |
| 5227 | 2.38 | 1.45 | 0.53 | 0.48 | 0.07 | 0.02 |
| CAP-2'O-ethyl | 5.41 | 4.80 | 1.73 | 0.57 | 0.09 | 0.02 |
| N-7113 | 5.10 | 4.33 | 1.49 | 0.49 | 0.05 | 0.02 |
| m6A | 2.35 | 2.12 | 0.66 | 0.52 | 0.08 | 0.02 |

TABLE 8

Multiple of total radiation intensity relative to m6A

| Name | 6 h | 12 h | 24 h | 48 h | 96 h |
|---|---|---|---|---|---|
| YK-CAP-101 | 0.8 | 0.5 | 0.5 | 0.4 | 1.5 |
| YK-CAP-106 | 2.5 | 3.2 | 2.7 | 1.0 | 2.6 |
| YK-CAP-107 | 3.4 | 3.2 | 2.9 | 1.2 | 2.5 |
| YK-CAP-108 | 2.7 | 2.8 | 2.6 | 2.0 | 1.3 |
| YK-CAP-109 | 2.6 | 2.8 | 2.8 | 1.0 | 2.7 |
| YK-CAP-110 | 4.1 | 5.0 | 4.6 | 4.4 | 1.0 |
| YK-CAP-111 | 3.7 | 4.4 | 4.2 | 3.8 | 1.1 |
| YK-CAP-112 | 3.8 | 3.5 | 3.7 | 2.8 | 1.3 |
| YK-CAP-113 | 2.6 | 3.6 | 3.1 | 2.5 | 1.2 |
| YK-CAP-114 | 3.8 | 2.7 | 3.5 | 2.9 | 1.2 |
| YK-CAP-115 | 2.6 | 2.6 | 2.8 | 2.3 | 1.2 |
| YK-CAP-116 | 3.9 | 3.1 | 3.0 | 2.8 | 1.1 |
| YK-CAP-117 | 3.8 | 3.8 | 3.2 | 3.3 | 0.9 |
| YK-CAP-118 | 3.0 | 3.0 | 3.1 | 2.6 | 1.2 |
| YK-CAP-119 | 3.2 | 3.1 | 3.3 | 2.4 | 1.3 |
| 5227 | 1.0 | 0.7 | 0.8 | 0.9 | 0.9 |
| CAP-2'O-ethyl | 2.3 | 2.3 | 2.6 | 1.1 | 2.4 |
| N-7113 | 2.2 | 2.0 | 2.3 | 0.9 | 2.4 |
| m6A | 1.0 | 1.0 | 1.0 | 1.0 | 1.0 |

1) The ribose-modified cap analogs of the present disclosure show a significant difference in the total radiation intensity and duration of the protein expressed by mRNA in mice. YK-CAP-106 to 119 have significantly higher total radiation intensity than that of YK-CAP-101 to 105. YK-CAP-110 has the highest total radiation intensity, which is 11.0 and 12.1 times that of YK-CAP-101 (the lowest) at 12 hours and 48 hours, respectively.

As can be seen from the data in Table 7, the different ribose-modified cap analogs of the present disclosure vary greatly in the total radiation intensity of the protein expressed by mRNA in mice. YK-CAP-106 to 119 all have very high total radiation intensity of in vivo imaging in mice, among which YK-CAP-110 has the highest total radiation intensity, reaching 10.55×$10^8$ p/s at 12 hours and still reaching 2.30×$10^8$ p/s at 48 hours, while YK-CAP-111 has the second highest total radiation intensity, reaching 9.34×$10^8$ p/s at 12 hours and still reaching 1.95×$10^8$ p/s at 48 hours.

YK-CAP-101 has the lowest total radiation intensity, which is 0.96×$10^8$ p/s at 12 hours and only 0.19×$10^8$ p/s at 48 hours. The total radiation intensity of YK-CAP-110 is 11.0 times that of YK-CAP-101 at 12 hours and 12.1 times that of YK-CAP-101 at 48 hours. The total radiation intensity of YK-CAP-111 is 9.7 times that of YK-CAP-101 at 12 hours and 10.3 times that of YK-CAP-101 at 48 hours.

2) Compared to the ribose-modified cap analogs with similar or vastly different structures in the prior art, the ribose-modified cap analogs of the present disclosure show a significant increase in the total radiation intensity and duration of the protein expressed by mRNA in mice. For example, the total radiation intensity of YK-CAP-110 is 5.0 times that of m6A at 12 hours and 4.4 times that of m6A at 48 hours.

N-7113 and m6A have a total radiation intensity of $4.33\times10^8$ p/s and $2.12\times 10^8$ p/s at 12 hours, and $0.49\times10^8$ p/s and $0.52\times 10^8$ p/s at 48 hours.

The total radiation intensity of YK-CAP-110 in the present disclosure is 2.4 times that of N-7113 and 5.0 times that of m6A at 12 hours, and 4.7 times that of N-7113 and 4.4 times that of m6A at 48 hours.

The total radiation intensity of YK-CAP-111 in the present disclosure is 2.2 times that of N-7113 and 4.4 times that of m6A at 12 hours, and 4.0 times that of N-7113 and 3.8 times that of m6A at 48 hours.

3) The ribose-modified cap analogs with similar structures vary greatly in the total radiation intensity and duration of the protein expressed by mRNA in mice, making it impossible to predict the total radiation intensity and duration of the protein expressed by mRNA in mice based on structure.

The ribose-modified cap analogs YK-CAP-117 to 119 designed in the present disclosure have structures that are very similar. This series of compounds is also very similar in structure to 5227, but they vary greatly in the total radiation intensity of the protein expressed by mRNA in mice. For example, compounds YK-CAP-117 to 119 in the present disclosure differ from 5227 only in the substituent at the C4 position of the first sugar ring, i.e., the C4-substituent of 5227 is methoxy; the C4-substituents of YK-CAP-117 to 119 are methoxymethyl, 1-fluoromethyl, and difluoromethyl, respectively. The other structures are exactly identical. However, the total radiation intensity of the protein expressed by mRNA in mice of YK-CAP-117 to 119 is 3.8 times, 3.0 times, and 3.1 times that of 5227 at 6 hours, respectively, showing a significant increase.

Similarly, the ribose-modified cap analogs YK-CAP-113 to 116 designed in the present disclosure have structures that are very similar. This series of compounds is also very similar in structure to CAP-2'O-ethyl, but they vary greatly in the total radiation intensity of the protein expressed by mRNA in mice. For example, compounds YK-CAP-113 to 116 in the present disclosure differ from CAP-2'O-ethyl only in the substituent at the C2 position of the second sugar ring, i.e., the C2-substituent of CAP-2'O-ethyl is ethoxy; the C2-substituents of YK-CAP-113 to 116 are methoxymethyl, acetamidomethyl, 1-fluoromethyl, and difluoromethyl, respectively. The other structures are exactly identical. However, the total radiation intensity of the protein expressed by mRNA in mice of YK-CAP-114 and YK-CAP-116 is 1.6 times and 1.7 times that of CAP-2'O-ethyl at 6 hours, respectively, showing a significant increase.

It can be seen that Fluc-mRNAs prepared from ribose-modified cap analogs with similar structures do not necessarily have similar amount and duration of protein expression in mice. On the contrary, there may be a huge difference.

As can be seen from the animal experiments, the ribose-modified cap analogs in the present disclosure, such as YK-CAP-106 to 119, show a significant increase in the amount and duration of protein expression by mRNA in mice compared to both ribose-modified cap analogs with similar structures (including YK-CAP-101 to 105 in the present disclosure as well as 5227, N-7113, and CAP-2'O-ethyl in the prior art) and ribose-modified cap analogs with vastly different structures (m6A).

In vivo experiments further demonstrate that the mRNA transcribed using YK-CAP-106 to 119 in the present disclosure can be effectively delivered into the body by LNP delivery vectors and efficiently and continuously expressed. Moreover, Fluc-mRNAs prepared from ribose-modified cap analogs with similar structures do not necessarily have similar amount and duration of protein expression in mice. On the contrary, there may be a huge difference.

In summary, the ribose-modified cap analogs YK-CAP-106 to 119 in the present disclosure show a significant increase in the in vitro transcription yield of mRNA, capping rate, translation efficiency of mRNA, decapping enzyme stability, and amount and duration of protein expression in animals compared to the ribose-modified cap analogs in the prior art (including 5227, CAP-2'O-ethyl, N-7113, compound 14, HN3002, and m6A). It indicates that the YK-CAP-106 to 119 cap structures provided by the present disclosure can significantly enhance the resistance of ribose-modified structures to decapping enzymes as well as their binding affinity to capping enzymes, providing a novel and efficient ribose-modified cap structure for in vitro transcription of mRNA.

1. The compounds of the present disclosure have chemical structures that are very similar. This series of compounds has some similarities and some significant differences in structure compared to the mRNA cap analogs disclosed in the prior art.

1) The first sugar ring of compounds YK-CAP-101 and YK-CAP-102 in the present disclosure is a 6-membered ring, while the first sugar ring of N7113 is a 5-membered ring. The other structures are exactly identical.

2) The group attached to the first sugar ring and guanine of compound YK-CAP-103 in the present disclosure is different from that of N7113, i.e., there is one more methylene group at the C1 position. The other structures are exactly identical.

3) The first sugar ring of compounds YK-CAP-104 to 106 in the present disclosure has two substituents at the C3 position, which is different from N7113, i.e., the C3-substituents of N7113 are hydroxyl and hydrogen; the C3-substituents of YK-CAP-104 are dimethylaminomethyl and fluorine, respectively; the C3-substituents of YK-CAP-105 are cyano and methyl, respectively; the C3-substituents of YK-CAP-106 are acetamido and methyl, respectively. The other structures are exactly identical.

4) The substituents at the C3 position of the first sugar ring of compounds YK-CAP-107 to 112 in the present disclosure are different from those of N7113 and HN3002, i.e., the C3-substituents of N7113 and HN3002 are hydroxyl and methoxymethyl; the C3-substituents of YK-CAP-107 to 112 are 1-methoxyethyl, 1-acetamidoethyl, 1-fluoroethyl, difluoromethyl, N,N-diacetamido, and N,N-dipropionamido, respectively. The other structures are exactly identical.

5) The substituents at the C2 position of the second sugar ring of compounds YK-CAP-113 to 116 in the present disclosure are different from those of N7113 and CAP-2'O-ethyl, i.e., the C2-substituents of N7113 and CAP-2'O-ethyl are methoxy and ethoxy; the C2-substituents of YK-CAP-113 to 116 are methoxymethyl, acetamidomethyl, 1-fluoromethyl, and difluoromethyl, respectively. The other structures are exactly identical.

6) The substituents at the C4 position of the first sugar ring of compounds YK-CAP-117 to 119 in the present disclosure are different from those of N7113 and 5227, i.e., the C4-substituents of N7113 and 5227 are hydrogen and methoxy; the C4-substituents of YK-CAP-117 to 119 are methoxymethyl, 1-fluoromethyl, and difluoromethyl, respectively. The other structures are exactly identical.

7)Compounds YK-CAP-101 to 119 in the present disclosure differ greatly in structure from compound 14 and m6A, specifically, the first sugar ring of compound 14 is a locked nucleic acid sugar ring, i.e., there is a methylene bridge between 2'-O and C4'; the second base of m6A, adenine, is methylated.

2. The ribose-modified cap analogs of the present disclosure show a significant difference in the in vitro transcription yield of mRNA and capping rate. Compared to the ribose-modified cap analogs in the prior art, the ribose-modified cap analogs of the present disclosure show a significant increase in both in vitro transcription yield of mRNA and capping rate.

1) The ribose-modified cap analogs of the present disclosure show a significant difference in the in vitro transcription yield and capping rate of mRNA. YK-CAP-106 to 119 have significantly higher in vitro transcription yield and capping rate of mRNA than those of YK-CAP-101 to 105. YK-CAP-111 has the highest transcription yield and capping rate, with the transcription yield being 5.3 times that of YK-CAP-101 (the lowest) and the capping rate being 3.2 times that of YK-CAP-102 (the lowest).

2)Compared to the ribose-modified cap analogs in the prior art, the ribose-modified cap analogs of the present disclosure show a significant increase in both in vitro transcription yield of mRNA and capping rate. For example, the transcription yield of YK-CAP-111 is 40.8% higher than that of compound 14, and the capping rate of YK-CAP-111 is 36.4% higher than that of 5227.

3) The ribose-modified cap analogs with similar structures vary greatly in the in vitro transcription yield of mRNA and capping rate. For example, the in vitro transcription yield of mRNA of YK-CAP-117 to 119 is 14.2%, 28.3% and 14.9% higher than that of 5227, respectively, and the capping rate of YK-CAP-117 to 119 is 32.3%, 35.2%, and 33.9% higher than that of 5227, respectively.

3. The ribose-modified cap analogs of the present disclosure show a significant difference in translation efficiency of mRNA. Compared to the ribose-modified cap analogs in the prior art, the ribose-modified cap analogs of the present disclosure show a significant increase in the translation efficiency of mRNA.

1) The ribose-modified cap analogs of the present disclosure show a significant difference in translation efficiency of mRNA. YK-CAP-106 to 119 have significantly higher translation efficiency than that of YK-CAP-101 to 105. YK-CAP-111 has the highest translation efficiency, which is 9.6 times that of YK-CAP-101 (the lowest).

2)Compared to the ribose-modified cap analogs with similar or vastly different structures in the prior art, the ribose-modified cap analogs of the present disclosure show a significant increase in the translation efficiency of mRNA. For example, the translation efficiency of YK-CAP-111 is 5.6 times that of m6A.

3) The ribose-modified cap analogs with similar structures vary greatly in the translation efficiency of mRNA. For example, the translation efficiency of mRNA of YK-CAP-117 to 119 is 2.2 times, 2.0 times, and 1.8 times that of 5227, respectively.

4. The ribose-modified cap analogs of the present disclosure show a significant difference in decapping rate. Compared to the ribose-modified cap analogs with similar or vastly different structures in the prior art, the ribose-modified cap analogs of the present disclosure show a significant decrease in the decapping rate.

1) The ribose-modified cap analogs of the present disclosure show a significant difference in decapping rate. YK-CAP-106 to 119 have a significantly lower decapping rate than that of YK-CAP-101 to 105. YK-CAP-117 has the lowest decapping rate, which is 36.3% lower than that of YK-CAP-104 (the highest).

2)Compared to the ribose-modified cap analogs with similar or vastly different structures in the prior art, the ribose-modified cap analogs of the present disclosure show a significant decrease in the decapping rate. For example, the decapping rate of YK-CAP-117 is 34.0% lower than that of N-7113.

3) The ribose-modified cap analogs with similar structures vary greatly in the decapping rate. For example, the mRNA decapping rate of YK-CAP-113 to 116 is 13.0%, 14.1%, 13.0%, and 11.0% lower than that of CAP-2'O-ethyl, respectively.

5. The ribose-modified cap analogs of the present disclosure show a significant difference in the total radiation intensity (corresponding to the amount of protein expression) and duration of the protein expressed by mRNA in mice. Compared to the ribose-modified cap analogs with similar or vastly different structures in the prior art, the ribose-modified cap analogs of the present disclosure show a significant increase in the amount and duration of protein expression by mRNA in mice.

1) The ribose-modified cap analogs of the present disclosure show a significant difference in the total radiation intensity and duration of the protein expressed by mRNA in mice. YK-CAP-106 to 119 have significantly higher total radiation intensity than that of YK-CAP-101 to 105. YK-CAP-110 has the highest total radiation intensity, which is 11.0 and 12.1 times that of YK-CAP-101 (the lowest) at 12 hours and 48 hours, respectively.

2)Compared to the ribose-modified cap analogs with similar or vastly different structures in the prior art, the ribose-modified cap analogs of the present disclosure show a significant increase in the total radiation intensity and duration of the protein expressed by mRNA in mice. For example, the total radiation intensity of YK-CAP-110 is 5.0 times that of m6A at 12 hours and 4.4 times that of m6A at 48 hours.

3) The ribose-modified cap analogs with similar structures vary greatly in the total radiation intensity and duration of the protein expressed by mRNA in mice. For example, the total radiation intensity of the protein expressed by mRNA in mice of YK-CAP-117 to 119 is 3.8 times, 3.0 times, and 3.1 times that of 5227 at 6 hours, respectively.

The applicant declares that the present disclosure illustrates the ribose-modified cap analogs of the present disclosure and the use thereof through the above examples. However, the present disclosure is not limited to these examples, which does not mean that the present disclosure must be implemented depending on these examples. It should be understood by those skilled in the art that any improvements to the present disclosure, equivalent substitutions of starting materials for the products of the present disclosure, additions of auxiliary ingredients, selections of specific means, etc., all fall within the scope of protection and disclosure of the present disclosure.

What is claimed is:

1. A ribose-modified cap analog or a pharmaceutically acceptable salt thereof, wherein the ribose-modified cap analog has a structure of YK-CAP-106, YK-CAP-107, YK-CAP-108, YK-CAP-109, YK-CAP-110, YK-CAP-111, YK-CAP-112, YK-CAP-113, YK-CAP-114, YK-CAP-115, YK-CAP-116, YK-CAP-117, YK-CAP-118, or YK-CAP-119 as shown below:

YK-CAP-106

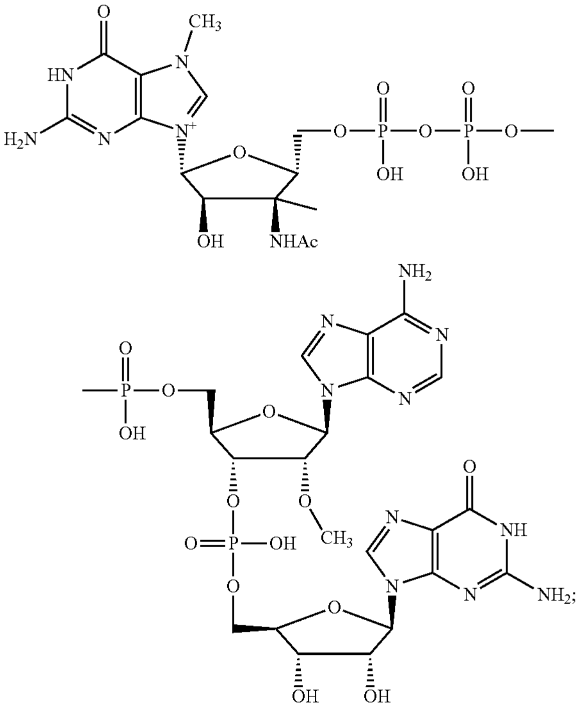

YK-CAP-107

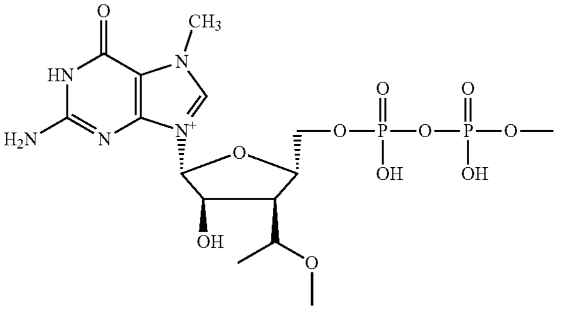

-continued

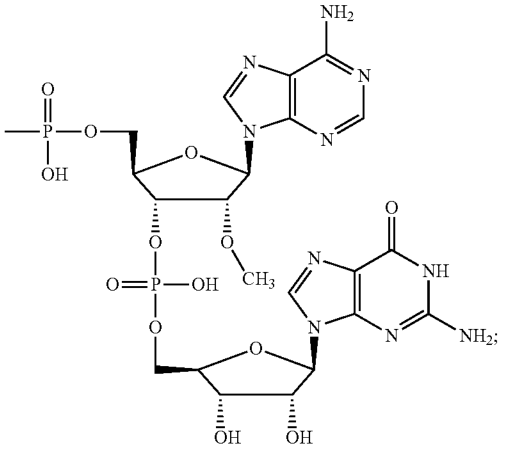

YK-CAP108

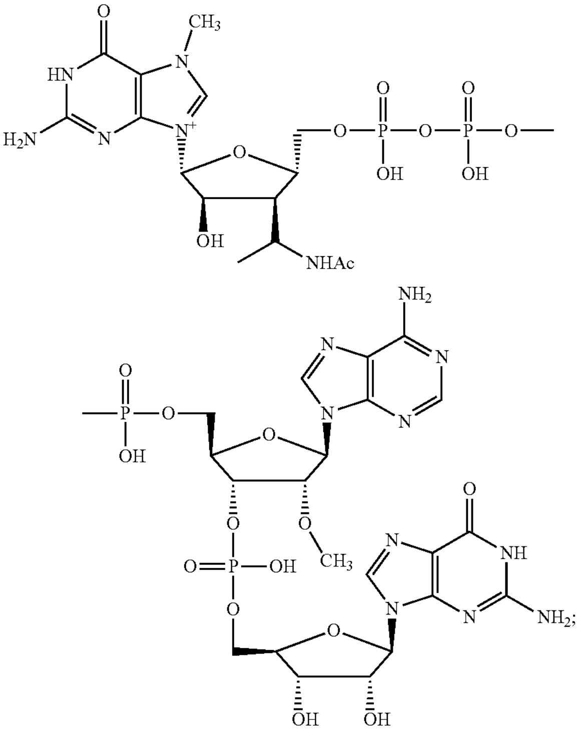

YK-CAP-109

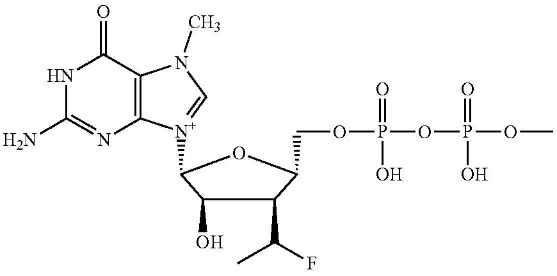

-continued
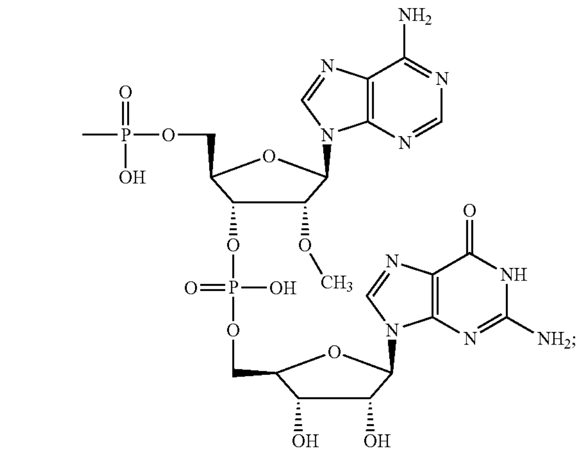
YK-CAP-110
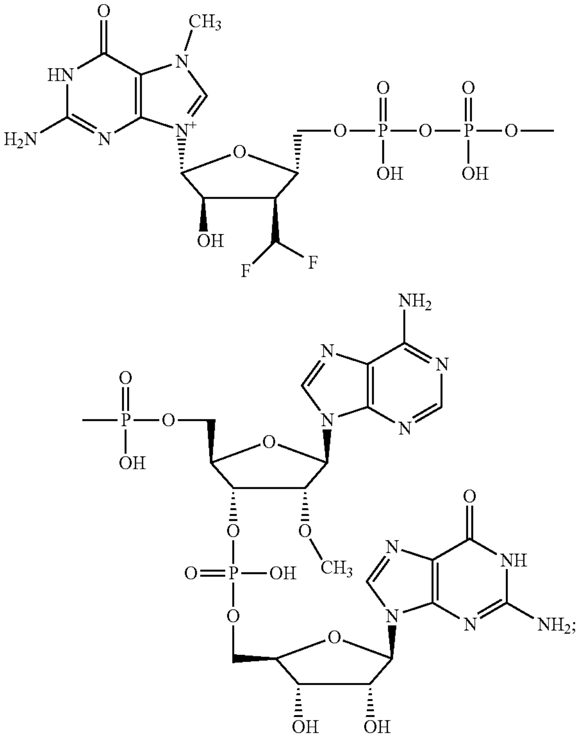
YK-CAP-111
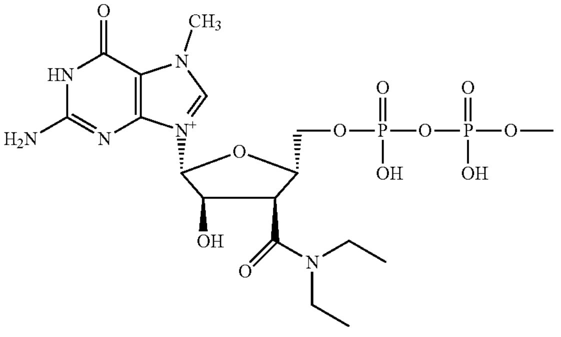
-continued
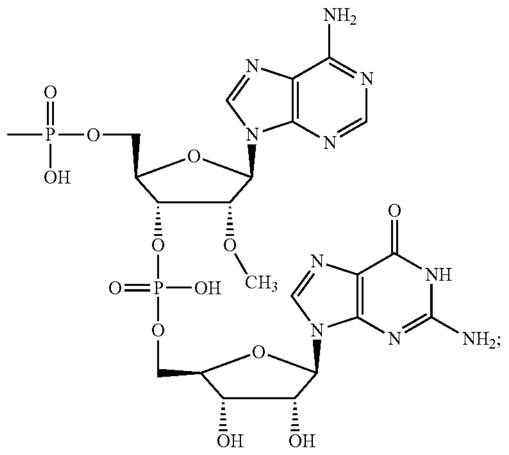
YK-CAP-112
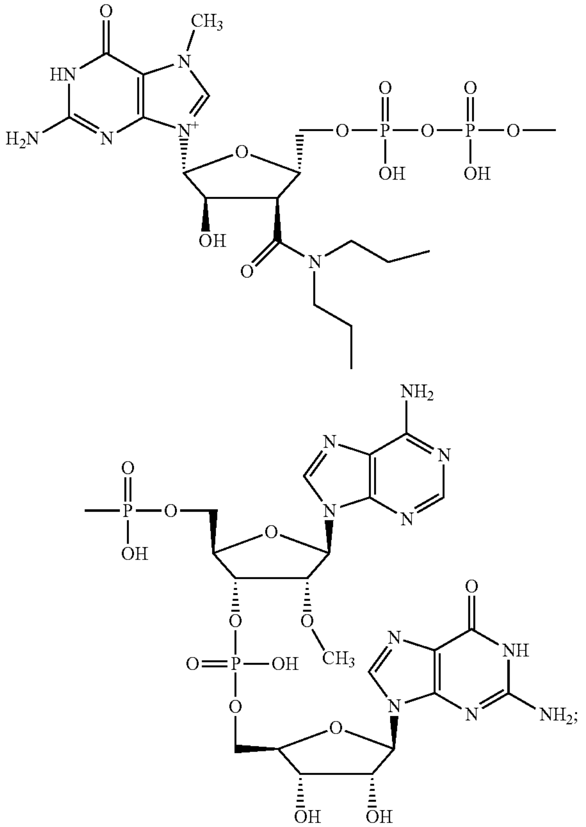
YK-CAP-113
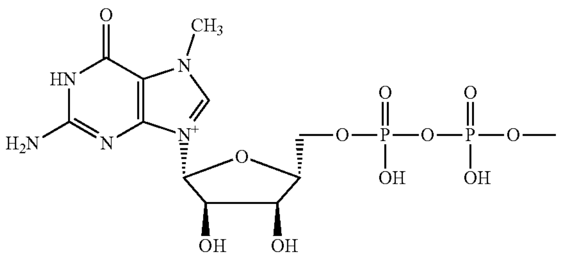

-continued
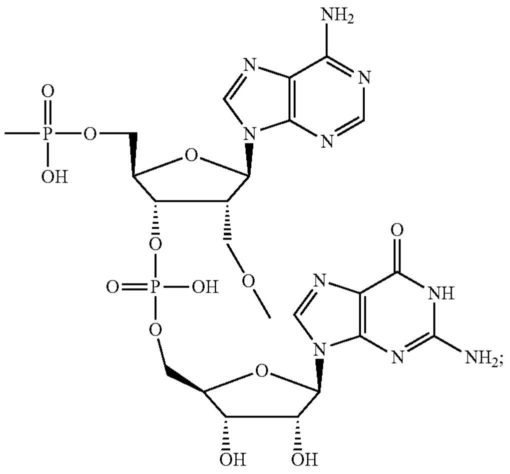
YK-CAP-114
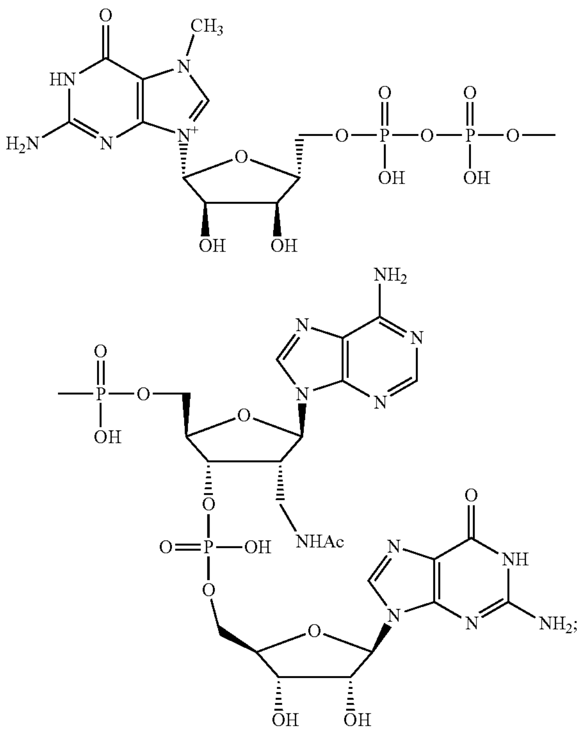
YK-CAP-115
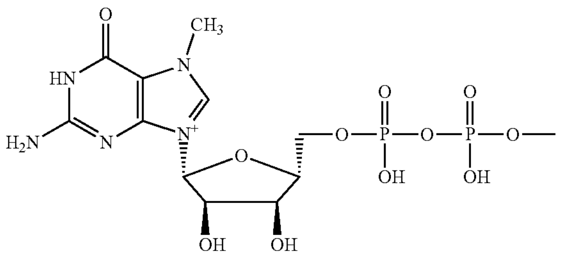
-continued
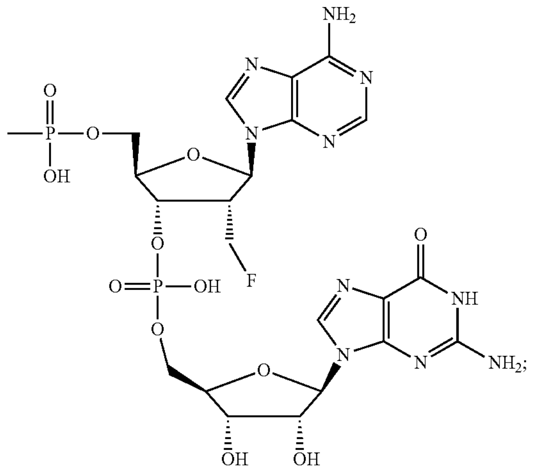
YK-CAP-116
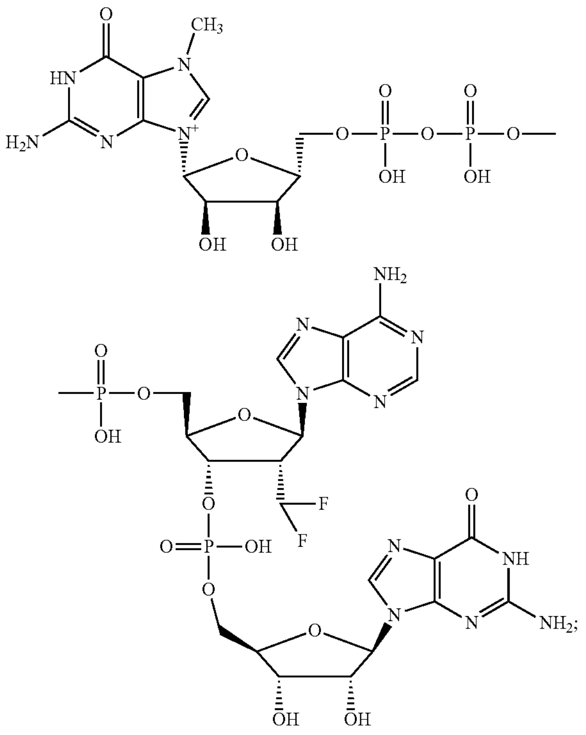
YK-CAP-117
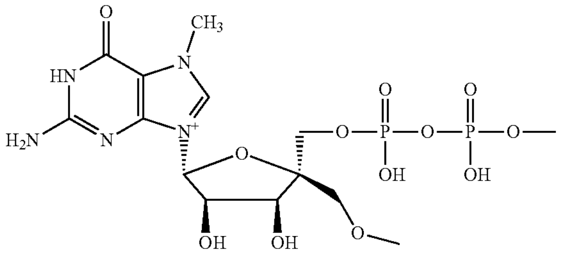

-continued

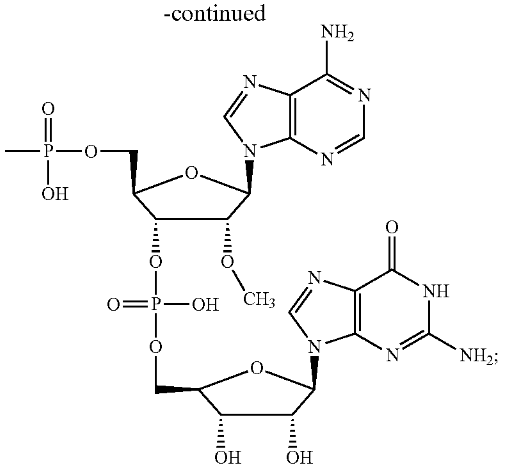

YK-CAP-118

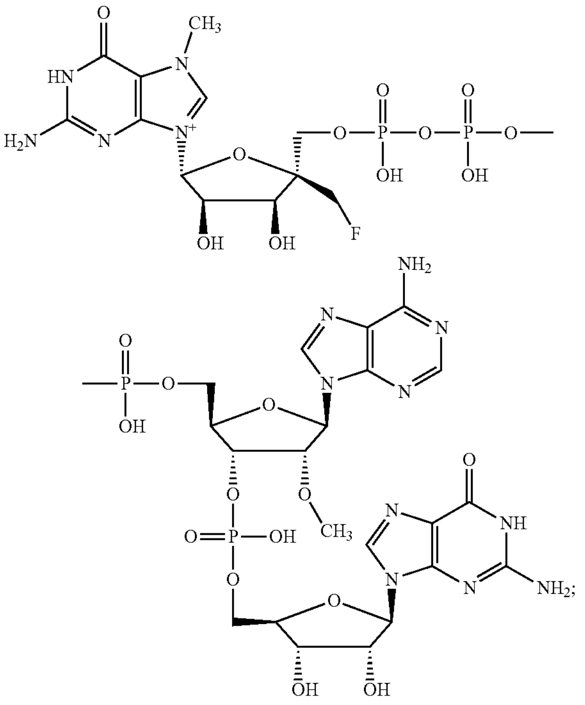

-continued

YK-CAP-119

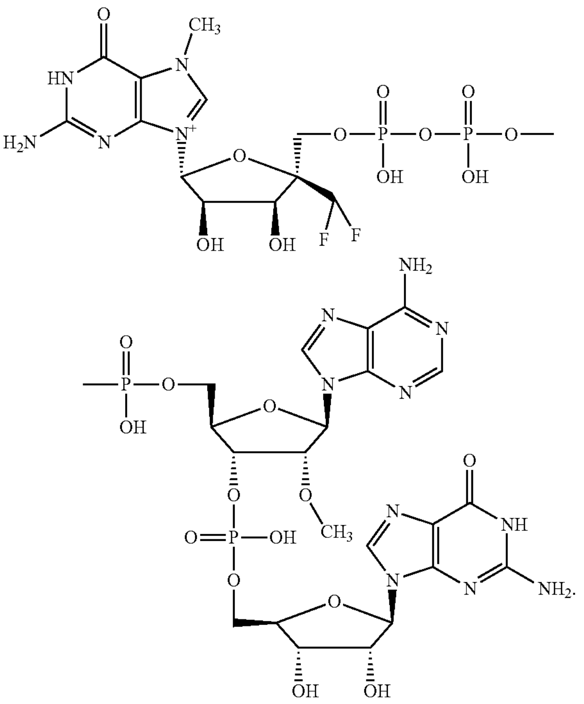

2. An RNA molecule, comprising the ribose-modified cap analog or the pharmaceutically acceptable salt thereof according to claim 1 as a cap structure.

3. A pharmaceutical composition, comprising the RNA molecule according to claim 2.

4. A kit comprising:

(1) the ribose-modified cap analog, or the stereoisomer, the pharmaceutically acceptable salt thereof according to claim 1; and (2) a nucleotide triphosphate molecule and an RNA polymerase.

5. The kit according to claim 4, wherein the kit further comprises one or a combination of at least two of an RNAase inhibitor, an inorganic pyrophosphatase, $Mg^{2+}$, or a buffer.

* * * * *